(12) United States Patent
Huertas Fernandez et al.

(10) Patent No.: US 12,427,318 B2
(45) Date of Patent: Sep. 30, 2025

(54) SPINAL CORD STIMULATION SYSTEM DETERMINING OPTIMAL SUB-PERCEPTION THERAPY BY USING NEURAL DOSE

(71) Applicant: Boston Scientific Neuromodulation Corporation, Valencia, CA (US)

(72) Inventors: Ismael Huertas Fernandez, Madrid (ES); Que T. Doan, West Hills, CA (US); Michael A. Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 850 days.

(21) Appl. No.: 17/596,340

(22) PCT Filed: Jul. 1, 2020

(86) PCT No.: PCT/US2020/040529
§ 371 (c)(1),
(2) Date: Dec. 8, 2021

(87) PCT Pub. No.: WO2021/003290
PCT Pub. Date: Jan. 7, 2021

(65) Prior Publication Data
US 2022/0233867 A1 Jul. 28, 2022

Related U.S. Application Data

(63) Continuation-in-part of application No. 16/738,786, filed on Jan. 9, 2020, now Pat. No. 11,951,314, and a
(Continued)

(51) Int. Cl.
*A61N 1/36* (2006.01)
*A61N 1/05* (2006.01)
*A61N 1/372* (2006.01)

(52) U.S. Cl.
CPC ....... *A61N 1/36171* (2013.01); *A61N 1/0551* (2013.01); *A61N 1/36175* (2013.01); *A61N 1/37235* (2013.01)

(58) Field of Classification Search
CPC .............. A61N 1/36171; A61N 1/0551; A61N 1/36175; A61N 1/37235; A61N 1/36071;
(Continued)

(56) References Cited

U.S. PATENT DOCUMENTS 6,181,969 B1   1/2001   Gord
6,516,227 B1   2/2003   Meadows et al.
(Continued)

FOREIGN PATENT DOCUMENTS

CN   202933390   5/2013
EP   2923727    9/2015
(Continued)

OTHER PUBLICATIONS

First Office Action regarding corresponding Chinese Patent Application No. 202080048202.7, mailed Jun. 26, 2024.
(Continued)

*Primary Examiner* — Mark W. Bockelman
(74) *Attorney, Agent, or Firm* — Lewis & Reese, PLLC

(57) ABSTRACT

Methods and systems for determining sub-perception stimulation for a patient having a spinal cord stimulator device are disclosed. In one example, an external device includes an algorithm configured to determine a stimulation program for the stimulator device. The algorithm includes a model that comprises pre-determined energy values that cause sub-perception stimulation. The algorithm is configured to determine stimulation parameters for the stimulation program that yield an energy value within the first model. The energy values in the model may be expressed as a function of frequency. The model in particular provides optimal sub-
(Continued)

perception stimulation at low frequencies, such as at 1 kHz and below, or even at 400 Hz and below.

17 Claims, 73 Drawing Sheets

Related U.S. Application Data continuation-in-part of application No. 16/657,560, filed on Oct. 18, 2019, and a continuation-in-part of application No. 16/460,640, filed on Jul. 2, 2019, and a continuation-in-part of application No. 16/460,655, filed on Jul. 2, 2019, now Pat. No. 11,338,127.

(60) Provisional application No. 62/986,365, filed on Mar. 6, 2020.

(58) Field of Classification Search
CPC ............ A61N 1/36062; A61N 1/3615; A61N 1/36164
See application file for complete search history.

(56) References Cited

U.S. PATENT DOCUMENTS

| | | | |
|---|---|---|---|
| 7,603,177 | B2 | 10/2009 | Sieracki et al. |
| 8,180,451 | B2 | 5/2012 | Hickman et al. |
| 8,359,102 | B2 | 1/2013 | Alataris et al. |
| 8,515,546 | B2 | 8/2013 | Goddard et al. |
| 8,606,360 | B2 | 12/2013 | Butson et al. |
| 8,606,362 | B2 | 12/2013 | He et al. |
| 8,620,436 | B2 | 12/2013 | Parramon et al. |
| 8,712,533 | B2 | 4/2014 | Alataris et al. |
| 8,792,988 | B2 | 7/2014 | Alataris et al. |
| 9,259,574 | B2 | 2/2016 | Aghassian et al. |
| 9,327,125 | B2 | 5/2016 | Alataris et al. |
| 9,333,357 | B2 | 5/2016 | Alataris et al. |
| 9,446,243 | B2 | 9/2016 | Marnfeldt et al. |
| 9,480,842 | B2 | 11/2016 | Alataris et al. |
| 9,789,252 | B2 | 10/2017 | Gerber et al. |
| 9,792,412 | B2 | 10/2017 | Moffitt et al. |
| 2010/0023090 | A1 | 1/2010 | Jaax et al. |
| 2010/0274312 | A1 | 10/2010 | Alataris et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2013/0053923 | A1 | 2/2013 | Jaax et al. |
| 2013/0268026 | A1 | 10/2013 | Rao et al. |
| 2014/0277251 | A1 | 9/2014 | Gerber et al. |
| 2014/0364919 | A1 | 12/2014 | Doan |
| 2015/0080982 | A1 | 3/2015 | Funderburk |
| 2015/0231402 | A1 | 8/2015 | Aghassian |
| 2015/0335893 | A1 | 11/2015 | Parker |
| 2015/0360038 | A1 | 12/2015 | Zottola et al. |
| 2016/0082265 | A1 | 3/2016 | Moffitt et al. |
| 2016/0114166 | A1 | 4/2016 | Kaula et al. |
| 2016/0144183 | A1 | 5/2016 | Marnfeldt |
| 2016/0158551 | A1 | 6/2016 | Kent et al. |
| 2016/0317815 | A1 | 11/2016 | Doan et al. |
| 2016/0361543 | A1 | 12/2016 | Kaula et al. |
| 2016/0367822 | A1 | 12/2016 | Parramon |
| 2017/0056642 | A1 | 3/2017 | Moffitt et al. |
| 2017/0080234 | A1 | 3/2017 | Gillespie et al. |
| 2017/0106197 | A1 | 4/2017 | Wechter et al. |
| 2017/0165490 | A1 | 6/2017 | Wechter |
| 2017/0173326 | A1 | 6/2017 | Bloch et al. |
| 2017/0173335 | A1 | 6/2017 | Min et al. |
| 2017/0189685 | A1 | 7/2017 | Steinke et al. |
| 2018/0043172 | A1 | 2/2018 | Serrano Carmona |
| 2018/0071513 | A1 | 3/2018 | Weiss et al. |
| 2018/0071520 | A1 | 3/2018 | Weerakoon et al. |
| 2018/0104493 | A1 | 4/2018 | Doan et al. |
| 2018/0193651 | A1 | 7/2018 | Annoni et al. |
| 2019/0046800 | A1 | 2/2019 | Doan et al. |
| 2019/0083796 | A1 | 3/2019 | Weerakoon et al. |
| 2019/0175915 | A1 | 6/2019 | Brill et al. |
| 2019/0209844 | A1 | 7/2019 | Esteller et al. |
| 2019/0290900 | A1 | 9/2019 | Esteller et al. |
| 2019/0366104 | A1 | 12/2019 | Doan et al. |

FOREIGN PATENT DOCUMENTS

| | | |
|---|---|---|
| WO | 2017/106539 | 6/2017 |
| WO | 2020/251899 | 12/2020 |

OTHER PUBLICATIONS

L. Kapural et al., "Novel 10-kHz High-frequency Therapy (HF10 Therapy) Is Superior to Traditional Low-frequency Spinal Cord Stimulation for the Treatment of Chronic Back and Leg Pain," Anesthesiology 2015; 123:851-60 (Oct. 2015).

S. Thomson et al., "The PROCO Randomised Controlled Trial: Effects of Pulse Rate On Clinical Outcomes in Kilohertz Frequency Spinal Cord Stimulation—A Multicentre, Double-blind, Crossover Study," presented at the International Neuromodulation Society (INS) Meeting on May 31, 2017.

E.C. Celik et al., "The effect of low-frequency TENS in the treatment of neuropathic pain in patients with spinal cord injury," Spinal Cord 51:34-337 (2013).

Y. Maeda et al., "Low frequencies, but not high frequencies of bi-polar spinal cord stimulation reduce cutaneous and muscle hyperalgesia induced by nerve injury," Pain 138:143-152 (2008).

S. Thomson et al., "Neural Dosing and Energy Requirements in Kilohertz Frequency Spinal Cord Stimulation (SCS)," poster presented at the International Neuromodulation Society (INS) Meeting on May 31, 2017.

S. Paz et al., "Improved Efficacy of SCS Implants Using Multiple Waveforms and Field Shape Options," poster presented at the International Neuromodulation Society (INS) Meeting on May 31, 2017.

S. Paz et al., "Evaluation of Customized Field Shape for Subperception SCS in a Case Series of Chronic Pain Patients," poster presented at the North American Neuromodulation Society (NANS) Meeting on Jan. 11-14, 2018.

S.J. Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21(1), pp. 67-76 (2018) (published on-line Dec. 8, 2017).

J.M. North et al., "Clinical Outcomes of 1 kHz Subperception Spinal Cord Stimulation in Implanted Patients With Failed Paresthesia-Based Stimulation: Results of a Prospective Randomized Controlled Trial," Neuromodulation: Technology at the Neural Interface, vol. 19(7), pp. 731-737 (2016).

Yearwood, Thomas, et al., Handout titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.

Yearwood, Thomas, et al., Poster titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 7 pages.

Yearwood, Thomas, "Neuropathic Extremity Paid and Spinal Cord Stimulation," Pain Medicine, vol. 7, No. S1, 2006, 6 pages.

A. Al-Kaisy et al., "Prospective, Randomized, Sham-Control, Double Blind, Crossover Trial of Subthreshold Spinal Cord Stimulation at Various Kilohertz Frequencies in Subjects Suffering From Failed Back Surgery Syndrome (SCS Frequency Study)," Neuromodulation, vol. 21(5), pp. 457-465 (2018).

M. De Jaeger M et al., "High-Density in Spinal Cord Stimulation: Virtual Expert Registry (Discover): Study Protocol for a Prospective Observational Trial," Anesth. Pain Med., vol. 7(3) (2017).

(56) References Cited

OTHER PUBLICATIONS

T.E. Hamm-Faber et al., "High-Dose Spinal Cord Stimulation for Treatment of Chronic Low Back Pain and Leg Pain in Patients With FBSS, 12-Month Results: A Prospective Pilot Study," Neuromodulation, E-pub ahead of print, DOI:10.1111/ner. 12940 (2019).

L. Kapural et al., "Novel 10-kHz High-frequency Therapy (HF10 Therapy) Is Superior to Traditional Low-frequency Spinal Cord Stimulation for the Treatment of Chronic Back and Leg Pain: The SENZA-RCT Randomized Controlled Trial," Anesthesiology, vol. 123(4), pp. 851-860 (2015).

J.P. Miller et al., "Parameters of Spinal Cord Stimulation and Their Role in Electrical Charge Delivery: A Review," Neuromodulation, vol. 19(4), pp. 373-384 (2016).

Z. Chen et al., "The Impact of Electrical Charge Delivery on Inhibition of Mechanical Hypersensitivity in Nerve-Injured Rats by Sub-Sensory Threshold Spinal Cord Stimulation," Neuromodulation, vol. 22(2), pp. 163-171 (2019).

F. Yang et al., "Modulation of Spinal Nociceptive Transmission by Sub-Sensory Threshold Spinal Cord Stimulation in Rats After Nerve Injury," Neuromodulation, E-pub ahead of print, DOI: 10.1111/ner.12975 (2019).

S.L. Leong et al., "Potential Therapeutic Effect of Low Amplitude Burst Spinal Cord Stimulation on Pain," Neuromodulation, E-pub ahead of print, DOI: 10.1111/ner.13090 (2019).

T. Deer et al., "Success Using Neuromodulation With Burst (Sunburst) Study: Results From a Prospective, Randomized Controlled Trial Using a Novel Burst Waveform," Neuromodulation, vol. 21(1), pp. 56-66 (2018).

F. Wille et al., "Altering Conventional to High Density Spinal Cord Stimulation: An Energy Dose-Response Relationship in Neuropathic Pain Therapy," Neuromodulation, vol. 20(1), pp. 71-80 (2017).

J. Vesper et al., "Burst SCS Microdosing Is as Efficacious as Standard Burst SCS in Treating Chronic Back and Leg Pain: Results From a Randomized Controlled Trial," Neuromodulation, vol. 22(2), pp. 190-193 (2019).

E. Tavel et al., "Lower Amplitudes for Burst SCS Programming Associated with Improved Outcomes: SUNBURST Sub-Analysis," International Neuromodulation Society (INS) annual meeting, poster, (2017).

International Search Report and Written Opinion regarding corresponding PCT Application No. PCT/US2020/040529, mailed Oct. 16, 2020.

Examination Report No. 1 for Standard Patent Application regarding corresponding Australian Application No. 2020299381, mailed Nov. 10, 2022.

Examiner's Report regarding corresponding Canadian Application No. 3,143,251, mailed Jan. 30, 2023.

Extended European Search Report regarding corresponding European Application No. 23194504.9, mailed Jan. 15, 2024.

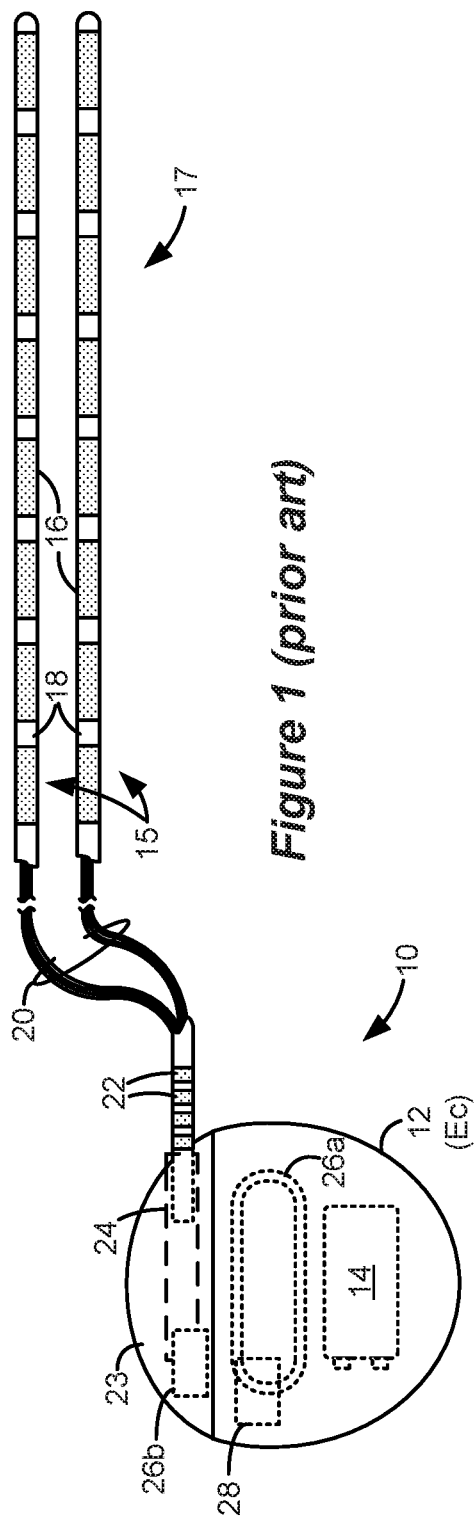
Figure 1 (prior art)
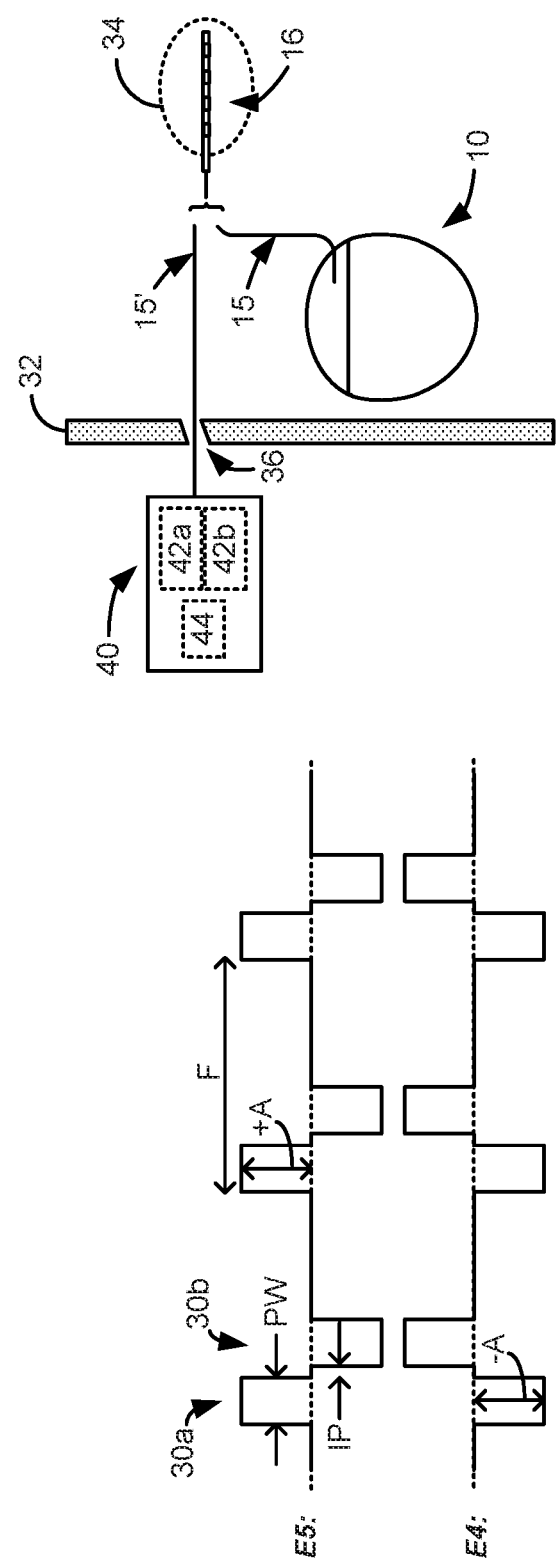
Figure 2 (prior art)
Figure 3 (prior art)

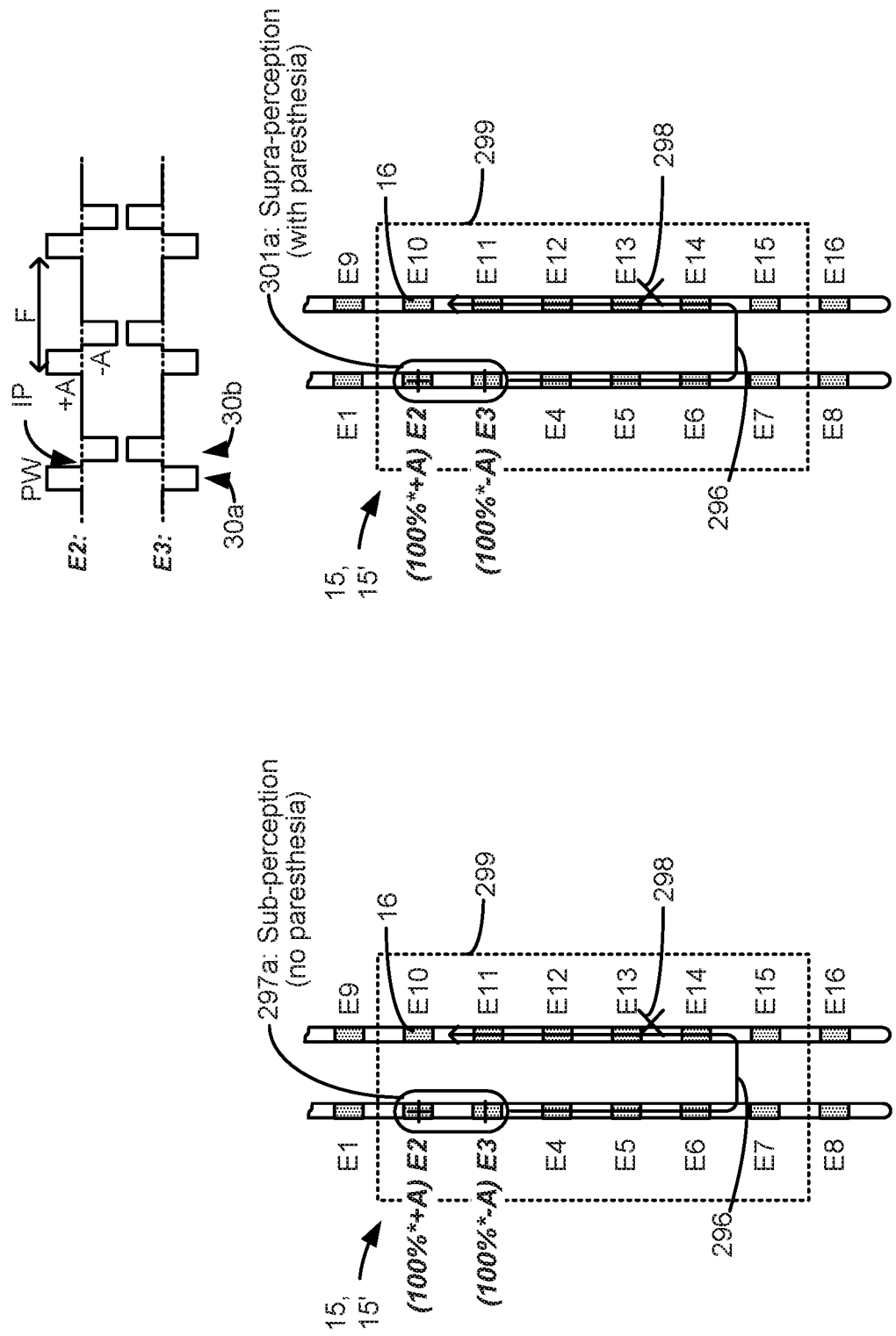

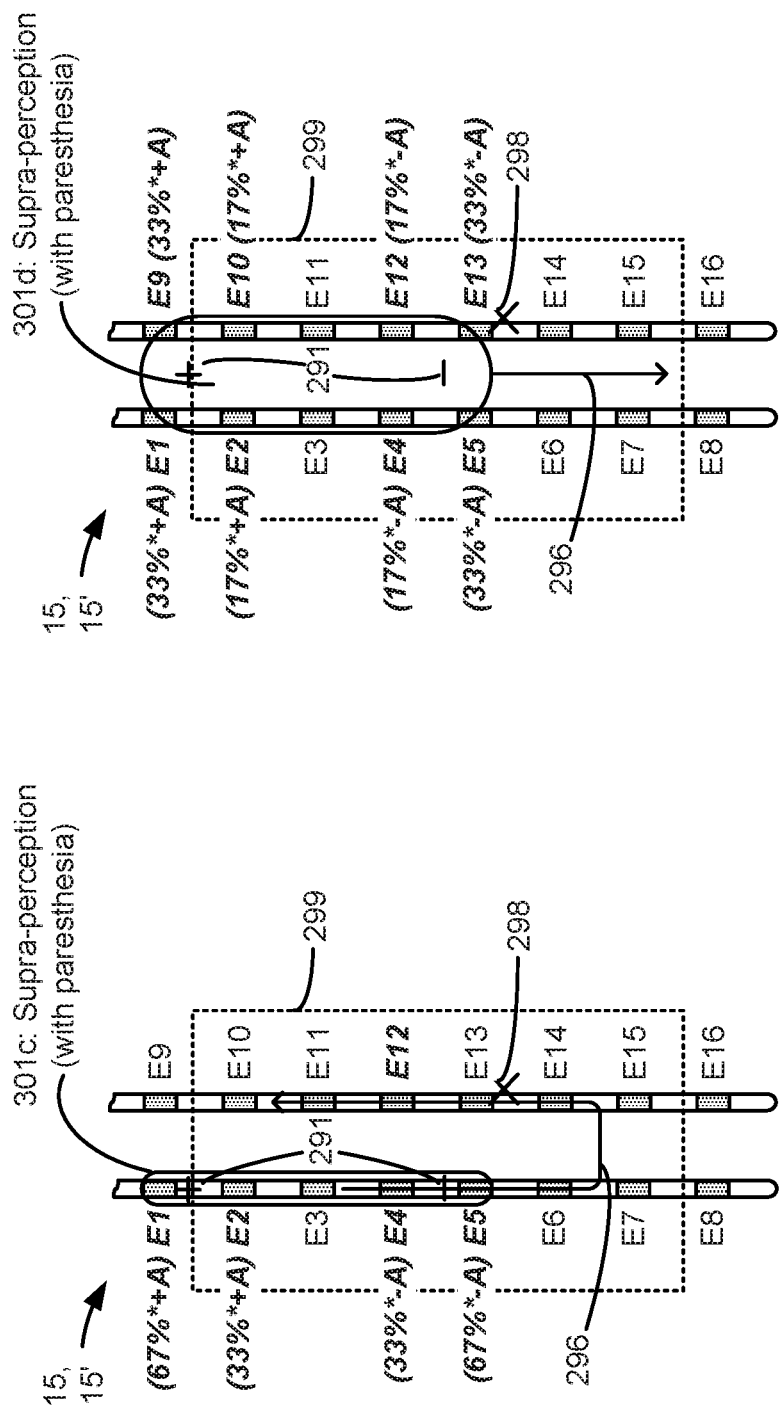

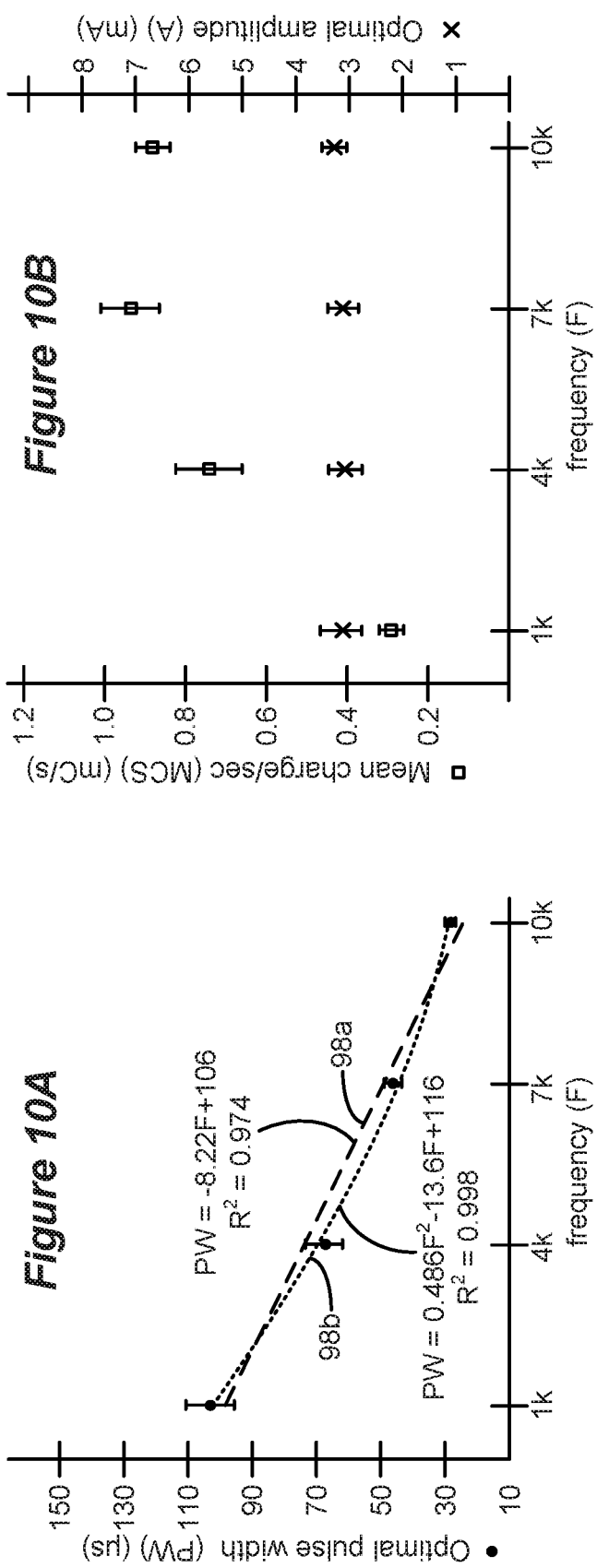
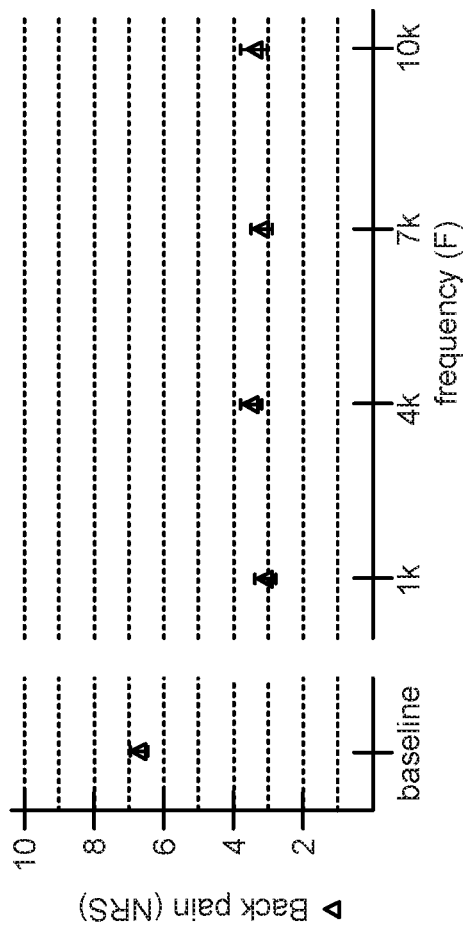
Figure 10A
Figure 10B
Figure 10C

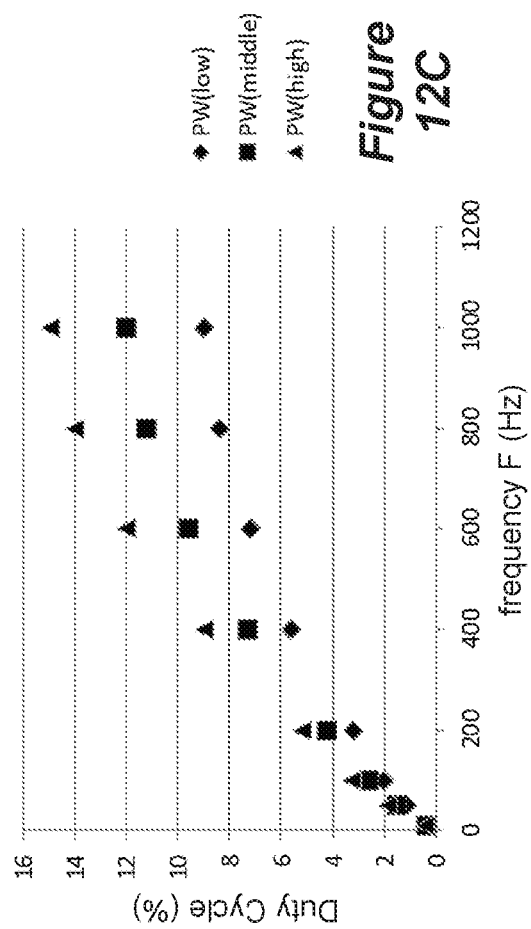
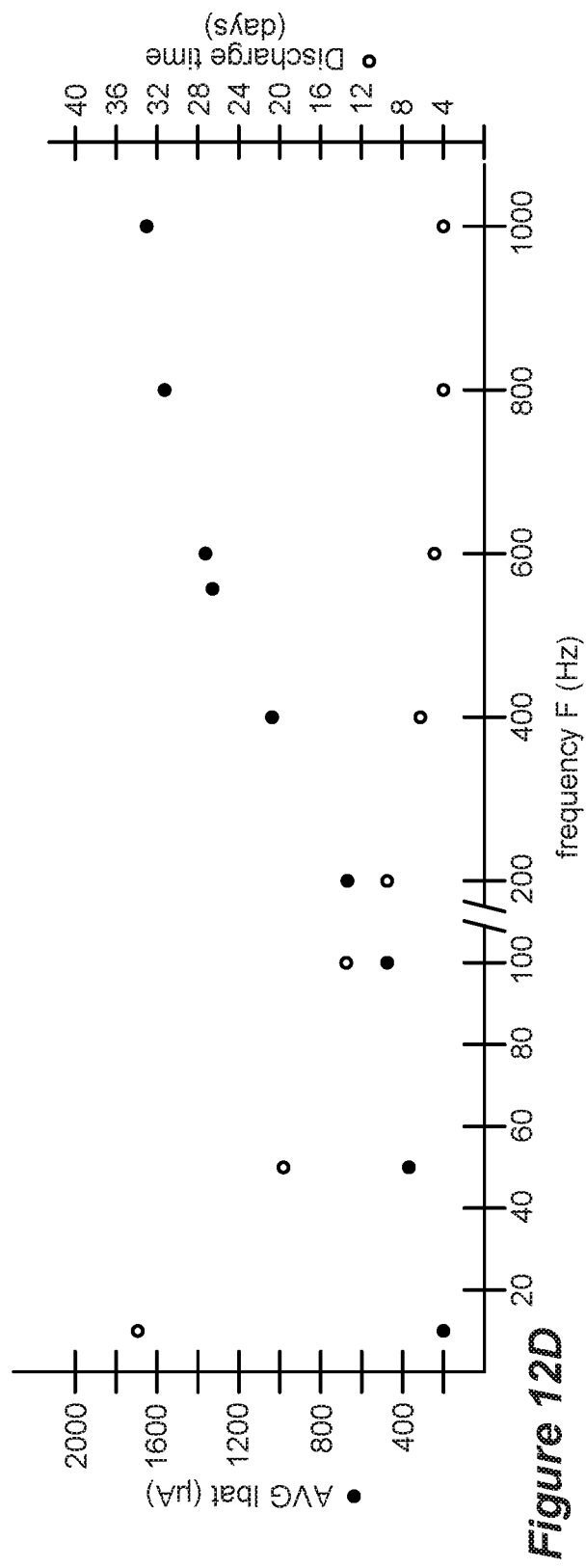
Figure 12C
Figure 12D

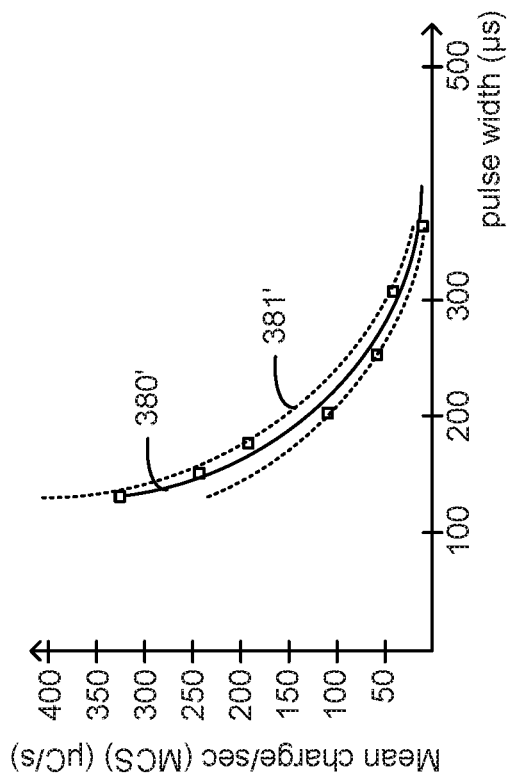
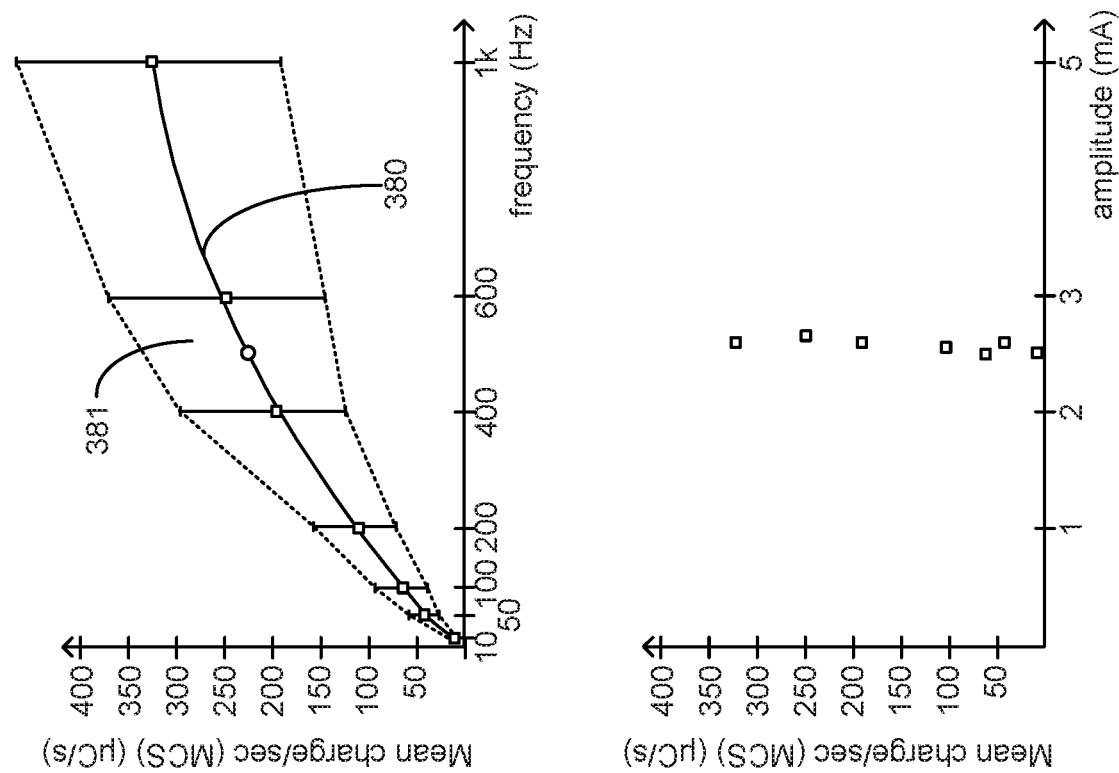
*Figure 17F*

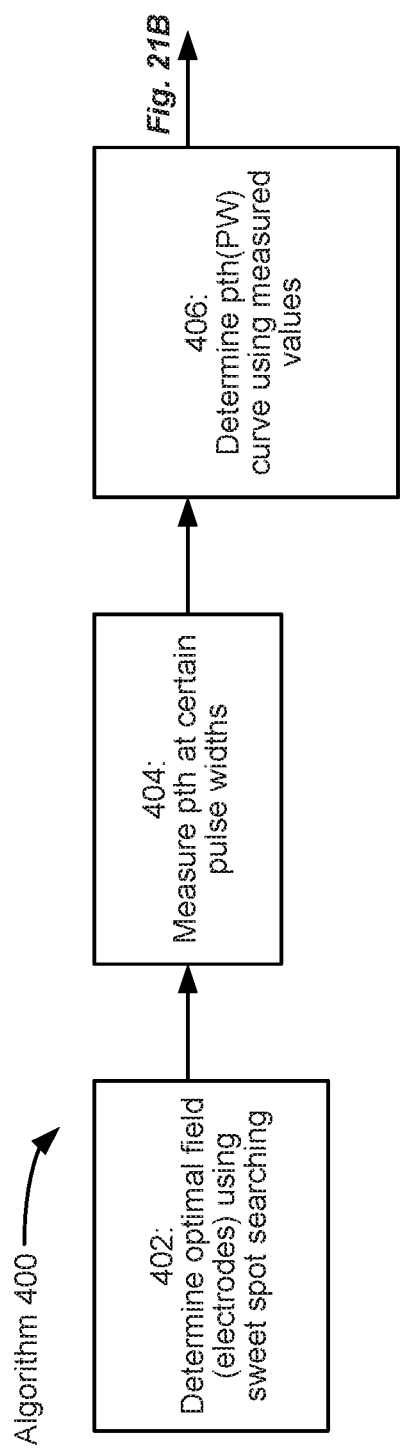
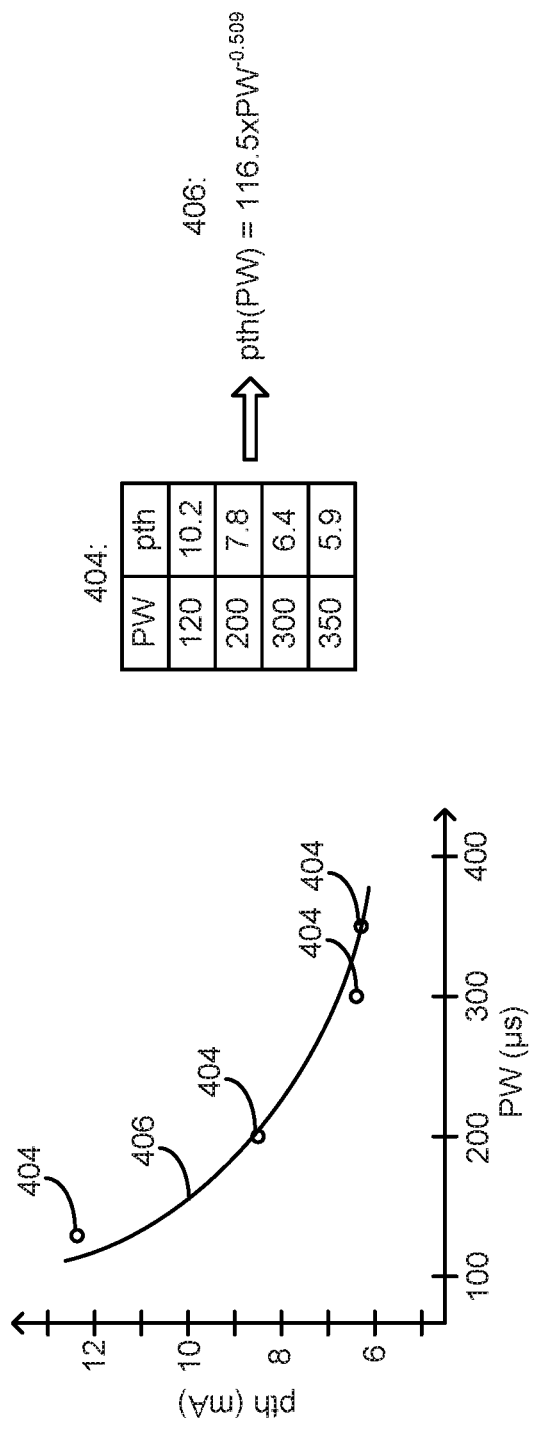
*Figure 21A*

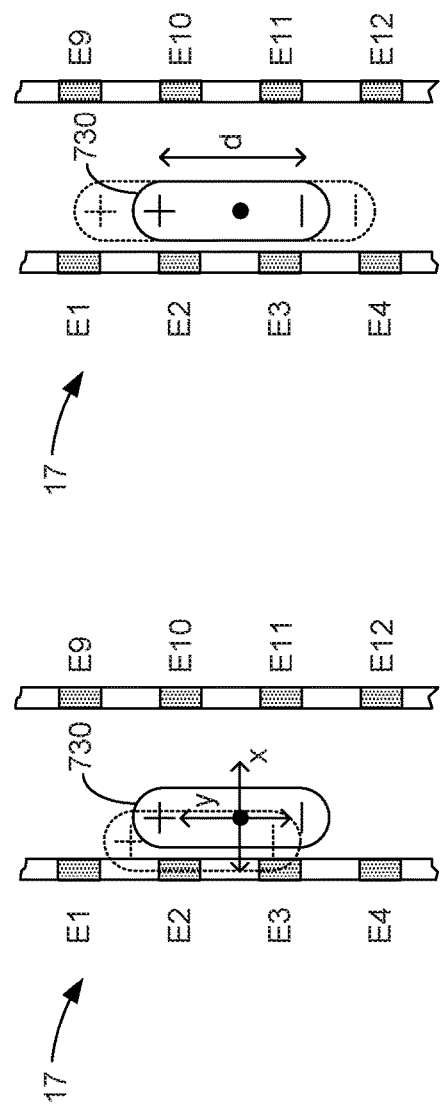
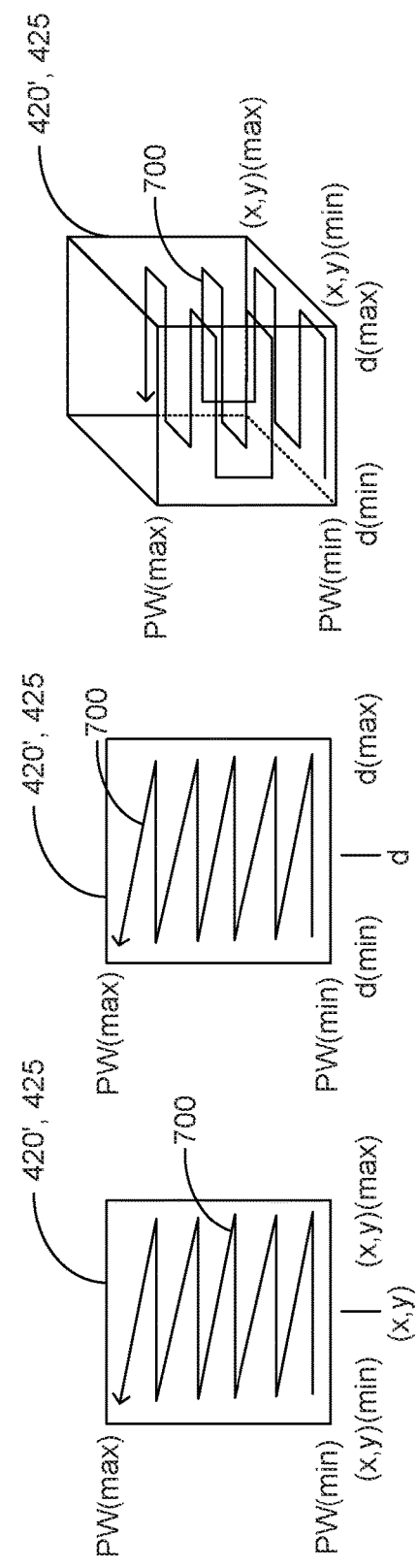
Figure 35

Fitting information 760 / Pain information 770

| | X1 | X2 | X3 | X4 | | Xx | |
|---|---|---|---|---|---|---|---|
| Pain | 1 | 1 | 1 | 0 | ••• | 0 | 0=no, 1=yes |
| Pain intensity | 3 | 5 | 7 | 0 | | 0 | out of 10 |
| Pain sensation | 1 | 2 | 2 | 0 | | 0 | 0=n/a, 1=burn, 2=numb, 3=sharp, etc. |
| Pain type | 1 | 1 | 1 | 0 | | 0 | 0=other, 1=neuropathic |

Fitting information 760

Phenotype information 800

Spatial field information 790 of applied stimulation

F {
- Pulse type: 1 — 0=mono w/ passive, 1=bi w/active, 2=bi w/passive
- Pole config: 0 — 0=bipole, 1= tripole, 2=spread bipole, 3=spread tripole
- Focus distance: 10 mm
- Field area: 25 mm²
- Anode1: +1.2 mA
- Anode2: +0.8mA
- ...
- Cathode1: -0.6 mA
- Cathode2: -1.4 mA
- ...
- Max V: 2.3
- Max dV/dx: 2.3
- Max d²V/dx²: 2.3
- Volume of Activation: 2.3 mm³

Physiological coordinates {
- x1,y1,z1
- x2,y2,z2
- x3,y3,z3
- x4,y4,z4
- x5,y5,z5
- x6,y6,z6
- x7,y7,z7
- x8,y8,z8

Y {
- Gender: 1 — 0=male, 1=female
- Age: 56
- Disease indication: 2 — (e.g., disease type)
- Disease duration: 35 — (e.g., in months)
- Time since implant: 4 — (e.g., in months)
- Posture/activity: 1 — (1=sit, 2=stand, 3=supine, 4=walking, ...)

*Figure 39C*

Fitting information 760/Different postures 820

| | posture | | | |
|---|---|---|---|---|
| | sit | stand | supine | prone |
| Pain information 770 | P1 | P2 | P3 | P4 |
| Mapping information 780 | M1 | M2 | M3 | M4 |
| Spatial field 790 | F1 | F2 | F3 | F4 |

Patient phenotype  Y

*Figure 40*

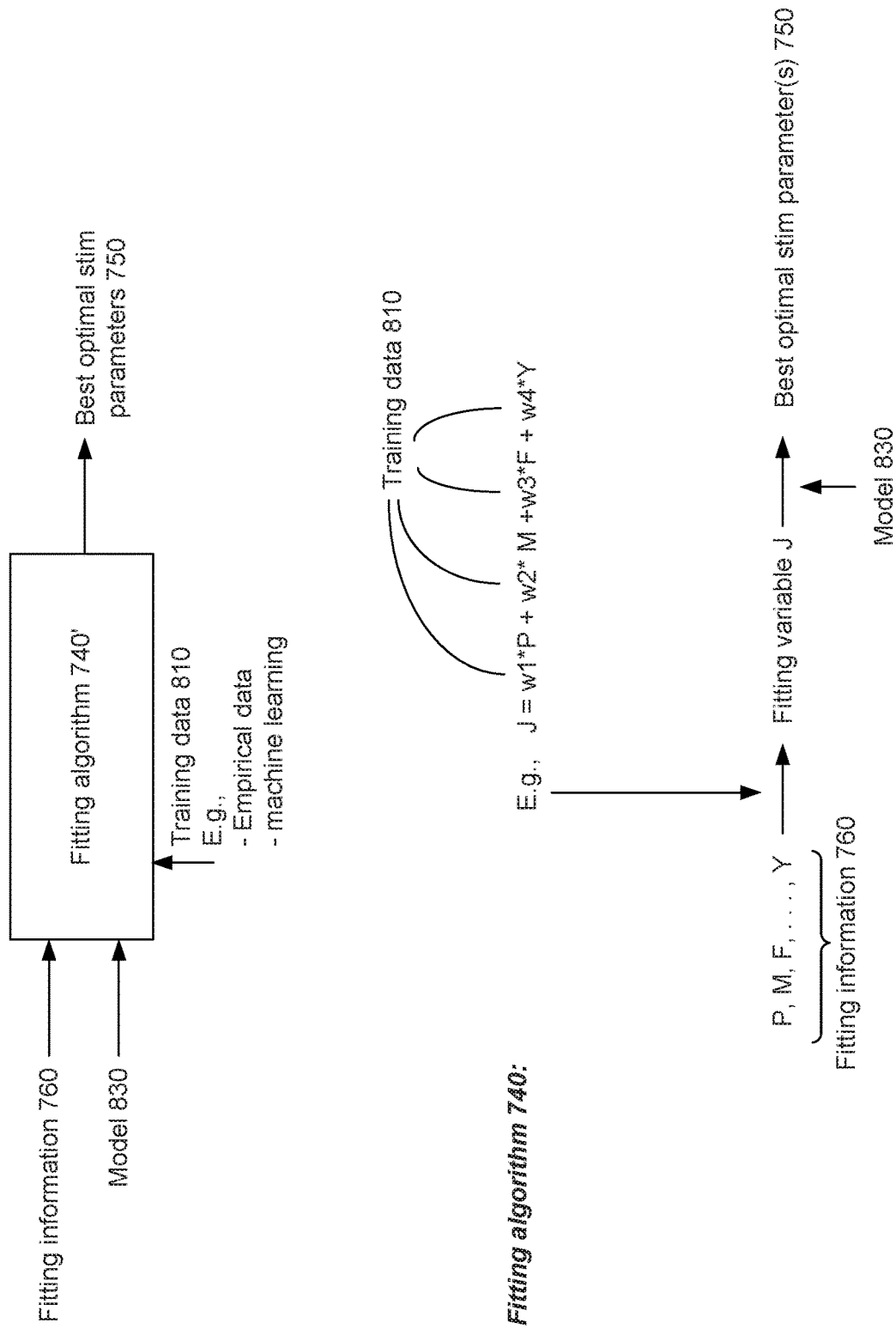

SPINAL CORD STIMULATION SYSTEM DETERMINING OPTIMAL SUB-PERCEPTION THERAPY BY USING NEURAL DOSE

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

In the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal electrodes 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

In the example of FIG. 2, electrode E5 has been selected as an anode, and thus provides pulses which source a positive current of amplitude +A to the tissue. Electrode E4 has been selected as a cathode, and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripole stimulation, quadripole stimulation, etc.).

The pulses as shown in FIG. 2 are biphasic, comprising a first phase 30a, followed quickly thereafter by a second phase 30b of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30a and discharged (be recovered) during the second phase 30b. In the example shown, the first and second phases 30a and 30b have the same duration and amplitude (although opposite polarities), which ensures the same amount of charge during both phases. However, the second phase 30b may also be charged balance with the first phase 30a if the integral of the amplitude and durations of the two phases are equal in magnitude, as is well known. The width of each pulse, PW, is defined here as the duration of first pulse phase 30a, although pulse width could also refer to the total duration of the first and second pulse phases 30a and 30b as well. Note that an interphase period (IP) during which no stimulation is provided may be provided between the two phases 30a and 30b.

IPG 10 includes stimulation circuitry 28 that can be programmed to produce the stimulation pulses at the electrodes as defined by the stimulation program. Stimulation circuitry 28 can for example comprise the circuitry described in U.S. Patent Application Publications 2018/0071513 and 2018/0071520, or described in U.S. Pat. Nos. 8,606,362 and 8,620,436. These references are incorporated herein by reference.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer 50. Both of devices 45 and 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

The external controller 45 can also have control circuitry 48 such as a microprocessor, microcomputer, an FPGA, other digital logic structures, etc., which is capable of executing instructions an electronic device. Control circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

If the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 5. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A. Likewise, electrode E4 has been selected as the only cathode to sink current, and this electrode receives X=100% of that cathodic current, −A.

The GUI 64 as shown specifies only a pulse width PW of the first pulse phase 30a. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30a and 30b (e.g., each having a duration of PW, and with opposite polarities +A and −A). An advanced menu 88 can also be used (among other things) to define the relative durations and amplitudes of the pulse phases 30a and 30b, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion.

While GUI 64 is shown as operating in the clinician programmer 50, the user interface of the external controller 45 may provide similar functionality.

BRIEF DESCRIPTION OF THE DRAWINGS

FIG. 1 shows an Implantable Pulse Generator (IPG) useable for Spinal Cord Stimulation (SCS), in accordance with the prior art.

FIG. 2 shows an example of stimulation pulses producible by the IPG, in accordance with the prior art.

FIG. 3 shows use of an External Trial Stimulator (ETS) useable to provide stimulation before implantation of an IPG, in accordance with the prior art.

FIG. 6 shows sweet spot searching to determine effective electrodes for a patient using a movable sub-perception bipole.

FIGS. 7A-7D show sweet spot searching to determine effective electrodes for a patient using a movable supra-perception bipole.

FIGS. 10A-10C show various results of the study as a function of stimulation frequency in the 1 kHz to 10 kHz frequency range, including average optimal pulse width (FIG. 10A), mean charge per second and optimal stimulation amplitude (FIG. 10B), and back pain scores (FIG. 10C).

FIG. 12C shows the duty of cycle of the optimal pulse widths as a function of frequencies at or below 1 kHz.

FIG. 12D shows the average battery current and battery discharge time at the optimal pulse widths as a function of frequencies at or below 1 kHz.

FIG. 17F shows that the model of energy can be viewed from the perspective of other stimulation parameters besides frequency. For example, energy can be modeled versus pulse width.

FIGS. 21A-21F show an algorithm used to derive a range of optimal sub-perception stimulation parameters (e.g., F, PW, and A) for a patient using the modelling information of FIGS. 18-20, and using perception threshold measurements taken on the patient.

FIG. 35 shows that the position or focus of the pole configuration may also be varied in addition to the one or more stimulation parameters within the determined optimal stimulation parameters.

FIGS. 39A-39C show receipt at a GUI of an external device of patient fitting information, including pain information, mapping information, field information, and patient phenotype information.

FIG. 40 shows that fitting information can be determined and used by the fitting algorithm as a function of patient posture.

FIG. 42 shows an alternative fitting algorithm in which best optimal stimulation parameters are determined using patient fitting information and a non-patient-specific model.

DETAILED DESCRIPTION

Figure 4:
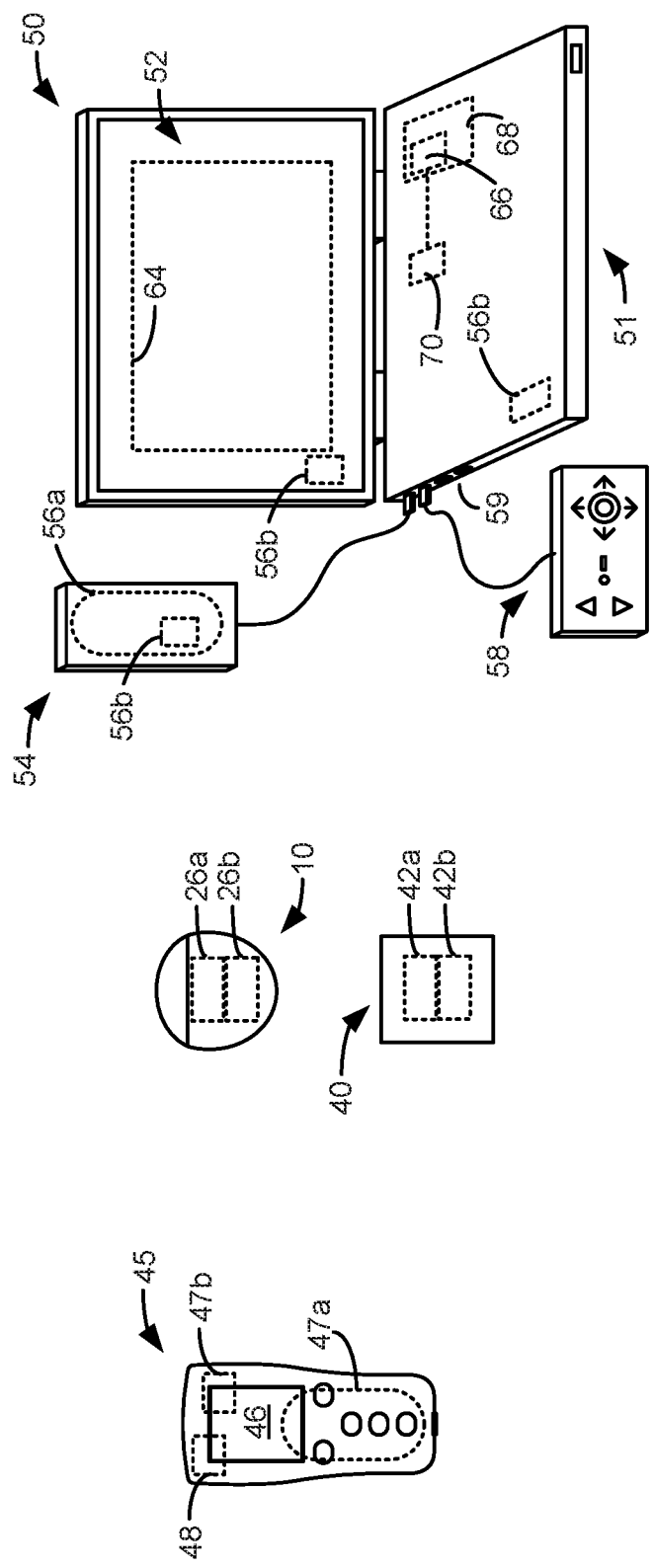
FIG. 4 shows various external devices capable of communicating with and programming stimulation in an IPG and ETS, in accordance with the prior art.

While Spinal Cord Stimulation (SCS) therapy can be an effective means of alleviating a patient's pain, such stimulation can also cause paresthesia. Paresthesia—sometimes referred to a "supra-perception" therapy—is a sensation such as tingling, prickling, heat, cold, etc. that can accompany SCS therapy. Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing.

Nonetheless, at least for some patients, SCS therapy would ideally provide complete pain relief without paresthesia—what is often referred to as "sub-perception" or sub-threshold therapy that a patient cannot feel. Effective sub-perception therapy may provide pain relief without paresthesia by issuing stimulation pulses at higher frequencies. Unfortunately, such higher-frequency stimulation may require more power, which tends to drain the battery 14 of the IPG 10. See, e.g., U.S. Patent Application Publication 2016/0367822. If an IPG's battery 14 is a primary cell and not rechargeable, high-frequency stimulation means that the IPG 10 will need to be replaced more quickly. Alternatively, if an IPG battery 14 is rechargeable, the IPG 10 will need to be charged more frequently, or for longer periods of time. Either way, the patient is inconvenienced.

In an SCS application, it is desirable to determine a stimulation program that will be effective for each patient. A significant part of determining an effective stimulation program is to determine a "sweet spot" for stimulation in each patient, i.e., to select which electrodes should be active (E) and with what polarities (P) and relative amplitudes (X %) to recruit and thus treat a neural site at which pain originates in a patient. Selecting electrodes proximate to this neural site of pain can be difficult to determine, and experimentation is typically undertaken to select the best combination of electrodes to provide a patient's therapy.

As described in U.S. Pat. No. 11,160,987, which is hereby expressly incorporated by reference, selecting electrodes for a given patient can be even more difficult when sub-perception therapy is used, because the patient does not feel the stimulation, and therefore it can be difficult for the patient to feel whether the stimulation is "covering" his pain and therefore whether selected electrodes are effective. Further, sub-perception stimulation therapy may require a "wash in" period before it can become effective. A wash in period can take up to a day or more, and therefore sub-perception stimulation may not be immediately effective, making electrode selection more difficult.

FIG. 6 briefly explains the '987 Patent's technique for a sweet spot search, i.e., how electrodes can be selected that are proximate to a neural site of pain 298 in a patient, when sub-perception stimulation is used. The technique of FIG. 6 is particularly useful in a trial setting after a patient is first implanted with an electrode array, i.e., after receiving their IPG or ETS.

In the example shown, it is assumed that a pain site 298 is likely within a tissue region 299. Such region 299 may be deduced by a clinician based on the patient symptoms, e.g., by understanding which electrodes are proximate to certain vertebrae (not shown), such as within the T9-T10 interspace. In the example shown, region 299 is bounded by electrodes E2, E7, E15, and E10, meaning that electrodes outside of this region (e.g., E1, E8, E9, E16) are unlikely to have an effect on the patient's symptoms. Therefore, these electrodes may not be selected during the sweet spot search depicted in FIG. 6, as explained further below.

In FIG. 6, a sub-perception bipole 297a is selected, in which one electrode (e.g., E2) is selected as an anode that will source a positive current (+A) to the patient's tissue, while another electrode (e.g., E3) is selected as a cathode that will sink a negative current (−A) from the tissue. This is similar to what was illustrated earlier with respect to FIG. 2, and biphasic stimulation pulses can be used employing active charge recovery. Because the bipole 297a provides sub-perception stimulation, the amplitude A used during the sweet spot search is titrated down until the patient no longer feels paresthesia. This sub-perception bipole 297a is provided to the patient for a duration, such as a few days, which allows the sub-perception bipole's potential effectiveness to "wash in," and allows the patient to provide feedback concerning how well the bipole 297a is helping their symptoms. Such patient feedback can comprise a pain scale ranking. For example, the patient can rank their pain on a scale from 1-10 using a Numerical Rating Scale (NRS) or the Visual Analogue Scale (VAS), with 1 denoting no or little pain and 10 denoting a worst pain imaginable. As discussed in the '987 Patent, such pain scale ranking can be entered into the patient's external controller 45.

After the bipole 297a is tested at this first location, a different combination of electrodes is chosen (anode electrode E3, cathode electrode E4), which moves the location of the bipole 297 in the patient's tissue. Again, the amplitude of the current A may need to be titrated to an appropriate sub-perception level. In the example shown, the bipole 297a is moved down one electrode lead, and up the other, as shown by path 296 in the hope of finding a combination of electrodes that covers the pain site 298. In the example of FIG. 6, given the pain site 298's proximity to electrodes E13 and E14, it might be expected that a bipole 297a at those electrodes will provide the best relief for the patient, as reflected by the patient's pain score rankings. The particular stimulation parameters chosen when forming bipole 297a can be selected at the GUI 64 of the clinician programmer 50 or other external device (such as a patient external controller 45) and wirelessly telemetered to the patient's IPG or ETS for execution.

While the sweet spot search of FIG. 6 can be effective, it can also take a significantly long time when sub-perception stimulation is used. As noted, sub-perception stimulation is provided at each bipole 297 location for a number of days, and because a large number of bipole locations are chosen, the entire sweet spot search can take up to a month to complete.

The inventors have determined via testing of SCS patients that even if it is desired to eventually use sub-perception therapy for a patient going forward after the sweet spot search, it is beneficial to use supra-perception stimulation during the sweet spot search to select active electrodes for the patient. Use of supra-perception stimulation during the sweet spot search greatly accelerates determination of effective electrodes for the patient compared to the use of sub-perception stimulation, which requires a wash in period at each set of electrodes tested. After determining electrodes for use with the patient using supra-perception therapy, therapy may be titrated to sub-perception levels keeping the same electrodes determined for the patient during the sweet spot search. Because the selected electrodes are known to be recruiting the neural site of the patient's pain, the application of sub-perception therapy to those electrodes is more likely to have immediate effect, reducing or potentially eliminating the need to wash in the sub-perception therapy that follows. In short, effective sub-perception therapy can be achieved more quickly for the patient when supra-perception sweet spot searching is utilized. Preferably, supra-perception sweet spot searching occurs using symmetric biphasic pulses occurring at low frequencies—such as between 40 and 200 Hz in one example.

In accordance with one aspect of the disclosed technique, a patient will be provided sub-perception therapy. Sweet spot searching to determine electrodes that may be used during sub-perception therapy may precede such sub-perception therapy. In some aspects, when sub-perception therapy is used for the patient, sweet spot searching may use a bipole 297a that is sub-perception (FIG. 6), as just described. This may be relevant because the sub-perception sweet spot search may match the eventual sub-perception therapy the patient will receive.

However, the inventors have determined that even if sub-perception therapy is eventually to be used for the patient, it can be beneficial to use supra-perception stimulation—that is, stimulation with accompanying paresthesia—during the sweet spot search. This is shown in FIG. 7A, where the movable bipole 301a provides supra-perception stimulation that can be felt by the patient. Providing bipole 301a as supra-perception stimulation can merely involve increasing its amplitude (e.g., current A) when compared to the sub-perception bipole 297a of FIG. 6, although other stimulation parameters might be adjusted as well, such as by providing longer pulse widths.

The inventors have determined that there are benefits to employing supra-perception stimulation during the sweet spot search even though sub-perception therapy will eventually be used for the patient.

First, as mentioned above, the use of supra-perception therapy by definition allows the patient to feel the stimulation, which enables the patient to provide essentially immediate feedback to the clinician whether the paresthesia seems to be well covering his pain site 298. In other words, it is not necessary to take the time to wash in bipole 301*a* at each location as it is moved along path 296. Thus, a suitable bipole 301*a* proximate to the patient's pain site 298 can be established much more quickly, such as within a single clinician's visit, rather than over a period of days or weeks. In one example, when sub-perception therapy is preceded with supra-perception sweet spot searching, the time needed to wash in the sub-perception therapy can be one hour or less, ten minutes or less, or even a matter of seconds. This allows wash in to occur during a single programming session during which the patient's IPG or ETS is programmed, and without the need for the patient to leave the clinician's office. Furthermore, the sub-perception therapy is noted to continue to be effective for some period of time after such therapy ceases, i.e., the therapy is effective during a "wash out" period after the cessation of therapy. The wash out period may be ten minutes or longer, or even an hour or longer. Note that this is beneficial because it means that therapy can be curtailed for some period of time (during the washout period), or rather that the sub-perception therapy can be cycled on and off. In short, the IPG does not need to continually provide the sub-perception therapy, and can effectively be off for periods of time, which saves power in the IPG.

Second, use of supra-perception stimulation during the sweet spot search ensures that electrodes are determined that well recruit the pain site 298. As a result, after the sweet spot search is complete and eventual sub-perception therapy is titrated for the patient, wash in of that sub-perception therapy may not take as long because the electrodes needed for good recruitment have already been confidently determined.

Figure 7B:
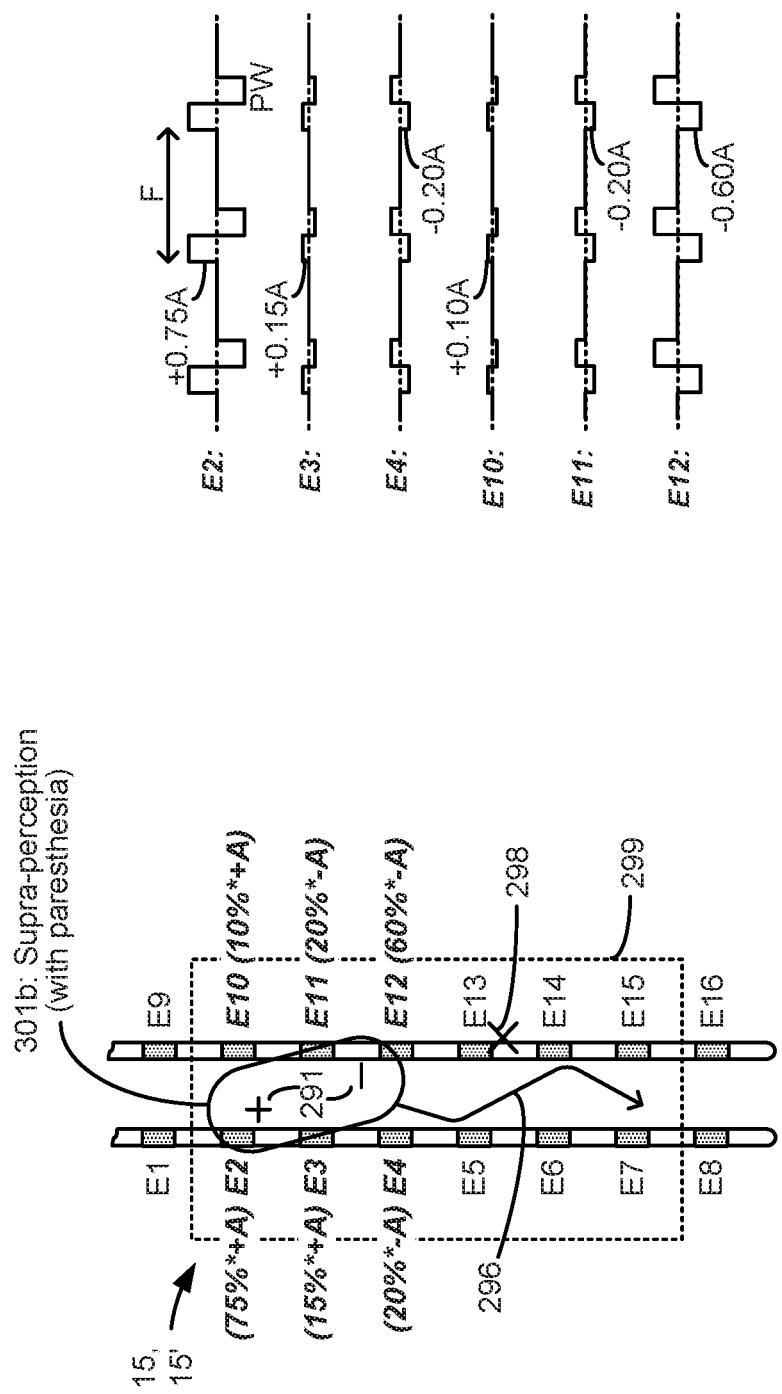

FIGS. 7B-7D show other supra-perception bipoles 301*b*-301*d* that may be used, and in particular show how the virtual bipoles may be formed using virtual poles by activating three or more of the electrodes 16. Virtual poles are discussed further in U.S. Patent Application Publication 2019/0175915, which is incorporated herein by reference in its entirety, and thus virtual poles are only briefly explained here. Forming virtual poles is assisted if the stimulation circuitry 28 or 44 used in the IPG or ETS is capable of independently setting the current at any of the electrodes—what is sometimes known as a Multiple Independent Current Control (MICC), which is explained further below with reference to FIG. 8.

When a virtual bipole is used, the GUI 64 (FIG. 5) of the clinician programmer 50 (FIG. 4) can be used to define an anode pole (+) and a cathode pole (−) at positions 291 (FIG. 7B) that may not necessarily correspond to the position of the physical electrodes 16. The control circuitry 70 in the clinician programmer 50 can compute from these positions 291 and from other tissue modeling information which physical electrodes 16 will need to be selected and with what amplitudes to form the virtual anode and virtual cathode at the designated positions 291. As described earlier, amplitudes at selected electrodes may be expressed as a percentage X % of the total current amplitude A specified at the GUI 64 of the clinician programmer 50.

For example, in FIG. 7B, the virtual anode pole is located at a position 291 between electrodes E2, E3 and E10. The clinician programmer 50 may then calculate based on this position that each of these electrodes (during first pulse phase 30*a*) will receive an appropriate share (X %) of the total anodic current +A to locate the virtual anode at this position. Since the virtual anode's position is closest to electrode E2, this electrode E2 may receive the largest share of the specified anodic current +A (e.g., 75%*+A). Electrodes E3 and E10 which are proximate to the virtual anode pole's position but farther away receive lesser shares of the anodic current (e.g., 15%*+A and 10%*+A respectively). Likewise, it can be seen that from the designated position 291 of the virtual cathode pole, which is proximate to electrodes E4, E11, and E12, that these electrodes will receive an appropriate share of the specified cathodic current −A (e.g., 20%*−A, 20%*−A, and 60%*−A respectively, again during the first pulse phase 30*a*). These polarities would then be flipped during the second phases 30*b* of the pulses, as shown in the waveforms of FIG. 7B. In any event, the use of virtual poles in the formation of bipole 301*b* allows the field in the tissue to be shaped, and many different combinations of electrodes can be tried during the sweet spot search. In this regard, it is not strictly necessary that the (virtual) bipole be moved along an orderly path 296 with respect to the electrodes, and the path may be randomized, perhaps as guided by feedback from the patient.

FIG. 7C shows a useful virtual bipole 301*c* configuration that can be used during the sweet spot search. This virtual bipole 301*c* again defines a target anode and cathode whose positions do not correspond to the position of the physical electrodes. The virtual bipole 301*c* is formed along a lead—essentially spanning the length of four electrodes from E1 to E5. This creates a larger field in the tissue better able to recruit the patient's pain site 298. This bipole configuration 301*c* may need to be moved to a smaller number of locations than would a smaller bipole configuration compared 301*a* of FIG. 7A) as it moves along path 296, thus accelerating pain site 298 detection. FIG. 7D expands upon the bipole configuration of FIG. 7C to create a virtual bipole 301*d* using electrodes formed on both leads, e.g., from electrodes E1 to E5 and from electrodes E9 to E13. This bipole 301*d* configuration need only be moved along a single path 296 that is parallel to the leads, as its field is large enough to recruit neural tissue proximate to both leads. This can further accelerate pain site detection.

In some aspects, the supra-perception bipoles 301*a*-301*d* used during the sweet spot search comprise symmetric biphasic waveforms having actively-driven (e.g., by the stimulation circuitry 28 or 44) pulse phases 30*a* and 30*b* of the same pulse width PW and the same amplitude (with the polarity flipped during the phases) (e.g., $A_{30a}=A_{30b}$, and $PW_{30a}=PW_{30b}$). This is beneficial because the second pulse phase 30*b* provides active charge recovery, with in this case the charge provided during the first pulse phase 30*a* ($Q_{30a}$) equaling the charge of the second pulse phase 30*b* ($Q_{30b}$), such that the pulses are charge balanced. Use of biphasic waveforms are also believed beneficial because, as is known, the cathode is largely involved in neural tissue recruitment. When a biphasic pulse is used, the positions of the (virtual) anode and cathode will flip during the pulse's two phases. This effectively doubles the neural tissue that is recruited for stimulation, and thus increases the possibility that the pain site 298 will be covered by a bipole at the correct location.

The supra-perception bipoles 301*a*-301*d* do not however need to comprise symmetric biphasic pulses as just described. For example, the amplitude and pulse width of the two phases 30*a* and 30*b* can be different, while keeping the charge (Q) of the two phases balanced (e.g., $Q_{30a}=A_{30a}*PW_{30a}=A_{30b}*PW_{30b}=Q_{30b}$). Alternatively, the two phases 30*a* and 30*b* may be charge imbalanced (e.g., $Q_{30a}=A_{30a}*PW_{30a}>A_{30b}*PW_{30b}=Q_{30b}$, or $Q_{30a}=A_{30a}*PW_{30a}<A_{30b}*PW_{30b}=Q_{30b}$). In short, the pulses in bipoles 301-301*d* can be biphasic symmetric (and thus inherently charge balanced), biphasic asymmetric but still charge balanced, or biphasic asymmetric and charge imbalanced.

In a preferred example, the frequency F of the supra-perception pulses 301a-301d used during the supra-perception sweet spot search may be 10 kHz or less, 1 kHz or less, 500 Hz or less, 300 Hz or less, 200 Hz or less, 130 Hz or less, or 100 Hz or less, or ranges bounded by two of these frequencies (e.g., 100-130 Hz, or 100-200 Hz). In particular examples, frequencies of 90 Hz, 40 Hz, or 10 Hz can be used, with pulses comprising biphasic pulses which are preferably symmetric. However, a single actively-driven pulse phase followed by a passive recovery phase could also be used. The pulse width PW may also comprise a value in the range of hundreds of microseconds, such as 150 to 400 microseconds. Because the goal of supra-perception sweet spot searching is merely to determine electrodes that appropriately cover a patient's pain, frequency and pulse width may be of less importance at this stage. Once electrodes have been chosen for sub-perception stimulation, frequency and pulse width can be optimized, as discussed further below.

It should be understood that the supra-perception bipoles 301a-301d used during sweet spot searching need not necessarily be the same electrodes that are selected when later providing the patient with sub-perception therapy. Instead, the best location of the bipole noticed during the search can be used as the basis to modify the selected electrodes. Suppose for example that a bipole 301a (FIG. 7A) is used during sweep spot searching, and it is determined that bipole provides the best pain relief when located at electrodes E13 and E14. At that point, sub-perception therapy using those electrodes E13 and E14 can be tried for the patient going forward. Alternatively, it may be sensible to modify the selected electrodes to see if the patient's symptoms can be further improved before sub-perception therapy is tried. For example, the distance (focus) between the cathode and anode can be varied, using virtual poles as already described. Or, a tripole (anode/cathode/anode) consisting of electrodes E12/E13/E14 or E13/E14/E15 could be tried. See U.S. Patent Application Publication 2019/0175915 (discussing tripoles). Or electrodes on a different lead could also be tried in combination with E13 and E14. For example, because electrodes E5 and E6 are generally proximate to electrodes E13 and E14, it may be useful to add E5 or E6 as sources of anodic or cathodic current (again creating virtual poles). All of these types of adjustments should be understood as comprising "steering" or an adjustment to the "location" at which therapy is applied, even if a central point of stimulation doesn't change (as can occur for example when the distance or focus between the cathode and anode is varied).

Figure 8:
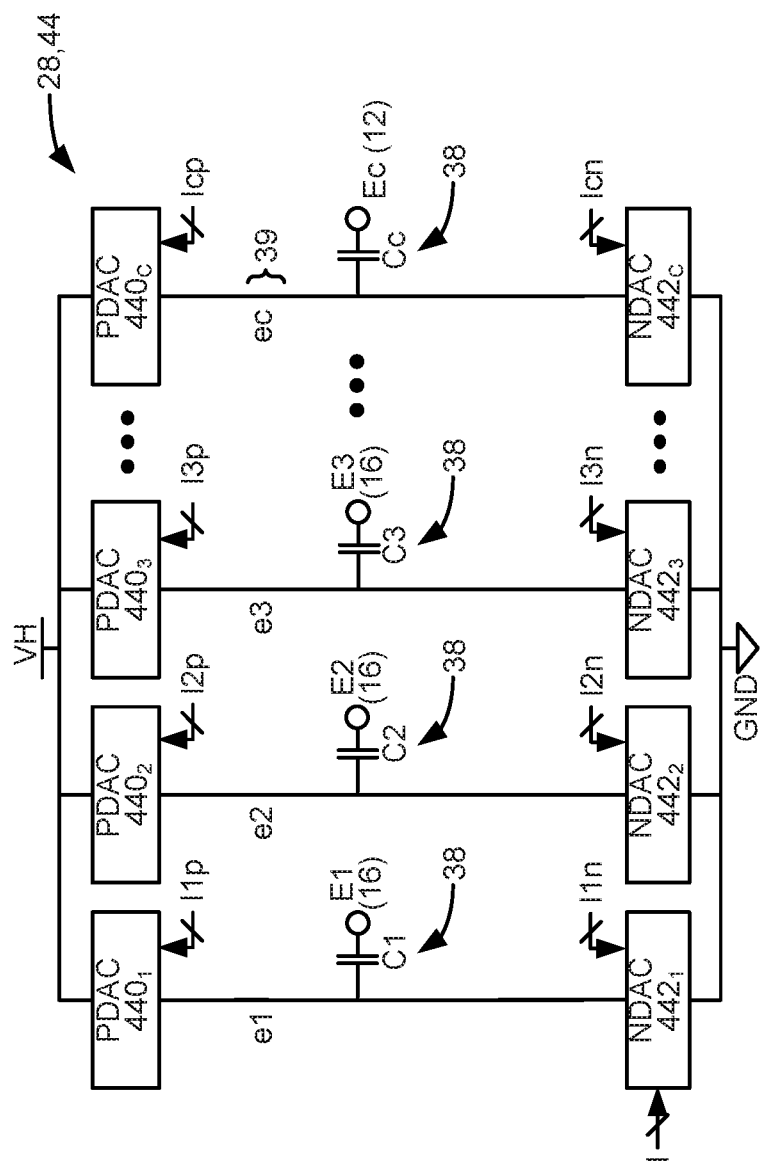
FIG. 8 shows stimulation circuitry useable in the IPG or ETS capable of providing Multiple Independent Current Control to independently set the current at each of the electrodes.

Multiple Independent Current Control (MICC) is explained in one example with reference to FIG. 8, which shows the stimulation circuitry 28 (FIG. 1) or 44 (FIG. 3) in the IPG or ETS used to form prescribed stimulation at a patient's tissue. The stimulation circuitry 28 or 44 can control the current or charge at each electrode independently, and using GUI 64 (FIG. 5) allows the current or charge to be steered to different electrodes, which is useful for example when moving the bipole 301i along path 296 during the sweet spot search (FIG. 7A-7D). The stimulation circuitry 28 or 44 includes one or more current sources $440_i$ and one or more current sinks $442_i$. The sources and sinks $440_i$ and $442_i$ can comprise Digital-to-Analog converters (DACs), and may be referred to as PDACs $440_i$ and NDACs $442_i$ in accordance with the Positive (sourced, anodic) and Negative (sunk, cathodic) currents they respectively issue. In the example shown, a NDAC/PDAC $440_i/442_i$ pair is dedicated (hardwired) to a particular electrode node ei 39. Each electrode node ei 39 is preferably connected to an electrode Ei 16 via a DC-blocking capacitor Ci 38, which act as a safety measure to prevent DC current injection into the patient, as could occur for example if there is a circuit fault in the stimulation circuitry 28 or 44. PDACs $440_i$ and NDACs $442_i$ can also comprise voltage sources.

Proper control of the PDACs $440_i$ and NDACs $442_i$ via GUI 64 allows any of the electrodes 16 and the case electrode Ec 12 to act as anodes or cathodes to create a current through a patient's tissue. Such control preferably comes in the form of digital signals Iip and Iin that set the anodic and cathodic current at each electrode Ei. If for example it is desired to set electrode E1 as an anode with a current of +3 mA, and to set electrodes E2 and E3 as cathodes with a current of −1.5 mA each, control signal I1p would be set to the digital equivalent of 3 mA to cause PDAC $440_1$ to produce +3 mA, and control signals I2n and I3n would be set to the digital equivalent of 1.5 mA to cause NDACs $442_2$ and $442_3$ to each produce −1.5 mA. Note that definition of these control signals can also occur using the programmed amplitude A and percentage X % set in the GUI 64. For example, A may be set to 3 mA, with E1 designated as an anode with X=100%, and with E2 and E3 designated at cathodes with X=50%. Alternatively, the control signals may not be set with a percentage, and instead the GUI 64 can simply prescribe the current that will appear at each electrode at any point in time.

In short, the GUI 64 may be used to independently set the current at each electrode, or to steer the current between different electrodes. This is particularly useful in forming virtual bipoles, which as explained earlier involve activation of more than two electrodes. MICC also allows more sophisticated electric fields to be formed in the patient's tissue.

Other stimulation circuitries 28 can also be used to implement MICC. In an example not shown, a switching matrix can intervene between the one or more PDACs $440_i$ and the electrode nodes ei 39, and between the one or more NDACs $442_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, and U.S. Patent Application Publications 2018/0071513, 2018/0071520, and 2019/0083796.

Much of the stimulation circuitry 28 or 44, including the PDACs $440_i$ and NDACs $442_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with the IPG's or ETS's telemetry antennas), circuitry for generating the compliance voltage VH that powers the stimulation circuitry, various measurement circuits, etc.

While it is preferred to use sweet spot searching, and in particular supra-perception sweet spot searching, to determine the electrodes to be used during subsequent sub-perception therapy, it should be noted that this is not strictly necessary. Sub-perception therapy can be preceded by sub-perception sweet spot searching, or may not be preceded by sweet spot searching at all. In short, sub-perception therapy as described next is not reliant on the use of any sweet spot search.

In another aspect of the invention, the inventors have determined via testing of SCS patients that statistically significant correlations exists between pulse width (PW) and frequency (F) where an SCS patient will experience a reduction in back pain without paresthesia (sub-perception). Use of this information can be helpful in deciding what pulse width is likely optimal for a given SCS patient based on a particular frequency, and in deciding what frequency is likely optimal for a given SCS patient based on a particular pulse width. Beneficially, this information suggests that paresthesia-free sub-perception SCS stimulation can occur at frequencies of 10 kHz and below. Use of such low frequencies allows sub-perception therapy to be used with much lower power consumption in the patient's IPG or ETS.

Figure 9:
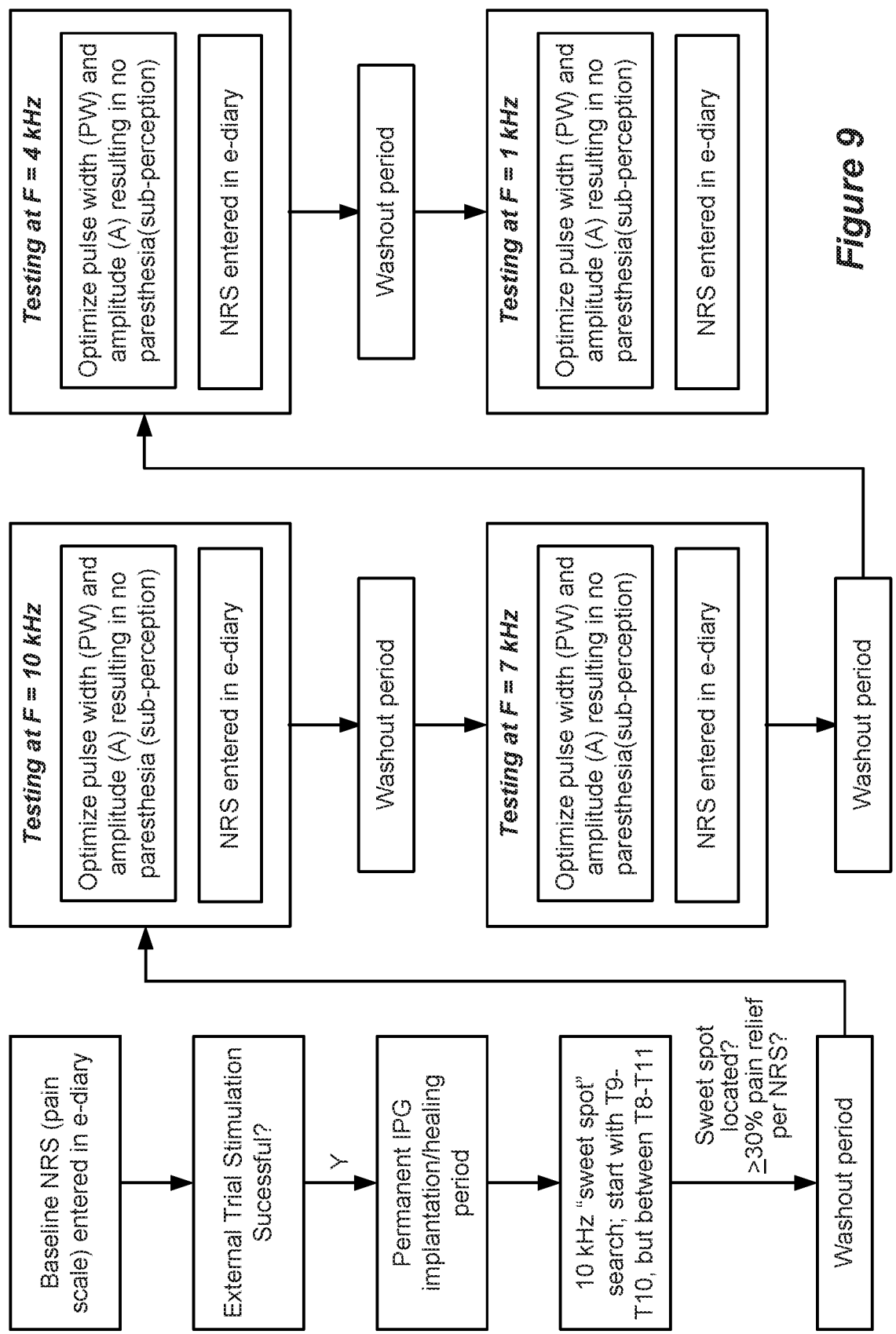
FIG. 9 shows a flow chart of a study conducted on various patients with back pain designed to determine optimal sub-perception SCS stimulation parameters over a frequency range of 1 kHz to 10 kHz.

FIGS. 9-11C shows results derived from testing patients at frequencies within a range of 1 kHz to 10 kHz. FIG. 9 explains how data was gathered from actual SCS patients, and the criteria for patient inclusion in the study. Patients with back pain, but not yet receiving SCS therapy, were first identified. Key patient inclusion criteria included having persistent lower back pain for greater than 90 days; a NRS pain scale of 5 or greater (NRS is explained below); stable opioid medications for 30 days; and a Baseline Oswestry Disability index score of greater than or equal to 20 and lower than or equal to 80. Key patient exclusion criteria included having back surgery in the previous 6 months; existence of other confounding medical/psychological conditions; and untreated major psychiatric comorbidity or serious drug related behavior issues.

Figure 5:
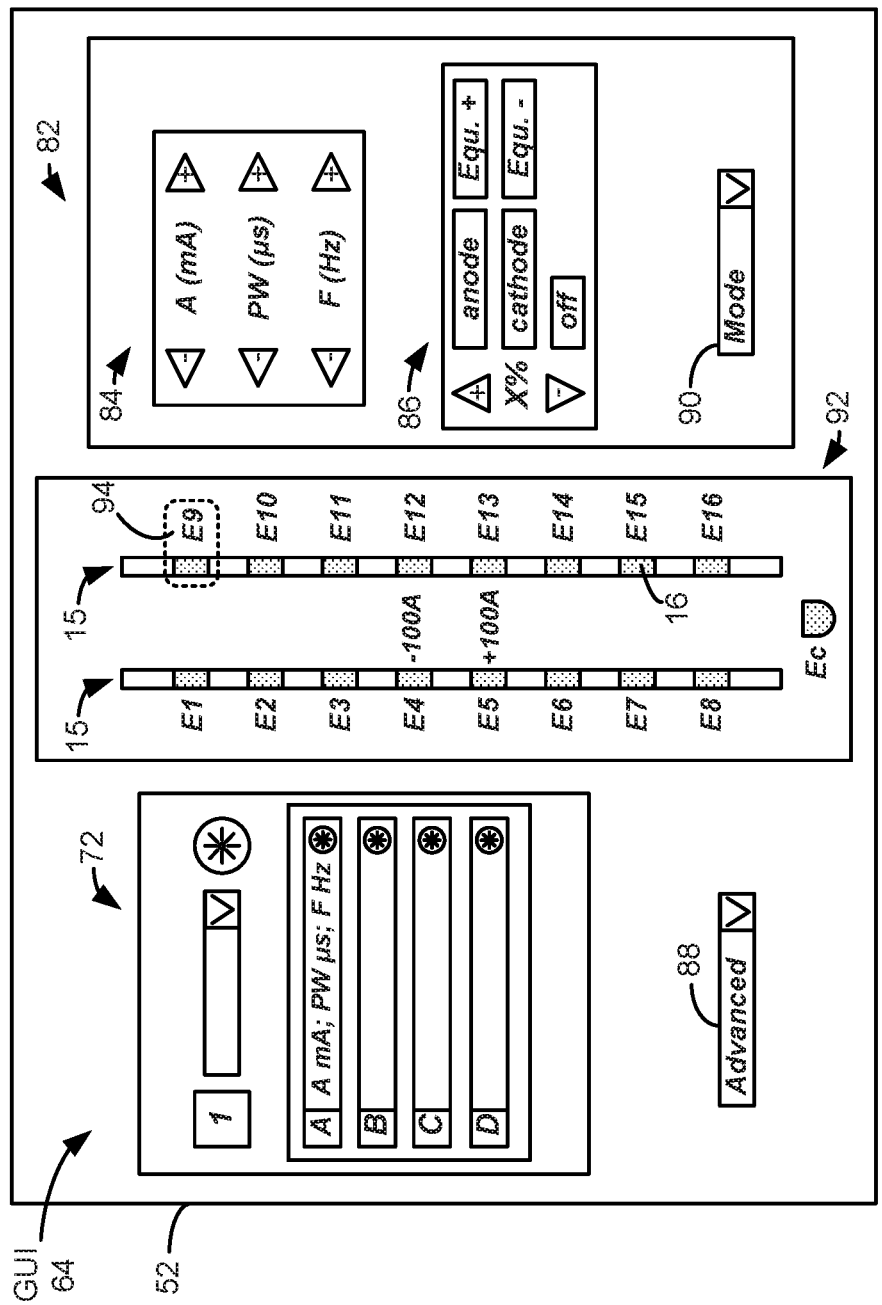
FIG. 5 shows a Graphical User Interface (GUI) of a clinician programmer external device for setting or adjusting stimulation parameters, in accordance with the prior art.

After such initial screening, patients periodically entered a qualitative indication of their pain (i.e., a pain score) into a portable e-diary device, which can comprise a patient external controller 45, and which in turn can communicate its data to a clinician programmer 50 (FIG. 4). Such pain scores can comprise a Numerical Rating Scale (NRS) score from 1-10, and were input to the e-diary three times daily. As shown in FIG. 10C, the baseline NRS score for patients not eventually excluded from the study and not yet receiving sub-perception stimulation therapy was approximately 6.75/10, with a standard error, SE (sigma/SQRT(n)) of 0.25.

Returning to FIG. 9, patients then had trial leads 15' (FIG. 3) implanted on the left and right sides of the spinal column, and were provided external trial stimulation as explained earlier. A clinician programmer 50 was used to provide a stimulation program to each patient's ETS 40 as explained earlier. This was done to make sure that SCS therapy was helpful for a given patient to alleviate their pain. If SCS therapy was not helpful for a given patient, trial leads 15' were explanted, and that patient was then excluded from the study.

Those patients for whom external trial stimulation was helpful eventually received full implantation of a permanent IPG 10, as described earlier. After a healing period, and again using clinician programmer 50, a "sweet spot" for stimulation was located in each patient, i.e., which electrodes should be active (E) and with what polarities (P) and relative amplitudes (X %) to recruit and thus treat a site 298 of neural site in the patient. The sweet spot search can occur in any of the manners described earlier with respect to FIGS. 6-7D, but in a preferred embodiment would comprise supra-perception stimulation (e.g., e.g., FIG. 7A-7D) because of the benefits described earlier. However, this is not strictly necessary, and sub-perception stimulation can also be used during the sweet spot search. In the example of FIG. 9, sweet spot searching occurred at 10 kHz, but again the frequency used during the sweet spot search can be varied. Symmetric biphasic pulses were used during sweet spot searching, but again, this is not strictly required. Deciding which electrodes should be active started with selecting electrodes 16 present between thoracic vertebrae T9 and T10. However, electrodes as far away as T8 and T11 were also activated if necessary. Which electrodes were proximate to vertebrae T8, T9, T10, and T1 was determined using fluoroscopic images of the leads 15 within each patient.

During sweet spot searching, bipolar stimulation using only two electrodes was used for each patient, and using only adjacent electrodes on a single lead 15, similar to what was described in FIGS. 6 and 7A. Thus, one patient's sweet spot might involve stimulating adjacent electrodes E4 as cathode and E5 as anode on the left lead 15 as shown earlier in FIG. 2 (which electrodes may be between T9 and T10), while another patient's sweet spot might involve stimulating adjacent electrodes E9 as anode and E10 as cathode on the right lead 15 (which electrodes may be between T10 and T11). Using only adjacent-electrode bipolar stimulation and only between vertebrae T8 to T11 was desired to minimize variance in the therapy and pathology between the different patients in the study. However, more complicated bipoles such as those described with respect to FIGS. 7B-7D could also be used during sweet spot searching. If a patient had sweet spot electrodes in the desired thoracic location, and if they experienced a 30% or greater pain relief per an NRS score, such patients were continued in the study; patients not meeting these criteria were excluded from further study. While the study started initially with 39 patients, 19 patients were excluded from study up to this point in FIG. 9, leaving a total of 20 patients remaining.

The remaining 20 patients were then subjected to a "washout" period, meaning their IPGs did not provide stimulation for a time. Specifically, patients' NRS pain scores were monitored until their pain reached 80% of their initial baseline pain. This was to ensure that previous benefits of stimulation did not carry over to a next analysis period.

Thereafter, remaining patients were subjected to sub-perception SCS therapy at different frequencies in the range from 1 kHz to 10 kHz using the sweet spot active electrodes determined earlier. This however isn't strictly necessary, because as noted earlier the current at each electrode could also be independently controlled to assist in shaping of the electric filed in the tissue. As shown in FIG. 9, the patients were each tested using stimulation pulses with frequencies of 10 kHz, 7 kHz, 4 kHz, and 1 kHz. FIG. 9 for simplicity shows that these frequencies were tested in this order for each patient, but in reality the frequencies were applied to each patient in random orders. Testing at a given frequency, once complete, was followed by a washout period before testing at another frequency began.

At each tested frequency, the amplitude (A) and pulse width (PW) (first pulse phase 30a; FIG. 2) of the stimulation was adjusted and optimized for each patient such that each patient experienced good pain relief possible but without paresthesia (sub-perception). Specifically, using clinician programmer 50, and keeping as active the same sweet spot electrodes determined earlier (although again this isn't strictly necessary), each patient was stimulated at a low amplitude (e.g., 0), which amplitude was increased to a maximum point (perception threshold) where paresthesia was noticeable by the patient. Initial stimulation was then chosen for the patient at 50% of that maximum amplitude, i.e., such that stimulation was sub-perception and hence paresthesia free. However, other percentages of the maximum amplitude (80%, 90%, etc.) could be chosen as well, and can vary with patient activity or position, as explained further below. In one example, the stimulation circuitry 28 or 44 in the IPG or ETS is configurable to receive an instruction from the GUI 64 via a selectable option (not shown) to reduce the amplitude of the stimulation pulses to or by a set amount or percentage to render the so that the pulses can be made sub-perception if they are not already. Other stimulation parameters may also be reduced (e.g., pulse width, charge) to the same effect.

The patient would then leave the clinician's office, and thereafter and in communication with the clinician (or her technician or programmer) would make adjustments to his stimulation (amplitude and pulse width) using his external controller 45 (FIG. 4). At the same time, the patient would enter NRS pain scores in his e-diary (e.g., the external controller), again three times a day. Patient adjustment of the amplitude and pulse width was typically an iterative process, but essentially adjustments were attempted based on feedback from the patient to adjust the therapy to decrease their pain while still ensuring that stimulation was sub-perception. Testing at each frequency lasted about three weeks, and stimulation adjustments might be made every couple of days or so. At the end of the testing period at a given frequency, optimal amplitude and pulse widths had been determined and were logged for each patient, along with patient NRS pain scores for those optimal parameters as entered in their e-diaries.

In one example, the percentage of the maximum amplitude used to provide sub-perception stimulation could be chosen dependent on an activity level or position of the patient. In regard, the IPG or ETS can include means for determining patient activity or position, such as an accelerometer. If the accelerometer indicates a high degree of patient activity or a position where the electrodes would be farther away from the spinal cord (e.g., lying down), the amplitude could be increased to a higher percentage to increase the current (e.g., 90% of the maximum amplitude). If the patient is experiencing a lower degree of activity or a position where the electrodes would be closer to the spinal card (e.g., standing), the amplitude can be decreased (e.g., to 50% of the maximum amplitude). Although not shown, the GUI 64 of the external device (FIG. 5) can include an option to set the percentage of the maximum amplitude at which paresthesia become noticeable to the patient, thus allowing the patient to adjust the sub-perception current amplitude.

Preferably, Multiple Independent Current Control (MICC) is used to provide or adjust the sub-perception therapy, as discussed earlier with reference to FIG. 8. This allows the current at each electrode to be independently set, which promotes the steering of current or charge between electrodes, facilitates the formation of virtual bipoles, and more generally allows the electric field to be shaped in the patient's tissue. In particular, MICC, can be used to steer sub-perception therapy to different locations in the electrode array and thus the spinal cord. For example, once a set of sub-perception stimulation parameters has been chosen for the patient, one or more of the stimulation parameters can be changed. Such changes may be warranted or dictated by the therapy location. The physiology of the patient may vary at different vertebral positions, and tissue may be more or less conductive at different therapy locations. Therefore, if the sub-perception therapy location is steered to a new location along the spinal cord (which location change may comprise changing the anode/cathode distance or focus), it may be warranted to adjust at least one of the stimulation parameters, such as amplitude. As noted earlier, making sub-perception adjustment is facilitated, and can occur within a programming session, because a substantial wash in period may not be necessary.

Adjustment to sub-perception therapy can also include varying other stimulation parameters, such as pulse width, frequency, and even the duration of the interphase period (IP) (FIG. 2). The interphase duration can impact the neural dose, or the rate of charge infusion, such that higher sub-perception amplitudes would be used with shorter interphase durations. In one example, the interphase duration can be varied between 0-3 ms. After a washout period, a new frequency was tested, using the same protocol as just described.

The sub-perception stimulation pulses used were symmetric biphasic constant current amplitude pulses, having first and second pulses phases 30a and 30b with the same duration (see FIG. 2). However, constant voltage amplitude pulses could be used as well. Pulses of different shapes (triangles, sine waves, etc.) could also be used. Pre-pulsing—that is, providing a small current prior to providing the actively-driven pulse phase(s)—to affect polarization or depolarization of neural tissue can also occur when providing sub-perception therapy. See, e.g., U.S. Pat. No. 9,008, 790, which is incorporated herein by reference.

FIGS. 10A-10C show the results of testing the patients at 10 kHz, 7 kHz, 4 Hz and 1 kHz. Data is shown in each figure as average values for the 20 remaining patients at each frequency, with error bars reflecting standard error (SE) between the patients.

Starting with FIG. 10B, the optimized amplitude A for the 20 remaining patients are shown at the tested frequencies. Interestingly, the optimal amplitude at each frequency was essentially constant—around 3 mA. FIG. 10B also shows the amount of energy expended at each frequency, more specifically a mean charge per second (MCS) (in mC/s) attributable to the pulses. MCS is computed by taking the optimal pulse width (FIG. 10A, discussed next) and multiplying it by the optimal amplitude (A) and the frequency (F), which MCS value can comprise a neural dose. MCS correlates to the current or power that the battery in the IPG 10 must expend to form the optimal pulses. Significantly, the MCS is significantly lower at lower frequencies: for example, the MCS at F=1 kHz is approximately ⅓ of its value at higher frequencies (e.g., F=7 kHz or 10 kHz). This means that optimal SCS therapy—that alleviates back pain without paresthesia—is achievable at lower frequencies like F=1 kHz, with the added benefit of lower power draws that are more considerate of the IPG 10's (or ETS 40's) battery.

FIG. 10A shows optimal pulse width as a function of frequency for the 1 kHz to 10 kHz frequency range tested. As shown, the relationship follows a statistically significant trend: when modeled using linear regression 98a, PW=−8.22F+106, where pulse width is measured in microseconds and frequency is measured in kiloHertz, with a correlation coefficient $R^2$ of 0.974; when modeled using polynomial regression 98b, PW=0.486$F^2$−13.6F+116, again with pulse width measured in microseconds and frequency measured in kiloHertz, with an even better correlation coefficient of $R^2$=0.998. Other fitting methods could be used to establish other information relating frequency and pulse width at which stimulation pulses are formed to provide pain relief without paresthesia in the frequency range of 1 kHz to 10 kHz.

Figure 11A:
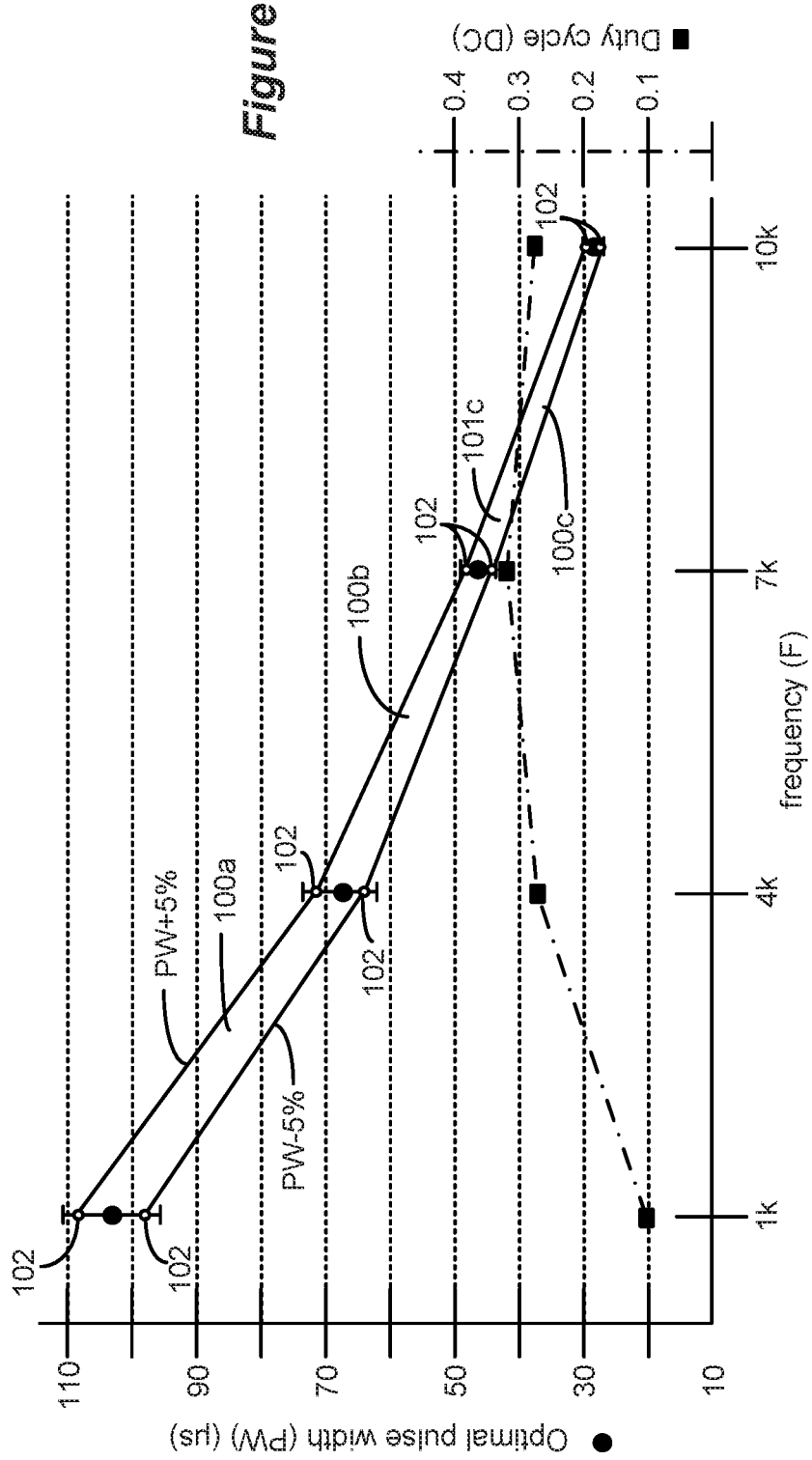
FIGS. 11A-11C show further analysis of relationships between average optimal pulse width and frequency in the 1 kHz to 10 kHz frequency range, and identifies statistically-significant regions of optimization of these parameters.

Note that the relationship between optimal pulse width and frequency is not simply an expected relationship between frequency and duty cycle (DC), i.e., the duration that a pulse is 'on' divided by its period (1/F). In this regard, notice that a given frequency has a natural effect on pulse width: one would expect that a higher frequency pulses would have smaller pulse widths. Thus, it might be expected for example that a 1 kHz waveform with a 100 microsecond pulse width would have the same clinical results as a 10 kHz waveform with a 10 microsecond frequency, because the duty cycle of both of these waveforms is 10%. FIG. 11A shows the resulting duty cycle of the stimulation waveforms using the optimal pulse width in the frequency range of 1 kHz to 10 kHz. Here, duty cycle is computed by considering the total 'on' time of the first pulse phase 30a (FIG. 2) only; the duration of the symmetric second pulse phase is ignored. This duty cycle is not constant over the 1 kHz to 10 kHz frequency range: for example, the optimal pulse width at 1 kHz (104 microseconds) is not merely ten times the optimal pulse width at 10 kHz (28.5 microseconds). Thus, there is significance to the optimal pulse widths beyond a mere scaling of the frequency.

FIG. 10C shows average patient pain scores at the optimal stimulation parameters (optimal amplitude (FIG. 7B) and pulse width (FIG. 7A)) for each frequency in the range of 1 kHz to 10 kHz. As noted earlier, patients in the study, prior to receiving SCS therapy, initially reported pain scores with an average of 6.75. After SCS implantation and during the study, and with amplitude and pulse width optimized during the provisional of sub-perception therapy, their average pain scores dropped significantly, to an average score of about 3 for all frequencies tested.

FIG. 11A provides a deeper analysis of the resulting relationship between optimal pulse width and frequency in the frequency range of 1 kHz to 10 kHz. The chart in FIG. 11A shows the average optimal pulse width for the 20 patients in the study at each frequency, along with the standard error resulting from variations between them. These are normalized at each frequency by dividing the standard error by the optimal pulse width, ranging in variations at each frequency between 5.26% and 8.51%. From this, a 5% variance (lower than all computed values) can be assumed as a statistically-significant variance at all frequencies tested.

From this 5% variance, a maximum average pulse width (PW+5%) and a minimum average pulse width (PW+5%) can be calculated for each frequency. For example, the optimal average pulse width PW at 1 kHz is 104 microseconds, and 5% above this value (1.05*104 µs) is 109 µs; 5% below this value (0.95*104) is 98.3 µs. Likewise, the optimal average pulse width AVG(PW) at 4 kHz is 68.0 microseconds, and 5% above this value (1.05*68.0 µs) is 71.4 µs; 5% below this value (0.95*68.0 µs) is 64.6 µs. Thus, a statistically-significant reduction in pain without paresthesia occurs in or on the linearly bounded region 100a of points 102 of (1 kHz, 98.3 µs), (1 kHz, 109 µs), (4 kHz, 71.4 µs), and (4 kHz, 64.6 µs). A linearly bounded region 100b around points 102 is also defined for frequencies greater than or equal to 4 kHz and less than or equal to 7 kHz: (4 kHz, 71.4 µs), (4 kHz, 64.6 µs), (7 kHz, 44.2 µs), (7 kHz, 48.8 µs). A linear bounded region 100c around points 102 is also defined for frequencies greater than or equal to 7 kHz and less than or equal to 10 kHz: (7 kHz, 44.2 µs), (7 kHz, 48.8 µs), (10 kHz, 29.9 µs), (10 kHz, 27.1 µs). Such regions 100 thus comprise information relating frequency and pulse width at which stimulation pulses are formed to provide pain relief without paresthesia in the frequency range of 1 kHz to 10 kHz.

Figure 11B:
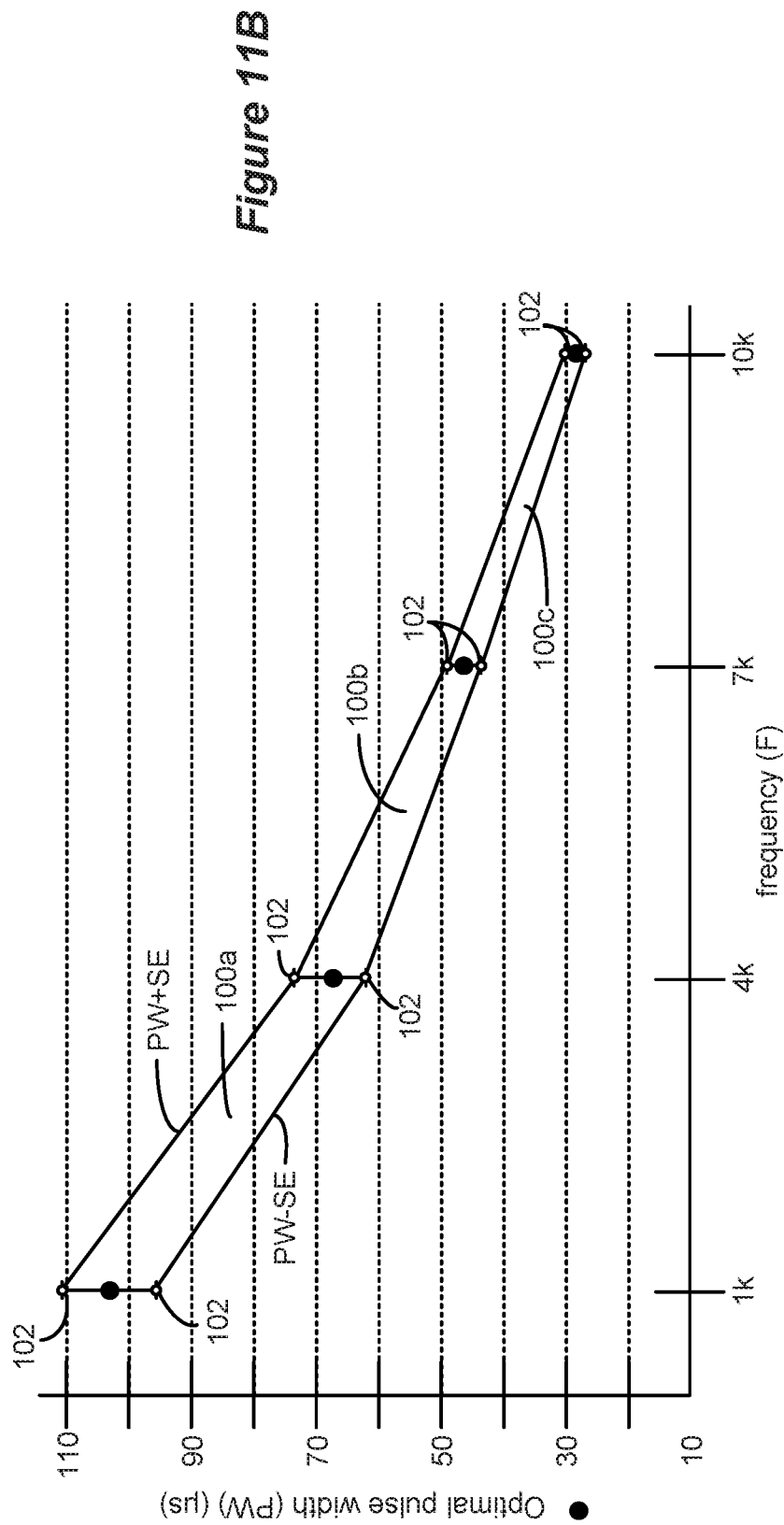

FIG. 11B provides an alternative analysis of the resulting relationship between optimal pulse width and frequency. In this example, regions 100a-100c are defined based upon the standard error (SE) calculated at each frequency. Thus, points 102 defining the corners of the regions 100a-c are simply located at the extent of the SE error bars at each frequency (PW+SE, and PW−SE), even though these error bars are of different magnitudes at each frequency. Thus, a statistically-significant reduction in pain without paresthesia occurs in or on the linearly bounded region 100a of points (1 kHz, 96.3 µs), (1 kHz, 112 µs), (4 kHz, 73.8 µs), and (4 kHz, 62.2 µs). The linear bounded regions 100b and 100c are similar, and because the points 102 defining them are set forth in chart at the top of FIG. 11B, they are not repeated here.

Figure 11C:
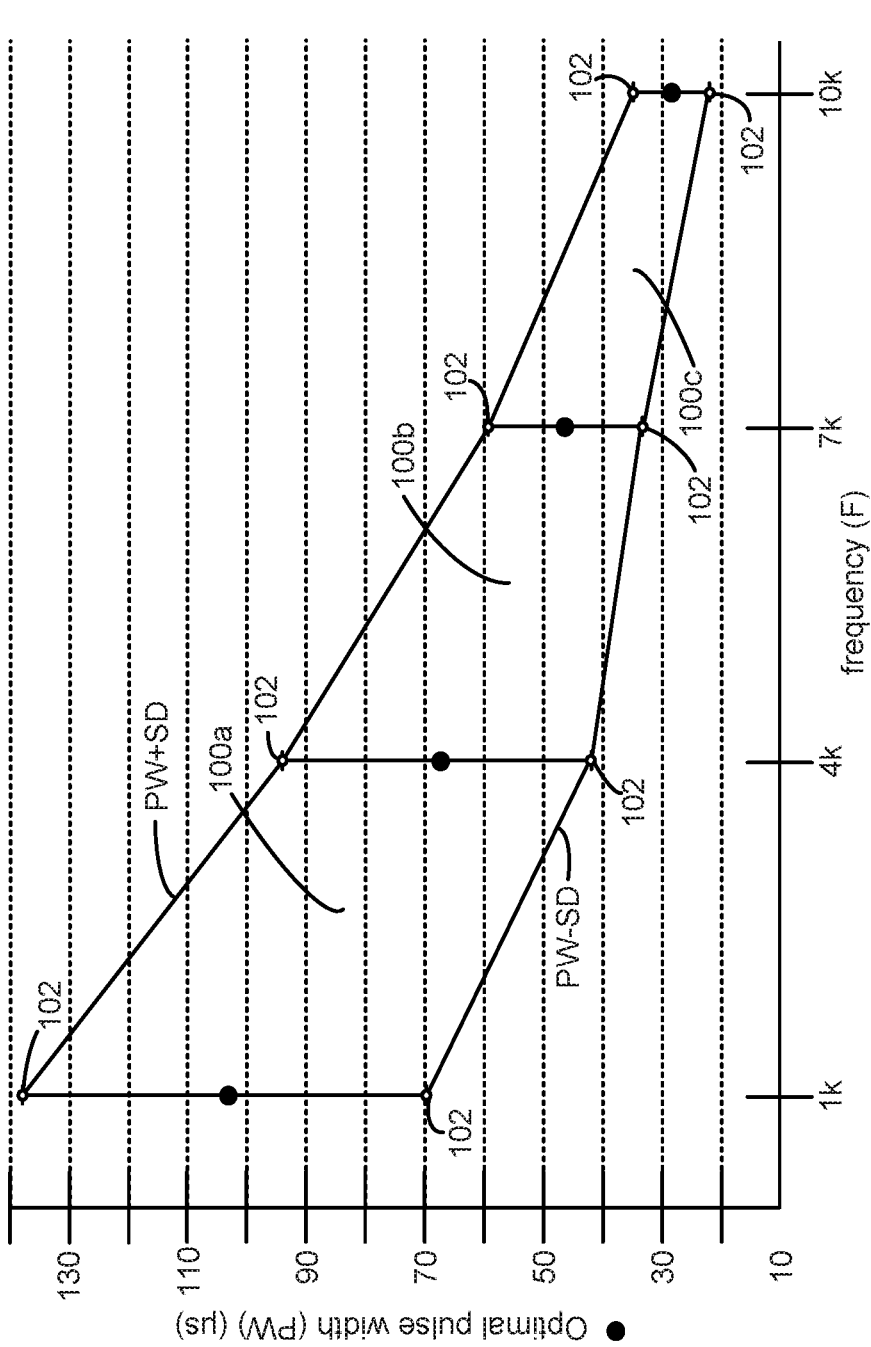

FIG. 11C provides another analysis of the resulting relationship between optimal pulse width and frequency. In this example, regions 100a-100c are defined based upon the standard deviation (SD) calculated at each frequency, which is larger than the standard error (SE) metric used to this point. Points 102 defining the corners of the regions 100a-c are located at the extent of the SD error bars at each frequency (PW+SD, and PW−SD), although points 102 could also be set within the error bars, similar to what was illustrated earlier with respect to FIG. 11A. In any event, a statistically-significant reduction in pain without paresthesia occurs in or on the linearly bounded region 100a of points (1 kHz, 69.6 µs), (1 kHz, 138.4 µs), (4 kHz, 93.9 µs), and (4 kHz, 42.1 µs). The linear bounded regions 100b and 100c are similar, and because the points 102 defining them are set forth in chart at the top of FIG. 11C, they are not repeated here.

More generally, although not illustrated, regions within the frequency range of 1 kHz to 10 kHz where sub-perception efficacy was achieved comprises linearly-bounded region 100a (1 kHz, 50.0 µs), (1 kHz, 200.0 µs), (4 kHz, 110.0 µs), and (4 kHz, 30.0 µs); and/or linearly-bounded region 100b (4 kHz, 110.0 µs), (4 kHz, 30.0 µs), (7 kHz, 30.0 µs), and (7 kHz, 60.0 µs); and/or linearly-bounded region 100c (7 kHz, 30.0 µs), (7 kHz, 60.0 µs), (10 kHz, 40.0 µs), and (10 kHz, 20.0 µs).

In summary, one or more statistically-significant regions 100 can be defined for the optimal pulse width and frequency data taken for the patients in the study to arrive at combinations of pulse width and frequency that reduce pain without the side effect of paresthesia within the frequency range of 1 kHz to 10 kHz, and different statistical measures of error can be used to so define the one or more regions.

FIGS. 12A-12D show the results of testing other patients with sub-perception stimulation therapy at frequencies at or below 1 kHz. Testing of the patients generally occurred after supra-perception sweep spot searching occurred to select appropriate electrodes (E), polarities (P) and relative amplitudes (X %) for each patient (see FIGS. 7A-7D), although again the sub-perception electrodes used could vary from those used during the supra-perception sweet spot search (e.g., using MICC). Patients were tested with sub-perception stimulation using symmetric biphasic bipoles, although the form of pulses used during sub-perception therapy could vary.

Figure 12A:
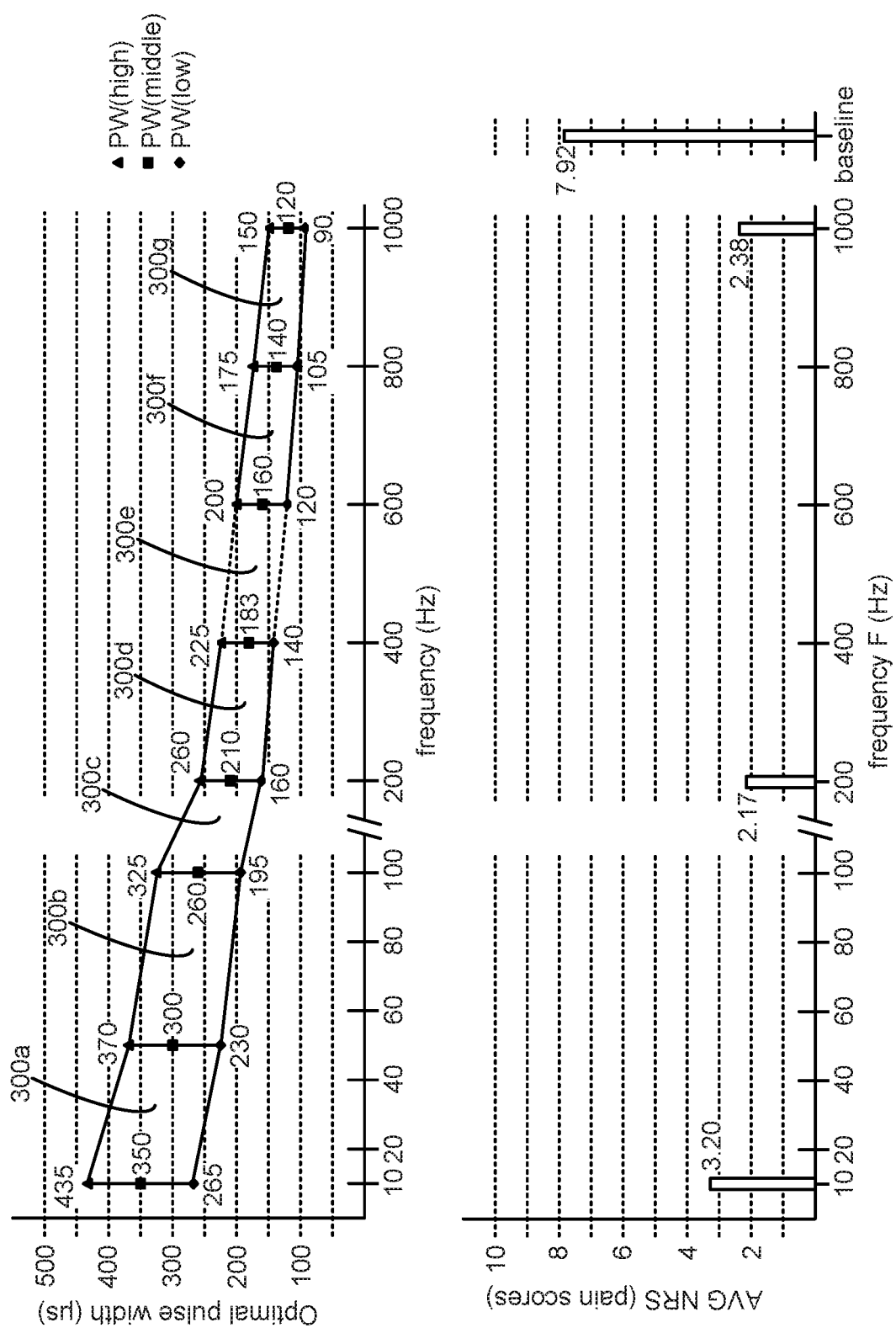
FIG. 12A shows results of patients tested with sub-perception therapy at frequencies at or below 1 kHz, and shows optimal pulse width ranges determined at tested frequencies, and optimal pulse width v. frequency regions for sub-perception therapy.

FIG. 12A shows the relationship between frequency and pulse width at which effective sub-perception therapy was reported by patients for frequencies of 1 kHz and below. Note that the same patient selection and testing criteria described earlier (FIG. 9) can be used when evaluating frequencies at or below 1 kHz, with the frequencies adjusted as appropriate.

As can be seen, at each frequency tested, the optimal pulse width again fell within a range. For example, at 800 Hz, patients reported good results when the pulse width fell within a range of 105-175 microseconds. The upper end of the pulse width range at each frequency is denoted PW(high), while the lower end of the pulse width range at each frequency is denoted PW(low). PW(middle) denotes the middle (e.g., average) of the PW(high) and PW(low) at each frequency. At each of the tested frequencies the amplitude of the current provided (A) was titrated down to sub-perception levels, such that the patient could not feel paresthesia. Typically, the current was titrated to 80% of the threshold at which paresthesia could be sensed. Because each patient's anatomy is unique, the sub-perception amplitude A could vary from patient to patient. The pulse width data depicted comprises the pulse width of only the first phase of the stimulation pulses.

Table 1 below expresses the optimal pulse width versus frequency data of FIG. 12A in tabular form for frequencies at or below 1 kHz, with the pulse widths expressed in microseconds:

TABLE 1

| Frequency (Hz) | PW(low) (µs) | PW(middle) (µs) | PW(high) (µs) |
|---|---|---|---|
| 1000 | 90 | 120 | 150 |
| 800 | 105 | 140 | 175 |
| 600 | 120 | 160 | 200 |
| 400 | 140 | 183 | 225 |
| 200 | 160 | 210 | 260 |
| 100 | 195 | 260 | 325 |
| 50 | 230 | 300 | 370 |
| 10 | 265 | 350 | 435 |

As with the analysis described earlier for frequencies in a range of 1 kHz to 10 kHz (FIGS. 10A-11C), the data may be broken down to define different regions 300i at which effective sub-perception therapy is realized below 1 kHz. For example, regions of effective sub-perception therapy may be linearly bounded between various frequencies and the high and low pulse widths that define effectiveness. For example, at 10 Hz, PW(low)=265 microseconds and PW(high)=435 microseconds. At 50 Hz, PW(low)=230 microseconds and PW(high)=370 microseconds. Therefore, a region 300a that provides good sub-perception therapy is defined by the linearly bounded region of points (10 Hz, 265 µs), (10 Hz, 435 µs), (50 Hz, 370 µs), and (50 Hz, 230 µs). Table 2 defines the points that linearly bind each of the regions 300a-300g shown in FIG. 12A:

TABLE 2

| region | Bounded by points (Hz, µs) |
|---|---|
| 300a | (10, 265), (10, 435), (50, 370), (50, 230) |
| 300b | (50, 230), (50, 370), (100, 325), (100, 195) |
| 300c | (100, 195), (100, 325), (200, 260), (200, 160) |
| 300d | (200, 160), (200, 260), (400, 225), (400, 140) |
| 300e | (400, 140), (400, 225), (600, 200), (600, 120) |
| 300f | (600, 120), (600, 200), (800, 175), (800, 105) |
| 300g | (800, 105), (800, 175), (1000, 150), (1000, 90) |

Regions of sub-perception therapeutic effectiveness at frequencies at or below 1 kHz may be defined in other statistically-significant ways, such as those described earlier for frequencies in the range of 1 kHz to 10 kHz (FIGS. 11A-11C). For example, regions 300i may be defined by reference to the pulse width at the middle of the ranges at each frequency, PW(middle). PW(middle) may comprise for example an average optimal pulse width reported by patients at each frequency, rather than as a strict middle of an effective range reported by those patients. PW(high) and PW(low) may then be determined as a statistical variance from the average PW(middle) at each frequency, and used to set the upper and lower bounds of effective sub-perception regions. For example, PW(high) may comprise average PW(middle) plus a standard deviation or standard error, or a multiples of such statistical measures; PW(low) may likewise comprise average PW(middle) minus a standard deviation or standard error, or a multiple of such statistical measures. PW(high) and PW(low) may also be determined from average PW(middle) in other ways. For example, PW(high) may comprise average PW(middle) plus a set percentage, while PW(low) may comprise PW(middle) minus a set percentage. In summary, one or more statistically-significant regions 300 can be defined for the optimal pulse width and frequency data at frequencies at or below 1 kHz that reduce pain using sub-perception stimulation without the side effect of paresthesia.

Also shown in FIG. 12A are average patient pain scores (NRS scores) reported by patients when optimal pulse widths are used for different frequencies at 1 kHz or below. Prior to receiving SCS therapy, patients initially reported pain scores with an average of 7.92. After SCS implantation, and using the sub-perception stimulation at optimal pulse widths with the ranges shown at each frequency, the patients' average pain scores dropped significantly. At 1 kHz, 200 Hz, and 10 Hz, patients reported average pain scores of 2.38, 2.17, and 3.20 respectively. Thus clinical significance with respect to pain relief is shown when the optimal pulse widths are used at or below 1 kHz with sub-perception therapy.

Figure 12B:
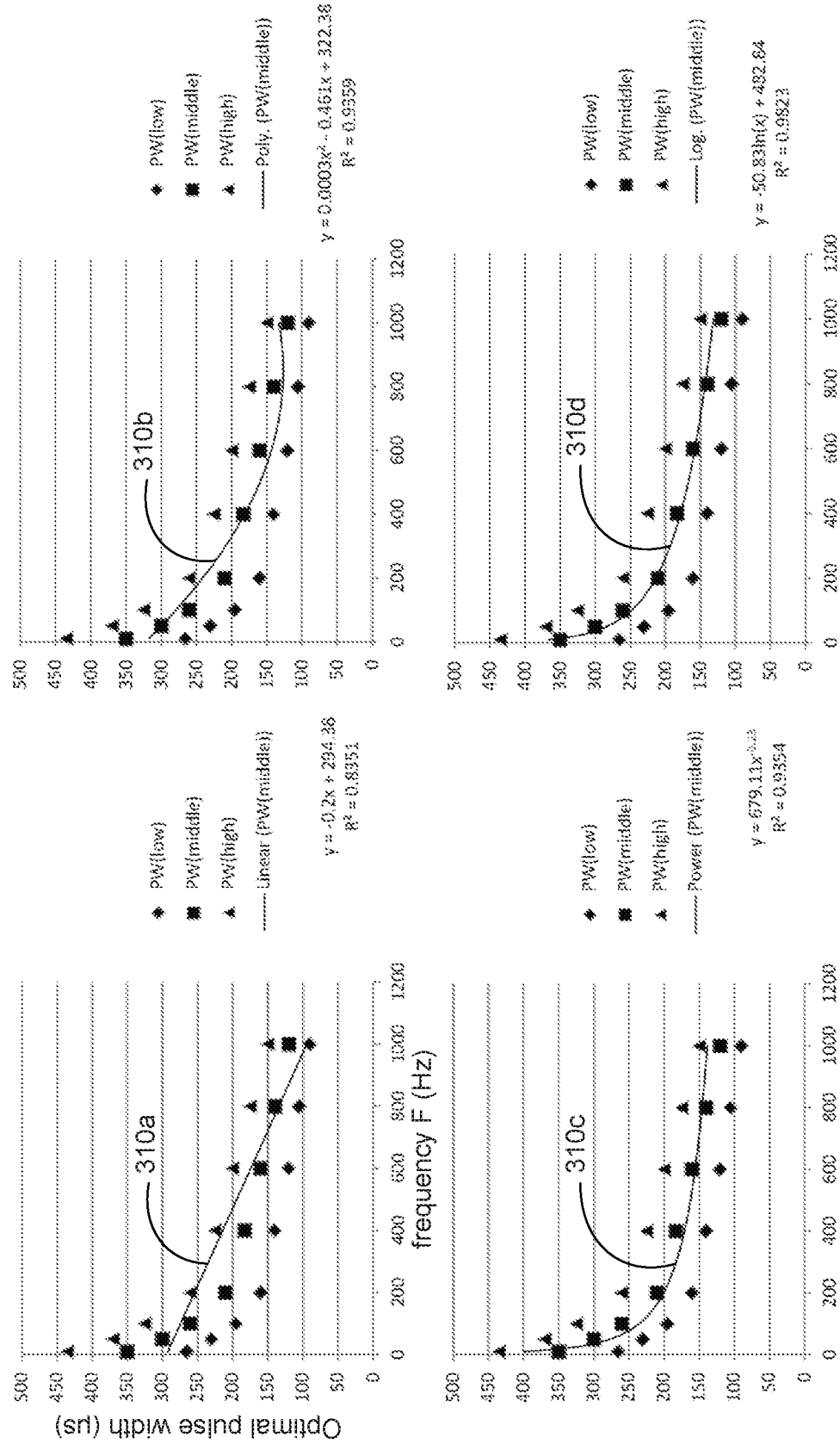
FIG. 12B shows various modelled relationships between average optimal pulse width and frequency at or below 1 kHz.

The optimal pulse width versus frequency data of FIG. 12A for frequencies at or below 1 kHz is analyzed in FIG. 12B from the perspective of the middle pulse width, PW(middle) at each frequency (F). As shown, the relationships 310a-310d follows statistically significant trends, as evidenced by the various regression models shown in FIG. 12B and summarized in Table 3 below:

TABLE 3

| Regression model | Relationship (PW(middle) in µs) | Correlation coefficient $R^2$ |
|---|---|---|
| Linear (310a) | PW(middle) = −0.2F + 294.4 | 0.835 |
| Polynomial (310b) | PW(middle) = $0.0002F^2$ − 0.461F + 332.38 | 0.936 |
| Power (310c) | PW(middle) = $679.1x^{-0.23}$ | 0.935 |
| Logarithmic (310d) | PW(middle) = −50.83ln(F) + 482.8 | 0.982 |

Other fitting methods could be used to establish other information relating frequency and pulse width at which stimulation pulses are formed to provide sub-perception pain relief without paresthesia.

Regression analysis can also be used to define statistically relevant regions such as 300a-300g where sub-perception therapy is effective at or below 1 kHz. For example, and although not shown in FIG. 12B, regression can be performed for PW(low) v. F to set a lower boundary of relevant regions 300i, and regression can be performed for PW(high) v. F to set an upper boundary of relevant regions 300i.

Note that the relationship between optimal pulse width and frequency depicted in FIG. 12A is not simply an expected relationship between frequency and duty cycle (DC), as FIG. 12C shows. As was the case when the 1 kHz to 10 kHz frequency range was tested (FIG. 11A), the duty cycle of the optimal pulse widths is not constant at 1 kHz and below. Again, there is significance to the optimal pulse widths beyond a mere scaling of the frequency. Nonetheless, most of the pulse widths observed to be optimal at 1 kHz and below are greater than 100 microseconds. Such pulse widths are not even possible at higher frequencies. For example, at 10 kHz, both pulse phases have to fit within a 100 us period, so PW longer than 100 are not even possible.

FIG. 12D shows further benefits achieved in using sub-perception at frequencies of 1 kHz and below, namely reduced power consumption. Two sets of data are graphed. The first data set comprises the average current drawn by the battery in the patients' IPG or ETS (AVG Ibat) at each frequency using the optimal pulse width for that patient (FIG. 12A) and the current amplitude A necessary to achieve sub-perception stimulation for that patient (again, this amplitude can vary for each of the patients). At 1 kHz, this average battery current is about 1700 microamps. However, as the frequency is reduced, this average battery current drops, to about 200 microamps at 10 Hz. The second data set looks at power consumption from a different vantage point, namely the number of days that an IPG or ETS with a fully-charged rechargeable battery can operate before a recharge is required ("discharge time"). As would be expected based on the average battery current data, the discharge time is lower at higher frequencies when the average battery current is higher (e.g., about 3.9 days at 1 kHz, depending on various charging parameters and settings), and is higher at lower frequencies when the average battery current is lower (e.g., about 34 days at 10 Hz, depending on various charging parameters and settings). This is significant: not only can effective sub-perception therapy be provided at 1 kHz and below when optimal pulse widths are used; power consumptions is greatly lowered, which places less stress on the IPG or ETS, and allows it to operate from longer periods of time. As noted above, excessive power consumption is a significant problem when sub-perception therapy is traditionally used at higher frequencies. Note that the data of FIG. 12D could also be analyzed in terms of mean charge-per-second (MSC), as described earlier for the 1 kHz to 10 kHz data (FIG. 10B).

Figure 13A:
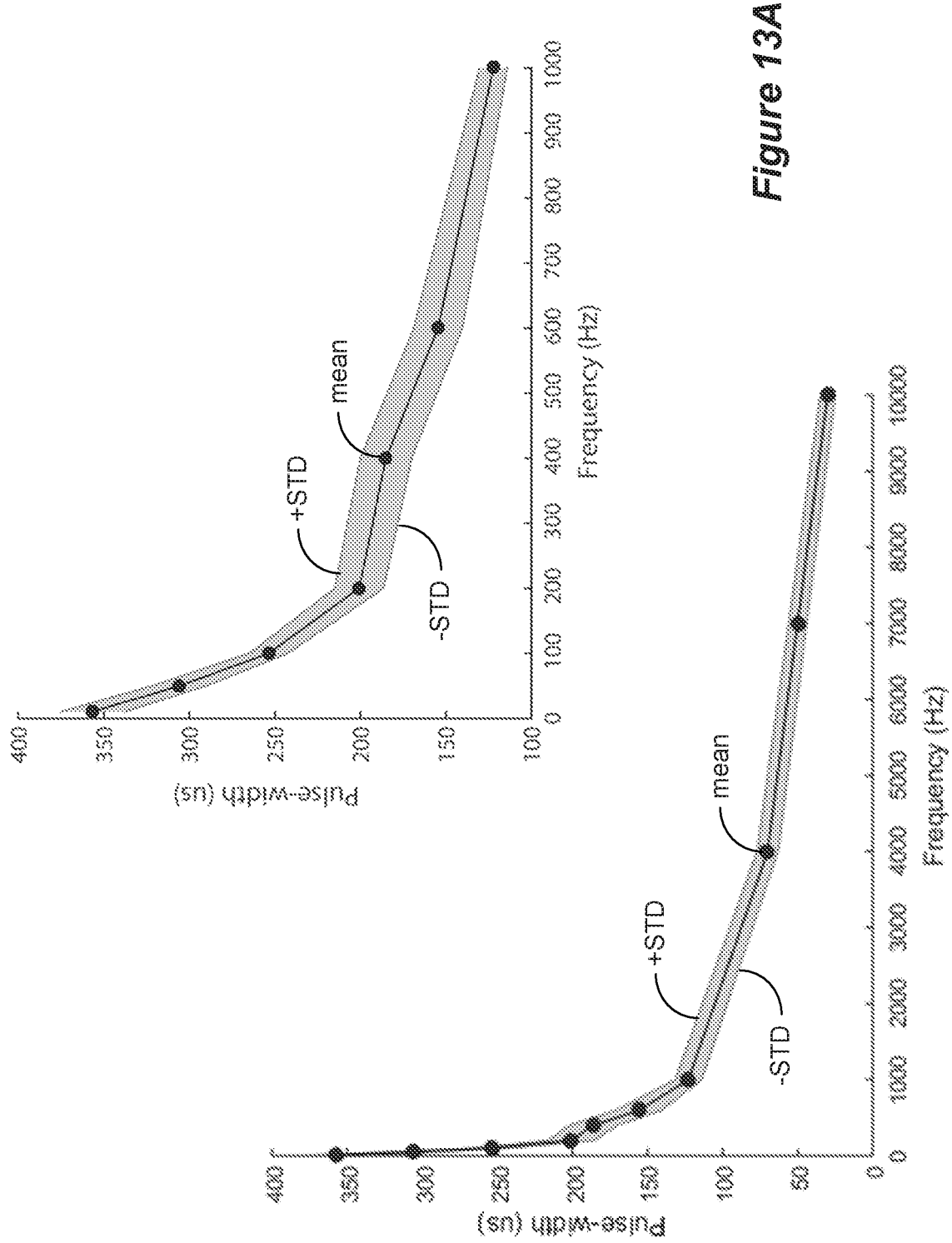
FIGS. 13A and 13B show the results of additional testing that verifies the frequency versus pulse width relationships presented earlier.
Figure 13B:
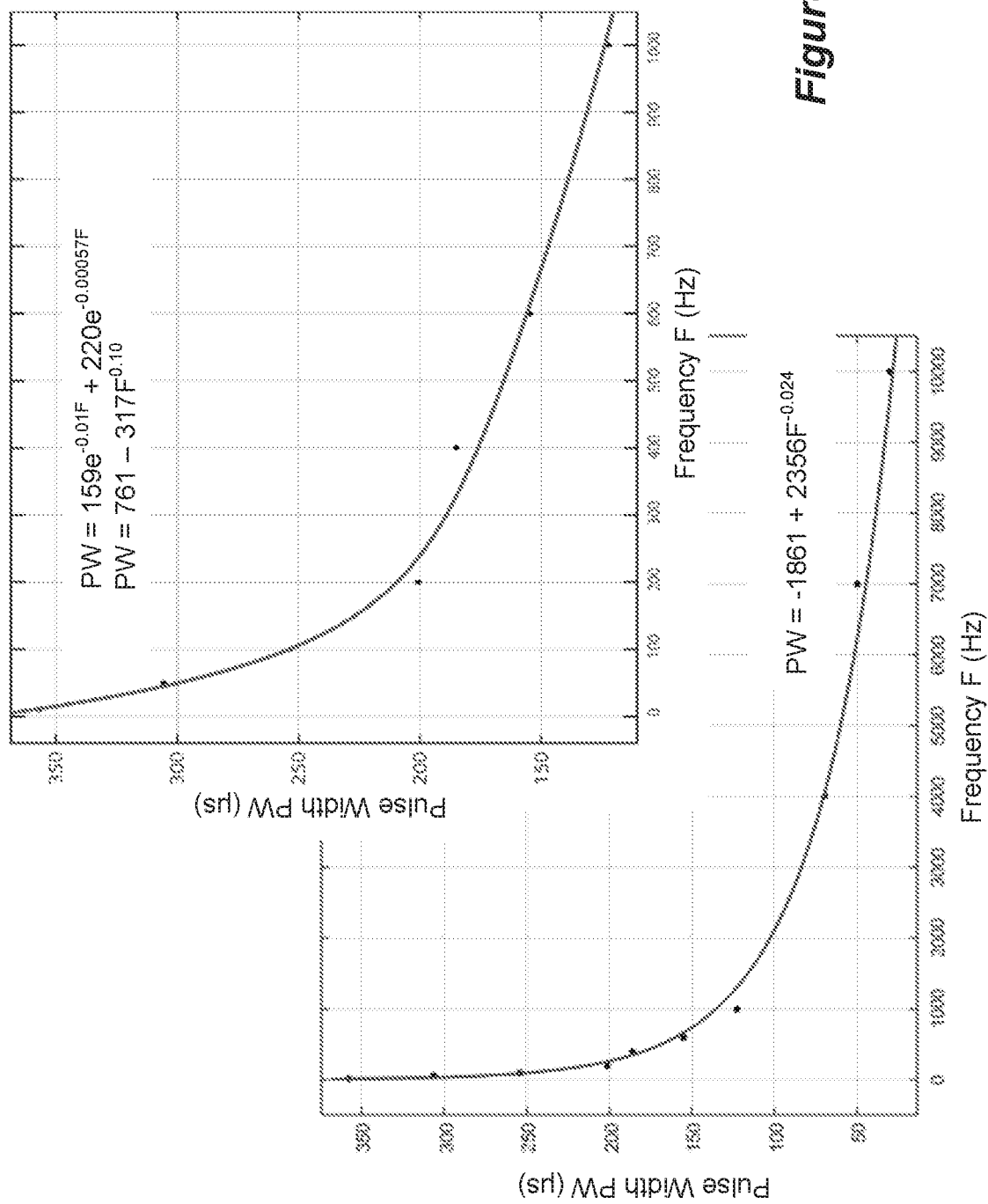

FIGS. 13A and 13B shows the results of additional testing that verifies the frequency versus pulse width relationships just presented. Here, data is shown for 25 patients tested using sub-perception stimulation at frequencies of 10 kHz and below. FIG. 13A shows two different graphs showing the result for frequencies of 10k and below (lower graph) and for frequencies of 1 kHz and below (upper graph). Mean values are shown frequencies and pulse width values at which optimal sub-perception therapy is produced. Upper and lower bands denote one standard deviation's variance (+STD and −STD) above and below the mean. FIG. 13B shows curve fitting results as determined using mean values. Data for 1 kHz and below is fit with an exponential function and with a power function, resulting in relationship $PW=159e^{-0.01F}+220e^{-0.00057F}$ and $PW=761-317F^{0.10}$, both of which well fit to the data. Data for 10 kHz and below is fit with a power function, yielding $PW=-1861+2356F^{-0.024}$, again with a good fit. The data could bit fit to other mathematical functions as well.

Once determined, the information 350 relating frequency and pulse width for optimal sub-perception therapy without paresthesia can be stored in an external device used to program the IPG 10 or ETS 40, such as the clinician programmer 50 or external controller 45 described earlier.

Figure 14:
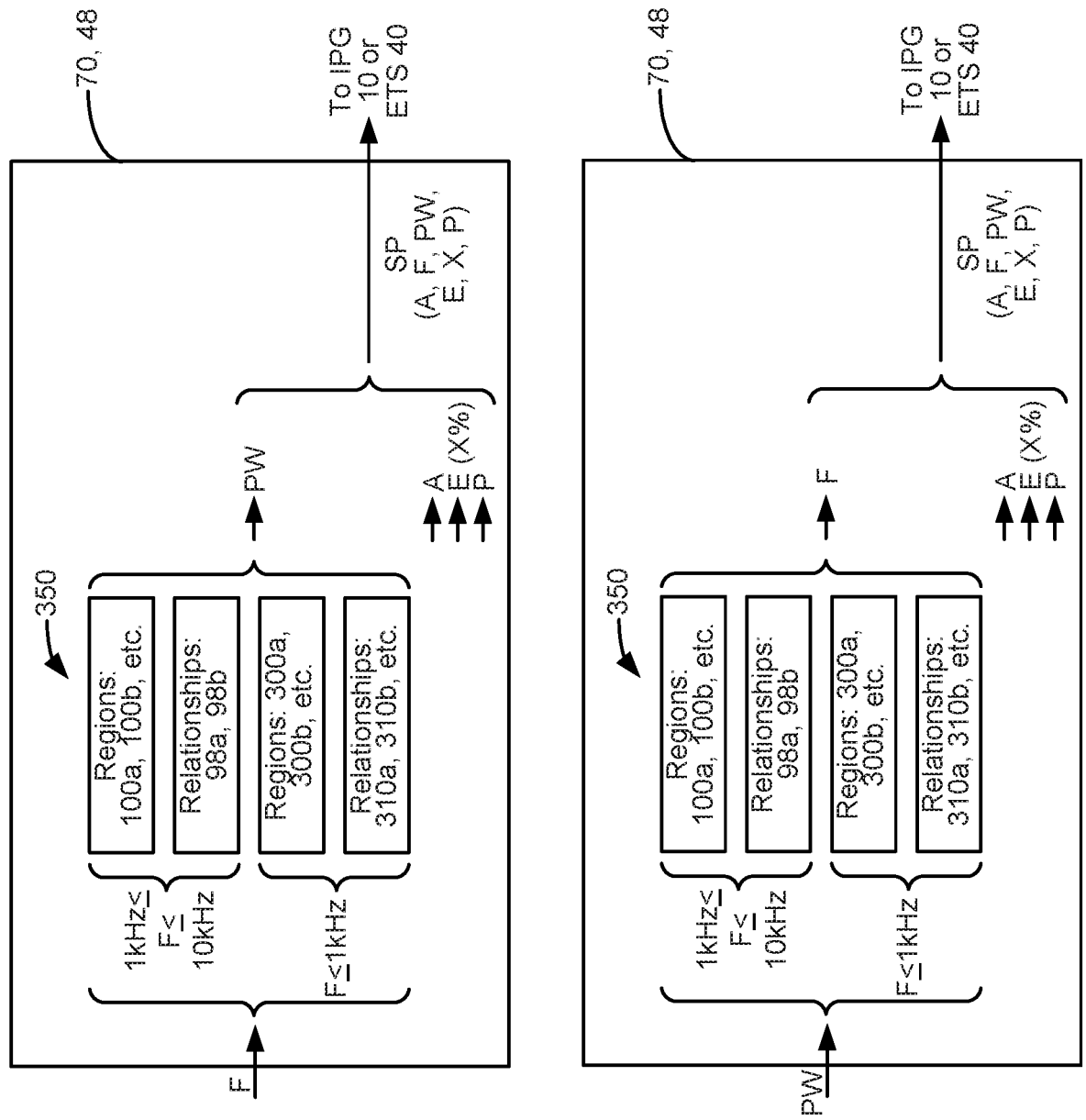
FIG. 14 shows a fitting module showing how the relationships and regions determined relating optimal pulse width and frequency (≤10 kHz) can be used to set sub-perception stimulation parameters for an IPG or ETS.

This is shown in FIG. 14, in which the control circuitry 70 or 48 of the clinician programmer or external controller is associated with region information 100i or relationship information 98i for frequencies in the 1 kHz to 10 kHz range, and region information 300i or relationship information 310i for frequencies at or below 1 kHz. Such information can be stored in memory within or associated with the control circuitry. Storing of this information with the external device is useful to assisting the clinician with sub-perception optimization, as described further below. Alternatively, and although not shown, the information relating frequency and pulse width can be stored in the IPG 10 or ETS 40, thus allowing the IPG or ETS to optimize itself without clinician or patient input.

Information 350 can be incorporated into a fitting module. For example, fitting module 350 could operate as a software module within clinician programmer software 66, and may perhaps be implemented as an option selectable within the advanced 88 or mode 90 menu options selectable in the clinician programmer GUI 64 (FIG. 6). Fitting module 350 could also operate in the control circuitry of the IPG 10 or ETS 40.

The fitting module 350 can be used to optimize pulse width when frequency is known, or vice versa. As shown at the top of FIG. 14, the clinician or patient can enter a frequency F into the clinician programmer 50 or external controller 45. This frequency F is passed to the fitting module 350 to determine a pulse width PW for the patient, which is statistically likely to provide suitable pain relief without paresthesia. Frequency F could for example be input to the relationships 98i or 310i to determine the pulse width PW. Or, the frequency could be compared to the relevant region 100i or 300i within which the frequency falls. Once the correct region 100i or 300i is determined, F can be compared to the data in regions to determine a pulse width PW, which may perhaps be a pulse width between the PW+X and PW−X boundaries at the given frequency, as described earlier. Other stimulation parameters, such as amplitude A, active electrodes E, their relative percentage X %, and electrode polarity P can be determined in other manners, such as those described below, to arrive at a complete stimulation program (SP) for the patient. Based on the data from FIG. 10B, an amplitude near 3.0 mA might be a logical starting point, as this amplitude was show to be preferred by patients in the 1 kHz to 10 kHz range. However, other initial starting amplitudes may be chosen as well, which amplitudes for sub-perception therapy may be dependent on frequency. The bottom of FIG. 14 shows use of the fitting module 350 in reverse—that is to pick a frequency given a pulse width. Note that in the algorithms that follow or even when used outside of any algorithm, in one example, the system can allow the user to associate the frequency and pulse width such that when the frequency or pulse width is changed, the other of the pulse width or frequency is automatically changed to correspond to an optimal setting. In some embodiments, associating the frequency and pulse width in this manner can comprise a selectable feature (e.g., in GUI 64) useable when sub-perception programming is desired, and associating the frequency and pulse width can be unselected or unselectable for use with other stimulation modes.

Figure 15:
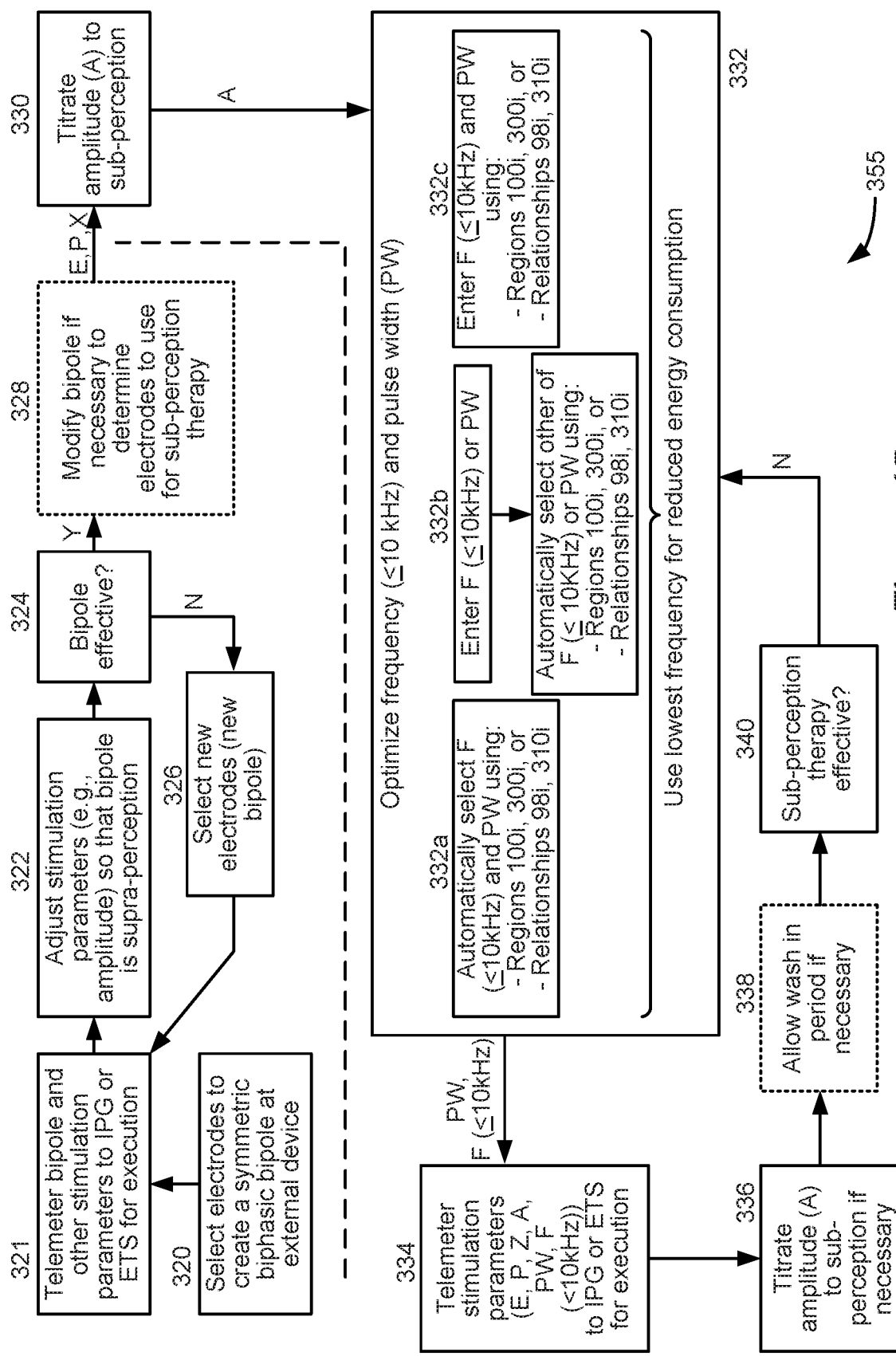
FIG. 15 shows an algorithm used for supra-perception sweet spot searching followed by sub-perception therapy, and possible optimization of the sub-perception therapy using the fitting module.

FIG. 15 shows an algorithm 355 that can be used to provide sub-perception therapy to an SCS patient at frequencies of 10 kHz or lower, and summarizes some of the steps already discussed above. Steps 320-328 describe the supra-perception sweep spot search. A user (e.g., clinician) selects electrodes to create a bipole for the patient (320), for example, by using the GUI of the clinician programmer. This bipole is preferably a symmetric biphasic bipole and may comprise a virtual bipole, as described earlier.

This bipole is telemetered along with other simulation parameters to the IPG or ETS for execution (321). Such other stimulation parameters can also be selected in the clinician programmer using the GUI. As a default, the frequency F can equal 90 Hz and the pulse width (PW) can equal 200 microseconds, although this is not strictly necessary and these values can be modified. At this point, if the bipole provided by the IPG or ETS is not supra-perception, i.e., if paresthesia is not felt by the patient, the amplitude A or other stimulation parameters can be adjusted to make it so (322). The bipole's effectiveness is then gauged by the patient (324) to see how well the bipole is covering the patient's pain site. NRS or other score rating systems can be used to judge effectiveness.

If the bipole is not effective, or if it is still desired to search, a new bipole can be tried (326). That is new electrodes can be selected preferably in manner which moves the bipole to a new location, along a path 296 as described earlier with reference to FIGS. 7A-7D. This new bipole can then again be telemetered to the IPG or ETS (321) and adjustments made if necessary to render the bipole supra-perceptive (322). If the bipole is effective, or if the searching is done and a most effective bipole has been located, that bipole may optionally be modified (328) prior to sub-perception therapy. Such modification as described above can involve selecting other electrodes proximate to the selected bipole's electrodes to modify the field shape in the tissue to perhaps better cover the patient's pain. As such, the modification of step 328 may change the bipole used during the search to a virtual bipole, or a tripole, etc.

Modification of other stimulation parameters can also occur at this point. For example, the frequency and pulse width can also be modified. In one example, a working pulse width can be chosen which provides good, comfortable paresthesia coverage (>80%). This can occur by using a frequency of 200 Hz for example, and starting with a pulse width of 120 microseconds for example. The pulse width can be increased at this frequency until good paresthesia coverage is noted. An amplitude in the range of 4 to 9 mA may be used for example.

At this point, the electrodes chosen for stimulation (E), their polarities (P), and the fraction of current they will receive (X %) (and possible a working pulse width) are known and will be used to provide sub-perception therapy. To ensure that sub-perception therapy is provided, the amplitude A of the stimulation is titrated downward to a sub-perception, paresthesia free level (330), and telemetered to the IPG or ETS. As described above, the amplitude A may be set below an amplitude threshold (e.g., 80% of the threshold) at which the patient can just start to feel paresthesia.

At this point, it can be useful to optimize the frequency and pulse width of the sub-perception therapy that is being provided to the patient (332). While the frequency (F) and pulse width (PW) used during sweet spot searching can be used for sub-perception therapy, benefit is had by additionally adjusting these parameters to optimal values in accordance with the regions 100$i$ or relationships 98$i$ established at frequencies in the 1 kHz to 10 kHz range, or the regions 300$i$ or relationships 310$i$ established at frequencies at or below 1 kHz. Such optimization may use the fitting module 350 of FIG. 14, and can occur in different ways, and a few means of optimization 332a-332c are shown in FIG. 15. Option 332a for instance allows the software in either the clinician programmer or the IPG or ETS to automatically select both a frequency (≤10 kHz) and pulse width using the region or relationship data correlating frequency to pulse width. Option 332a might use the working pulse width determined earlier (328), and choose a frequency using the regions or relationships. Option 332b by contrast allows the user (clinician) to specify (using the GUI of the clinician program) either the frequency (≤10 kHz) or the pulse width. The software can then select an appropriate value for the other parameter (pulse width or frequency (≤10 kHz), again using regions or the relationships. Again, this option might use the working pulse width determined earlier to select an appropriate frequency. Option 332c allows the user to enter both the frequency (≤10 kHz) and the pulse width PW, but in a manner that is constrained by the regions or the relationships. Again, this option may allow the use to enter the working pulse width and a frequency that is appropriate for that working frequency, depending on the regions or relationships. The GUI 64 of the clinician programmer might in this example not accept inputs for F and PW that do not fall within the regions or along the relationships because such values would not provide optimal sub-perception therapy.

Frequency or pulse width optimization can occur other ways that more effectively search the desired portion of the parameter space. For example, a gradient descent, binary search, simplex method, genetic algorithm, etc. can be used for the search. A machine learning algorithm that has trained using data from patients could be considered.

Preferably, when optimizing the frequency (≤10 kHz) and pulse width at step 332, these parameters are selected in a manner that reduces power consumption. In this regard, it is preferable that the lowest frequency be chosen, as this will reduce mean charge per second (MCS), reduce the average current drawn from the battery in the IPG or ETS, and thus increase the discharge time, as discussed earlier with respect to FIGS. 10B and 12D. Lowering the pulse width if possible will also reduce battery draw and increase the discharge time.

At this point all relevant stimulation parameters (E, P, X, I, PW, and F (≤10 kHz)) are determined and can be sent from the clinician programmer to the IPG or ETS for execution (334) to provide sub-perception stimulation therapy for the patient. It is possible that adjustment of the optimal pulse width and frequency (≤10 kHz) (332) may cause these stimulation parameters to provide paresthesia. Therefore, the amplitude of the current A can once again be titrated downward to sub-perception levels if necessary (336). If necessary, the prescribed sub-perception therapy can be allowed a period of time to wash in (338), although as mentioned earlier this may not be necessary as the supra-perception sweet spot search (320-328) has selected electrodes for situation that well recruit the patient's pain site.

If sub-perception therapy is not effective, or could use adjustment, the algorithm can return to step 332 to selection of a new frequency (≤10 kHz) and/or pulse width in accordance with the regions or relationships defined earlier.

It should be noted that not all parts of steps of the algorithm of FIG. 15 need be performed in an actual implementation. For example, if effective electrodes are already known (i.e., E, P, X), then the algorithm may begin with sub-perception optimization using the information relating frequency and pulse width.

Figure 16:
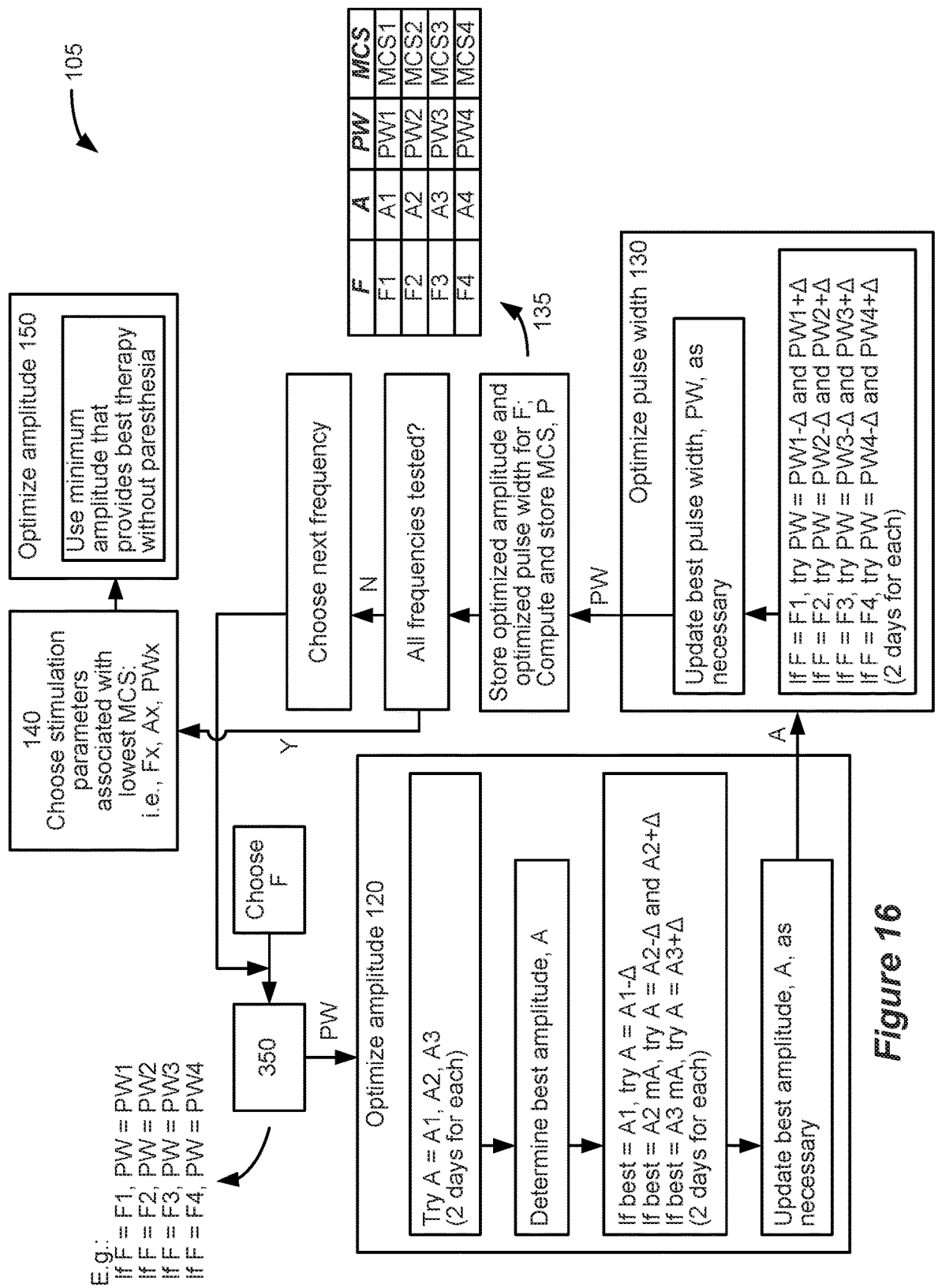
FIG. 16 shows an alternative algorithm for optimization of the sub-perception therapy using the fitting module.

FIG. 16 shows another manner in which fitting module 350 (FIG. 14) can be used to determine optimal sub-perception stimulation for a patient at frequencies of 10 kHz or less. In FIG. 16, the fitting module 350 is again incorporated within or used by an algorithm 105, which again can be executed on the external device's control circuitry as part of its software, or in the IPG 10. In the algorithm 105, the fitting module 350 is used to pick initial pulse widths given a particular frequency. Algorithm 105 is however more comprehensive as it will test and optimize amplitudes and further optimize pulse widths at different frequencies. As explained further below, algorithm 105 further optionally assists in picking optimized stimulation parameters that will result in the lowest power requirements that are most considerate of the IPG's battery 14. Some steps illustrated in FIG. 16 for algorithm 105 are optional, and other steps could be added as well. It is assumed that a sweet spot search for a patient being tested by algorithm 105 has already occurred, and that electrodes (E, P, X) have already been chosen and preferably will remain constant throughout operation of the algorithm. However, this is not strictly required, as these electrode parameters can also be modified, as described above.

Algorithm 105 begins by picking an initial frequency (e.g., F1) within the range of interest (e.g., ≤10 kHz). Algorithm 105 then passes this frequency to the fitting module 350, which uses the relationships and/or regions determined earlier to pick an initial pulse width PW1. For simplicity, fitting module 350 is illustrated in FIG. 16 as a simple look up table of pulse width versus frequency, which can comprise another form of information relating frequency and pulse width at which stimulation pulses are formed to provide pain relief without paresthesia. Selection of a pulse width using fitting module 350 could be more sophisticated, as described earlier.

After selection of a pulse width for the given frequency, stimulation amplitude A is optimized (120). Here, a number of amplitudes are chosen and applied to the patient. In this example, the chosen amplitudes are preferably determined using an optimal amplitude A determined at each frequency (see, e.g., FIG. 10B). Thus, amplitudes at A=A2, below (A1), and above (A3) are tried by the patient for a period (e.g., two days each). A best of these are picked by the patient. At this point, further adjustments to amplitude can be tried to try and hone in on an optimal amplitude for the patient. For example, if A2 is preferred, amplitudes slightly above (A2+Δ) and below (A2−Δ) below this can be tried for a period. If a lower value of A1 was preferred, an even lower amplitude (A1−Δ) can be tried. If a higher value of A3 was preferred, an even higher amplitude (A3+Δ) can be tried. Ultimately, such iterative testing of amplitude arrives at an effective amplitude for the patient that does not induce paresthesia.

Next, the pulse width can be optimized for the patient (130). As with amplitude, this can occur by slightly lowering or increasing the pulse width chosen earlier (350). For example, at a frequency of F1 and an initial pulse width of PW1, the pulse width may be lowered (PW1−Δ) and increased (PW1+Δ) to see if such settings are preferred by the patient. Further iterative adjustment of amplitude and pulse width may occur at this point, although this is not illustrated.

In short, at a given frequency, an initial pulse width (350) (and preferably also an initial amplitude (120)) are chosen for a patient, because it would be expected that these values would likely provide effective and paresthesia-free pain relief. Nonetheless, because each patient is different, the amplitude (120) and pulse width (130) are also adjusted from the initial values for each patient.

Thereafter, the optimal stimulation parameters determined for the patient at the frequency being tested are stored in the software (135). Optionally, a mean charge per second (MCS) indicative of the neural dose the patient receives, or other information indicative of power draw (e.g., average Ibat, discharge time) is also calculated and also stored. If still further frequencies in the range of interest have not been tested (e.g., F2), they are then tested as just described.

Once one or more frequencies have been tested, stimulation parameters can be chosen for the patient (140), using the optimal stimulation parameters stored earlier for the patient at each frequency (135). Because the stimulation parameters at each frequency are suitable for the patient, the stimulation parameters chosen can comprise that which results in the lowest power draw (e.g., the lowest) MCS. This is desired, because these stimulation parameters will be easiest on the IPG's battery. It might be expected that the stimulation parameters determined by algorithm 105 to have the lowest MCS would comprise those taken at the lowest frequency. However, every patient is different, and therefore this might not be the case. Once the stimulation parameters have been chosen, further amplitude optimization can be undertaken (150), with the goal of choosing a minimum amplitude that provides sub-perception pain relief without paresthesia.

As noted earlier, an interesting aspect of the disclosed trends and modeling of optimal sub-perception stimulation parameters is the realization that lower frequency stimulation can provide good results. The use of lower frequencies, as noted earlier, can result in stimulation parameters that require lower energy draws from the IPG. This was assessed earlier in several different ways. In FIG. 10B for example, it was explained for frequencies ranging from 1 kHz to 10 kHz that optimal sub-perception stimulation parameters (including pulse width and amplitude) result in mean charge per second (MCS) values that decline with frequency. In FIG. 12D, we see similarly for frequencies at and below 1 kHz that the total energy expended to produce optimal sub-perception stimulation decreases with frequency. In FIG. 12D, energy draw was represented by an assessment of the IPG's battery current (Ibat), and from the standpoint of a discharge time—i.e., the amount of time in which an IPG with a rechargeable battery can operate before it needs to be recharged. FIG. 12D shows that lower frequencies result in lower battery currents and longer discharge times, which reflects lower MCS values and lower energies used to form the optimal stimulation parameters.

Figure 17A:
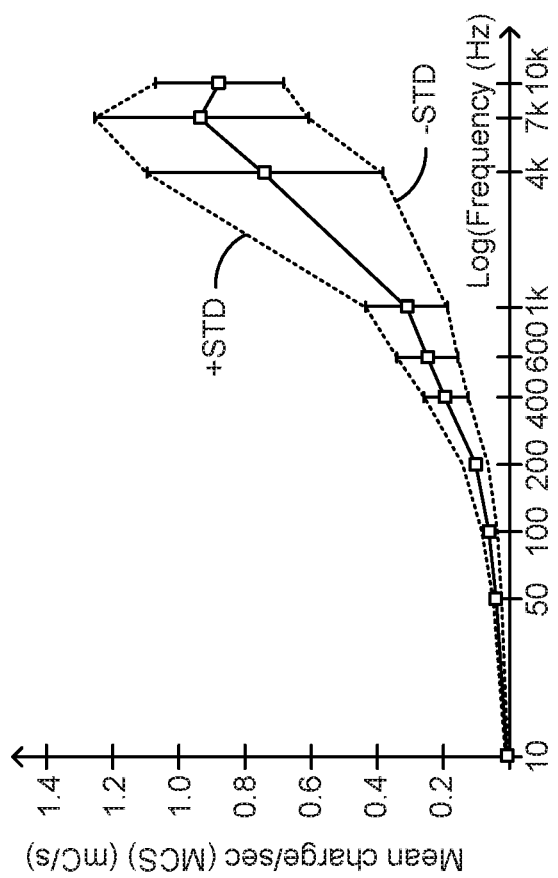
FIGS. 17A and 17B show an analysis of optimal sub-perception stimulation parameters, including a model of energy (mean charge per second) versus frequency.
Figure 17B:
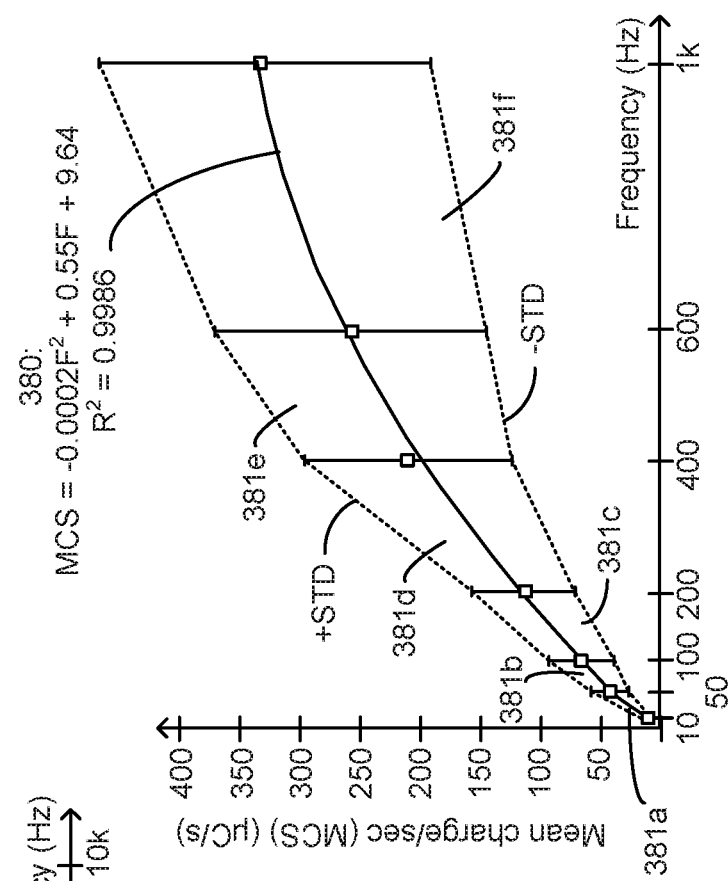

FIGS. 17A and 17B continue the analysis of neural dosing by again considering mean charge per second (MCS) data as a function of frequency for optimal stimulation parameters as taken from a population of patients. FIG. 17A shows MSC versus the logarithm of frequency for frequencies from 10 Hz to 10 kHz; FIG. 17B focuses more precisely on MSC data for a lower frequency range of 10 to 1 kHz. As noted earlier, MCS can be computed by multiplying the optimal frequency, pulse width, and amplitude for each of the patients tested. Because the optimal sub-perception stimulation parameters varied for each patient, error bars are associated with the MCS data in FIGS. 17A and 17B, which represent +/− one standard deviation (STD). As can be seen from both FIGS. 17A and 17B, the MCS data resulting from the optimal sub-perception parameters follows a predictable trend, and increases non-linearly with frequency, as discussed further below.

In FIG. 17B, the MSC data is analyzed with particularity for frequencies at 1 kHz and below, which as noted earlier is particularly interesting because such frequencies provide good sub-perception therapy results but at significantly lower energies. That being said, and although not shown, the data up to 10 kHz could also be analyzed and used in various algorithms such as those shown below, but this isn't shown. The data represented in FIG. 17B is shown in Table 4 below, which also shows the average optimal stimulation parameters for the patients tested:

TABLE 4

| Frequency (F) (Hz) | Pulse Width (PW) (µs) ± STD | Amplitude (A) (mA) ± STD | Duty cycle (PW*F) (%) | MCS (F*PW*A) (µC/s) ± STD |
|---|---|---|---|---|
| 1000 | 122 ± 14 | 2.60 ± 0.90 | 12.2 | 326 ± 145 |
| 600 | 153 ± 20 | 2.66 ± 0.86 | 9.2 | 249 ± 108 |
| 400 | 183 ± 21 | 2.62 ± 0.86 | 7.3 | 196 ± 78 |
| 200 | 209 ± 28 | 2.59 ± 0.93 | 4.2 | 109 ± 42 |
| 100 | 252 ± 19 | 2.62 ± 0.80 | 2.5 | 64 ± 24 |
| 50 | 308 ± 25 | 2.54 ± 0.89 | 1.5 | 41 ± 14 |
| 10 | 350 ± 24 | 2.56 ± 0.83 | 0.35 | 9 ± 3 |

Although the MCS versus frequency data could be curve fit to other functions, the data fits well when modeled as a polynomial (relationship 380), which results in MSC=−0.0002$F^2$+0.55F+9.64 ($R^2$=0.9986), with MSC calculated in microCoulombs per second. Statistically-significant regions 381$i$ around this relationship 380 can also be established, which region(s) may be defined by various error measures, as described above. In FIG. 17B, these regions 381$i$ are bounded by the standard-deviation error bars. For example, at 10 Hz, MCS−STD=6 µC/s and MCS+STD=12 µC/s. At 50 Hz, MCS−STD=27 µC/s and MCS+STD=55 µC/s. Therefore, a region 381$a$ that provides good sub-perception therapy is defined by the linearly bounded region of points (10 Hz, 6 µC/s), (10 Hz, 12 µC/s), (50 Hz, 55 µC/s), and (50 Hz, 27 µC/s). Table 4 defines the points that linearly bind each of the regions 381$a$-381$f$ shown in FIG. 17B:

TABLE 5

| region | Bounded by points (Hz, µC/s) |
|---|---|
| 381a | (10, 6), (10, 12), (50, 55), (50, 27) |
| 381b | (50, 27), (50, 55), (100, 88), (100, 40) |
| 381c | (100, 40), (100, 88), (200, 151), (200, 67) |
| 381d | (200, 67), (200, 151), (400, 274), (400, 118) |
| 381e | (400, 118), (400, 274), (600, 357), (600, 141) |
| 381f | (600, 141), (600, 357), (1000, 471), (1000, 181) |

Particularly interesting are the results for frequencies equal to or below 400 Hz (e.g., regions 381$a$-$d$). Such frequencies yield particularly low energy values (i.e., low MSC values), and are not understood by the inventors to have been investigated in the art of sub-perception therapy. As mentioned elsewhere, conventional sub-perception therapies are understood to focus on higher stimulation frequencies.

FIGS. 17A and 17B shows that the deviation in MCS grows as frequency increases. It is hypothesized that this occurs because MCS is more sensitive as frequency increases to the step sizes that were used to adjust amplitude (0.1 mA) and pulse width (10 µs). This suggests when using higher frequencies, use of smaller step sizes may be advisable. In this regard, and although not shown in the figures, algorithms may be employed to adjust the step sizes of amplitude and pulse width as a function of frequency, with larger step sizes used for lower frequencies and smaller step sizes used for higher frequencies. Note that the ability to adjust step size may depend on the clinician programmer software used to adjust the stimulation parameters, and may also depend on the DAC circuitry used for a given patient.

The data in Table 4, which expresses the spread of the amplitude and pulse width data across the population of patients further suggests specific optimal sub-perception parameters. Such optimal stimulation parameters may be expressed in terms of a volume in frequency, amplitude, and pulse width. For example, at 10 Hz, A−STD=1.73 mA, A+STD=3.39 mA, PW−STD=326 µs, and PW+STD=374 µs. At 50 Hz, A−STD=1.65 mA, A+STD=3.43 mA, PW−STD=283 µs, and PW+STD=333 µs. Therefore, a volume that provides good sub-perception therapy is defined by the linearly bounded volume of the following eight points: (10 Hz, 1.73 mA, 326 µs), (10 Hz, 1.73 mA, 374 µs), (10 Hz, 3.39 mA, 326 µs), (10 Hz, 3.39 mA, 374 µs), (50 Hz, 1.65 mA, 283 µs), (50 Hz, 1.65 mA, 333 µs), (50 Hz, 3.43 mA, 283 µs), (50 Hz, 3.43 mA, 333 µs). Table 6 below sets forth these optimal stimulation parameter volumes:

TABLE 6

| volume | Bounded by points F, A, PW (Hz, mA, µs) |
|---|---|
| a | (10, 1.73, 326), (10, 1.73, 374), (10, 3.39, 326), (10, 3.39, 374), (50, 1.65, 283), (50, 1.65, 333), (50, 3.43, 283), (50, 3.43, 333) |
| b | (50, 1.65, 283), (50, 1.65, 333), (50, 3.43, 283), (50, 3.43, 333), (100, 1.82, 233), (100, 1.82, 271), (100, 3.42, 233), (100, 3.42, 271) |
| c | (100, 1.82, 233), (100, 1.82, 271), (100, 3.42, 233), (100, 3.42, 271), (200, 1.66, 181), (200, 1.66, 237), (200, 3.52, 181), (200, 3.52, 237) |
| d | (200, 1.66, 181), (200, 1.66, 237), (200, 3.52, 181), (200, 3.52, 237), (400, 1.76, 162), (400, 1.76, 204), (400, 3.48, 162), (400, 3.48, 204) |
| e | (400, 1.76, 162), (400, 1.76, 204), (400, 3.48, 162), (400, 3.48, 204), (600, 1.80, 133), (600, 1.80, 173), (600, 3.52, 133), (600, 3.52, 173) |
| f | (600, 1.80, 133), (600, 1.80, 173), (600, 3.52, 133), (600, 3.52, 173), (1000, 1.70, 108), (1000, 1.70, 136), (1000, 3.50, 108), (1000, 3.50, 136) |

Figure 17C:
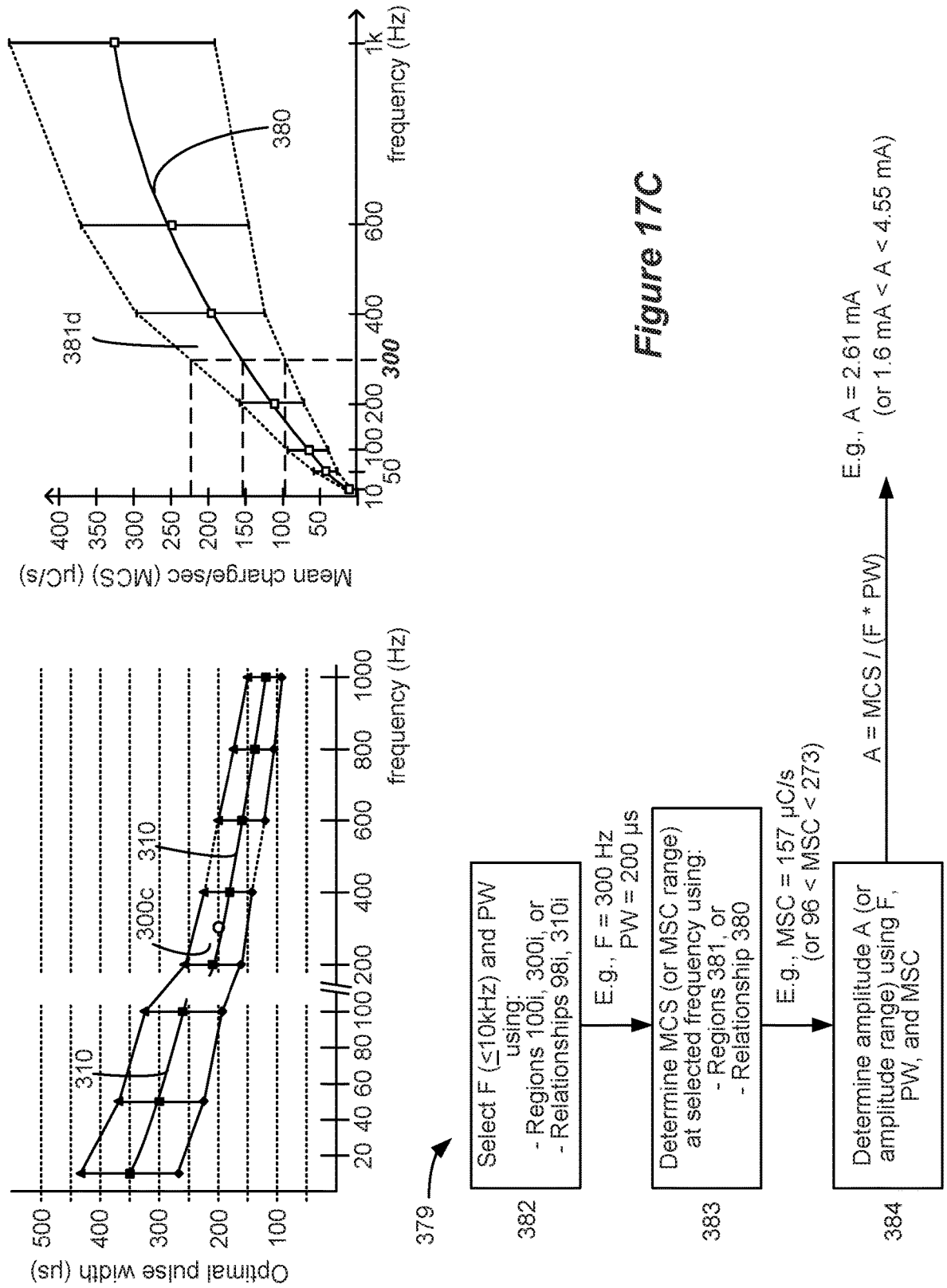
FIGS. 17C-17E show various algorithms by which the model of FIGS. 17A and 17B can be used to selected optimal sub-perception stimulation parameters.
Figure 17D:
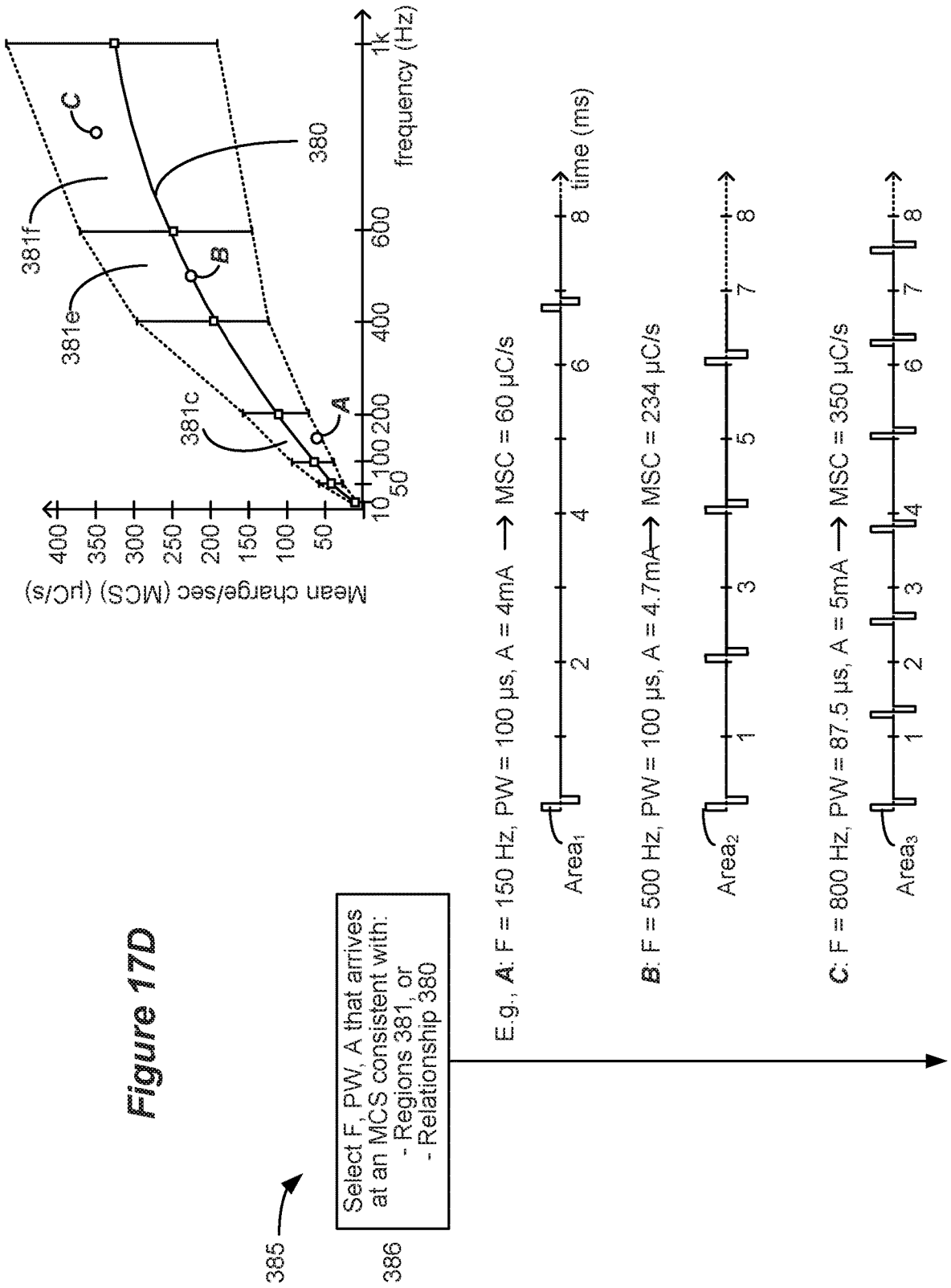
Figure 17E:
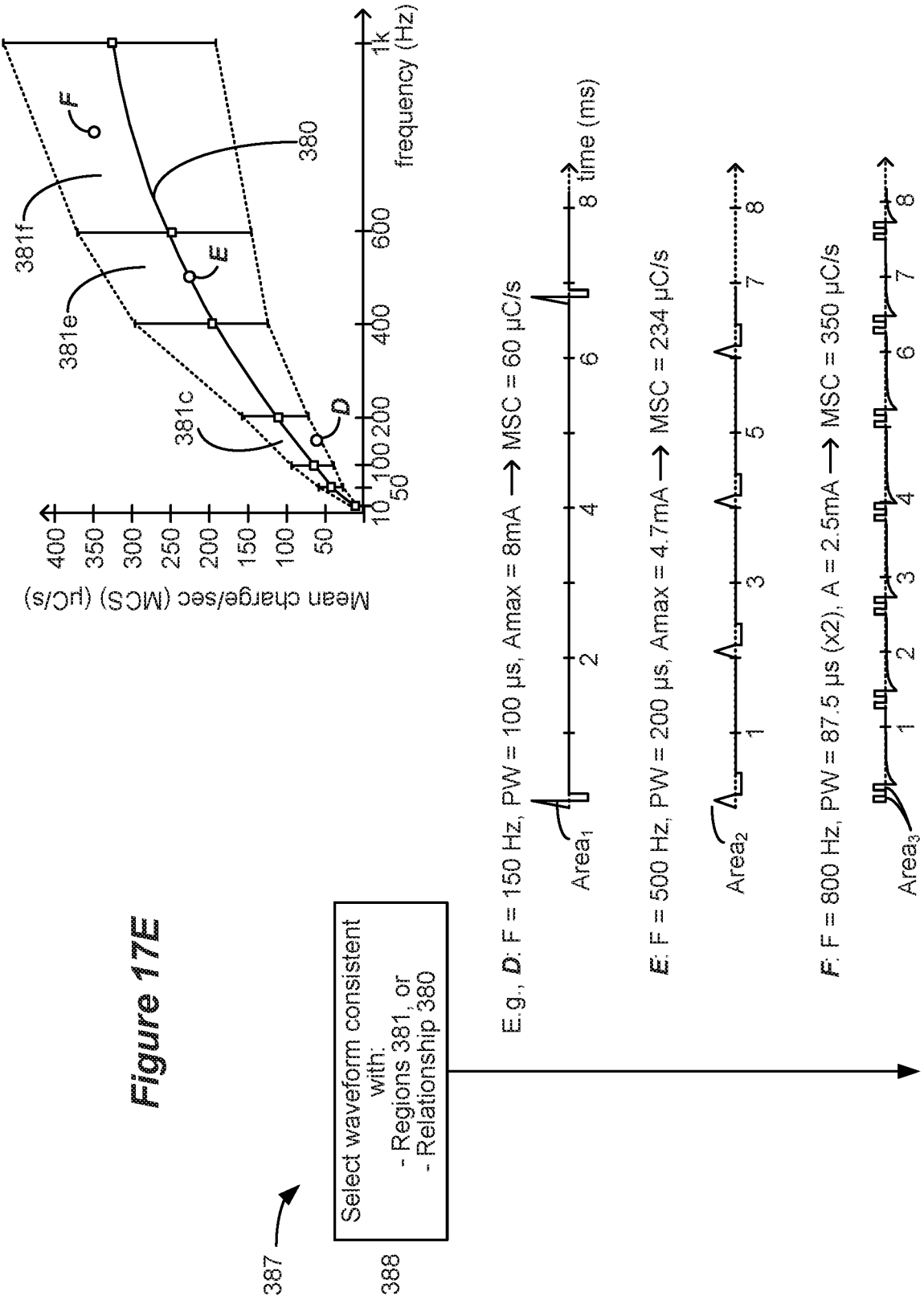

The fact that the MCS of optimal stimulation parameters follows a predictable trend across patients suggests that such trend data can be used to select optimal stimulation parameters for a given patient, and FIGS. 17C-17E shows different manners or algorithms in which this could occur. As mentioned elsewhere, the algorithms shown could be implemented as software in an external device used to control a patient's IPG or ETS. The algorithms could also be implemented in the IPG or ETS themselves, which would allow optimal sub-perception stimulation parameters to be at least semi-automatically picked for the patient.

Algorithms to select optimal sub-threshold stimulation parameters may use the MSC data alone, or may also consider other modelling data established earlier, such as the relationship between frequency and pulse width (see, e.g., FIGS. 10A and 12A). Algorithm 379 in FIG. 17C uses such frequency versus pulse width data in step 382 to select a frequency and pulse width consistent with the various relationships (98$i$, 310$i$) or statistically-significant regions (100$i$, 300$i$) described earlier. An example of frequency versus pulse width relationship 310 and region 300$c$ is reproduced in the left graph in FIG. 17C. In the example shown in FIG. 17C, a frequency of 300 Hz and 200 microseconds is selected at step 382, which point falls within region 300$c$ (see FIG. 12A). Alternatively, a frequency and pulse width could also be selected using relationship 310 (see FIG. 12B).

Next, in step 383, a MCS value or range is determined using the selected frequency, and either relationship 380 or one of the regions 381$i$. For example, using relationship 380, an MSC value of 157 µC/s can be calculated when F=300

Hz. Alternatively, the error bars defining region 381d (in which F=300 Hz falls) allows an MSC range to be determined at this frequency, such as between approximately 96 and 273 µC/s, as shown in the right graph in FIG. 17C.

From the determined MCS value (or range), an amplitude value (or range) can be determined, as shown in step 384. This amplitude will comprise the MSC value (or range) divided by the product of the selected frequency (300 Hz) and pulse width (200 µs), which yields a single amplitude value of 2.61 mA, or an amplitude range from 1.6 to 4.55 mA, in the example shown. In short, algorithm 379 yields optimal sub-perception stimulation parameters, including frequency (e.g., 300 Hz), pulse width (e.g., 200 µs), and amplitude (e.g., 2.61 mA). Because the underlying data may reflect some spread (e.g., regions 300, 381) algorithm 379 could determine a plurality of potential candidate stimulation parameters sets to try with a given patient. The plurality of different stimulation sets may also be applied to the patient in a time-multiplexed manner. This is described in further detail later with respect to FIGS. 33A-35.

The trend of MSC versus frequency suggests that it may not be strictly necessary when selecting optimal sub-perception parameters to select the pulse width dependent on frequency (or vice versa), and FIG. 17D shows another example of an algorithm 385 that may be used to select optimal sub-perception stimulation parameters. In this example, the frequency v. pulse width trends (e.g., regions 100i, 300i, or relationships 98i and 310i) discussed earlier are not used. Instead, only the MSC versus frequency trends (regions 381i or relationship 380 are used), with the goal of selecting a frequency, pulse width, and amplitude that are consistent with such trend data. Operation of the algorithm 385 may select a single stimulation parameter set (i.e., a single frequency, pulse width, and amplitude), although FIG. 17D shows the selection of three such sets. Set 'A' comprises the set F=150 Hz, PW=100 µs, and A=4 mA, which results in a MCS value of 60 µC/s. This stimulation parameter set 'A' is shown on the graph in FIG. 17D, and notice that it is within statistically-significant region 381c, although it is not a point on relationship 380. Set 'B' comprises the set F=500 Hz, PW=100 µs, and A=4.7 mA, which results in an MCS value of 234 µC/s. This point is within region 381e, although it is also assumed that this comprises a point on relationship 380—i.e., when F=500 Hz, relationship 380 calculates MSC as 234. Set 'C' comprises the set F=800 Hz, PW=87.5 µs, and A=5 mA, which results in a MCS value of 350 µC/s. This stimulation parameter set 'C' is within region 381f, although it is not a point on relationship 380.

Also shown in FIG. 17D are the resulting waveforms for these different stimulation parameter sets. In this example, it is assumed that active charge recovery is used, and that the active charge recovery phase (the second phase of each pulse) is symmetric with the first phase (but of opposite polarity). However, this is not strictly necessary, and the charge recovery phase could comprise non-symmetric active phases, or passive phases, as described earlier, and as shown subsequently in the examples of FIG. 17E. Notice that these stimulation parameter sets may include frequencies and pulse widths that are consistent with the pulse width v. frequency trends explained earlier (100i, 300i, 98i, 310i), or they may not. Similar to algorithm 379, algorithm 385 may select a single stimulation parameter set for a given patient, or a plurality of such sets which can be tried, or applied in a time-multiplexed manner.

Because the MSC versus frequency data ultimately reflects an energy of the stimulation, other algorithms may determine waveforms for patient use that are not strictly defined by pulses, or at least are not strictly defined by constant frequencies, pulse widths, or amplitudes. Algorithm 387 in FIG. 17E selects a waveform which is consistent with the MSC versus frequency trend data (either region 381 or relationships 380), where the waveform has an irregular shape. For example, the pulses in the waveform selected by algorithm 387 may not have constant amplitudes, or may be sub-divided into a plurality of pulses.

For example, the pulses in stimulation parameter set 'D' have the same pulse width (100 µs) and frequency (150 Hz) as the pulses in set 'A' (FIG. 17C). However, the amplitude of the pulses is not constant, and instead ramps from zero to a maximum amplitude (Amax) of 8 mA over the pulse width. As such, the area ($Area_1$) under the pulses in set 'D' is equal to the area under the pulses in set 'A'. Because MSC can also be defined as the pulse area times the frequency, the MSC of the pulses in sets 'A and 'D' are the same (60 µC/s), which is again consistent with the MSC versus frequency trends noted (380, 381).

In another example, the pulses in stimulation parameter set 'E' have the same maximum amplitude (4.7 mA) and frequency (500 Hz) as the pulses in set 'B' (FIG. 17C). However, the pulse width is doubled (to 200 µs), and the amplitude ramps both up and down during the pulse width. As such, the area ($Area_2$) under the pulses in set 'E' is equal to the area under the pulses in set 'B', and both sets again have the same MSC value (234 µC/s), which is again consistent with MSC trend data.

Stimulation parameter set 'F' shows that each pulse can be formed by algorithm 387 as a group of pulses, sometimes known as a "burst" of pulses. In this example, the pulses are similar to those in set 'C' (FIG. 17C), and have the same pulse width (87.5 µs) and frequency (800 Hz). However, set 'F' creates a plurality of pulses (two, although there could be more) for each pulse shown in set 'C', and with half the amplitude (2.5 mA). The sum of the area under the two pulses in 'F' ($Area_3$) equals that under a single pulse in 'C', and so the pulses in 'C' and 'F' again have the same MCS value (350 µC/s), which is again consistent with MSC trend data. In short, algorithm 387 allows more generally for a waveform to be defined consistent with MSC trend data.

To this point, MSC trend data (e.g., 380, 381) has been illustrated as varying with frequency. However, MSC trend data as useful in the disclosed algorithms could also be defined with respect to other stimulation parameters. For example, and as shown in FIG. 17F, and as Table 4 above illustrates, MSC values predictive of good sub-perception therapy also varies in a predictable manner with pulse width, as shown in relationship 380'. This relationship 380' could also be modeled (e.g., curve fit), and associated with error bars to determine regions 381', which could then in turn be used in the algorithms just described to assist is selecting optimal sub-perception stimulation parameters. Shown also in FIG. 17F, and again taken from Table 4, is the variation in MSC values with amplitude. Notice here that the amplitude is fairly constant (e.g., around 2.6 mA) as MSC varies. While this trend may not be as useful in selecting stimulation parameters, notice that it is consistent with optimal sub-perception stimulation amplitudes reported earlier (see, e.g., FIG. 10B).

The results of further investigations are shown in FIGS. 18-23D, with the goal of providing optimal sub-perception modelling that takes into account perception threshold (pth) as well and frequency (F) and pulse width (PW). Perception threshold can be a significant factor to consider when modelling sub-perception stimulation, and using such modeling information to determine optimal sub-threshold stimulation parameters for each patient. Perception threshold, pth, comprises a lowest magnitude at which the patient can feel the effects of paresthesia (e.g., in mA), with magnitudes below this causing sub-perception stimulation. It is a reality that different patients will have different perception thresholds. Different perception thresholds result in significant part because the electrode array in some patients may be closer to spinal neural fibers than in other patients. Such patients will thus experience perception at lower magnitudes, i.e., pth will be lower for such patients. If the electrode array in other patients is farther from spinal neural fibers, the perception threshold pth will be higher. Improved modelling takes an understanding of pth into account, because the inclusion of this parameter can be used to suggest an optimal amplitude A for a patient's sub-perception stimulation in additional to optimal frequencies and pulse widths.

Figure 18:
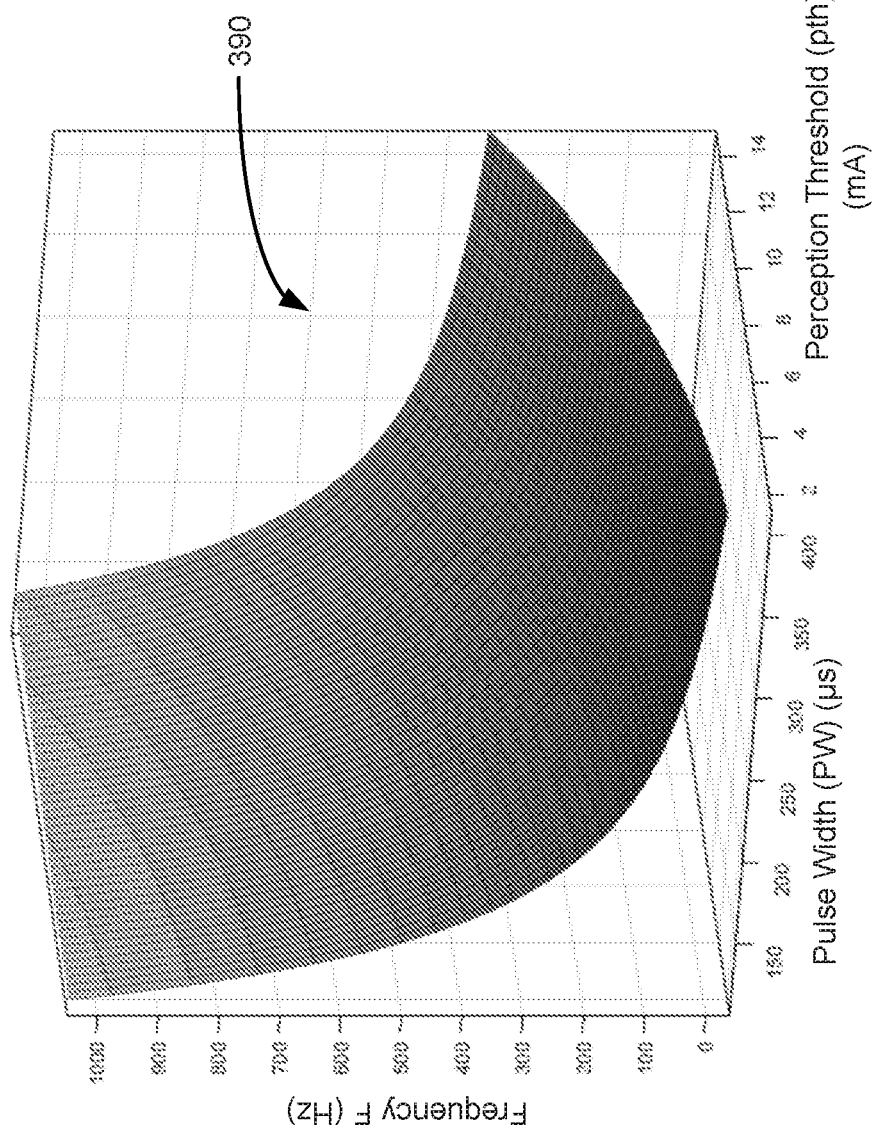
FIG. 18 shows a model derived from patients showing a surface denoting optimal sub-perception values for frequency and pulse width, and further including the patients' perception threshold pth as measured at those frequencies and pulse widths.

With this in mind, data was taken from patients to determine not only which frequencies and pulse widths they found optimal as described earlier, but also to determine the perception threshold at those frequencies and pulse widths. The resulting model 390 in shown in FIG. 18. This model 390 was determined based on testing with a sample of patients (N=25), with FIG. 18 showing mean values as determined by three-dimensional regression fitting, which yields model 390 as a surface in Frequency-Pulse Width-Perception Threshold space. Data as represented in FIG. 18 was taken at frequencies of 1 kHz and below. Data at these frequencies is of particular interest, because, as already mentioned, lower frequencies are more considerate of energy usage in an IPG or ETS, and hence is it particularly desirable to prove the utility of sub-perception stimulation in this frequency range. As can be seen by the equation in FIG. 18, data taken from the patient was modelled with a good fit by assuming that frequency varies with both pulse width (a(PW)b) and perception threshold pth (c(pth)d) in accordance with power functions. While these functions provided suitable fitting, other types of mathematical equations could be used for fitting as well. Model 390 as surface fit yields the following: $F(PW, pth) = 4.94 \times 10^8 (PW) - 2.749 + 1.358 (pth)^2$. Note that frequency, pulse width, and perception threshold are not simply proportionally related or inversely proportionately related model 390, but are instead related by non-linear functions.

Figure 19A:
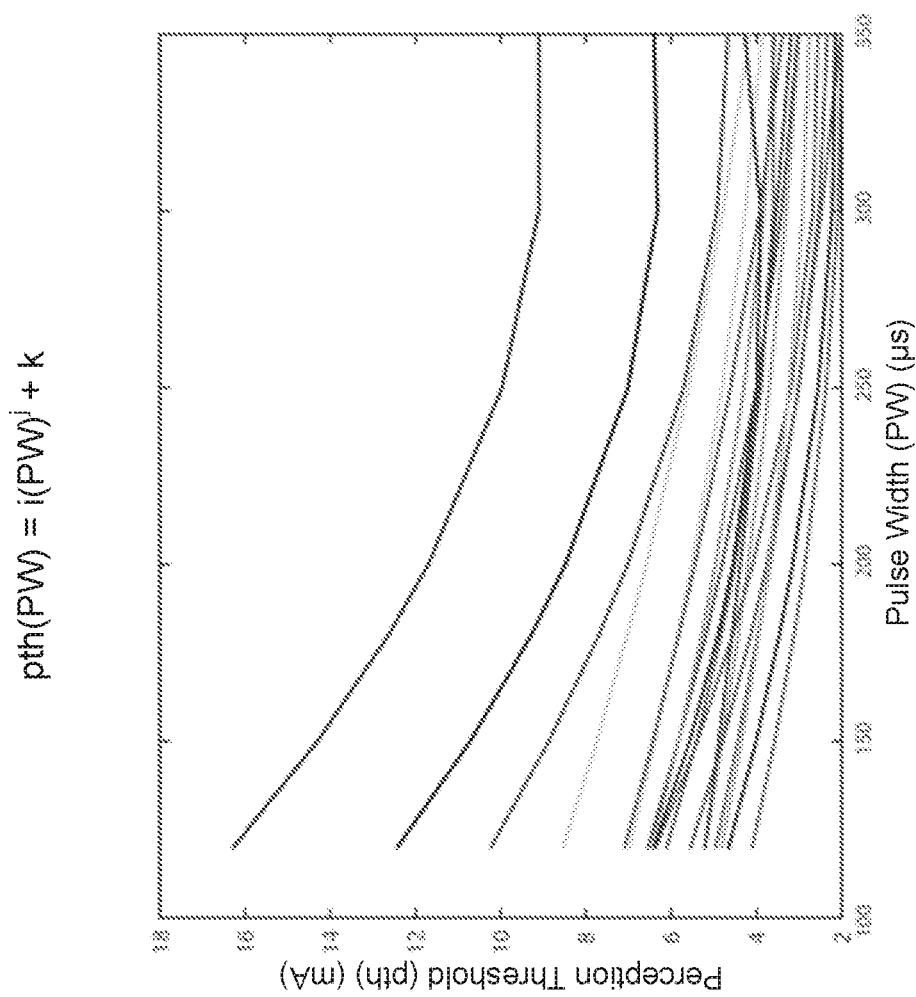
FIGS. 19A and 19B show the perception threshold pth plotted versus pulse width for a number of patients, and shows how results can be curve fit.
Figure 19B:
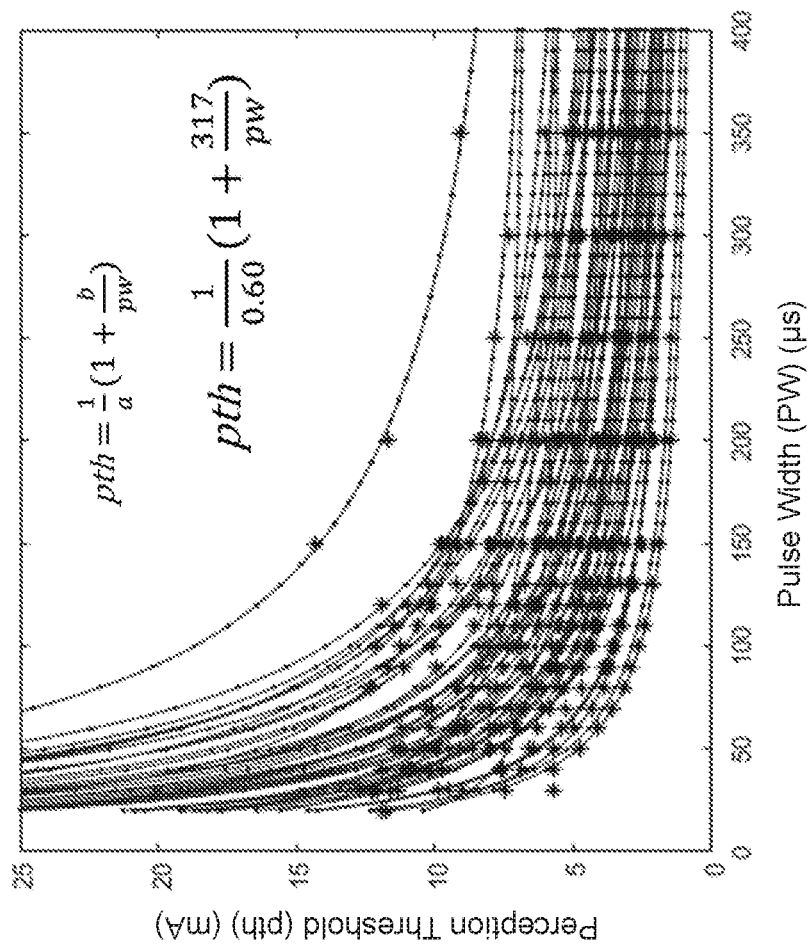

FIG. 19A shows further observations noticed from tested patients, and provides another modelling aspect that along with model 390 can be used to determine optimal sub-threshold stimulation parameters for a patient. FIG. 19A shows how perception threshold pth varies as a function of pulse width for the tested patients, with each patient being represented by a different line in the graph of FIG. 19A. Analysis of each of the lines suggests that the relationship between pth and PW can be well modeled with a power function, i.e., $pth(PW) = i(PW)j + k$, although again other mathematic functions could be used for fitting as well. The data of FIG. 19A was taken for each patient at a nominal frequency such as 200 to 500 Hz, with further analysis confirming that the results do not vary considerably with frequency (at least at frequencies of 150 Hz and higher, using biphasic pulses with active recharge). Pulse widths in FIG. 19A were limited to the range of approximately 100 to 400 microseconds. Limiting analysis to these pulse widths is reasonable, because previous testing (e.g., FIG. 12A) shows pulse widths in this range to have unique sub-perception therapeutic effectiveness at frequencies of 1 kHz and lower. FIG. 19B shows another example of pth versus pulse width for different patients, and shows another equation that can be used to model the data. Specifically, a Weiss-Lapicque, or strength-duration, equation is used in this example, which relates the amplitude and pulse width required to attain a threshold. The equation takes the form $pth = (1/a)(1 + b/PW)$, and when data for different patients are averaged, constants $a = 0.60$ and $b = 317$ result with good fitting results, where these values represent the mean constant parameters extracted from the population data.

Figure 20:
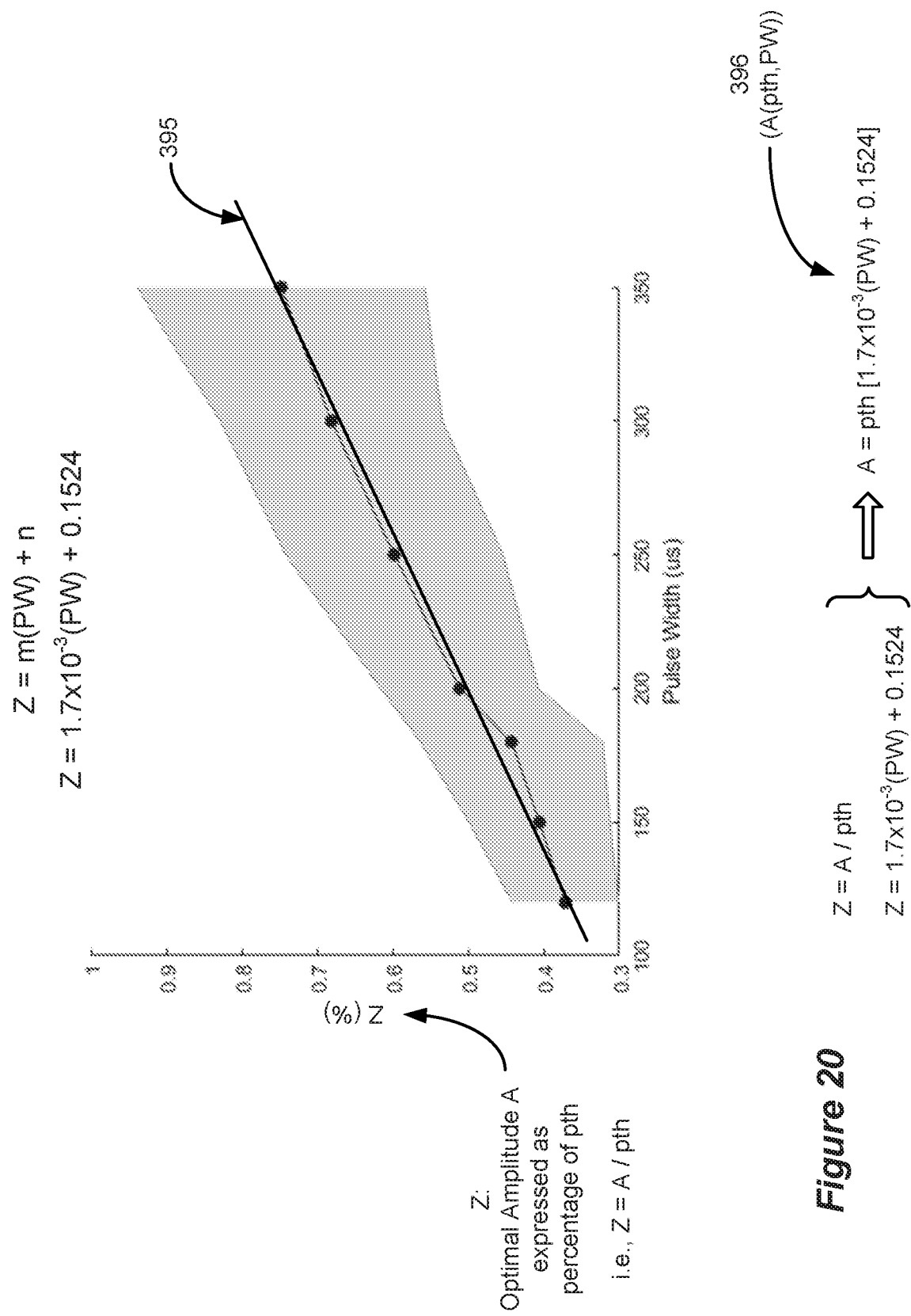
FIG. 20 shows a graph of parameter Z versus pulse width for patients, where Z comprises an optimal amplitude A for patients expressed as a percentage of perception threshold pth (i.e., Z=A/pth).

FIG. 20 shows still further observations noted from the tested patients, and provides yet another modeling aspect. FIG. 20 in effect shows how optimal sub-perception amplitudes A for patients vary in accordance with a patients' perception thresholds pth, as well as pulse width. In the graph in FIG. 20, the vertical axis plots a parameter Z, which relates a patients' perception thresholds pth and their optimal amplitudes A (which in a sub-perception therapy would be lower than pth). Specifically, Z is the optimal amplitude expressed as a percentage of pth, i.e., $Z = A/pth$. As FIG. 20 shows, Z varies with pulse width. At smaller pulse widths (e.g., 150 microsecond), Z is relatively low, meaning that the optimal amplitude A for patients was noted to be considerably lower than their perception thresholds (e.g., A=40% of pth). At longer pulse widths (e.g., 350 microseconds), Z is higher, meaning that the optimal amplitude A for patients was noted to be closer to their perception thresholds (e.g., A=70% of pth). Z and PW as noted from testing various patients generally have a linear relationship over the pulse widths tested, and so linear regression was used to determine their relationship, yielding $Z = 0.0017(PW) + 0.1524$ (395). Again, testing in FIG. 20 was limited to the general range of 100 to 400 microseconds noted to be useful for sub-perception therapy at less than 1 kHz. It might be expected that testing over a wider pulse width range (e.g., less than 100 microseconds, or greater than 400 microseconds) would show some variance from the linear relationship noted. For example, Z might level off to some value smaller than 1 for pulse widths higher than 400 microseconds, and might level off to a value greater than 0 for pulse widths shorter than 100 microseconds. Because Z varies with pulse width as curve fit, and because Z also varies with optimal amplitude A and perception threshold pth ($Z = A/pth$), the modelling of FIG. 20 allows optimal amplitude A to be modelled as a function of both perception threshold pth and pulse width PW, i.e., $A = pth [0.0017(PW) + 0.1524]$ (396). The inventors observe that optimal amplitude A is generally invariant to changes in frequency and pulse width. However, perception threshold varies with pulse width. Thus, Z varies with pulse width, while optimal amplitude A may not.

Recognizing and modeling these observations, the inventors have developed an algorithm 400 that can be used to provide personalized sub-perception therapy for particular patients. This algorithm 400 can largely be implemented on the clinician programmer 50, and results in the determination of a range of optimal sub-perception parameters (e.g., F, PW, and A) for the patient. Preferably, as last step in the algorithm 400, the range or volume of optimal sub-perception parameters is transmitted to the patient's external controller 45 to allow the patient to adjust their sub-perception therapy within this range or volume.

The algorithm 400, shown starting in FIG. 21A, starts in step 402 by determining for a given patient the sweet spot in the electrode array at which therapy should be applied—i.e., by identifying which electrodes should be active and with what polarities and percentages (X %). The results of sweet spot searching may already be known for a given patient, and thus step 402 should be understood as optional. Step 402 and subsequent steps may be accomplished using clinician programmer 50.

At step 404, a new patient is tested by providing situation pulses, and in the algorithm 400, such testing involves measuring the patient's perception threshold pth at various pulse widths during a testing procedure, using the sweet spot electrodes already identified at step 402. As discussed earlier with respect to FIGS. 19A and 19B, testing of different pulse widths can occur at a nominal frequency such as in the range of 200 to 500 Hz. Determining pth at each given pulse width involves applying the pulse width, and gradually increasing the amplitude A to a point where the patient reports feeling the stimulation (paresthesia), resulting in a pth expressed in terms of amplitude (e.g., milliamps). Alternatively, determining pth at each given pulse width can involve decreasing the amplitude A to a point where the patient reports no longer feels the stimulation (sub-threshold). Testing 404 of a particular patient is shown graphically and in tabular form in FIG. 21A. Here, it is assumed that the patient in question has a paresthesia threshold pth of 10.2 mA at a pulse width of 120 microseconds; a pth of 5.9 mA at a pulse width of 350 microseconds, and other values between these.

Next, in step 406, the algorithm 400 in the clinician programmer 50 models the pth v. PW data points measured in step 404, and curve fits them to a mathematical function. This mathematical function could be one noticed earlier to well model pth and PW in other patients, such as a power function $pth(PW)=i(PW)^j+k$ or the Weiss Lapicque equation, as discussed earlier with respect to FIGS. 19A and 19B. However, any other mathematical function could be used to curve fit the current patient's data measurements, such as a polynomial function, and exponential function, etc. In the illustrated data, a power function well models the data, yielding $pth(PW)=116.5 \times PW^{-0.509}$. (For simplicity, constant 'k' has been ignored). The measured data in table 404, as well as the determined curve-fit relationship pth(PW) 406 determined for the patient may be stored in memory in the clinician programmer 50 for use in subsequent steps.

Figure 21B:
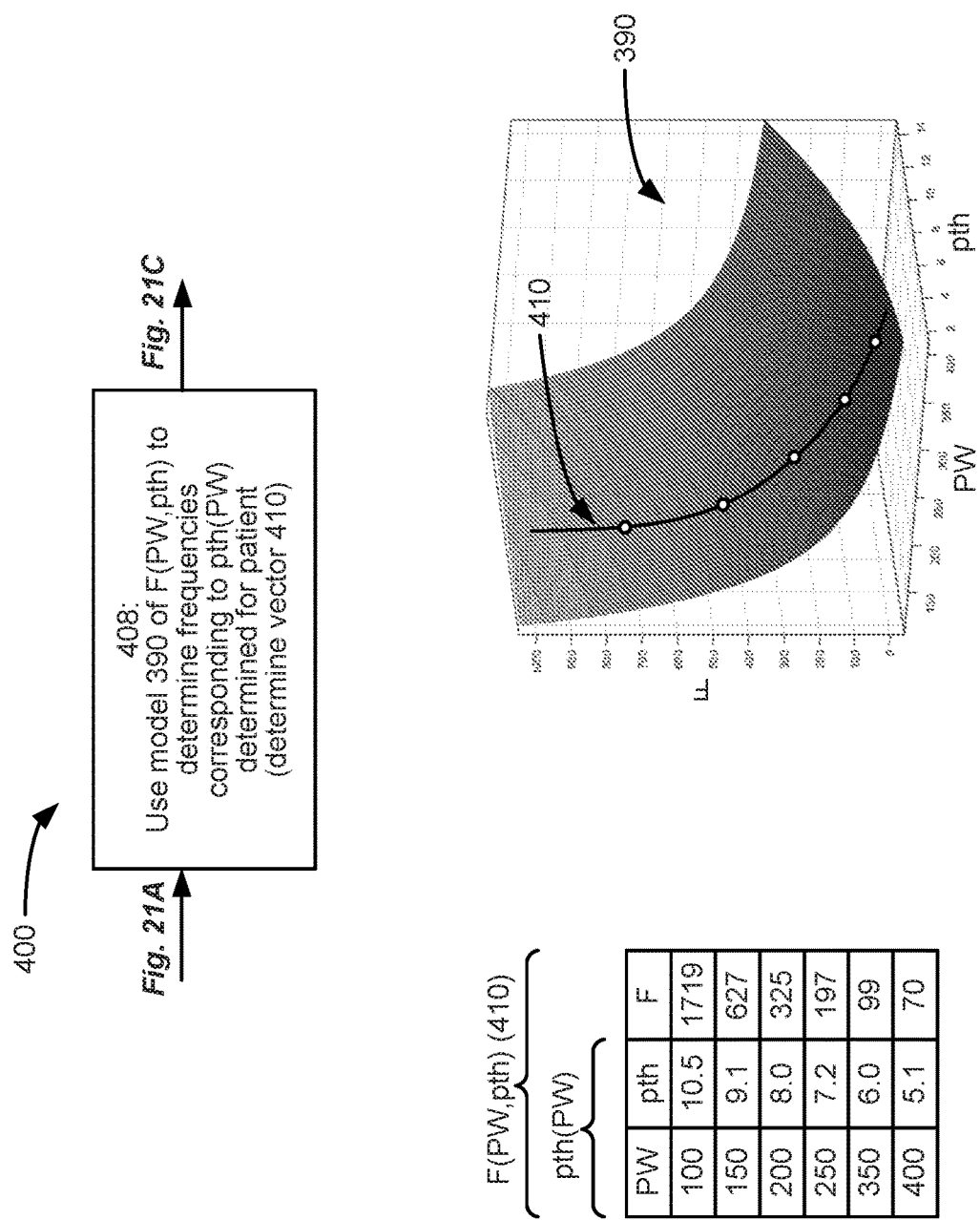

Next, and referring to FIG. 21B, algorithm 400 proceeds to compare the pth(PW) relationship determined in step 406 to the model 390. This is explained with reference to a table shown in FIG. 21B. In this table, values for pth and PW are populated, as determined by the pth(PW) (406) determined in FIG. 21A. As can be seen, discrete pulse width values of interest (100 microseconds, 150 microseconds, etc.) may be used (which may vary from the exact pulse widths used during patient testing in step 404). While only six rows of PW v. pth values are shown in the table of FIG. 21B, this could be a much longer vector of values, with pth determined at discrete PW steps (such as 10 microsecond steps).

The pth v. PW values (from function 406) are in step 408 compared against the three-dimensional model 390 to determine frequencies F that would be optimal at these various pth v. PW pairs. In other words, the pth and PW values are provided as variables into the surface fit equation (F(PW, pth)) 390 in FIG. 18 to determine optimal frequencies, which frequencies are also shown as populated into the chart in FIG. 21B. At this point, the table in FIG. 21B represents a vector 410 relating pulse widths and frequencies that are optimal for the patient, and that in addition include the perception threshold for the patient at these pulse width and frequencies values. In other words, a vector 410 represents values within the model 390 that are optimal for the patient. Note that vector 410 for the patient can be represented as a curved line along the three-dimensional model 390, as shown in FIG. 21B.

Figure 21C:
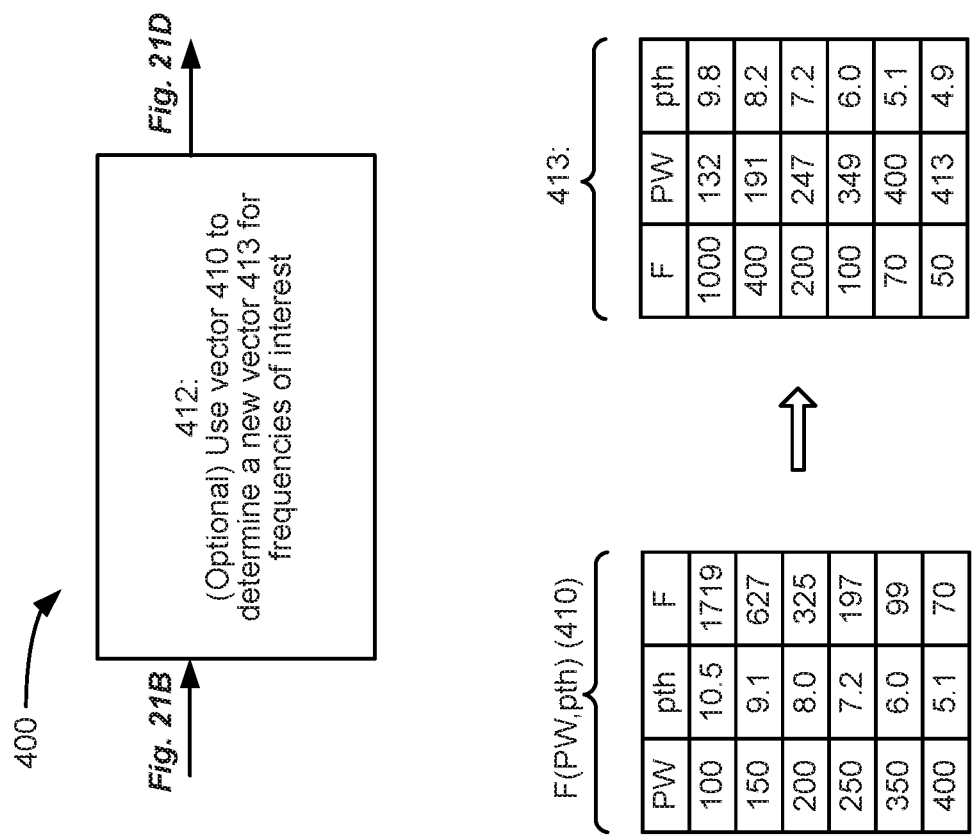

Next, and as shown in step 412 in FIG. 21C, the vector 410 can optionally be used to form another vector 413, which contains values of interest or more practically values that may be supportable by the IPG or ETS. For example, notice that vector 410 for the patient includes frequencies at higher values (e.g., 1719 Hz), or otherwise at odd values (such as 627 and 197 Hz). Frequencies at higher values may not be desirable to use, because even if effective for the patient, such frequencies will involve excessive power draws. See, e.g., FIG. 12D. Moreover, the IPG or ETS at issue may only be able to provide pulses with frequencies at discrete intervals (such as in 10 Hz increments). Therefore, in vector 413, frequencies of interest or that are supported are chosen (e.g., 1000 Hz, 400 Hz, 200 Hz, 100 Hz, etc.), and then corresponding values for PW and pth are interpolated using vector 410. Although not shown, it may be useful to formulate vector 410 as an equation F(PW,pth)) to make vector 413 easier to populate. Nonetheless, vector 413 includes essentially the same information as vector 410, albeit at desirable frequencies. Realize that only certain pulse widths may be supportable by the IPG or ETS (e.g., in 10 microsecond increments). Therefore, the pulse widths in vector 413 may be adjusted (e.g., rounded) to nearest supported values, although this isn't shown in the drawings.

Figure 21D:
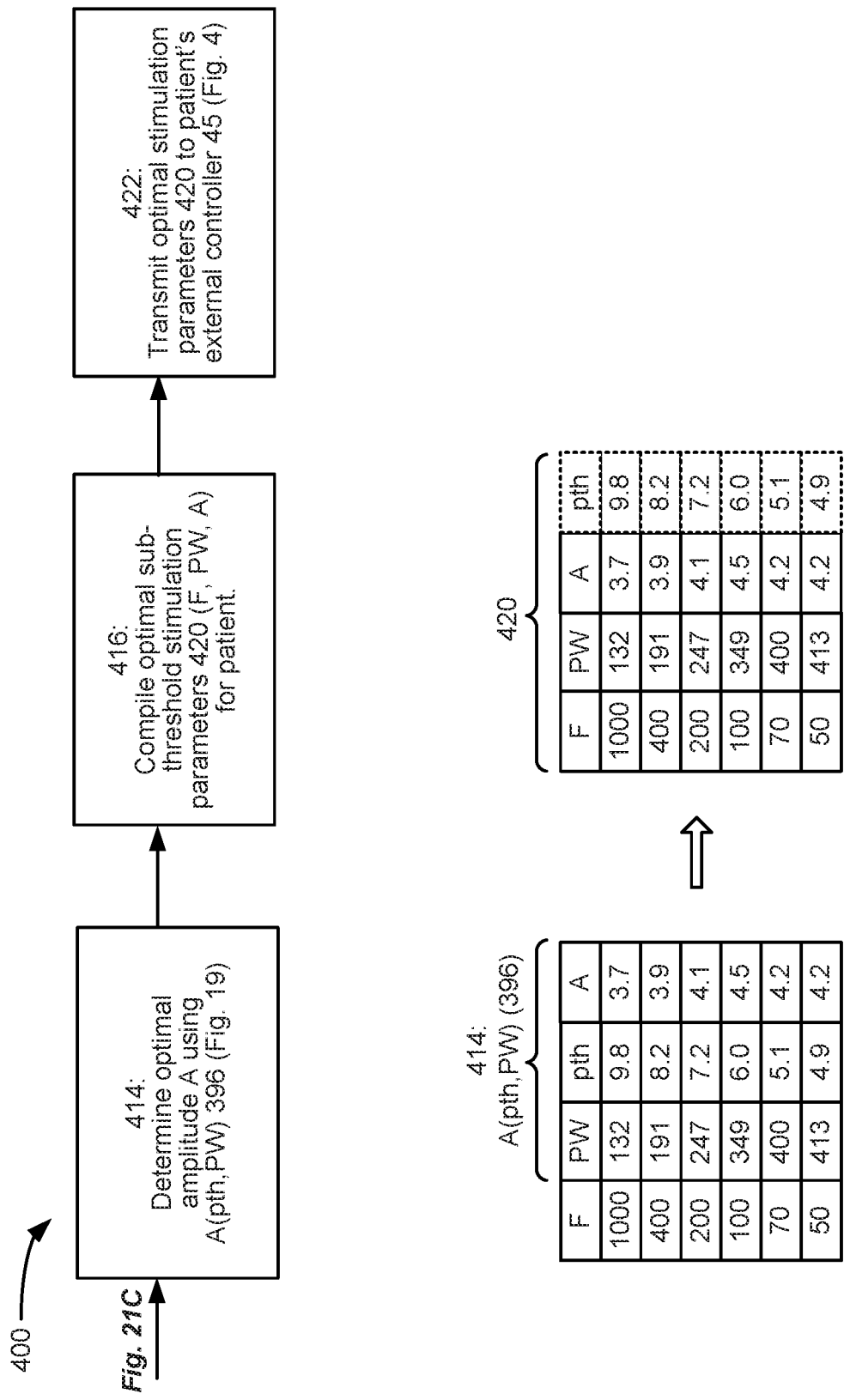

Next, and referring to FIG. 21D, the algorithm 400 in step 414 determines optimal amplitudes for the pulse width and pth values in vector 413 (or vector 410 if vector 413 isn't used). This occurs by using the amplitude function 396 determined earlier in FIG. 20, i.e., A(pth,PW). Using this function, an optimal amplitude A can be determined for each pth, PW pair in the table.

At this point, in step 416, optimal sub-threshold stimulation parameters F, PW, A 420 are determined as a model specific to the patient. Optimal stimulation parameters 420 may not need to include the perception threshold, pth: although pth was useful to determine optimal subthreshold amplitude A for the patient (step 414), it may no longer be a parameter of interest as it is not a parameter that the IPG or ETS produces. However, in other examples discussed later, it can be useful to include pth with the optimal parameters 420, as this can allow a patient to adjust their stimulation to a supra-perception level if desired. At this point, optimal stimulation parameters 420 may then be transmitted to the IPG or ETS for execution, or as shown in step 422, they may be transmitted to the patient's external controller 45, as described next.

Figure 21E:
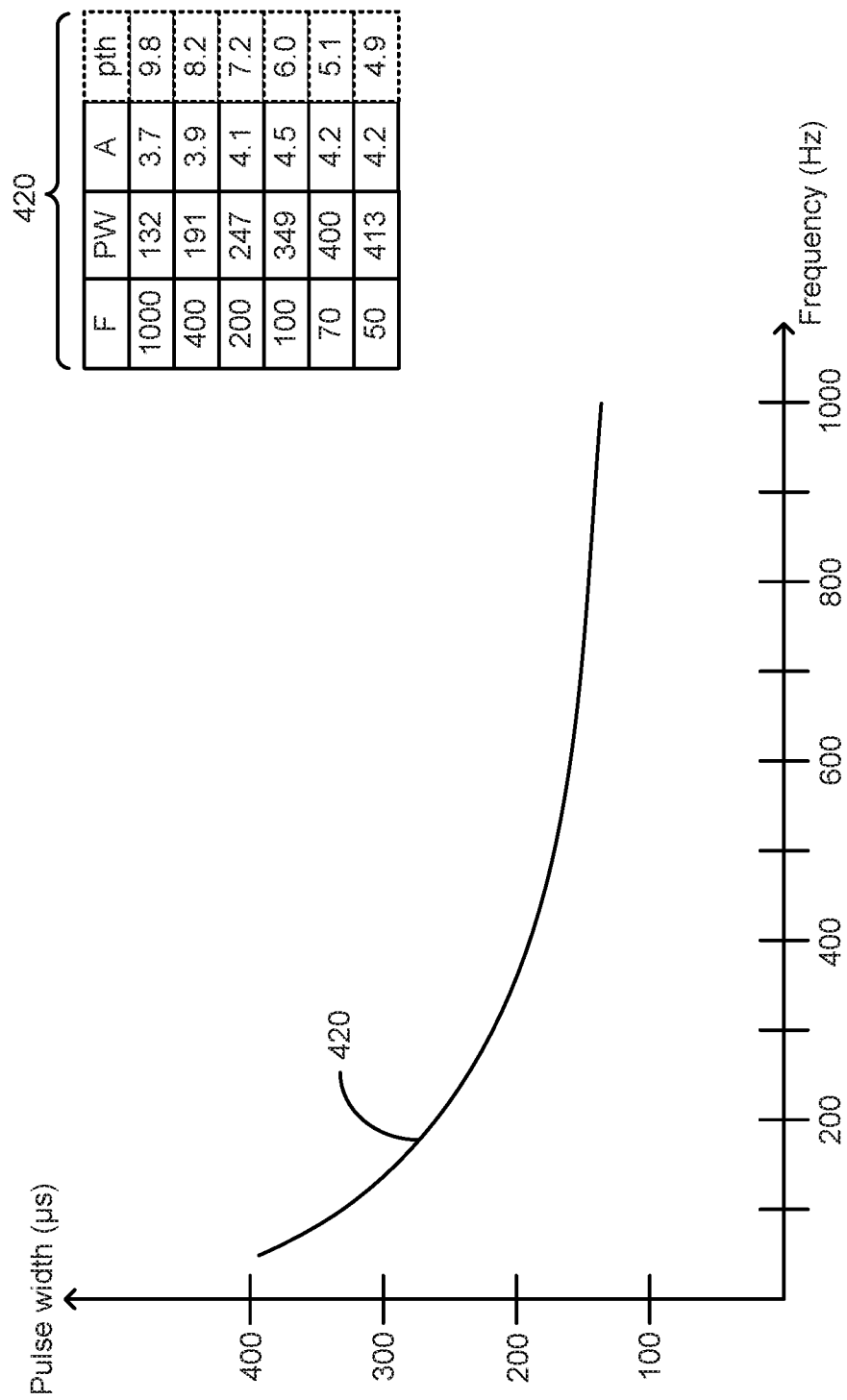
Figure 21F:
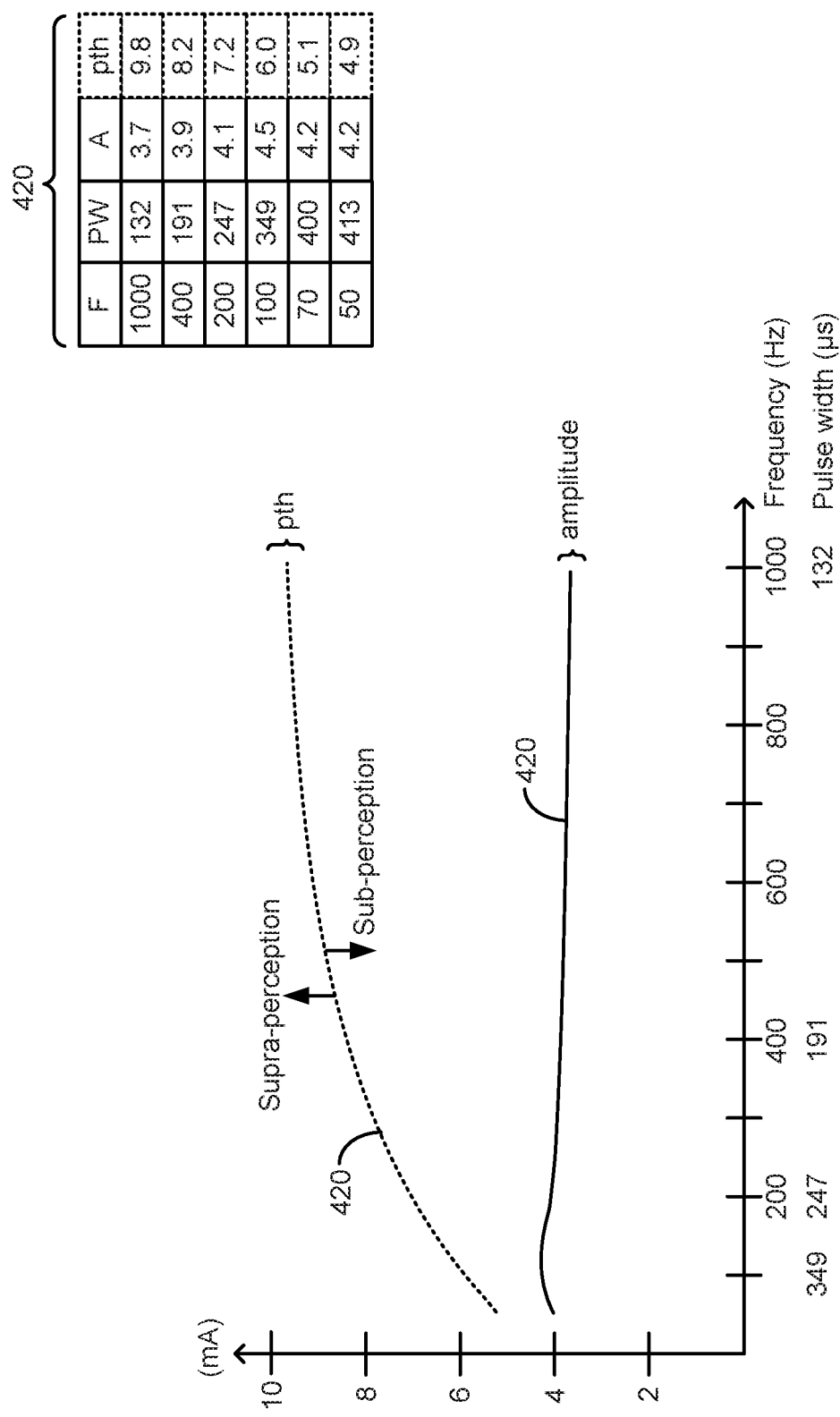

FIGS. 21E and 21F depict optimal parameters 420 in graphical form. While optimal parameters 420 in this example comprise a three-dimensional range or line of coordinates (F, PW, and A), they are depicted in two two-dimensional graphs for easier illustration: FIG. 21E shows the relationship between frequency and pulse width, and FIG. 21F shows the relationship between frequency and amplitude. Note also that FIG. 21F shows the paresthesia threshold pth, and additionally shows on the X-axis the pulse width corresponding to the various frequencies from FIG. 21E. Note that the shapes of the data on these graphs could vary from patient to patient (e.g., based on the pth measurements of FIG. 21A), and could also change depending on the underlying modelling used (e.g., FIGS. 18-20). The various shapes of the trends shown thus should not be construed as limiting.

The optimal stimulation parameters 420 determined by the algorithm 400 comprise a range or vector of values, comprising frequency/pulse width/amplitude coordinates that based on modeling (FIGS. 18-20), and on testing of the patient (step 404, FIG. 21A), will result in sub-threshold stimulation that is optimal for that patient. While optimal parameters 420 are shown for simplicity in tabular form in FIG. 22, it should be understood these optimal parameters (O) may be curve fit using an equation that includes frequency, pulse, and amplitude (i.e., O=f(F,PW,A)). Because each of these coordinates are optimal, it may be reasonable to allow the patient to use them with their IPG or ETS, and as a result the optimal parameters 420 may be sent from the clinician programmer 50 to the patient external controller 45 (FIG. 4) to allow the patient to select between them. In this regard, the optimal parameters 420, whether in tabular form or in the form of an equation, can be loaded into control circuitry 48 of the external controller 45.

Figure 22:
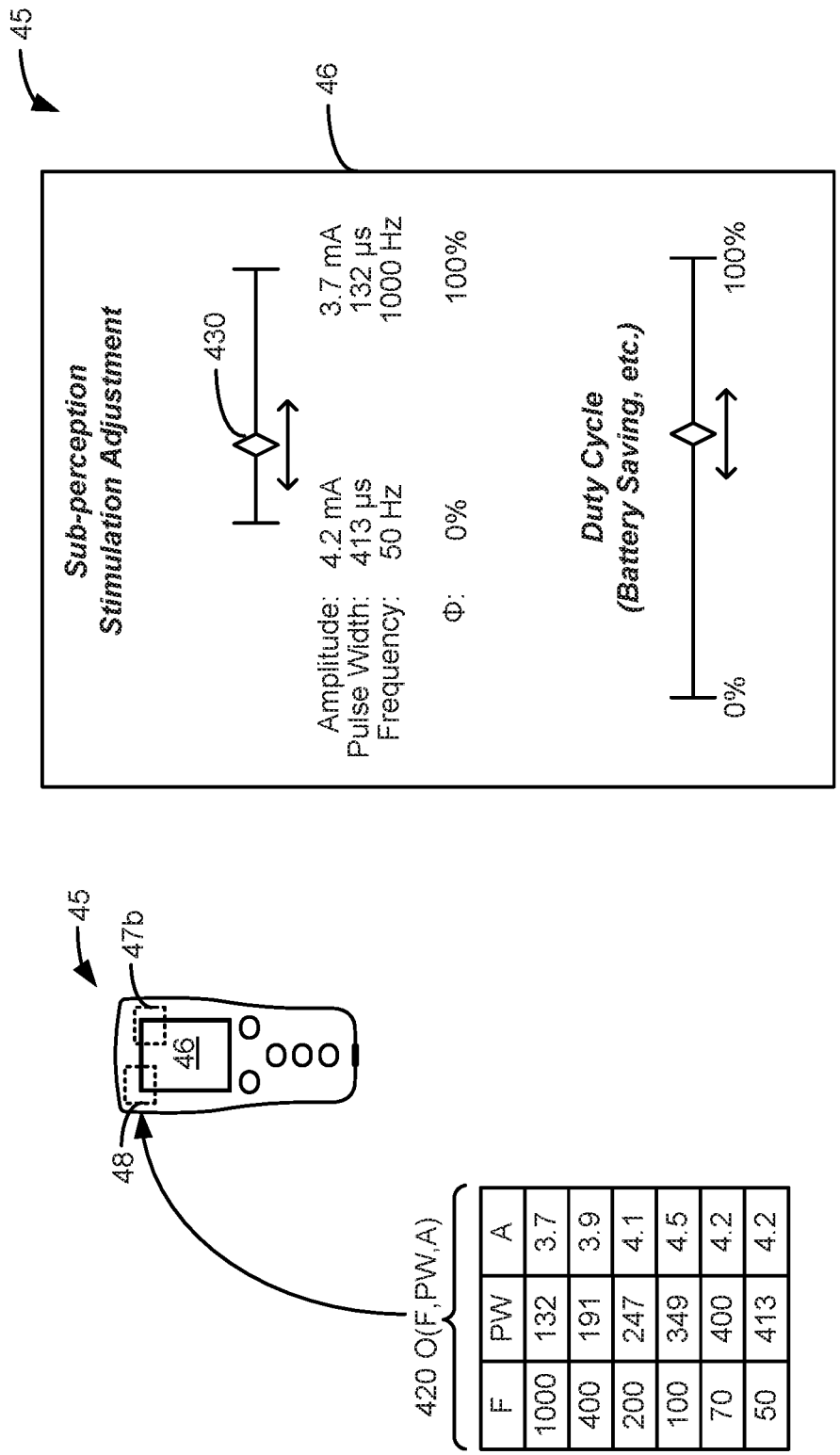
FIG. 22 shows use of the optimal stimulation parameters in a patient external controller, including a user interface that allows the patient to adjust stimulation within the range.

Once loaded, the patient can access a menu in the external controller 45 to adjust the therapy the IPG or ETS provides consistent with these optimal parameters 420. For example, FIG. 22 shows a graphical user interface (GUI) of the external controller 45 as displayed on its screen 46. The GUI includes means to allow the patient to simultaneously adjust the stimulation within the range of determined optimal stimulation parameters 420. In one example, a slider is included in the GUI with a cursor 430. The patient may select the cursor 430 and in this example move it to the left or right to adjust the frequency of stimulation pulses in their IPG or ETS. Moving it to the left reduces the frequency down to a minimum value included in the optimal parameters 420 (e.g., 50 Hz). Moving the cursor 430 to the right increases the frequency to a maximum values included in the optimal parameters (e.g., 1000 Hz). As the cursor 430 is moved and the frequency of stimulation is changed, the pulse widths and amplitudes are simultaneously adjusted as reflected in optimal parameters 420. For example, at F=50 Hz, the amplitude is automatically set to A=4.2 mA, and the pulse width is set to 413 microseconds. At F=1000 Hz, the amplitude is set to A=3.7 mA, and the pulse width is set to 132 microseconds. In effect the cursor 430 allows the patient to navigate through the optimal parameters 420 to find a F/PW/A setting they prefer, or simply to choose stimulation parameters that are still effective but require lower power draws from the IPG or ETS (e.g., at lower frequencies). Note that the frequency, pulse width, and amplitude may not be adjusted proportionately or inversely proportional with respect to each other but will follow non-linear relationships in accordance with the underlying modelling.

In another example, it may be useful to allow the patient to adjust stimulation without knowledge of the stimulation parameters, i.e., without displaying the parameters, which may be too technical for the patient to understand. In this regard, the slider can be labeled with a more generic parameter, such as $\varphi$, which the patient can adjust, such as between 0 and 100%. The three-dimensional simulation parameters A, PW, and F can be mapped to this one-dimensional parameter $\varphi$ (e.g., 4.2 mA, 413 µs, and 50 Hz can equal 0% as shown). Generally speaking, the patient may understand parameter $\varphi$ as a sort of "intensity" or "neural dose" which is higher at higher percentages. This may in fact be true given depending on the manner in which the optimal stimulation parameters 420 are mapped to $\varphi$. In another modification not shown, the optimal stimulation parameters can be selected using a mean charge per second (MSC) model (e.g., 380, 381), as described earlier with respect to FIGS. 17A-17F. The GUI can then also allow the user to navigate within a MSC model to select optimal stimulation parameters.

It should be appreciated that while the GUI of the external controller 45 does allow the patient some flexibility to modify stimulation parameters for his IPG or ETS, it is also simple, and beneficially allows the patient to adjust all three stimulation parameters simultaneously using a single user interface element, all while being ensured that the resulting stimulation parameters will provide optimal sub-threshold stimulation.

Other stimulation adjustment controls may be provided by the external controller 45 as well. For example, as shown in FIG. 22, another slider can allow the patient to adjust the duty cycle to control the extent to which pulses will be continually running (100%) or completely off (0%). A duty cycle in the middle (e.g., 50%) will mean that pulses will run for a period of time (from second to minutes) and will then be off for that exact same duration. Because "duty cycle" may be a technical concept that a patient would not intuitively understand, note that the duty cycle may be labeled in a more intuitive manner. Thus, and as shown, the duty cycle adjustment may be labeled differently. For example, because lower duty cycles would affect lower power draws, the duty cycle slider may be label as a "battery saving" feature, as a "total energy" feature, a "total neural charge dose" feature, or the like, which may be easier for the patient to understand. Duty cycling may also comprise a feature in the external controller 45 that is locked to the patient, and only made accessible to a clinician for example, upon entering an appropriate password or other credentials. Note that the duty cycle could be smoothly adjusted, or made adjustable in pre-set logical increments, such as 0%, 10%, 20%, etc. Duty cycle adjustment is not show in subsequent user interface examples for simplicity, but could be used in such examples as well.

FIGS. 23A-23D address the practicality that the modeling leading to the determination of optimal parameters 420 may not be perfect. For example, model 390—modeling frequency as a function of PW and pth (F(PW,pth); FIG. 18)—is averaged from various patients, and can have some statistical variance. This is illustrated simply in FIG. 23A by showing surfaces 390+ and 390− that are higher and lower from the mean as reflected in surface model 390. Surfaces 390+ and 390− may represent some degree of statistical variance or error measure, such as plus or minus one sigma, and may in effect generically comprise error bars beyond which the model 390 is no longer reliable. These error bars 390+ and 390− (which may not be constant over the entire surface 390) can also be determined from an understanding of the statistical variance in the various constants assumed during modeling. For example, values a, b, c, and d in model 390 may be determined with different measures of confidence. As shown in FIG. 18, constants a, b, and c vary within a 95% confidence interval. For example, constant 'a' can range from $5.53 \times 10^7$ to $9.32 \times 10^8$, as shown on the graph. (Here, it is assumed that constant d is simply 2 and does not vary). Likewise, values used to model the relationship of pth and pulse width (FIGS. 19A and 19B) may have different measure of confidence, as may values m and n used to model the relationship between optional amplitude, pth, and PW (FIG. 20). Over time, as data is taken on more patients, it would be expected that the confidence of these models would improve. In this regard, note that algorithm 400 can easily be updated with new modeling information from time to time by loading new modeling information into the clinician programmer 50.

Figure 23A:
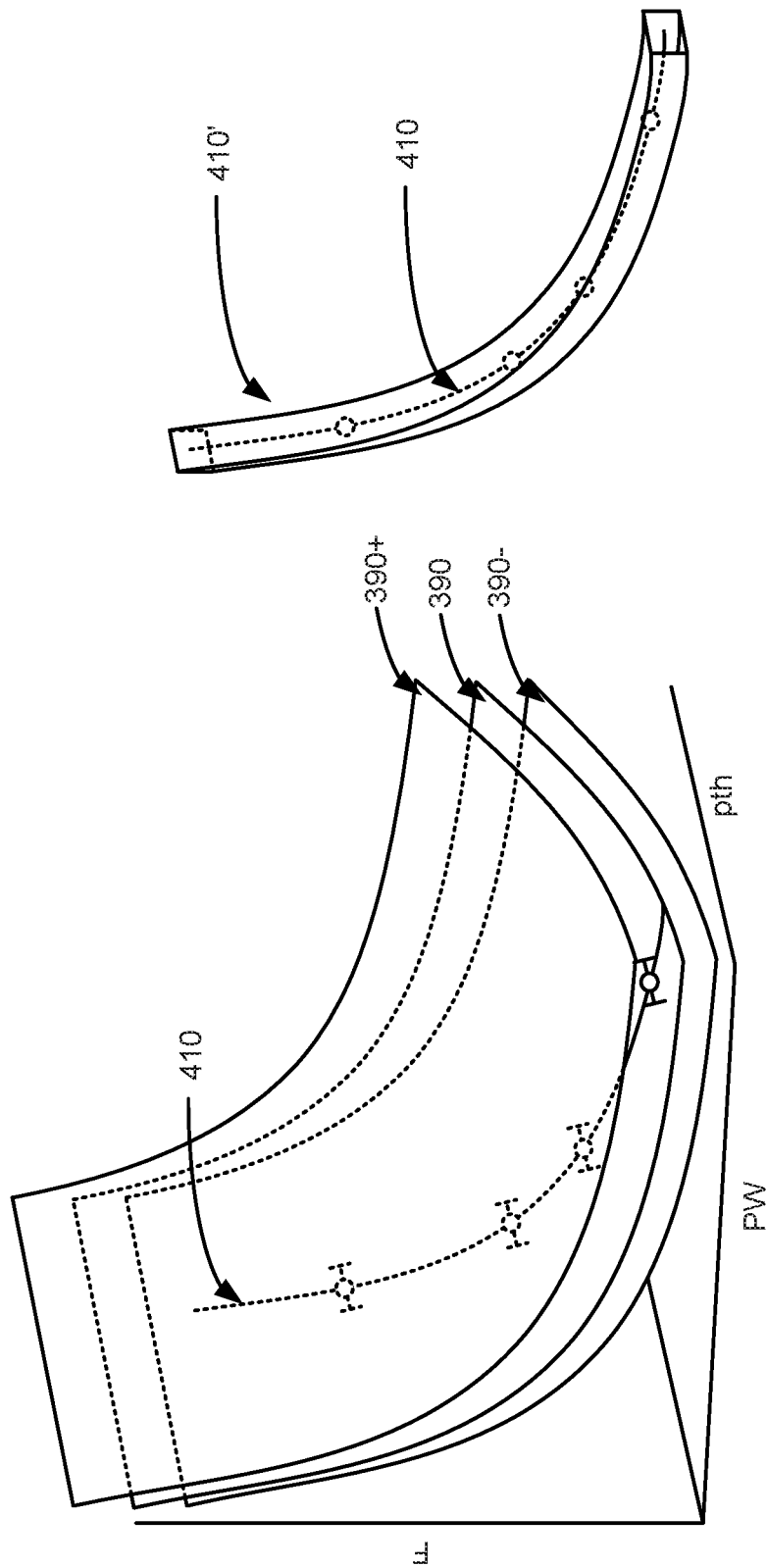
FIGS. 23A-23F show the effect of statistic variance in the modelling, leading to the result that determined optimal stimulation parameters for a patient may occupy a volume. User interfaces for the patient external controller are also shown to allow the patient to adjust stimulation within this volume.
Figure 23B:
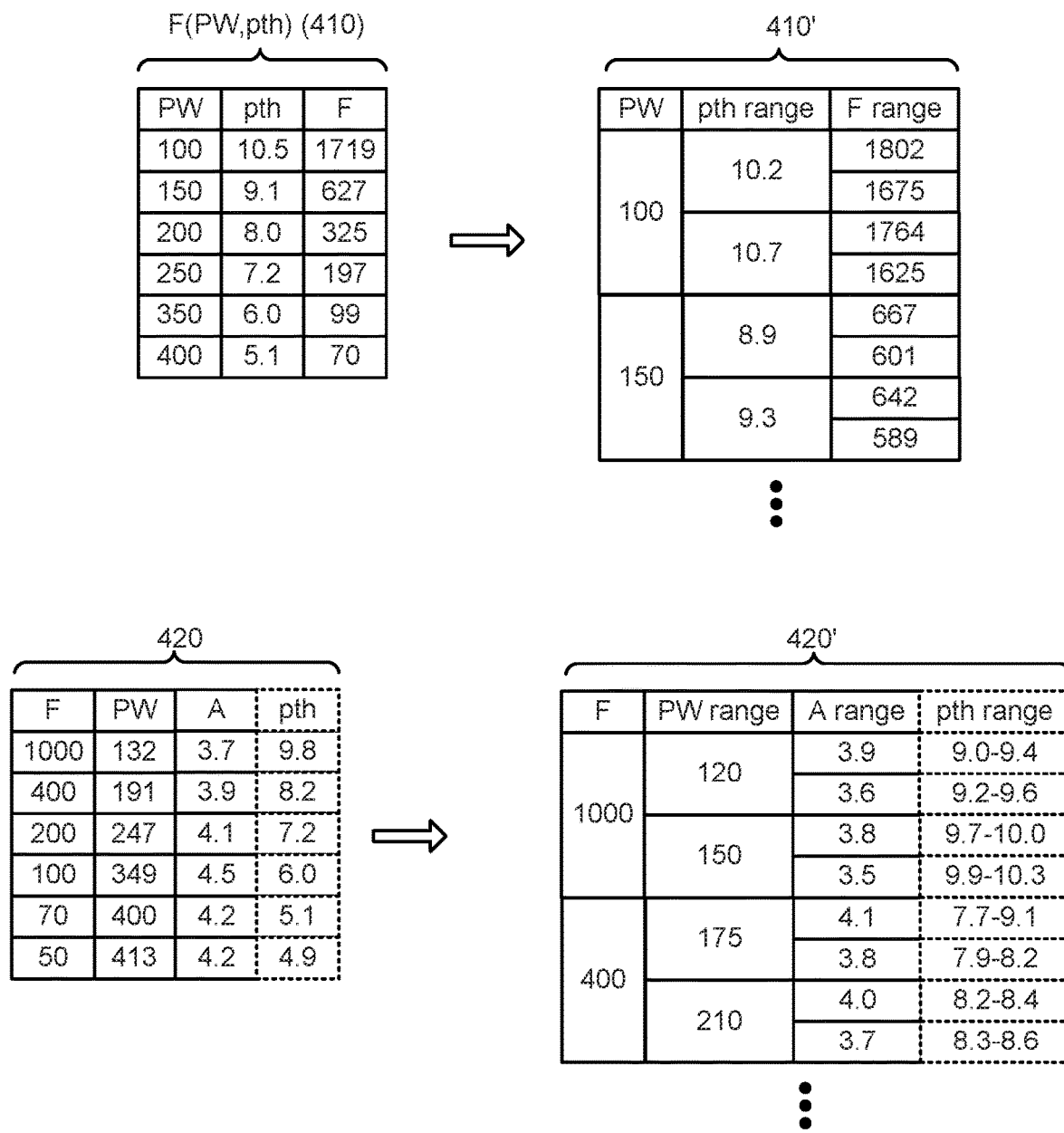

Statistical variance means that optimal stimulation parameters may not comprise discrete values, but may instead fall within a volume. This is illustrated in FIG. 23A as concerns the vector 410 determined for the patient (see FIG. 21B). Given statistical variance, vector 410 may comprise a rigid line within a volume 410'. In other words, there may not be a one-to-one correspondence of PW, pth, and F, as was the case for vector 410 in FIG. 21B. Instead, for any given variable (such as pulse width), the pth as determined for the patient (using the pth(PW) model in step 406) may vary in a range between statistically-significant maximum and minimum values, as shown in FIG. 23B. Statistical variation in model 390 (FIG. 18) may also mean that maximum and minimum frequencies may be determined for each maximum and minimum pth in step 408. As this trickles through the algorithm 400, the optimal stimulation parameters 420 may also not have one-to-one correspondence between frequency, pulse width, and amplitude. Instead, and as shown in FIG. 23B, for any frequency, there may be a range of maximum and minimum optimal pulse width of statistical significance, and a likewise a range of optimal amplitudes A. Effectively, then, optimal stimulation parameters 420' may define a statistically-significant volume of coordinates in Frequency-Pulse Width-Amplitude space rather than a line of coordinates. Paresthesia threshold pth may also vary within a range, and as noted earlier can be useful to include in the optimal stimulation parameters 420', because pth may be helpful to permitting the patient to vary stimulation from sub-perception to supra-perception, as discussed in some later examples.

Figure 23C:
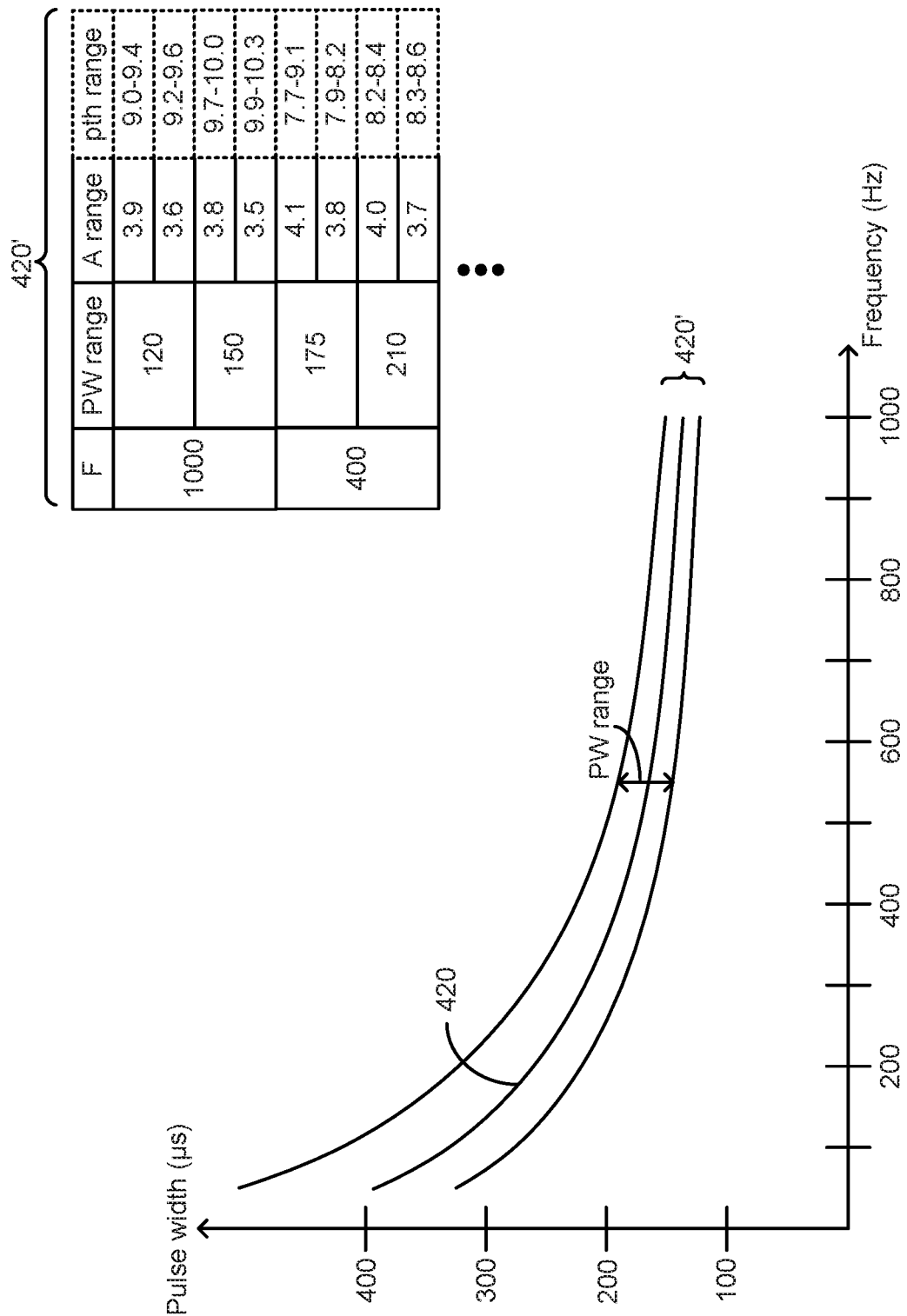
Figure 23D:
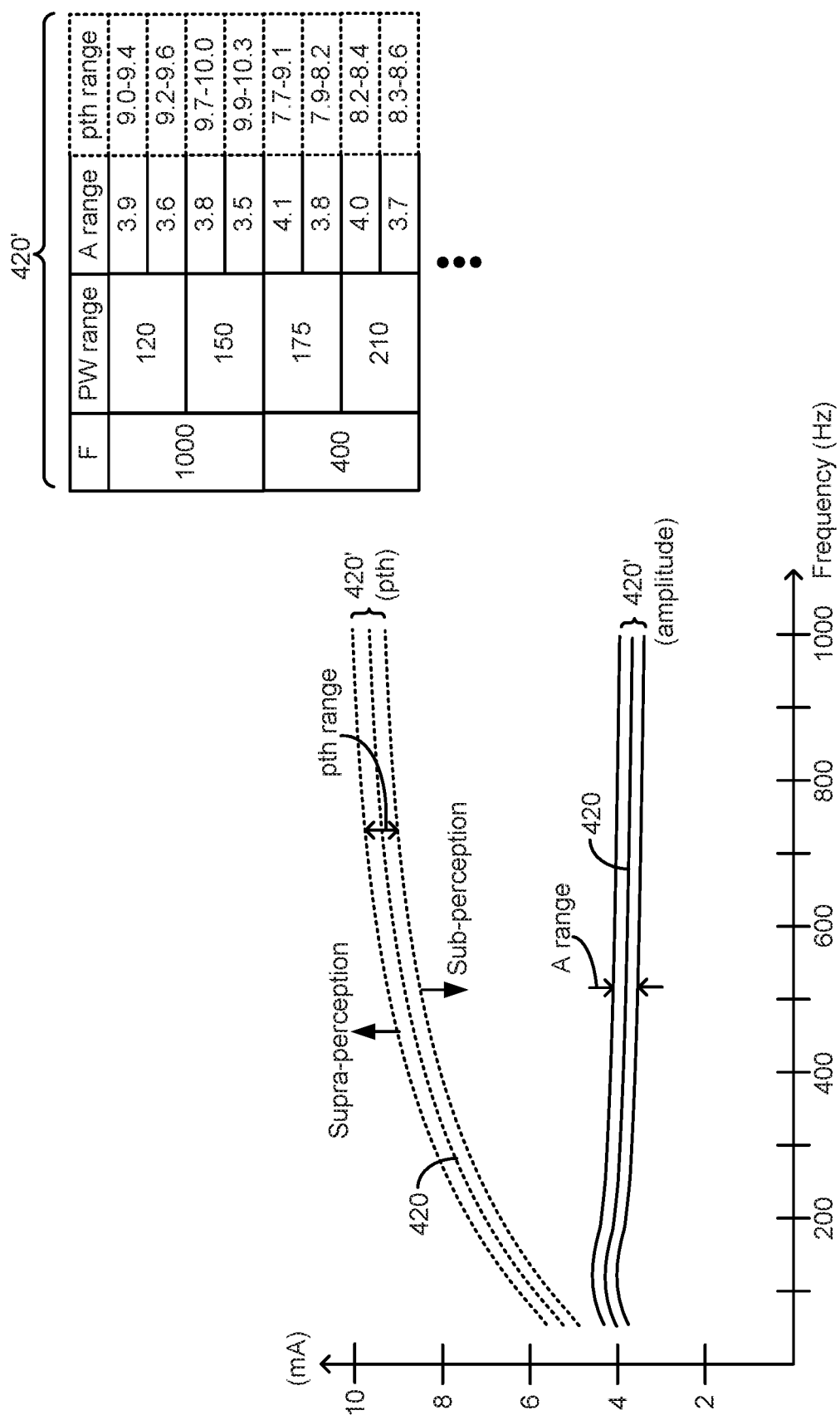
Figure 23E:
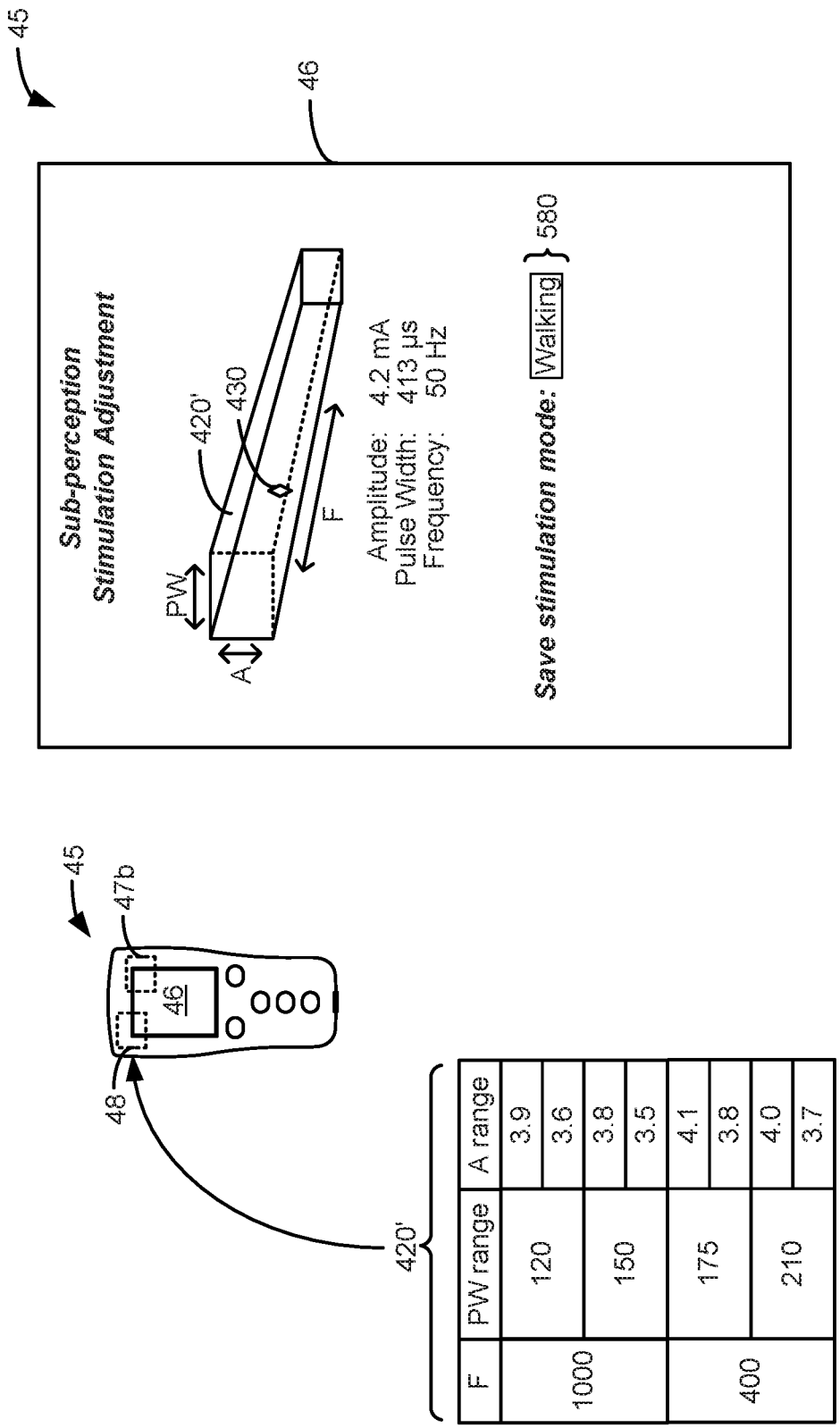

FIGS. 23C and 23D depict optimal parameters 420' in graphical form, showing at each frequency a statistically-relevant range of pulse widths, and a statistically-relevant range of amplitudes appropriate for the patient. While optimal parameters 420' in this example comprise a three-dimensional volume of coordinates (F, PW, and A), they are depicted in two two-dimensional graphs for easier illustration, similar to what occurred earlier in FIGS. 21E and 21F: FIG. 23C shows the relationship between frequency and pulse width, and FIG. 23D shows the relationship between frequency and amplitude. Note also that FIG. 23D shows the paresthesia threshold pth, which like pulse width and amplitude can statistically vary within a range. Optimal stimulation parameters 420 (determined without statistical variance, see FIGS. 21E and 21F) are also shown for each of the parameters, and as expected fall within the broader volume for the parameters specified by 420'.

With a volume of optimal parameters 420' defined, it may then be useful to allow the patient to use his external controller 45 to navigate different setting within this volume of optimal parameters 420'. This is shown in one example in FIG. 23E. Here, the GUI of the external controller 45 displays not a single linear slider, but a three-dimensional volume representative of the volume 420' of optimal parameters, with different axes representing changes the patient can make in frequency, pulse width, and amplitude. As before, the GUI of the external controller 45 allows the patient some flexibility to modify stimulation parameters for his IPG or ETS, and allows the patient to adjust all three stimulation parameters simultaneously through one adjustment action and using a single user interface element.

Figure 23F:
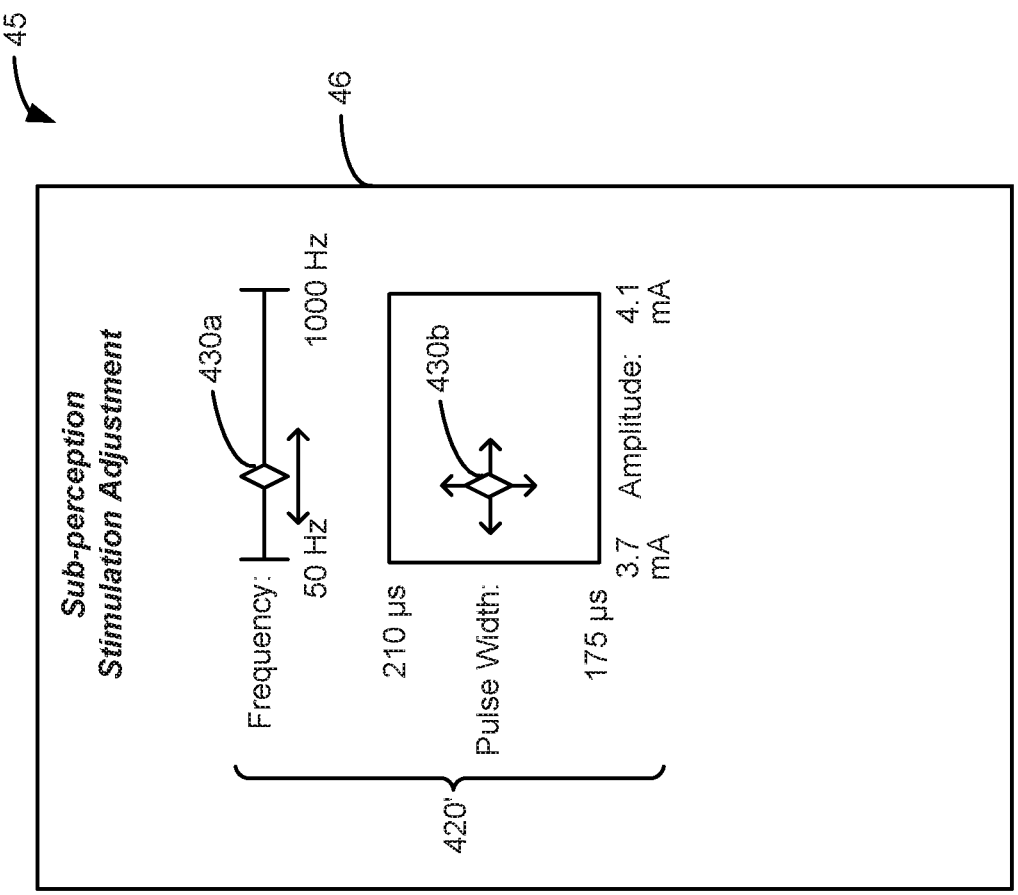

Different GUIs to allow the patient to navigate through the determined volume of optimal parameters 420' are possible, and FIG. 23F shows another example. In FIG. 23F, two sliders are shown. The first, a linear slider controlled by cursor 430a, allows the patient to adjust the frequency in accordance with frequencies reflected in the optimal volume 420'. A second two-dimensional slider controlled by cursor 430b allows the patient to adjust pulse width and amplitude at that frequency. Preferably, the range of pulse widths and amplitudes is constrained by the optimal parameters 420' and by the frequency already selected using cursor 430a. For example, if the user selected to use frequency F=400 Hz, the external controller 45 can consult optimal parameters 420' to automatically determine an optimal range of pulse widths (e.g., 175 to 210 microseconds) and amplitudes (3.7 to 4.1 mA) for the patient to use at that frequency. When the patient changes the frequency using cursor 430a, the range of permissible pulse widths and amplitudes selectable using cursor 430b can automatically change to ensure that sub-threshold stimulation remains within the volume 420' determined to be statistically useful for the patient. In another modification not shown, the optimal stimulation parameters can be selected using a mean charge per second (MSC) model (e.g., 380, 381), as described earlier with respect to FIGS. 17A-17F. The GUI can then also allow the user to navigate within a MSC model to select optimal stimulation parameters.

Figure 24:
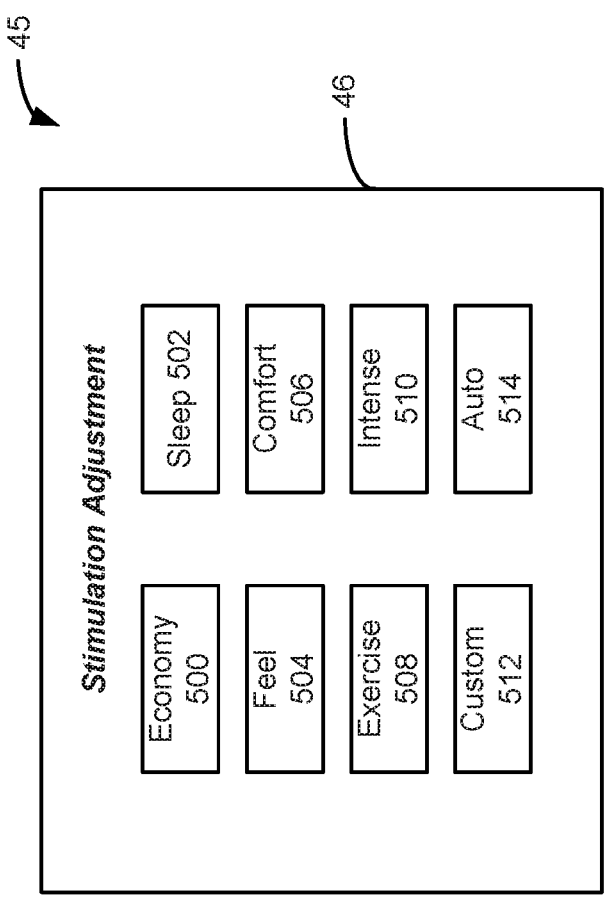
FIG. 24 shows a stimulation mode user interface, from which a patient may select different stimulation modes, resulting in providing stimulation, or allowing the patient to control stimulation, using different subsets of stimulation parameters determined using the optimal stimulation parameters.

FIG. 24 shows another example in which a user can program settings for his IPG 10 (or ETS) using the derived optimal stimulation parameters. Subsequent examples for completeness use determined volumes 420' of optimal stimulation parameters, but vectors or ranges 420 of optimal stimulation parameters could be used as well. Optimal stimulation parameters can also be selected using a mean charge per second (MSC) model (e.g., 380, 381), as described earlier with respect to FIGS. 17A-17F.

FIG. 24 shows a user interface on screen 46 of the patient's external controller 45, which allows the patent to select from a number of stimulation modes. Such stimulation modes can include various ways in which the IPG can be programmed consistent with optimal stimulation parameters 420' determined for the patient, such as: an economy mode 500 that provides stimulation parameters having a low power draw; a sleep mode 502 which optimizes the stimulation parameters for the patient while sleeping; a feel mode 504 which allows a patient to feel the stimulation (supra-perception); a comfort mode 506 for normal everyday use; an exercise mode 508 that provide stimulation parameters appropriate for when the patient is exercising; and an intense mode 510 usable for example if the patient is experiencing pain, and would benefit from more intense stimulation. Such stimulation modes can be indicative of a patient's posture or activity. For example, a sleep mode 502 provides stimulation optimized for sleep (e.g., when the patient is lying down and is not moving significantly), and an exercise mode 508 provides stimulation optimized for exercise (e.g., when the patient is standing up and is moving significantly). Although not shown, stimulation modes can also be included that provide stimulation optimized for different patient postures, such as supine, prone, standing, sitting, etc., or for different conditions such as cold or bad weather. While illustrated in the context of the patient's external controller, realize as in other examples that another external device usable to program a patient's IPG can be used as well to select the stimulation modes, such as the clinician programmer 50.

A patient can select from these stimulation modes, and such selections can program the IPG 10 to provide a subset of stimulation parameters useful for that mode governed by the optimal stimulation parameters 420'. For some stimulation modes, the subset of stimulation parameters may be wholly constrained by (wholly within) the volume of optimal stimulation parameters 420' determined for the patient, and hence would provide optimal sub-perception stimulation therapy for the patient. The subsets for other modes may only be partially constrained by the optimal stimulation parameters, as explained further below. In all cases however, the subsets are determined using the optimal stimulation parameters (either 420 or 420'). Preferably, the subsets are determined for the patient at the clinician programmer 50 and are transmitted to and stored in the patient's external controller 45. Alternatively, the determined optimal stimulation parameters can be transmitted to the external controller 45, leaving it to the external controller 45 to determine the subsets from the optimal stimulation parameters.

The number of stimulation modes made available for selection by the patient on the external controller 45 may be limited or programmed by a clinician. This may be warranted because some stimulation modes may not be relevant for certain patients. In this regard, the clinician may program the patient's external controller 45 to specify the stimulation modes available, such as by entering an appropriate clinician's password. Alternatively, the clinician may program the external controller 45 using clinician programmer 50 to program the external controller 45.

Figure 25A:
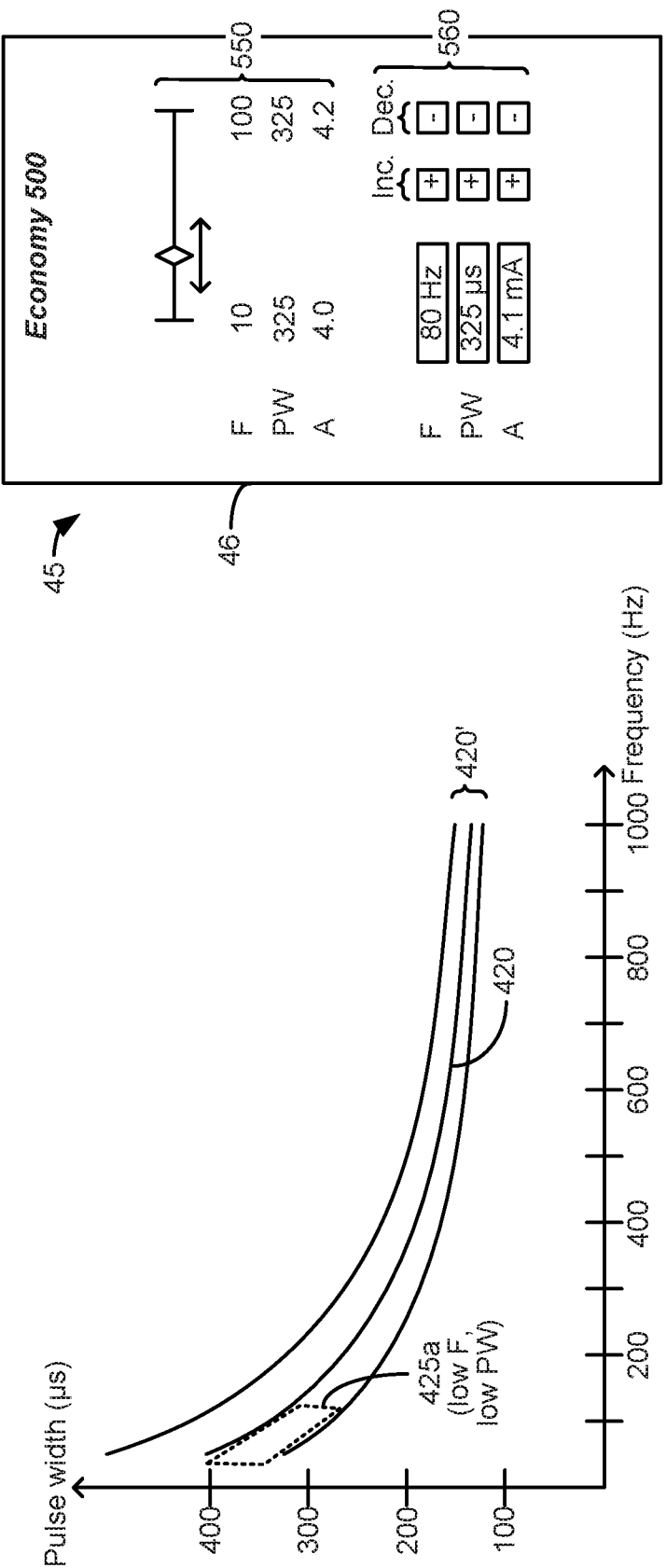
FIGS. 25A-30B show examples of different subsets of stimulation parameters based on the patient's selection of different stimulation modes. Figures labeled A (e.g., 25A) show frequencies and pulse widths of a subset, while figures labeled B (e.g., 25B) show amplitudes and perception thresholds for that subset. These figures show that subsets of stimulation parameters corresponding to different stimulation modes may comprise parameters wholly constrained by (i.e., wholly within) the determined optimal stimulation parameters, or may comprise parameters only partially constrained by the optimal stimulation parameters.
Figure 25B:
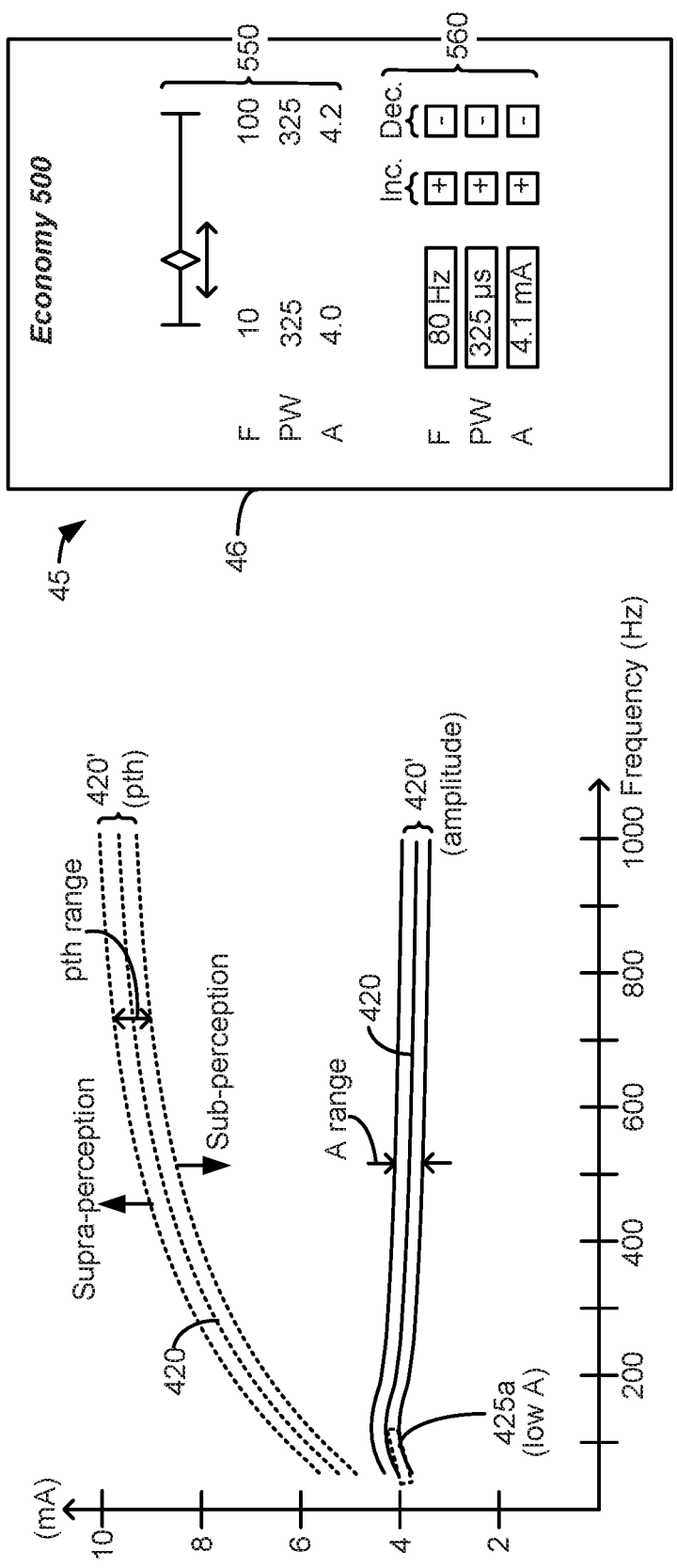

Examples of the subsets 425x of stimulation parameters are shown in FIGS. 25A-30B. FIGS. 25A and 25B show a subset 425a of stimulation parameters coordinates used when the economy mode 500 is selected, which comprises a subset of the optimal stimulation parameters 420' having a low power draw. Subset 425a may, like optimal stimulation parameters 420', comprise a three dimensional volume of F, PW, and A parameters, and again (compare FIGS. 23C and 23D), two two-dimensional graphs are used to represent subset 425a, with FIG. 25A showing the relationship between frequency and pulse width, and with FIG. 25B showing the relationship between frequency and amplitude.

To affect a low power draw, frequencies within subset 425a are low, such as limited to a frequency range of 10 to 100 Hz, even though the optimal stimulation parameters 420' may have been determined over a wider range, such as 10 to 1000 Hz. Further, while optimal pulse widths within this frequency range may vary more significantly in optimal stimulation parameters 420', subset 425a may be constrained to lower of these pulse widths, such as the lower half of such pulse widths, as shown in FIG. 25A. Again, using a lower pulse width will result in lower power draws. Furthermore, subset 425a may be constrained to lower amplitudes within optimal stimulation parameters 420' for the relevant frequency range, as shown in FIG. 25B, again resulting in lower power draws. In short, subset 425a can comprise a smaller volume of stimulation parameters wholly within the volume of optimal stimulation parameters 420' that provide adequate sub-threshold stimulation for the patient, while providing lower power draws from the IPG's battery 14. Not all subsets 425x corresponding to selected stimulation modes (FIG. 24) contain stimulation parameters that are necessarily wholly within the determined optimal stimulation parameters 420' as shown in some subsequent examples.

When economy mode 500 is selected, the external controller 45 could simply transmit a single low-power optimal parameter (F, PW, A) within subset 425a to the IPG for execution. However, and more preferably, the user interface will include means to allow the patient to adjust stimulation parameters to those within subset 425a. In this regard, the user interface can include a slider interface 550 and a parameter interface 560. The slider interface 550 can be as explained earlier (see FIG. 22), and can include a cursor to allow the patient to slide through parameters in subset 425a. In the example shown, slider interface 550 may not adjust the pulse width, which is set to a particular value (e.g., 325 µs), but the frequency and amplitude can vary. This is just one example, and all three of frequency, pulse, and amplitude may be variable by the slider in other examples, or other of the parameters may be held constant. Note that more complicated user interfaces can be used to allow the patient to navigate through subset 425a. For example, although not shown, user interface elements having a more three-dimensional quality, such as those discussed earlier in FIGS. 23E and 23F, can be used to navigate the volume of subset 425a. Parameter interface 560 can also allow the patient to navigate parameters within subset 425a, and is shown simply as having selectable buttons to increase or decrease the parameters within the determined subset 425a. Parameter interface 560 may also include fields displaying the current values for frequency, pulse width, and amplitude. Initially, these values may be populated with parameters that are roughly in the center of the determined subset 425a, thus allowing the patient to adjust the stimulation around that center.

Figure 26A:
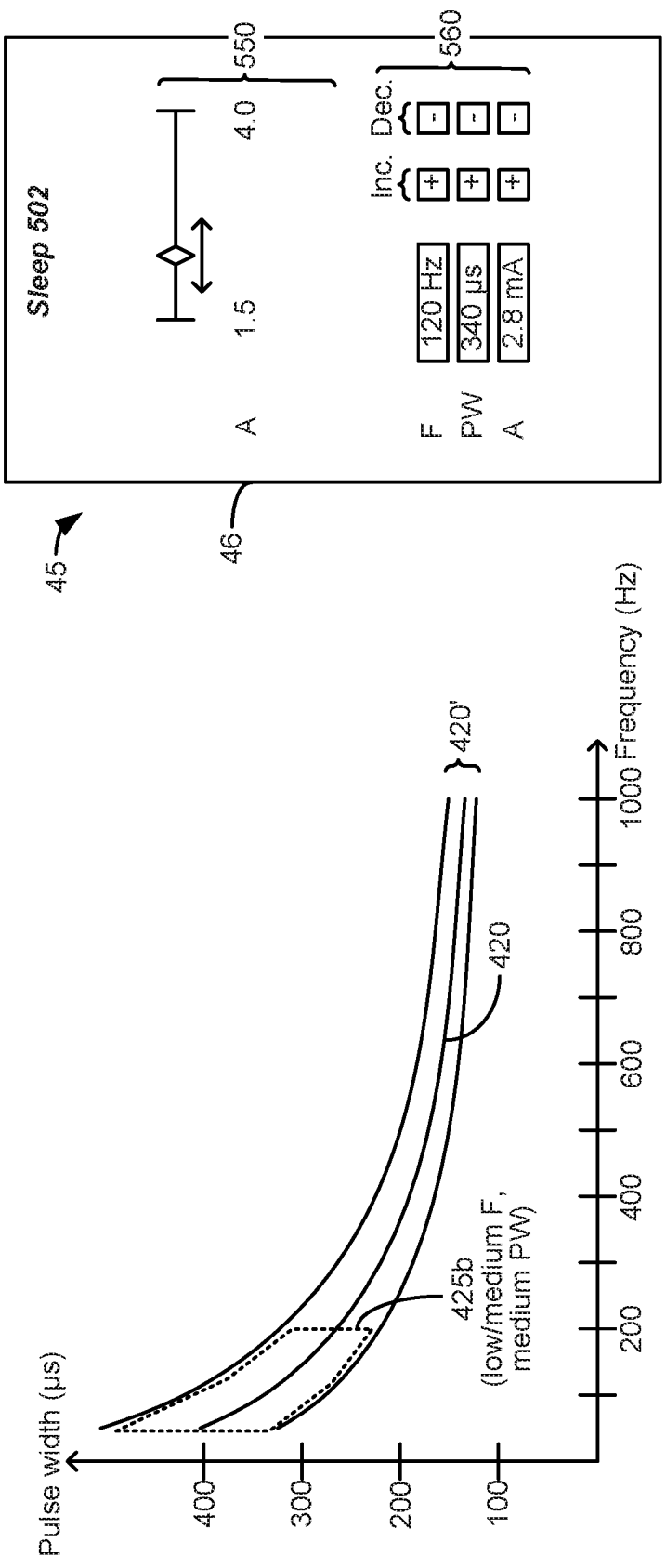
Figure 26B:
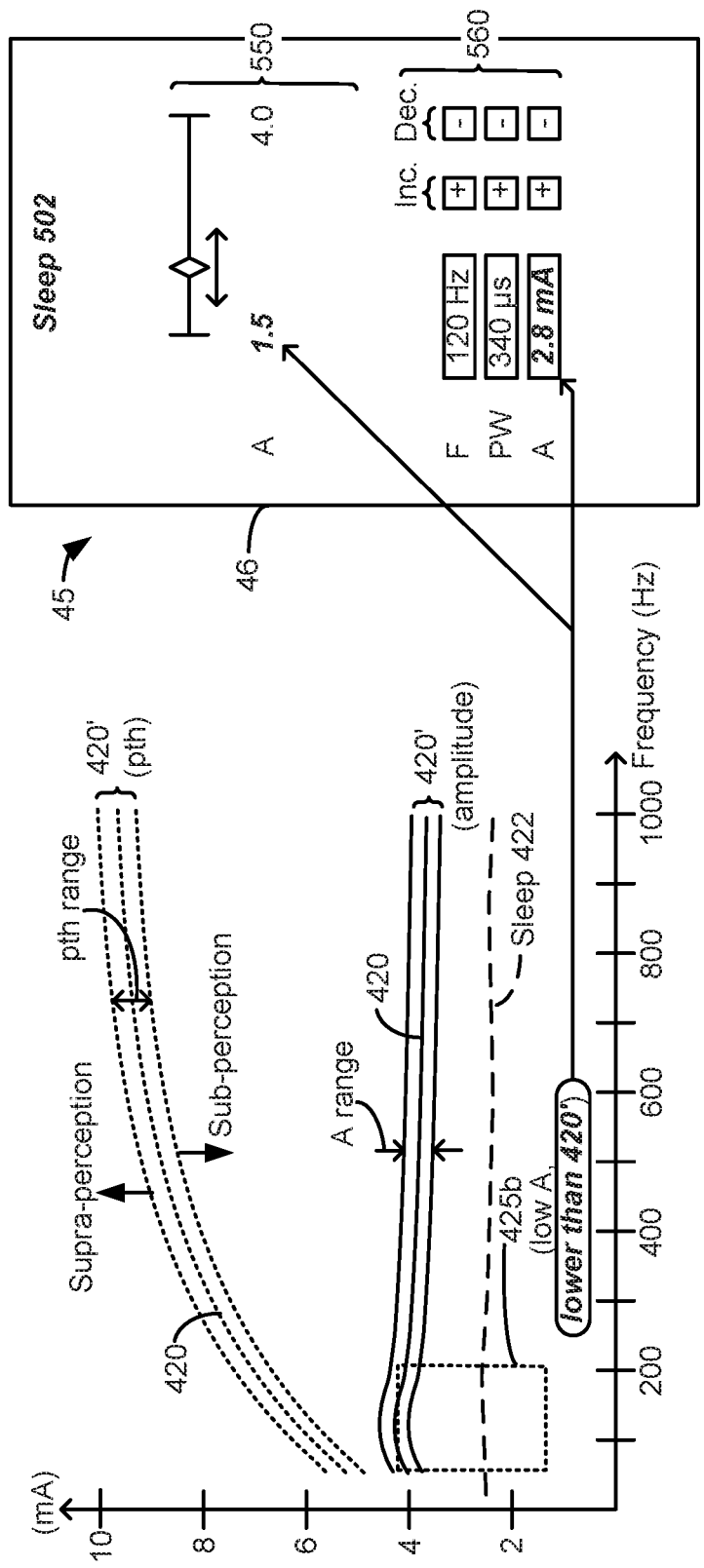

FIGS. 26A and 26B shows selection of sleep mode 502, and the subset 425b of optimal stimulation parameters 420' that results when this selection is chosen. Subset 425b in this example is determined using the optimal stimulation parameters 420' in a manner such that subset 425b is only partially constrained by optimal stimulation parameters 420'. Subset 425b may include low-to-medium frequencies (e.g., 40 to 200 Hz) within optimal stimulation parameters 420', and can include medium pulse widths otherwise permitted by 420' for this frequency range, as shown by FIG. 26A.

Because the intensity of the stimulation may not need to be as high during sleep, amplitudes within subset 425b may fall outside of amplitudes otherwise suggested by optimal parameters 420', as shown in FIG. 26B. For example, while optimal parameters 420' may suggest for example that the amplitude based on earlier modelling would fall within a range of 3.6 to 4.0 mA for the frequency and pulse width ranges of interest, the amplitude within subset 425b in this example be set to even lower values. Specifically, as shown in the slider interface 550, the amplitude can be set between 1.5 mA and 4.0 mA. To know where the lower boundary of amplitude should be set, modeling information can include an additional model 422, which may be determined separately from optimal stimulation parameters 420' based on patient testing. Permitting the use of amplitudes lower than those suggested by optimal parameters 420' may be warranted in the case of sleep due to expected changes in the location of the electrodes leads within a patient's spinal column when the patient is lying down. Further, a patient may be less bothered by pain while sleeping, and therefore lower amplitudes could still be reasonably effective. This being said, subset 425b could also comprise values (including amplitude) wholly within and constrained by optimal stimulation parameters 420', similar to what was shown for subset 425a in FIGS. 25A and 25B.

Figure 27A:
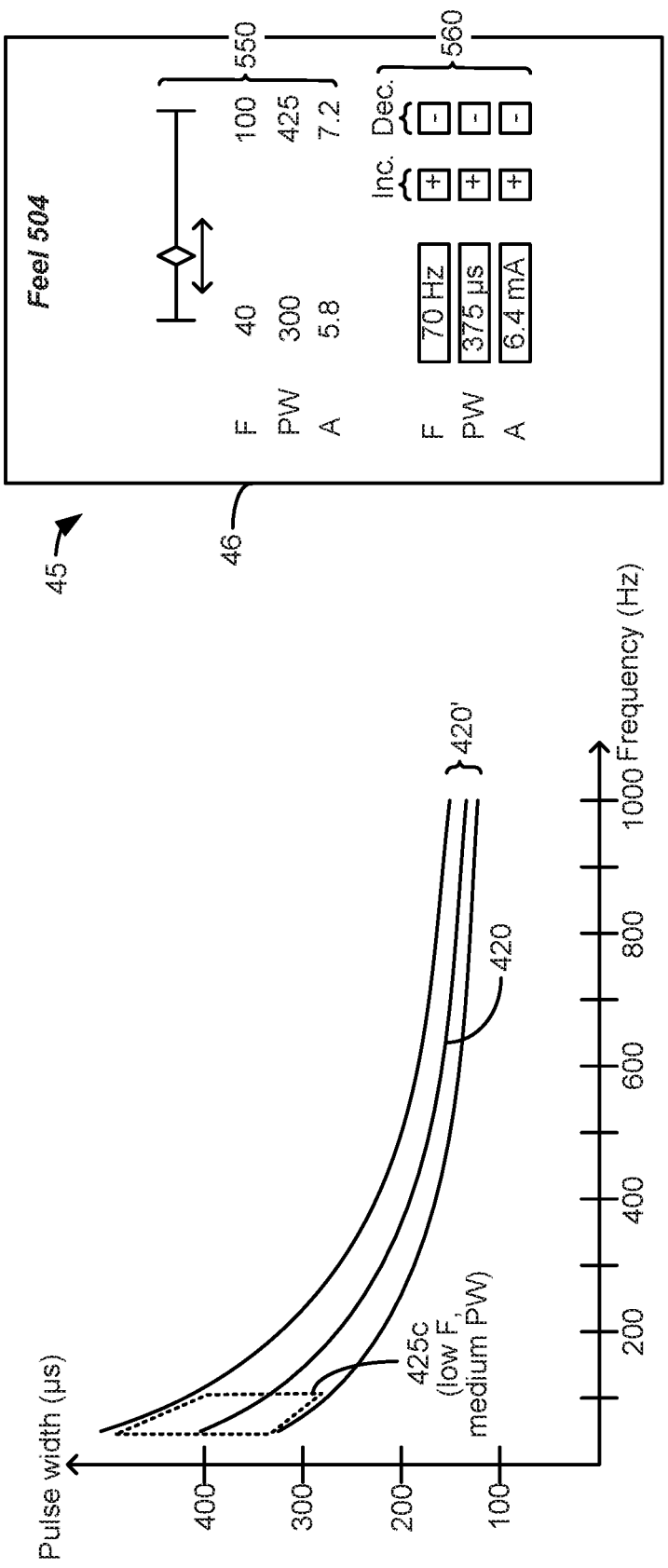
Figure 27B:
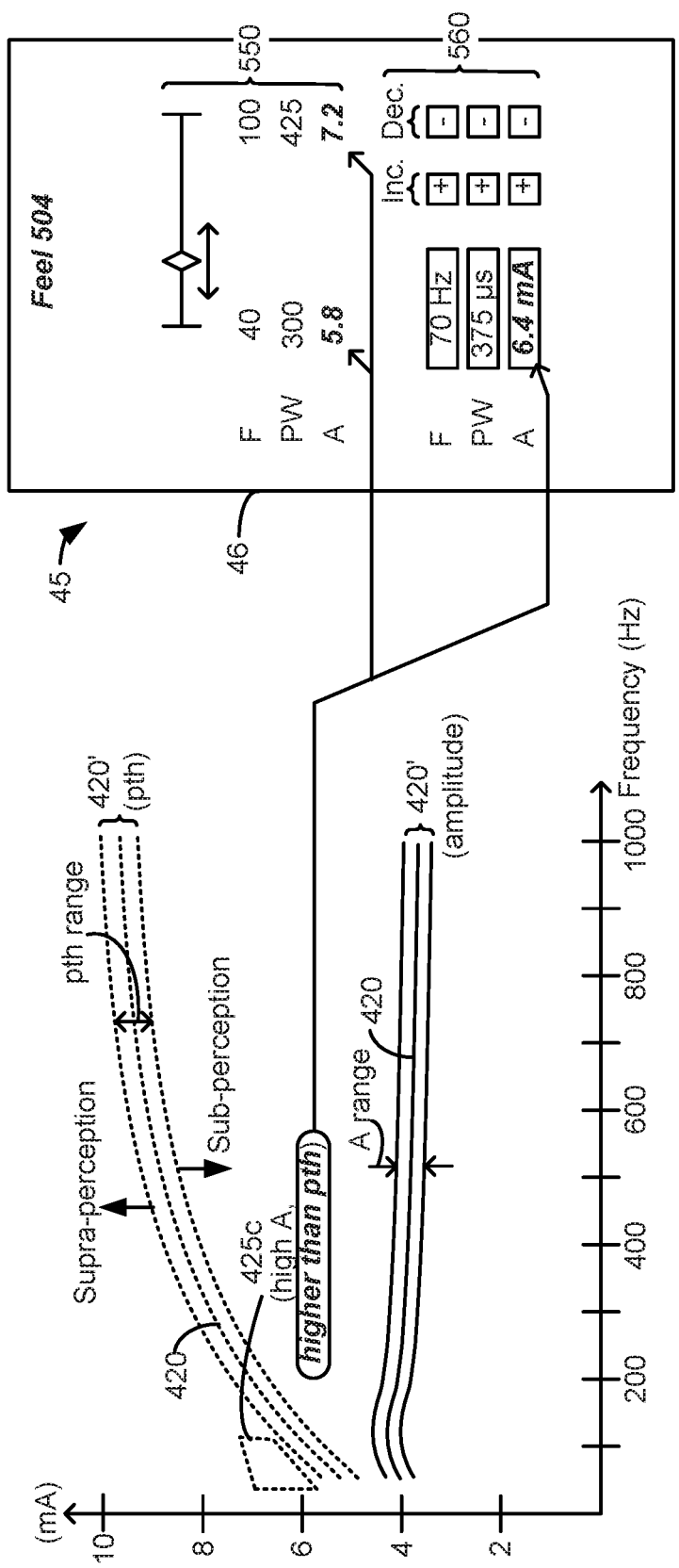

FIGS. 27A and 27B show selection of feel mode 504, and the resulting subset 425c useable for a given patient during this mode. The purpose of this mode is to allow the patient, at their discretion, to feel the stimulation that his IPG is providing. In other words, the stimulation provided to the patient in this mode is supra-perception. The optimal stimulation parameters 420' preferably define a volume of stimulation parameters in which sub-perception stimulation is optimized for the patient. However, as described earlier, perception threshold pth is measured and modelled as part of the determination of optimal sub-threshold stimulation parameters 420'. As such, perception threshold pth as determined earlier is useful during this mode to select amplitudes that a patients will feel—i.e., amplitudes that are higher than pth for the other stimulation parameters (particularly pulse width). The feel mode 504 is thus an example in which it is beneficial to include pth values (or pth ranges) within optimal stimulation parameters 420'.

It is generally easier for a patient to feel stimulation at lower frequencies, and thus selection of feel mode may constrain stimulation in subset 425c to lower frequencies (e.g., 40 to 100 Hz), as shown in FIG. 27A. Control of the pulse width may not be a primary concern, and thus the pulse width may have a medium range as permitted by 420' for this frequency range, again as shown by FIG. 27A.

However, because the patient in this mode intends to feel the stimulation, the amplitude within subset 425c is set to higher values, as shown in FIG. 27B. Specifically, the amplitudes for the relevant frequencies and pulse widths are set not only to be higher than the upper bound for amplitudes as determined for optimal stimulation parameters 420'; they are also set at or higher than the perception threshold, pth. As noted earlier, the perception threshold, pth, and more particularly significant ranges for pth as determined for the patient (when statistical variation is considered), can be included with the optimal stimulation parameters 420' (see FIG. 23D) to useful effect in this mode. Thus, subset 425c is be defined to set the amplitude at a value or within a range that should provide supra-perception stimulation based on earlier measurements and modelling. If pth is defined by a range in light of statistical variance, the permissible range of amplitude for the feel mode 504 may be set beyond the upper value of that range, as shown in FIG. 27B. Therefore, while the optimal (sub-perception) amplitude (per 420') for the frequency range of interest may range from about 3.7 to 4.5 mA, the amplitudes within subset 425c are set to about 5.8 to 7.2 mA, beyond the upper bound of the pth range to guarantee that the resulting stimulation is supra-perception for the patient in question. In this example, note that subset 425c is determined using the optimal stimulation parameters 420', but is only partially constrained by such optimal parameters. Frequency and pulse width are constrained; amplitude is not, because the amplitude in this subset 425c is set beyond 420', and more particularly beyond pth.

Figure 28A:
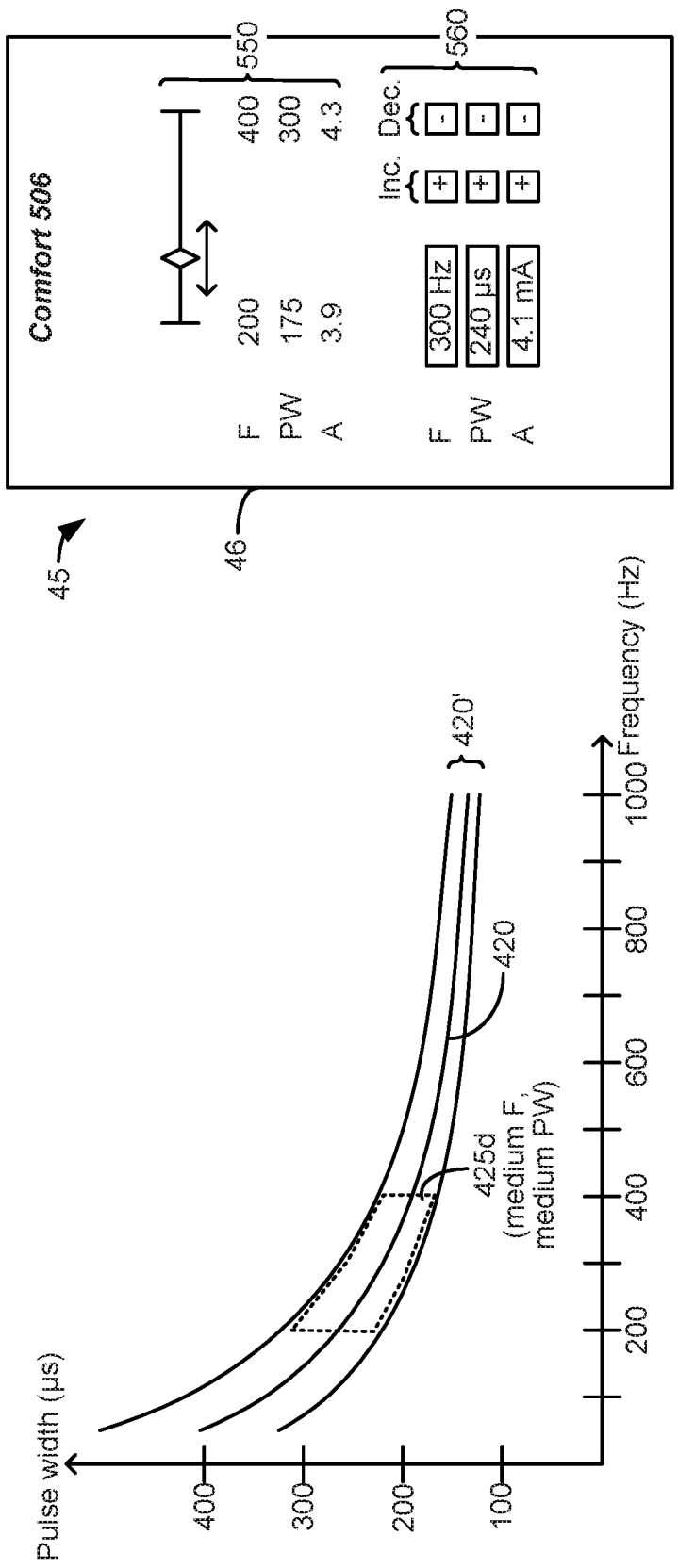
Figure 28B:
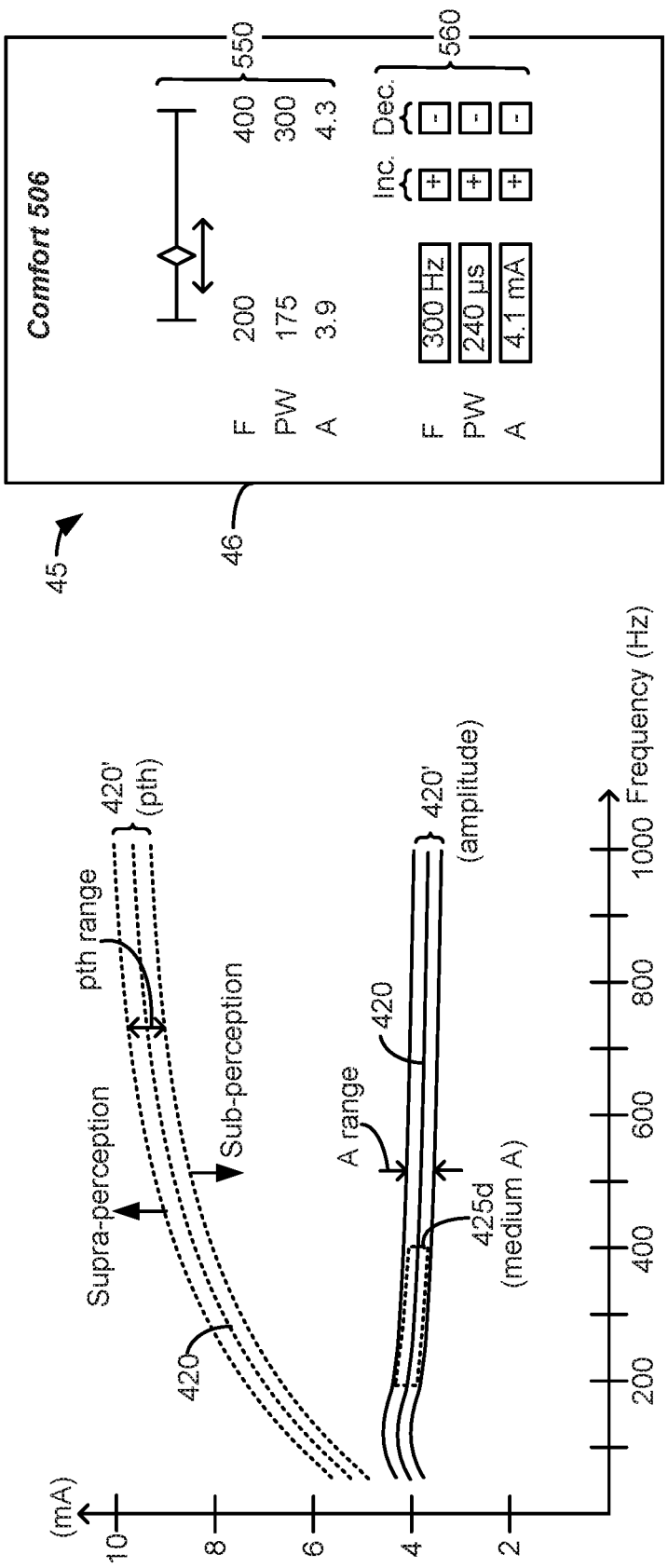

FIGS. 28A and 28B shows selection of a comfort mode 506, and the resulting subset 425d of stimulation parameters for this mode. In this mode, stimulation parameters are set via subset 425d to nominal values within the optimal stimulation parameters 420': medium frequencies such as 200 to 400 Hz, and medium pulse widths for those frequencies, such as 175 to 300 μs as shown in slider interface 550, as shown in FIG. 28A. Amplitudes within subset 425d may likewise be medium amplitudes within optimal stimulation parameters 420' for the frequencies and pulse widths at issue, as shown in FIG. 28B. In this example, the stimulation parameters in subset 425d are wholly constrained by optimal stimulation parameters 420', although as noted earlier, this doesn't have to be the case for every subset.

Figure 29A:
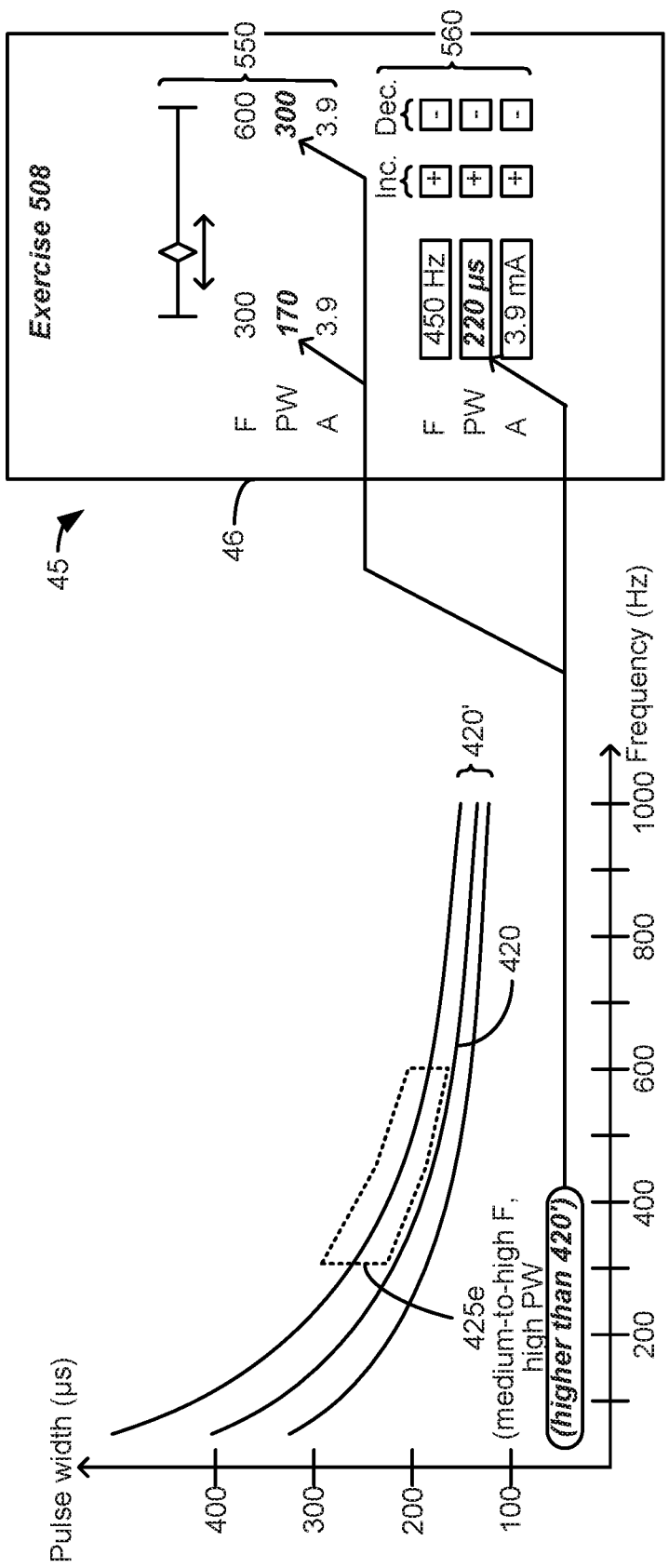
Figure 29B:
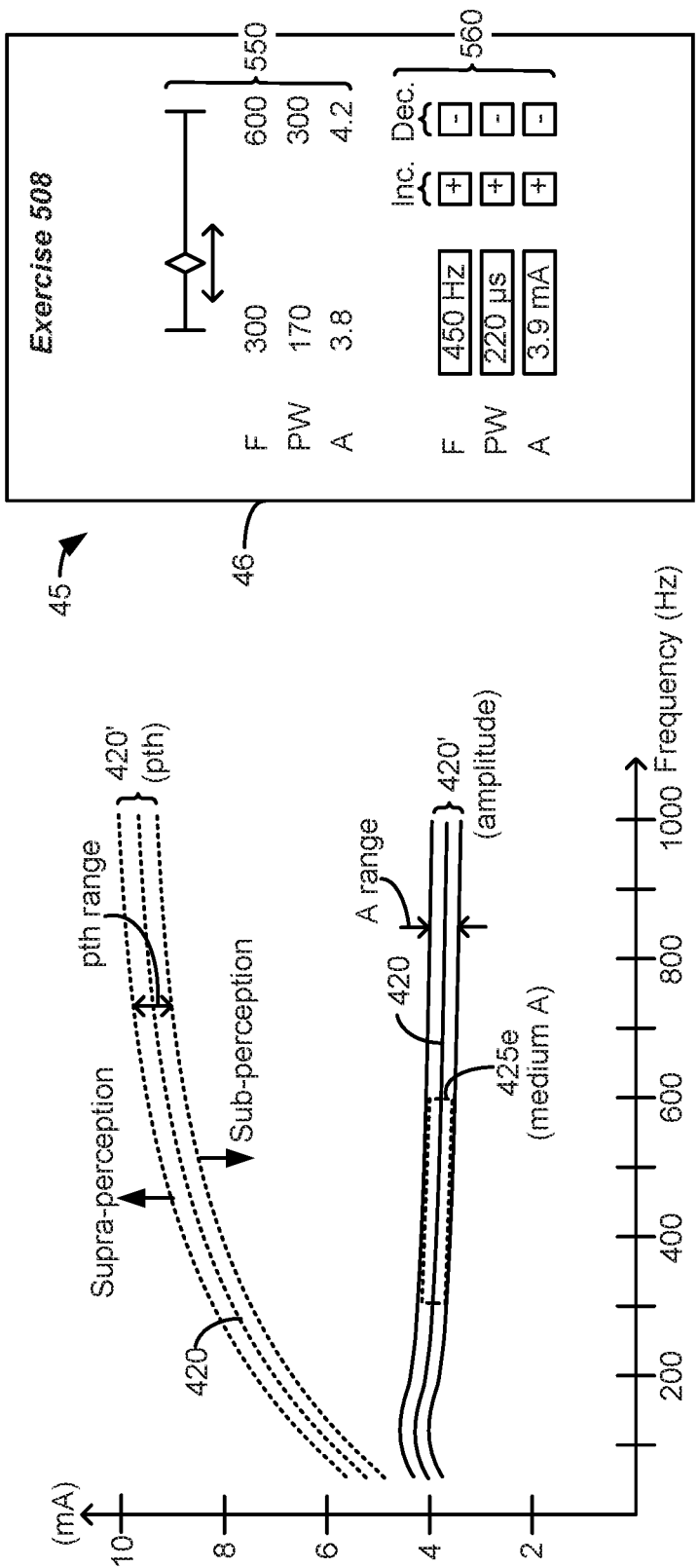

FIGS. 29A and 29B show selection of an exercise mode 508, and the subset 425e of stimulation parameters associated with this mode. In this mode, it may be warranted to use medium-to-high frequencies (e.g., 300-600 Hz), but pulse widths that are higher than those prescribed by optimal stimulation parameters 420' for these frequencies, as shown in FIG. 29A. This is because the position of the electrode leads in the patient may be more variable when the patient is moving, and hence it may be useful to provide higher injections of charge into the patient which higher pulse widths would achieve. As shown in FIG. 29B, the amplitudes used may span a medium range for the frequencies and pulse widths involved, but higher amplitudes beyond 420' (not shown) could also be used to provide additional charge injection as well. Subset 425e shows an example where the frequency and amplitude are constrained by optimal stimulation parameters 420', but pulse width in not; thus subset 425e is only partially constrained by optimal stimulation parameters 420'. Subset 425e in other examples could be wholly constrained within the optimal stimulation parameters 420' determined earlier.

Figure 30A:
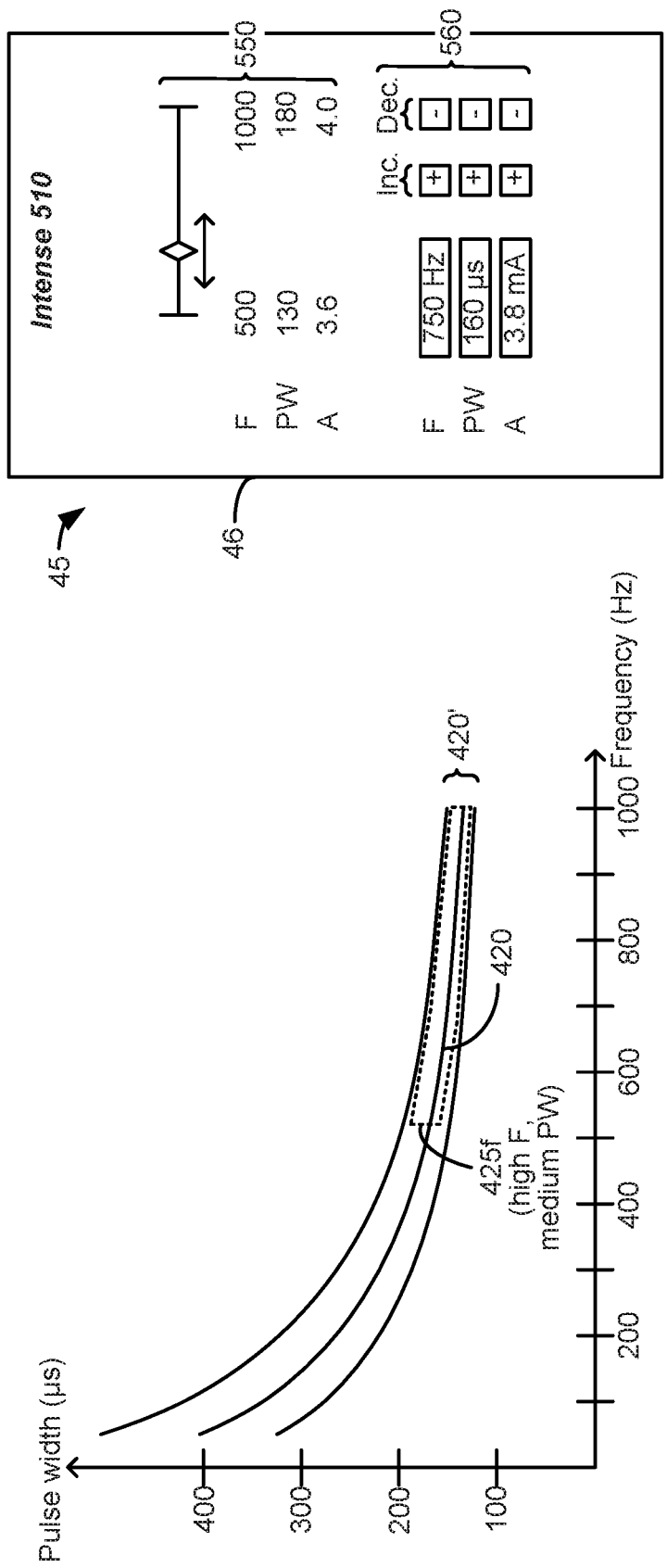
Figure 30B:
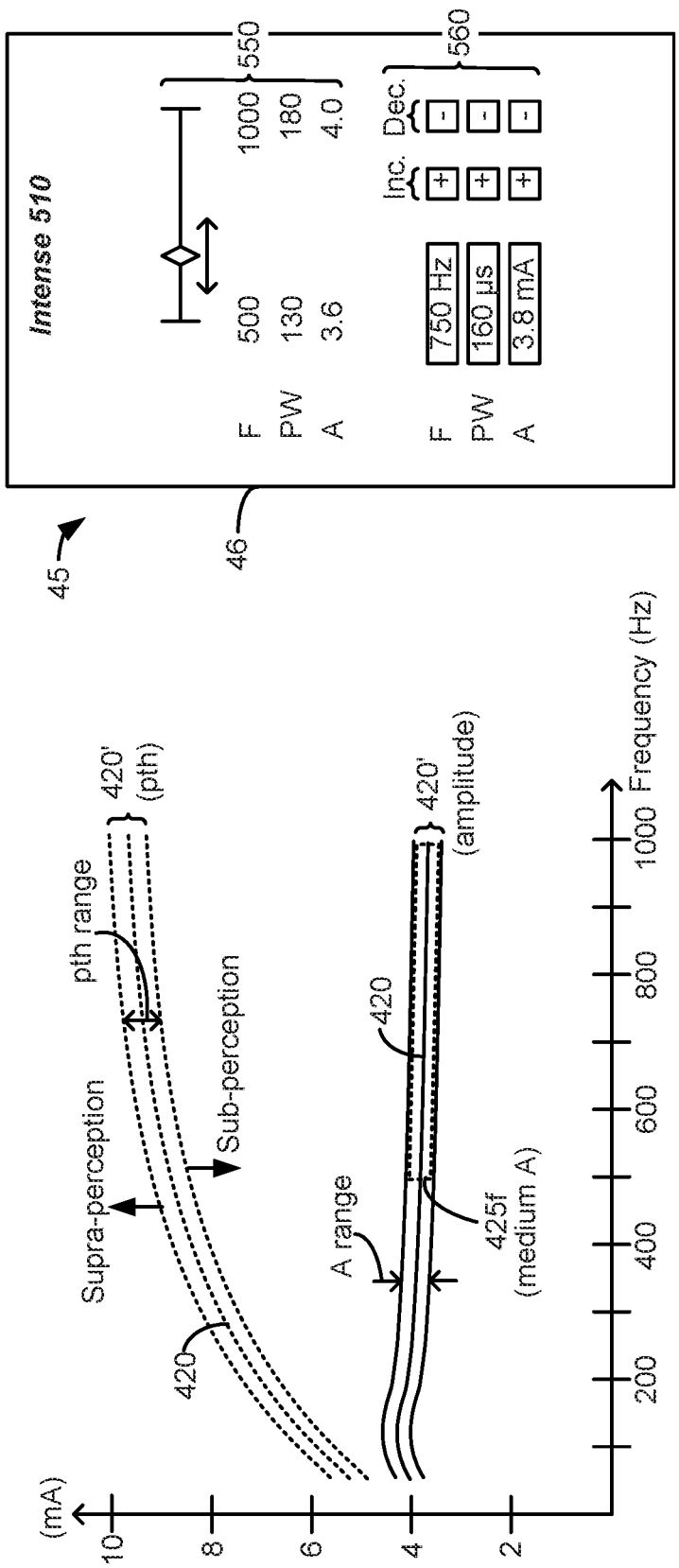

FIGS. 30A and 30B show selection of an intense mode 510 of stimulation. In this mode, stimulation is more aggressive, and the subset 425f of stimulation parameters may occur at higher frequencies (e.g., 500 to 1000 Hz). However, the pulse width and amplitudes at these frequencies may be medium for the frequencies involved, as shown in FIGS. 30A and 30B respectively. In this example, the subset of stimulation parameters in subset 425f may be wholly constrained by (contained within) optimal stimulation parameters 420'. As in earlier examples, the patient can use interfaces 550 or 560, or other interface elements not shown, to adjust stimulation within the subset 425x corresponding to the patient's stimulation mode selection (FIG. 24). Less preferably, selection of a stimulation mode may cause the external controller 45 to send a single set of stimulation parameters (F, PW, A) determined using the optimal stimulation parameters 420' (or 420).

Notice that the stimulation parameters in subsets 425x may overlap; some F, PW, and A values in one subset (e.g., 425a) may also be present in another subset (e.g., 425b). In other words, it is not strictly necessary that stimulation parameters in a given subset are unique to that subset, or the stimulation mode that that subset represents, although this could also be the case. Furthermore, the boundaries of the various subsets 425x may be adjustable. For example, although not shown, the external controller 45 could have options to change the boundaries for the various subsets. Using such options, a patient or clinician could for example change one or more of the stimulation parameters (e.g., frequency) in a subset (e.g., by increasing the frequencies within subset 425a from 10 to 100 Hz to 10 to 150 Hz). Adjustments to the subsets 425x may also be affected in response to certain feedback, such as patient pain ratings as may be entered into the external device 45, or detection of patient activity or posture. More complex adjustments may be locked to the patient, and only made accessible by the clinician, with such accessibility being provided by entering a password into the external controller 45 for example. Behind such password protection, the subsets 425x may be adjustable, and/or other stimulation modes (e.g., beyond those shown in FIG. 24) may be made accessible to the clinician only. As before, clinician adjustments of this sort may also be made by the clinician using clinician programmer 50.

The subsets 425x may also be automatically updated from time to time. This may be advantageous, because the underlying modelling leading to the generation of optimal stimulation parameters 420' may change or become better informed as data is taken on more patients. It may also later be learned that different stimulation parameters better produce the effects desired for the stimulation modes, and so it may be warranted to adjust which parameters are included in the subsets. Different stimulation modes, provided for different reasons or to produce different effects, may also become apparent later, and so such new modes and their corresponding subsets may be later programmed into the external controller 45, and presented to the patient in the stimulation mode user interface of FIG. 24. Updating of the subsets and/or stimulation modes can occur wirelessly, either by connection of the external controller 45 to a clinician's programmer, or to a network such as the Internet. It should be understood that the stimulation modes disclosed, and the subset of stimulation parameters 425x corresponding to such modes, are merely exemplary, and that different modes or subsets could be used.

Referring again to FIG. 24, the stimulation mode user interface can include an option 512 to allow the patient or clinician to define a custom mode of stimulation. This custom mode 512 may allow the user to select a frequency, pulse width, and amplitude, or to define a subset, at least partially defined by optimal stimulation parameters 420'. Selection of this option may provide a user interface that allows a patient to navigate different stimulation parameters within optimal stimulation parameters 420', such as those shown earlier in FIGS. 23E and 23F. Should the patient find stimulation parameters through this option that seem effective to operate as a simulation mode, the user interface can allow the stimulation mode to be stored for future use. For example, and referring to FIG. 23E, the patient may have found stimulation parameters within optimal stimulation parameters 420' that are beneficial when the patient is walking. Such parameters may then be saved by the patient, and appropriately labeled, as shown at user interface element 580 in FIG. 23D. This newly-saved stimulation mode may then be presented to the patient (FIG. 24) as a selectable stimulation mode. The logic in the external controller 45 may additionally define a subset 425 (e.g., 425g) of stimulation parameters through which the patient can navigate when this user-defined stimulation mode is later selected. Subset 425g may comprise for example stimulation parameters that bound the patient's selected parameters (e.g., +/−10% of the frequency, pulse width and amplitude selected by the patient), but which are still wholly or partially constrained by the optional stimulation parameters 420'.

As shown in FIG. 24, the stimulation mode user interface can also include an option 514 that automatically selects and adjusts the stimulation mode for the patient based on various factors that the IPG 10 may detect. Selection of this automatic mode 514 is shown in further detail in FIG. 31. Preferably, selection of the automatic mode 514 allows the patient to select 570 which of the stimulation modes he would like detected, and to be automatically used by his IPG 10. In the depicted example, the user has selected the sleep mode 502, the comfort mode 506, and the exercise mode 508. The IPG 10 will try to automatically detect when these stimulation modes should be entered, and in this regard the IPG 10 can include a stimulation mode detection algorithm 610. As shown, this algorithm may be programmed into the control circuitry 600 of the IPG 10. The control circuitry can comprise a microprocessor, microcomputer, an FPGA, other digital logic structures, etc., which is capable of executing instructions an electronic device. Alternatively, algorithm 610 in the IPG 10 can attempt to detect, and adjust stimulation for, all stimulation modes (e.g., 500-510) supported by the system, without the need for the user to select 570 stimulation modes of interest.

Algorithm 610 can receive different inputs relevant to detecting the stimulation mode, and hence subsets 425x, that should be used for a patient at any given time. For example, the algorithm 610 may receive input from various sensors that indicate the posture and/or activity level of the patient, such as an accelerometer 630. The algorithm 610 may also receive input from various other sensors 620. In one example, the sensors 620 can include the electrodes Ex of the IPG 10, which can sense various signals relevant to stimulation mode determination. For example, and as discussed in U.S. Pat. No. 9,446,243, signals sensed at the electrodes can be used to determine (complex) impedances between various pairs of the electrodes, which can be correlated in the algorithm 610 to various impedance signatures indicative of patient posture or activity. Signals sensed at the electrodes may comprise those resulting from stimulation, such as Evoked Compound Action Potentials (ECAPs). Review of various features of detected ECAPs can be used to determine patient posture or activity, as disclosed in U.S. Pat. No. 10,926,092. Signals sensed at the electrodes may also comprise stimulation artifacts resulting from the stimulations, which can also indicate patient posture or activity, as disclosed in PCT (Int'l) Patent Application Publication WO 2020/251899. Sensed signals at the electrodes can also be used to determine a patient's heart rate, which may also correlate to patient posture or activity, as disclosed in U.S. Pat. No. 10,974,042.

The algorithm 610 can receive other information relevant to determining stimulation modes. For example, clock 640 can provide time information to the algorithm 610. This can be relevant to determining, or confirming, whether the patient is involved in activities that occur during certain times of day. For example, it may be expected that the patient may be asleep during evening hours, or exercising during mornings or afternoon hours. Although not shown, the user interface may allow time ranges for expected activities to be programmed, such as whether a patient prefers to exercise in the morning or afternoon. The algorithm 610 can also receive input from the battery 14, such as the current state of the battery's voltage, Vbat, which may be provided by any number of voltage sensors, such as an Analog-to-Digital Converter (ADC; not shown). This can be useful for example in deciding when the economy mode 500 or other power-based stimulation mode should be automatically entered, i.e., if Vbat is low.

Figure 31:
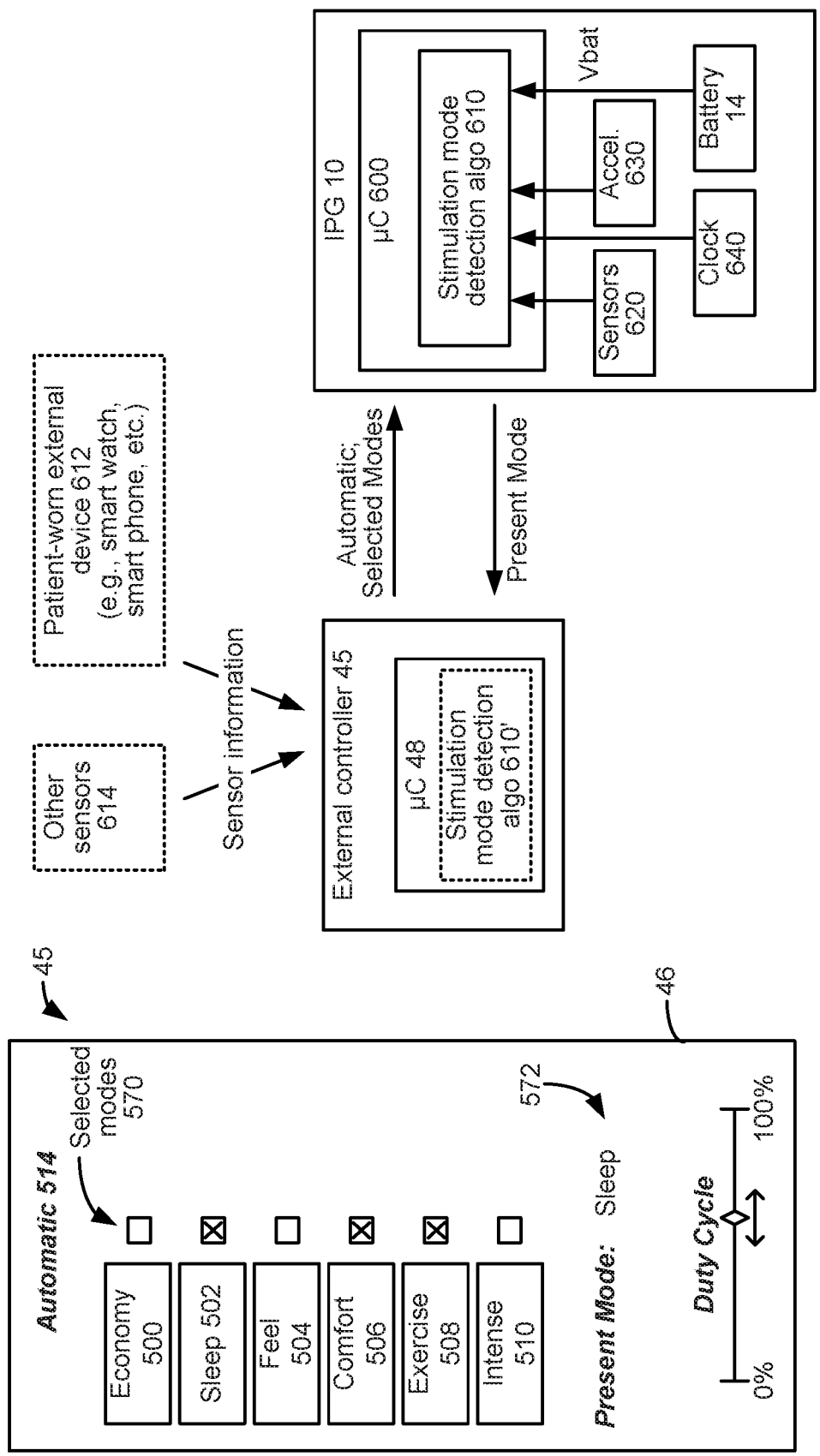
FIG. 31 shows an automatic mode in which the IPG and/or external controller are used to determine when particular stimulation modes should automatically be entered based on sensed information.

In any event, the stimulation mode detection algorithm 610 can wirelessly receive an indication that the automatic mode 514 has been selected, as well as any of the selected modes 570 of interest to the patient. The algorithm 610 can then determine using its various inputs when those modes should be entered, and thus will enable the use of the subsets 425x corresponding to the detected stimulation modes at appropriate times. In the example of FIG. 31 for example, the algorithm 610 may determine using the accelerometer 630, sensors 620, and the clock 640 that a person during evening hours is still, supine, or prone, and/or that his heart rate is slow, and thus determine that the person is presently sleeping. Algorithm 610 may at that time automatically activate sleep mode 502, and activate use of stimulation parameters within subset 425b (FIGS. 26A-26B) corresponding to this mode. Further, the IPG 10 may transmit notice of the present stimulation mode determination back to the external controller 45, which may be displayed at 572. This can be useful to allow the patient to review that the algorithm 610 has correctly determined the stimulation mode. Further, notifying the external controller 45 of the presently-determined mode can allow the proper subset 425x for that mode to be used by the external controller 45 to allow a patient adjustment to stimulation. That is, the external controller 45 can use the determined mode (sleep) to constrain adjustment (FIGS. 26A-26B) to the corresponding subset (425b) for that mode.

If the algorithm 610 determines using one or more of its inputs that a person is quickly changing position, is upright, and/or that his heart rate is high, it may determine that the person is presently exercising, a stimulation mode of interest selected by the patient. Algorithm 610 may at that time automatically activate exercise mode 508, and activate use of stimulation parameters within subset 425e (FIGS. 26A-26B) corresponding to this mode. Again, the IPG 10 may transmit notice of this present stimulation mode determination back to the external controller 45, to constrain adjustment (FIGS. 29A-29B) to the corresponding subset (425e) for that mode. If the algorithm 610 cannot determine that the patient is sleeping or exercising, it may default to a selection of the comfort mode 506, and provide stimulation, notification, and constrain adjustment (subset 425d, FIGS. 28A-28B) accordingly.

The external controller 45 may also be useful in determining the relevant stimulation mode to be used during selection of the automatic mode. In this regard, the external controller 45 can include sensors useful to determine patient activity or posture, such as an accelerometer, although this isn't shown in FIG. 31. The external controller 45 can also include a clock, and can wirelessly receive information from the IPG 10 concerning its battery voltage, and from sensors 620 regarding signals that are detected at the IPG's electrodes. Thus, the external controller 45 may also include a stimulation mode detection algorithm 610' responsive to such inputs. This algorithm 610' can take the place of algorithm 610 in the IPG 10, or can supplement the information determined from algorithm 610 to improve the stimulation mode determination. In short, and as facilitated by the bi-directional wireless communication between the external controller 45 and the IPG 10, the stimulation mode detection algorithm can effectively be split between the external controller and the IPG 10 in any desired fashion.

Further, the external controller 45 can receive relevant information to determine which stimulation mode should be entered from various other sensors. For example, the external controller 45 can receive information from a patient-worn external device 612, such as a smart watch or smart phone. Such smart devices 612 contain sensors indicative of movement (e.g., an accelerometer), and can include biological sensors as well (heart rate, blood pressure), which can be helpful to understanding different patient states, and thus different stimulation modes that should be used. Other sensors 614 more generically can also provide relevant information to the external controller 45. Such other sensors 614 could include other implantable devices that detect various biological states of the IPG patient (glucose, hear rate, etc.). Such other sensors 614 can provide still other information. For example, because cold or bad weather has been shown to affect an IPG patient stimulation therapy, sensor 614 could comprise weather sensors that provide weather information to the external controller 45. Note that sensor 614 may not need to communicate directly with the external controller 45. Information from such sensors 614 can be sent by a network (e.g., the Internet) and provided to the external controller 45 via various gateway devices (routers, WiFi, Bluetooth antennas, etc.).

Figure 32:
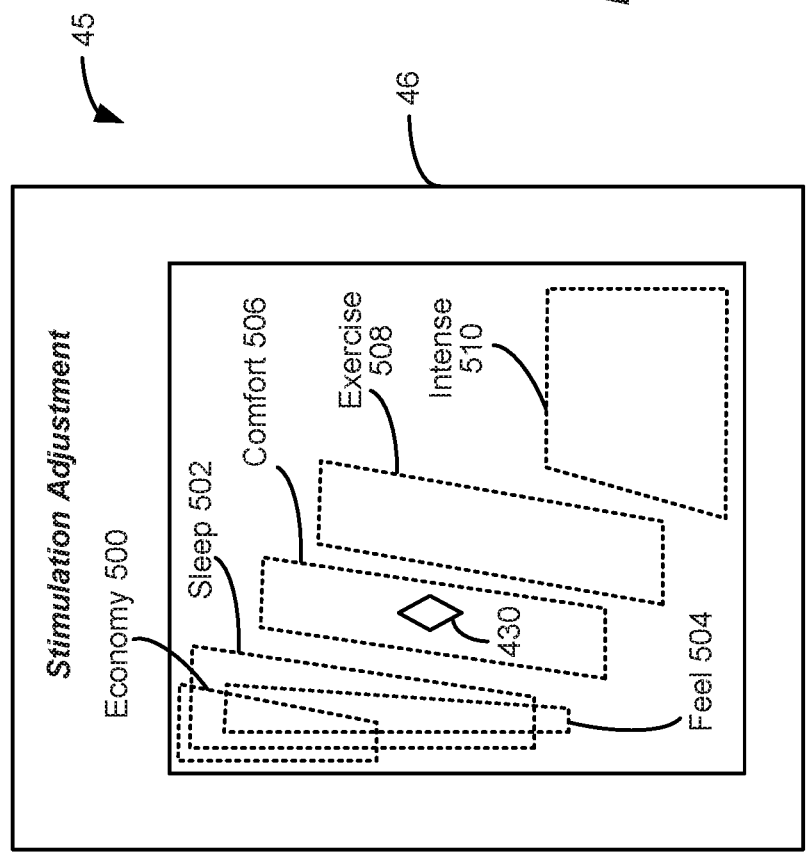
FIG. 32 shows another example of a simulation mode user interface, in which stimulation modes are presented for selection on a two-dimensional representation of stimulation parameters, although a three-dimensional representation indicative of subset volume can also be used.

FIG. 32 shows another example of a user interface on the patient's external controller 45 that allows a patient to select from different stimulation modes. In this example, the different stimulation modes (consistent with optimal stimulation parameters 420' determined for the patient) are displayed in a two-dimensional representation. In the example shown, the two-dimensional representation comprises a graph of pulse width (Y axis) versus frequency (X-axis), but any two stimulation parameters (amplitude versus frequency, or pulse width versus amplitude) could have been used as well. However, note that these X and Y axes may not be labeled, nor labeled with particular pulse width or frequency values, if the goal is to provide the patient with a simple user interface unencumbered by technical information that the patient may not understand.

Labeled in this two-dimensional representation are the different stimulation modes discussed earlier, with boundaries showing the extent of the subsets 425x of each stimulation mode. Using this representation, the patient can position a cursor 430 to select a particular stimulation mode, and in so doing select a frequency and pulse width, and its corresponding subset 425x. Because the subsets 425x may overlap, selection at a particular frequency and pulse width may select more than one stimulation mode, and more than one subset 425x, thus allowing the patient to navigate through more than one subset of stimulation parameters. Because amplitude is not represented in the two dimensional representation, the amplitude may automatically be adjusted to a suitable value given the stimulation mode/subset 425x, or the particular frequency/pulse width, selected. Alternatively, a separate slider can be included to allow the patient to additionally adjust the amplitude in accordance with subsets 425x for each of the stimulation modes. As explained above, the amplitude may be wholly constrained within optimal stimulation parameters 420' by the selected mode/subset, or may be allowed to range beyond 420' (e.g., FIGS. 26B, 27B). In a more complex example, the representation could include a three-dimensional space (F, PW, A) in which the patient can move the cursor 430, similar to that shown in FIG. 23E, with three-dimensional subsets 425x for the stimulation modes displayed.

Figure 33:
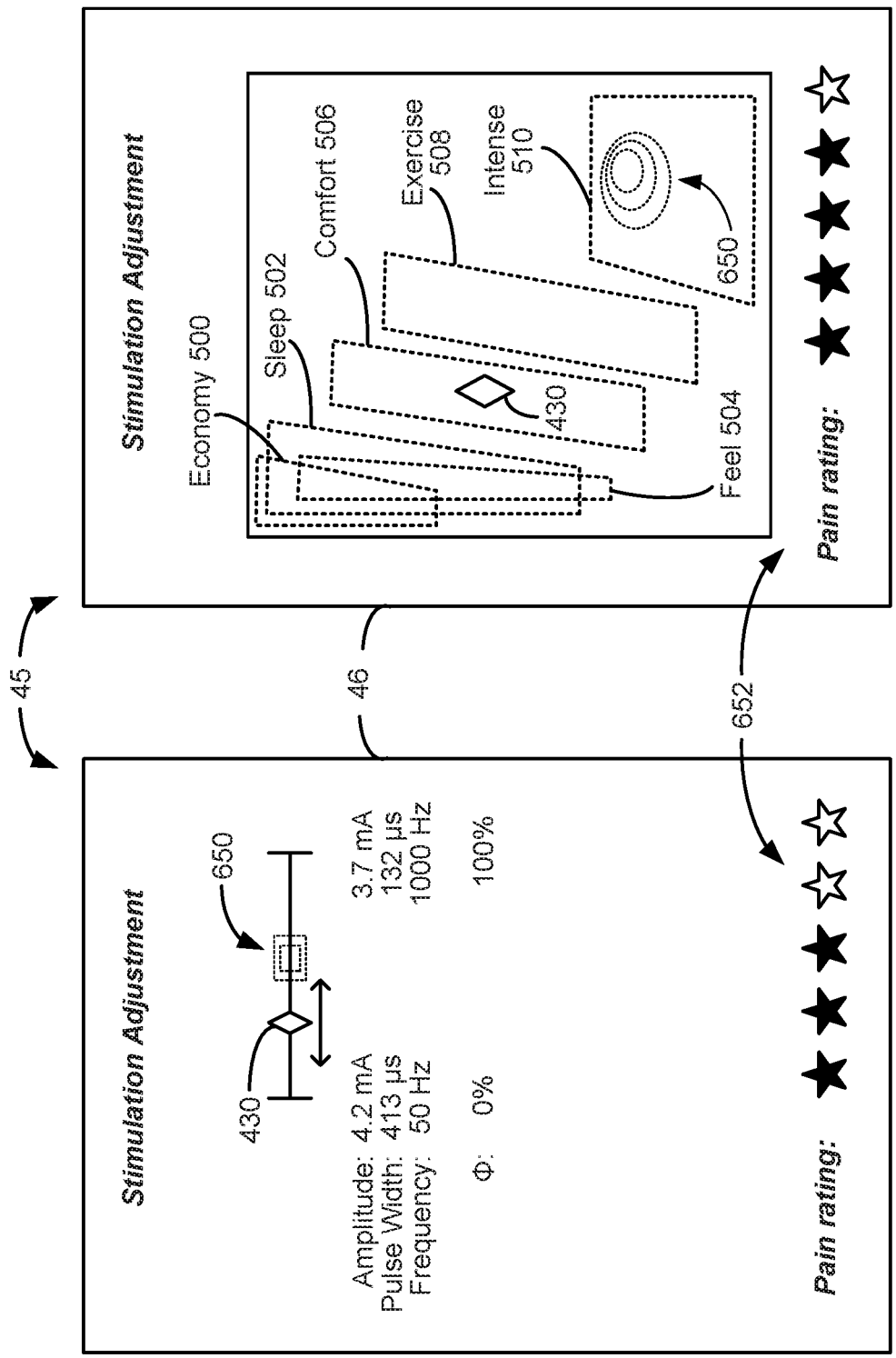
FIG. 33 shows GUI aspects that allows a patient to adjust stimulation, where a suggested stimulation region for the patient is shown in conjunction with adjustment aspects.

FIG. 33 shows another GUI aspect that allows a patient to adjust stimulation in accordance with the modelling developed for the patient. In these examples, a suggested stimulation region 650 is shown for the patient, overlaid on user interface elements that otherwise allow the patient to adjust stimulation. The examples in FIG. 33 show modification to the graphical user interfaces shown in FIGS. 22 and 32, but could be applied to other user interface examples as well. In these examples, suggested stimulation region 650 provides for the patient a visual indicator where the patient may want to select (using cursor 430 for example) stimulation settings consistent with optimal stimulation parameters 420 or 420', or subsets 425x. These regions 650 can be determined in different manners. They can be mathematically determined using the optimal stimulation parameters 420 or 420' or subsets 425x, such as by determining a center or "center of mass" of such regions. They may also be determined with specific focus on providing stimulation parameters that have an appropriate amplitude, intensity, or total charge for the patient. This may be particularly useful if the patient's previous selections have moved far away from such ideal values. Regions 650 may also be determined during a fitting procedure—by determining regions or volumes that the patient most prefers within optimal stimulation parameters 420 or 420' or subsets 425x.

Furthermore, regions 650 can be determined over time for the patient based on previously selected stimulation parameters. Thus, regions 650 can correlate to setting most often used by the patient. In an improved example, the patient may also provide feedback relevant to determining the location of regions 650. For example, the external device 45 can include an option 652 to allow a patient to provide an indication of their symptoms (e.g., pain) using a rating scale as shown. Over time, the external controller can track and correlate the pain ratings input at 652 with the stimulation parameters selected, and draw or update region 650 to appropriate locations overlaying the stimulation adjustment aspects where the patient has experienced the best symptomatic relief. Again, a mathematical analysis weighting stimulation parameters versus their pain ratings, or a center of mass approach, can be used.

It should be noted the use of the disclosed techniques should not necessarily be limited to the specific frequencies tested. Other data suggests applicability of the disclosed technique to provide pain relief without paresthesia at frequencies as low as 2 Hz.

To summarize to this point, modelling and patient fitting allows for the determination of optimal, and preferably sub-perception, stimulation parameters (in the form of ranges 420, volumes, 420' or subsets 425) for a given patient. However, once such optimal stimulation parameters are found, it may be desirable to vary such parameters over time as the stimulation is applied to the patient. This is because providing the same non-varying stimulation to neural tissue—even if ideal—can cause such tissue to habituate, such that the stimulation may not be effective as it once was.

Accordingly, once optimal stimulation parameters are determined, it may be useful to automatically vary the stimulation applied by the IPG 10 or ETS 40 within those parameters over time. This is shown in a first example in FIG. 34A. In this example, it is assumed that a subset 425 (in particular, 425e, see FIGS. 28A and 28B) of the volume of optimal stimulation parameters 420' has been determined for the patient's use. However, although not illustrated, optimal stimulation parameters can also be selected using a mean charge per second (MSC) model (e.g., 380, 381), as described earlier with respect to FIGS. 17A-17F.

To prevent habituation, the simulation applied to the patient varies over time within this subset 425, as denoted by adjustments 700. Adjustments 700 can vary any of the simulation parameters within subset 425, including the frequency, pulse width, and amplitude, and any one or more of these parameters may be changed at any given time. In the example shown at the top of FIG. 34A, frequency and pulse width are changed within subset 425 at different times (t1, t2, tec.), while the amplitude stays constant. In the example shown at the bottom of FIG. 34A, frequency and amplitude are changed within subset 425 at different times, while the pulse width stays constant.

Figure 34A:
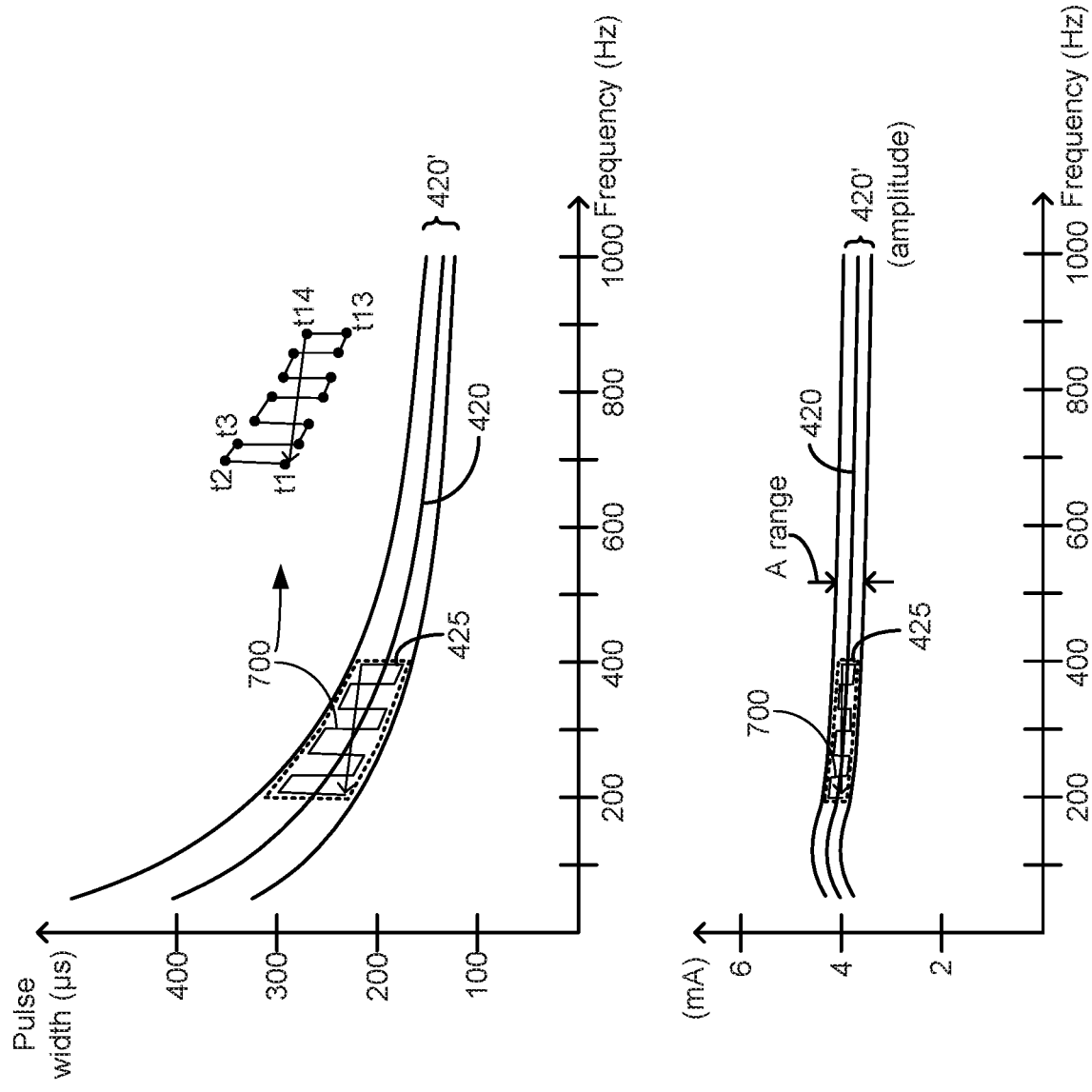
FIGS. 34A and 34C show different manners in which adjustments to one or more of the stimulation parameters can be automatically made within the range or volume of the determined optimal stimulation parameters.
Figure 34B:
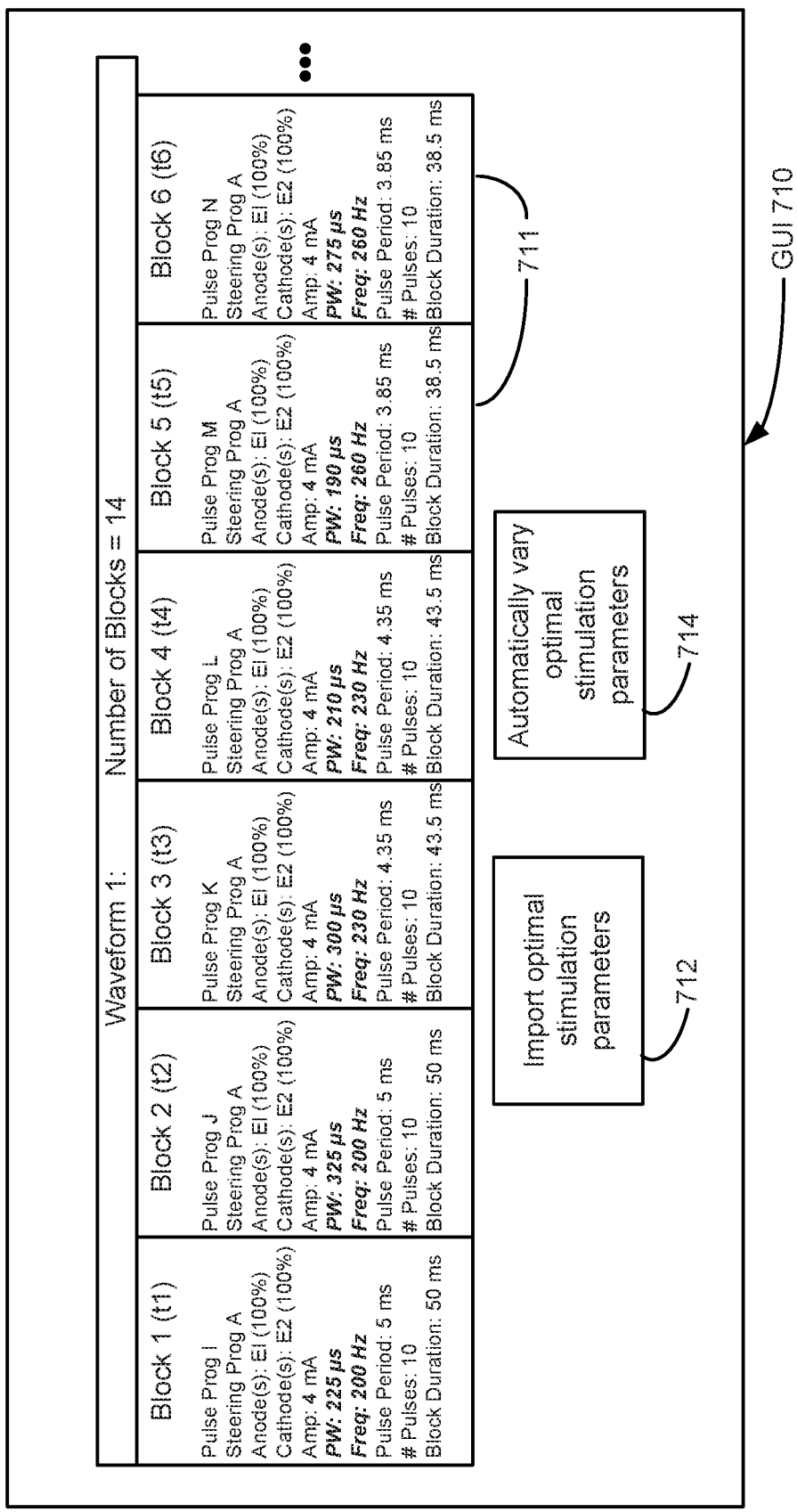
FIG. 34B shows a GUI that can be used to automatically generate the adjustments of FIG. 34A.

FIG. 34B shows an example of how adjustment 700 can be formulated, and how a program for the IPG comprising instructions can be generated. Shown in a Graphical User Interface (GUI) 710, which is described in further detail in PCT (Int'l) Patent Application Publication WO 2021/046120, with which the reader is assumed familiar. GUI 710 may operate on the clinician programmer 50 or the external controller 45, and allows the user to prescribe pulses in a manner to effect the variation desired by adjustment 700. The GUI 710 includes a number of blocks 711 where a user can specify a chronological sequence of pulses. The first block (1) prescribes pulses to be formed at t1, at electrodes (E1 and E2) as specified by a steering program A, and with a frequency (200 Hz), pulse width (225 µs), and amplitude (4 mA) within the volume of subset 25. The frequency, pulse width, and amplitude may be specified by a pulse program I, as explained in further detail in the '120 Publication. During time period t1 (and all other time periods in this example), ten of these pulses will be formed, although the number of pulses can vary and can be set in the GUI 170. The second block (2) prescribes 10 pulses to be formed at t2, at the same electrodes, and with a frequency (200 Hz), pulse width (325 µs), and amplitude (4 mA) as specified by a pulse program J. Thus, only the pulse width has been changed from time period t1 to t2. Other changes occur to the pulse width and frequency in the example of FIG. 34B to affect the adjustment 700 shown at the top of FIG. 34A. In this example, the pulse width and frequency are adjusted in a serpentine fashion between the different time periods, but this is just one example, and adjustments 700 within the optimal stimulation parameters can be made in different manners, or even randomly. The amplitudes determined within the optimal stimulation parameters could also be changed, as explained later with respect to FIG. 34C.

Even though certain stimulation parameters are changed via adjustment 700, they are still within the previously determined optimal stimulation parameters, and in particular within subset 425. Note that adjustment 700 need not however occur within a subset 425. More generally, adjustments to prevent habituation may occur within optimal stimulation parameters 420 or 420' as determined for the patient earlier.

The GUI 710 may include an option 712 to allow the user to import into the GUI 170 previously-determined optimal stimulation parameters (the model for the patient) which may be resident in either the clinician programmer 50 or external controller 45. Once imported, another option 714 can be used to automatically form adjustments 700 within those optimal stimulation parameters. Selecting option 714 can cause the GUI 710 to automatically populate blocks 711 in a manner to vary one or more stimulation parameters as necessary to produce the desired adjustment 700. Although not shown, option 714 may allow the user to select which of the one or more stimulation parameters (e.g., frequency, amplitude, pulse width) should be varied within the optimal stimulation parameters, and may further allow the user to determine an order or pattern within the optimal stimulation parameters within which the stimulation parameters may be varied. Option 714 may also allow the user to select that the stimulation parameters be randomly varied during adjustment 700. If necessary the user can adjust the stimulation parameters in the individual blocks 711 after they are automatically created to best affect a particular adjustment 700.

Figure 34C:
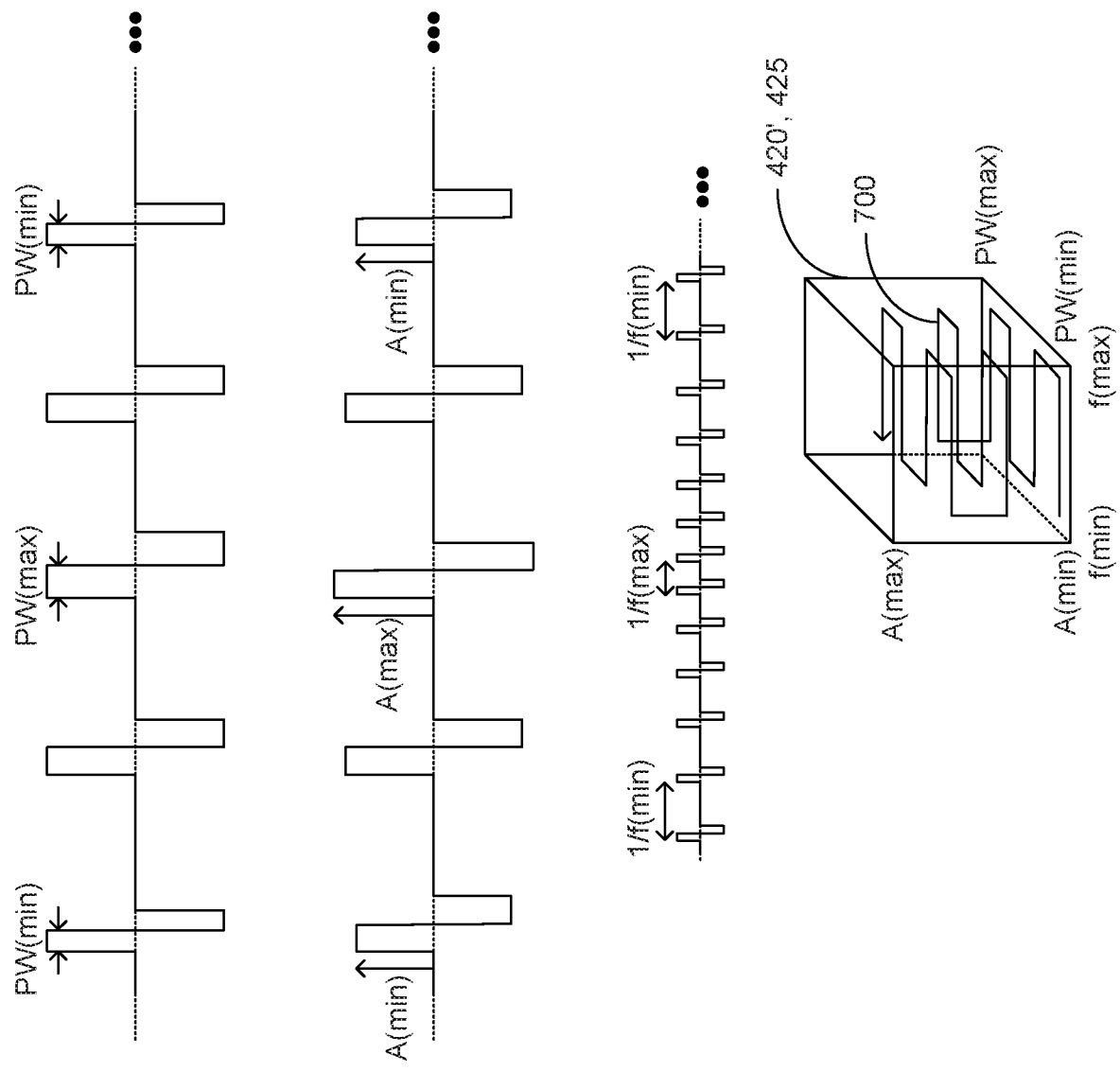

FIG. 34C shows further examples of manners in which an adjustment 700 within optimal stimulation parameters can be affected. As shown, pulse width, amplitude, and frequency of the stimulation pulses can be adjusted between maximum and minimum values (e.g., PW(min), PW(max)) within the optimal stimulation parameters. Note that these maximum and minimum value may not be constant, but may be affected by the value of other stimulation parameters. For example, and as FIG. 34A shows, PW(max) and PW(min) may comprise 325 and 225 µs when the frequency is 200 Hz, but may comprise 225 and 150 µs when the frequency is 400 Hz. The bottom of FIG. 34C shows an example in which an adjustment 700 varies amplitude, pulse width, and frequency within a volume of optimal stimulation parameters 420' or within a subset 425 of such parameters. Again, this is shown simplistically as a cube in which the parameters have maximum and minimum values, but the resulting volume may actually have a more random shape. In another modification not shown, different optimal stimulation parameters can be selected using a mean charge per second (MSC) model (e.g., 380, 381), as described earlier with respect to FIGS. 17A-17F, and applied at different times.

As well as helping to prevent tissue habituation, adjustments 700 are expected to be beneficial because the stimulation is adjusted over time within a range or volume of optimal stimulation parameters, thus making it more likely that best stimulation parameters (or combination of parameters) for the patient within this range will be at least occasionally be provided during the adjustment 700. This may be important because the leads may move within the patient, such as with activity, which may cause the best optimal stimulation parameters to change from time to time. Adjusting the stimulation parameters thus helps to ensure that the best parameters within the range or volume will be applied at least during some time periods of the adjustment 700. Further, when the stimulation parameters are adjusted, it may not be necessary to spend the time to fine tune stimulation to determine a single invariable set of optimal stimulation parameters for the patient.

FIG. 35 shows other adjustments 700 can be used which affect the electric field that is formed in the patient's tissue, and which can also be useful in preventing habituation of the tissue. Shown is a particular pole configuration 730 that has been selected for use with the patient. In the depicted example, the pole configuration 730 comprises a virtual bipole having a virtual anode pole (+) and a virtual cathode pole (−). By way of review, virtual poles are discussed further in U.S. Patent Application Publication 2019/0175915, and were discussed earlier with reference to FIG. 7B. The positions of the anode and cathode poles may not necessarily correspond to the position of the physical electrodes 16 in the electrode array, as discussed earlier. As also discussed earlier, the pole configuration 730 can have different numbers of poles, and may comprise tripoles or other configurations, although a bipole is depicted in FIG. 35 for simplicity.

The top of FIG. 35 shows different manners in which the pole configuration 730 can be moved in the electrode array 17. The top left of FIG. 35 shows how bipole 730 can be moved to different x-y locations in the electrode array 17, while still preserving the relative position of the poles with respect to each other. The top right shows how the focus—i.e., the distance d between poles—can be varied. Both of these means of adjusting the position of the poles can be made by varying activation of the electrodes 16 in the array, such as by providing particular polarities and current percentages to selected electrodes, as discussed earlier.

The bottom of FIG. 35 shows how adjustments to the location of the poles can be combined with adjustments consistent with the previously-determined optimal stimulation parameters. The left diagram shows how one of the stimulation parameters (in this case, pulse width) can be varied while also varying the x-y position of the pole configuration 730. Such adjustment 700 can vary over time the pulse width between maximum and minimum values (PW(max) and PW(min)) as determined for the optimal stimulation parameters 420' or 425. Such adjustment can also vary over time the x-y position of the pole configuration 730. Preferably, the (x,y) position of the pole configuration 730 was previously determined (using sweet spot searching, as explained earlier), but is varied during adjustment 700 from that position by maximum and minimum values. For example, position (x,y)(min) may comprise a position in which both x and y are 1 mm smaller, and position (x,y)(max) may comprise a position that in which both x and y are 1 mm larger. In other words, if optimal position (x,y) is located at (5 mm, 6 mm) in the electrode array, (x,y)(min) would comprise a position located at (4 mm, 5 mm), and (x,y)(max) would comprise a position located at (6 mm, 7 mm). Thus, adjustment 700 may move the position of the pole configuration 730 anywhere within the 2-dimensional region bounded by these maximum and minimum positions. The pulse width is also varied during adjustment 700, and other stimulation parameters (frequency, amplitude) could be varied as well, again between maximum and minimum values as determined using the optimal stimulation parameters 420' or 425. The stimulation parameters and poles can be adjusted over time pursuant to a pattern as shown, or at random between maximum and minimum values.

The middle diagram shows how one of the stimulation parameters (again, pulse width) can be varied while also varying the focus distance d of the pole configuration 730. Preferably, the focus distance d was previously determined (e.g., during sweet spot searching), but is varied during adjustment 700 from that distance by maximum and minimum values. For example, if d equals 10 mm, d(max) might be 12 mm while d(min) is 8 mm. Thus, adjustment 700 may move the focus of the pole configuration 730 anywhere within these maximum and minimum distances. The pulse width (and/or at least one other parameter such as amplitude or frequency) is also varied during adjustment 700 consistent with the previously-determined optimal stimulation parameters 420' or 425. Again, the stimulation parameters and focus distances can be adjusted over time pursuant to a pattern or at random between maximum and minimum values.

The right diagram shows that both the x-y position of the pole configuration 730 and the focus distance d of the pole configuration can be varied along with at least one other stimulation parameter (e.g., pulse width) during adjustment 700. In all of these examples, adjustments 700 which include slight adjustments to the positions of the poles in the pole configuration 730 are expected to be useful in preventing tissue habituation.

Adjustment 700 may prioritize the adjustment of certain parameters over others, and such prioritization may be based on a patient's status or symptoms. For example, if it is noticed that the patient is particularly sensitive to the location of the stimulation, it may be desirable that adjustment 700 prioritize variation to the position of the poles, either by varying the x-y position of the pole configuration 730 in the electrode array and/or by varying the focus distance d. By contrast, if the patient is particularly sensitive to the amount of stimulation (e.g., a received neural dose), it may be desirable that adjustment 700 prioritize variation to one or more of the stimulation parameters (pulse width, frequency, amplitude). Patient sensitivity as useful in prioritizing adjustment 700 can be determined using subjective or objective measures, such as by receiving patient feedback, or by taking measurements indicative of the efficacy of stimulation (e.g., by measuring ECAPs as described earlier).

Figure 36:
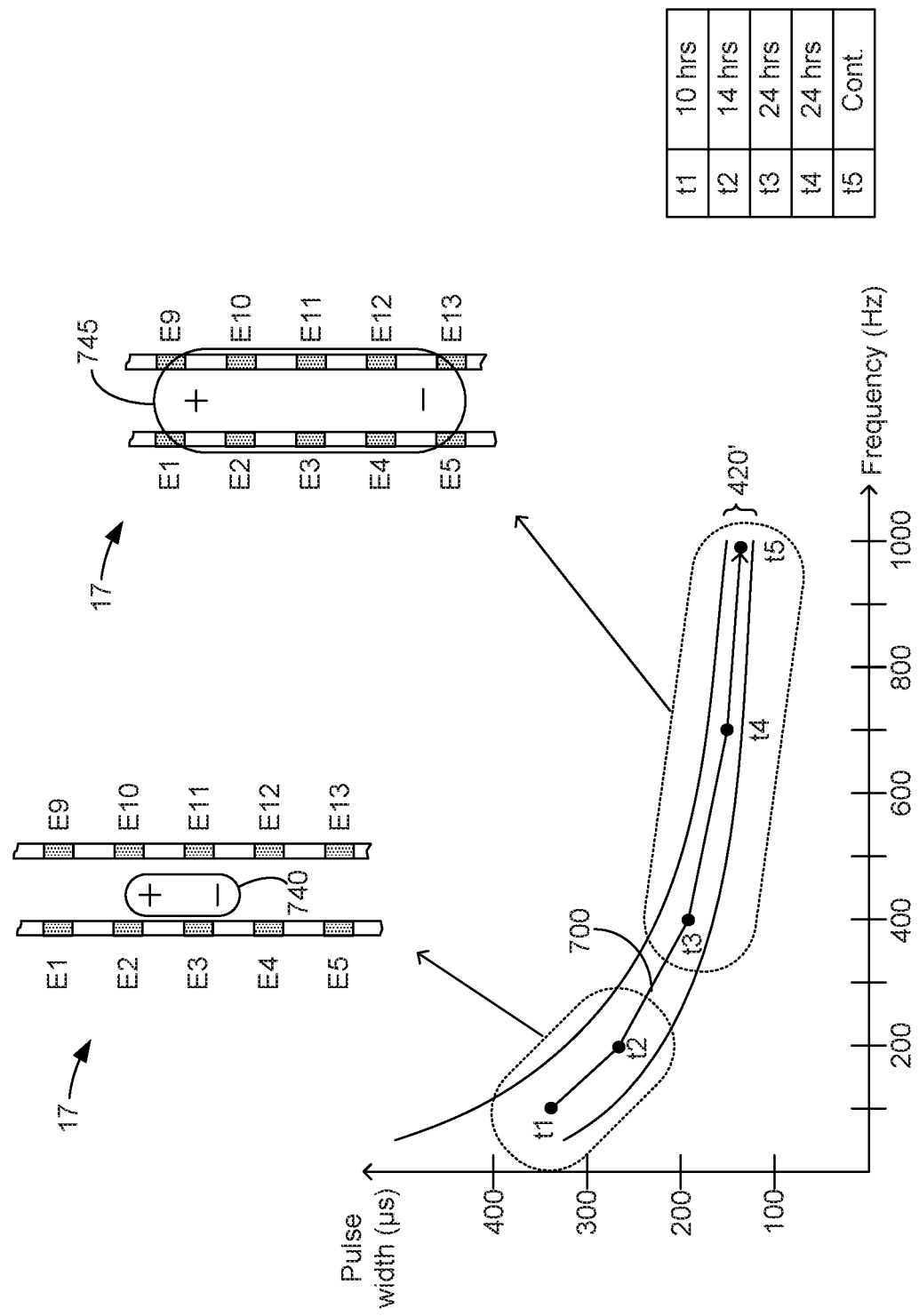
FIG. 36 shows a specific example of an adjustment within a range or volume of the determined optimal stimulation parameters in which the pulse width and frequency are adjusted between different time periods.

FIG. 36 shows another example of an adjustment 700 of stimulation parameters within optimal stimulation parameters 420'. In this example, the pulse width and frequency are adjusted between different time periods. Unlike previous examples, the stimulation at each time period is of a longer duration on the order of hours. Furthermore, the pole configuration is changed at different time periods to achieve different beneficial effects. For example, at time periods t1 and t2, a bipole 740 is used which forms a relatively small field in the tissue. This can be useful because, as described earlier, such a sub-perception bipole 740 can provide fast relief and with short wash in periods, and especially at the lower frequencies present during these time periods. However, a smaller bipole such as 740 may be sensitive: it creates only a small field in the tissue, and therefore if the leads in the electrode array 17 migrate within the tissue, bipole 740 may migrate away from the patient's pain site and become less effective. Therefore, at subsequent time periods (e.g., t3-t5), the pole configuration is changed to a larger bipole 745 which provides a larger field in the tissue. A larger field makes it less likely that lead migration will cause effective stimulation to move away from a patient's pain site, and hence such pain site is more easily recruited. Higher frequencies as used with the larger bipole 745 may additionally more easily recruit the patient's tissue, and be less susceptible to lead migration. Therefore, during adjustment 700, the bipole increases in size to promote a larger field in the tissue, and the frequency of the pulses increase, until at time t5 constant (but still optimal) stimulation therapy is provided.

Figure 37A:
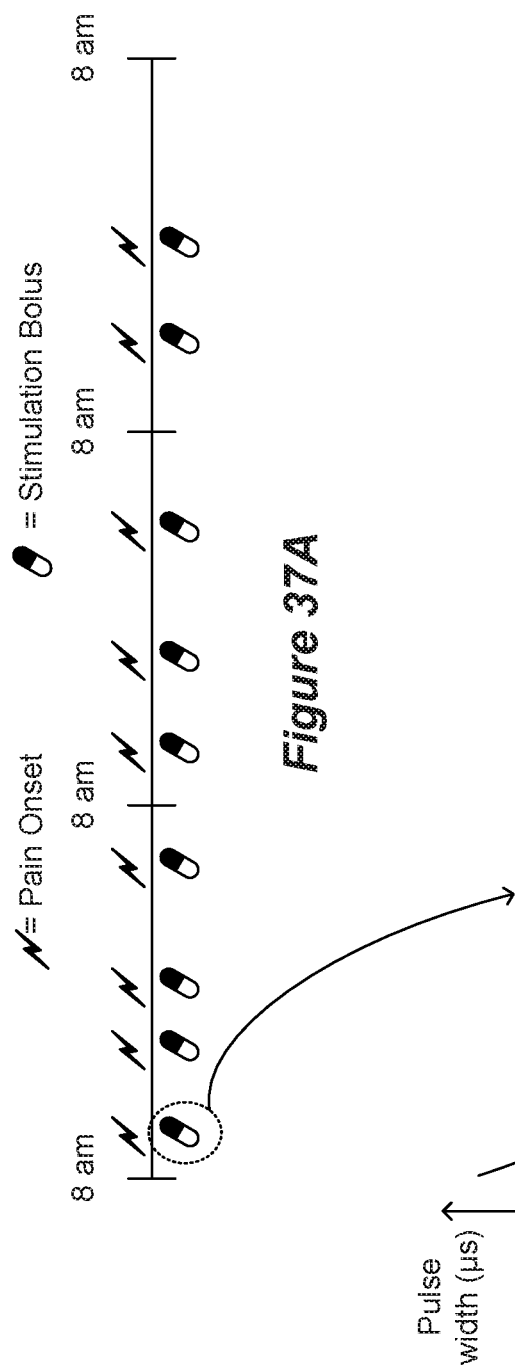
FIGS. 37A and 37B show specific examples of an adjustment within a range or volume of the determined optimal stimulation parameters, in which stimulation is provided by stimulation boluses.
Figure 37B:
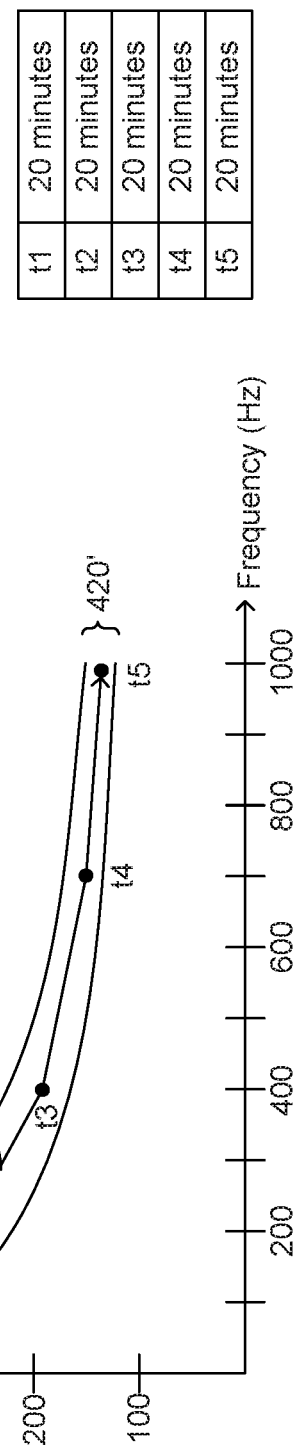
Figure 38:
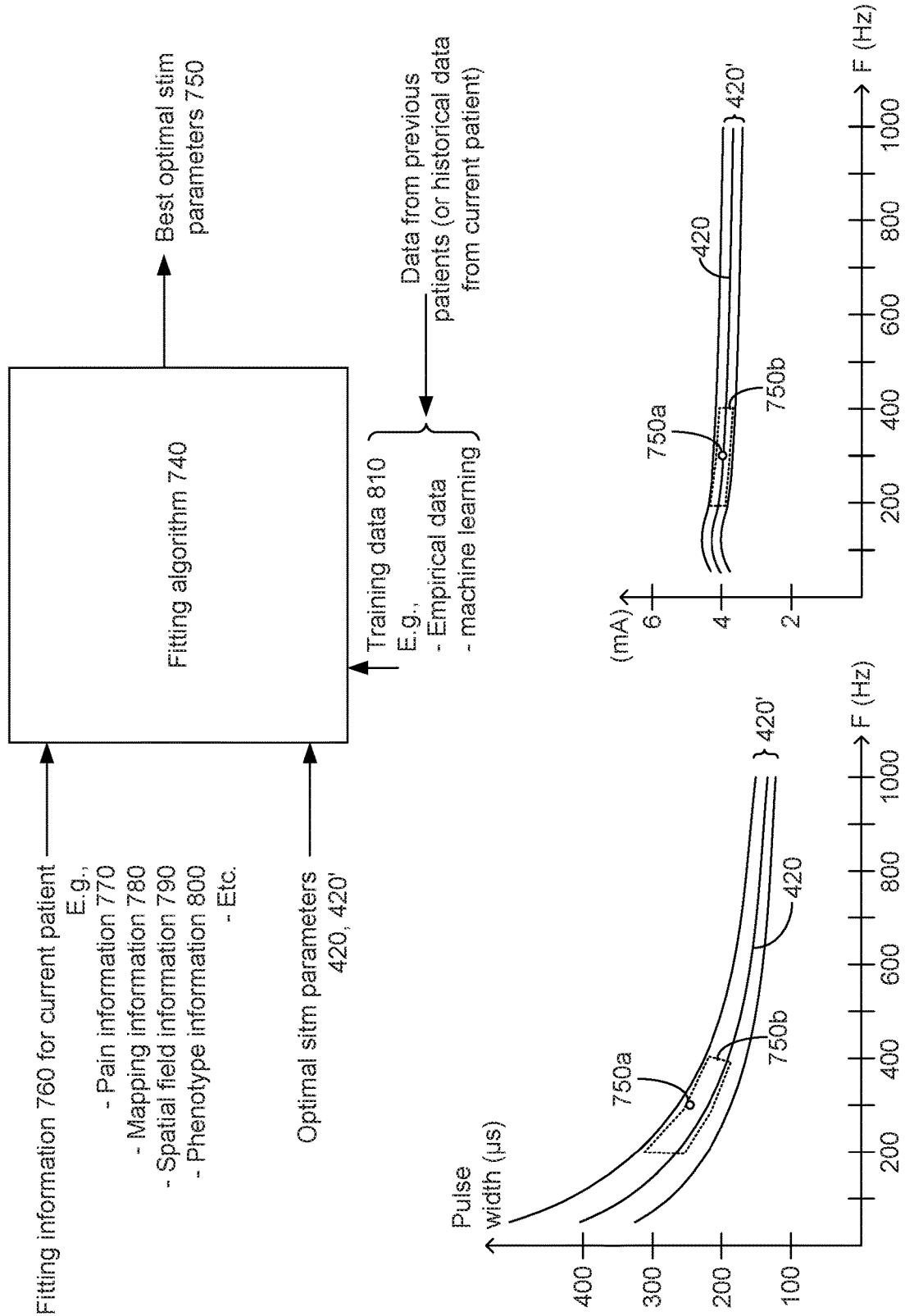
FIG. 38 shows use of a fitting algorithm that uses patient fitting information to select best stimulation parameters from a range or volume of optimal stimulation parameters determined for that patient.

Adjustment 700 within the previously-determined optimal stimulation parameters can also be used when stimulation is provided in a bolus, as shown in FIGS. 37A and 37B. Providing boluses of stimulation are described in further detail in U.S. Patent Application Publication 2020/0147400 filed concurrently herewith, which is incorporated herein by reference in its entirety. A bolus comprises stimulation that is provided for a set unit of time, such as ten minutes, thirty minutes, one hour, two hours, or any other duration that is effective, with gaps of time with no stimulation between the administration of boluses. It has been observed that some patients respond well to "bolus mode" treatment. A patient may initiate a bolus of stimulation (shown as a capsule in FIG. 37A) when they feel pain coming on (shown as a lightning bolt). FIG. 37A shows three days during which a patient has administered nine stimulation boluses. The administration of a bolus can also occur automatically, as discussed in the '400 Publication. Providing simulation in boluses can be beneficial because some patients experience extended pain relief, up to several hours or more, following receiving a bolus of stimulation, that is during the gaps between boluses during which no stimulation occurs. Furthermore, providing boluses of stimulation saves energy in the IPG because simulation is not continuous, and also helps to prevent over-stimulation and habituation of the tissue.

The stimulation parameters used during each stimulation bolus can be adjusted, as shown in FIG. 37B. Such adjustment 700 can be similar to that described in FIG. 36, but may occur on a shorter time scale. For example, the stimulation bolus shown is 100 minutes in length, and consists of five different time periods t1-t5, each lasting 20 minutes. As before, one or more stimulation parameters (e.g., pulse width and frequency) are adjusted during the different time periods within the optimal stimulation parameters 420' determined earlier. Preferably, the simulation parameters used initially (e.g., during t1) are designed to bring fast symptomatic relief. As before, the position, size, or focus distance of the pole configuration can also be changed during the different time periods comprising adjustment 700.

FIGS. 38-41B shows a fitting algorithm 740 that can be used to determine best 750 of the optimal stimulation parameters 420 or 420' for use with a given patient. In this example, a range or volume of preferred optimal stimulation parameters 420 or 420' are determined for the patient, which preferably prescribes sub-perception stimulation for the patient, as described earlier. Although not illustrated, the optimal stimulation parameters can be selected using a mean charge per second (MSC) model (e.g., 380, 381), as described earlier with respect to FIGS. 17A-17F.

The fitting algorithm 740 then uses fitting information 760 to determine one or more best of the optimal stimulation parameters for the patient to use. The best optimal stimulation parameters 750 may comprise a single set of stimulation parameters—e.g., a single frequency, pulse width, and amplitude value 750a—or a subset 750b of sets of parameters similar to the subsets 425 described earlier. In short, by using the additional information included in the fitting information 760, the fitting algorithm 740 can determine stimulation parameter(s) within the optimal stimulation parameters 420 or 420' that are most logical for the patient, and can set sub-perception stimulation in the patient's IPG accordingly.

The fitting information 760 is preferably taken during a fitting procedure after implantation, which usually occurs in a clinical setting. Accordingly, fitting algorithm 740 is preferably implemented as part of clinician programmer software 66 (FIG. 4) executable on a clinician programmer 50. However, the fitting algorithm 740 could also be used with any device or system capable of communicating with the patient's IPG, including the patient's external controller 45 (FIG. 4). Aspects of fitting algorithm 740 can be rendered as part of the clinician programmer GUI. Fitting algorithm 740 can also comprise instructions in a computer readable medium, as described elsewhere. Fitting algorithm 740 can be executed and fitting information 760 received in conjunction with other operations that may logically occur during a fitting procedure. For example, testing that occurs during algorithm 400—such as measuring the paresthesia threshold pth at different pulse widths (404, FIG. 21A) as used during determination of the optimal stimulation parameters 420 or 420'—can occur at the same time and during the same procedure when fitting information 760 is received.

The fitting information 760 can include various data indicative of the patient, his symptoms, and stimulation provided during the fitting procedure. For example, fitting information 760 can include pain information 770 that characterizes the patient's pain in the absence of stimulation. Fitting information 760 can also include mapping information 780 indicative of the effectiveness of stimulation used during the fitting procedure. Fitting information 760 can also include spatial field information 790 indicative of the stimulation used during the fitting procedure, and the electric field it creates in the patient's tissue. Fitting information 760 can also include phenotype information 800, such as the patient's age, gender, and other patient-specific particulars.

The fitting algorithm 740 also receives or includes training data 810. Essentially, the training data 810 is used to correlate the fitting information 760 with best outcomes, as will be described in further detail below. For example, the training data 810 may suggest that a particular patient's fitting information 760 warrants the use of lower-frequency therapy (e.g., 10-400 Hz) for that patient, and fitting algorithm 740 will thus choose lower-frequency stimulation when selecting best optimal stimulation parameters 750 from the optimal stimulation parameters 420 or 420' for that patient. Alternatively, the training data 810 may suggest that a particular patient's fitting information 760 warrants the use of higher-frequency therapy (e.g., 400-1000 Hz) for that patient, and fitting algorithm 740 will thus choose higher-frequency stimulation when selecting best optimal stimulation parameters 750 for that patient. Training data 810 may be arrived at over time and may be derived from the treatment of previous patients, and in this regard training data 810 would improve over time as further patients are treated and as data is received from larger numbers of patients. In this regard, information comprising training data 810 may be received at the fitting algorithm 740 from a source outside of the external device, for example from a server which can receive data from different patients to develop or update the training data 810 over time. The training data 810 can also comprise or include historical data taken from the current patient. In one example, the training data 810 can be arrived at using machine learning techniques, and can comprise weights or coefficient to be applied to various pieces of the fitting information 760, as explained further below.

Figure 39A:
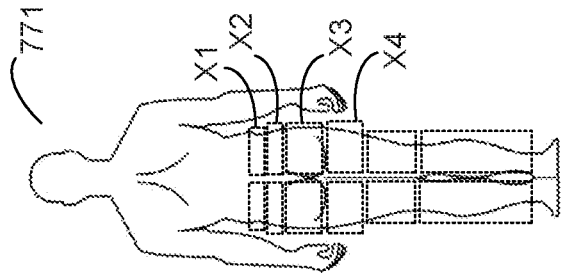
Figure 39B:
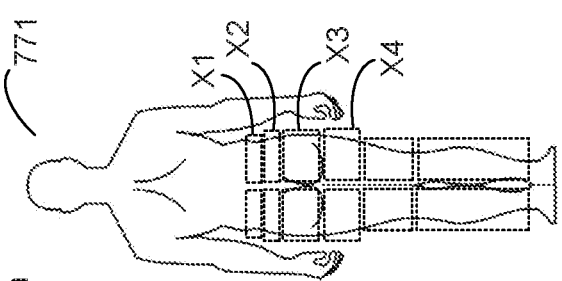

FIGS. 39A-39C show a GUI of the external system (e.g., the clinician programmer) that is useable during a fitting procedure to receive various pieces of fitting information 760, with FIG. 39A showing receipt of pain information 770, FIG. 39B showing receipt of mapping information 780, and FIG. 39C showing receipt of spatial field information 790 and patient phenotype information 800. It is not required that fitting algorithm 740 receive all pieces of fitting information illustrated in these figures, and algorithm 740 could receive additional un-illustrated pieces of information as might be relevant to predicting the best optimal stimulation parameters 750. In short, FIGS. 39A-39C merely provide examples of possibly relevant fitting information 760. Further, while it is sensible to divide relevant fitting information 760 as shown into the categories of pain information 770, mapping information 780, spatial field information 790, and patient phenotype information 800, the fitting information 760 could be subdivided into more or less categories. Alternatively, the fitting information 760 may not be subdivided into categories at all and may instead comprise one, more, or all of the pieces of information within these categories.

Referring first to FIG. 39A, pain information 770 is received at the GUI, which as noted earlier includes pieces of information that characterize the patient's pain in the absence of stimulation. In a preferred example, pain information 770 is provided for individual body regions Xx. In this respect, the GUI can include a graphic or image 771 that illustrates different body regions in which pain may occur. For example, in FIG. 39A, body region X1 denotes an upper portion of the lower back, while body region X2 denotes a lower portion of the lower back, with both of regions X1 and X2 appearing on the right side of the body. Body portion X3 denotes the right gluteus maximus, while region X4 denotes the upper portion of the right thigh. Other body regions are not labeled in graphic 771, and may appear on the left side of the body as well.

For each body region Xx, a number of different pain measures are recorded, and may be entered either by the patient or the clinician into the GUI. For example, and considering body region X1, one can record whether pain is present in that region (e.g., no (0), yes (1)), the intensity of pain in that region (e.g., 3 out of 10), how the patient senses pain in that region (e.g., as burning (1), numbness (2), sharp (3), etc.). The type of pain may also be classified; for example, 1 may denote neuropathic pain which an SCS can well treat, whereas 0 may denote pain originating from other mechanisms (bruising, arthritis, etc.) which SCS may not well treat. Such pain information 770 can be entered into the GUI for each body region as shown, resulting in a pain matrix P, which may also be viewed as a plurality of pain vectors each containing information about the patient's pain in different body regions Xx.

FIG. 39B shows receipt at the GUI of mapping information 780, which as noted earlier is indicative of the effectiveness of stimulation used during the fitting procedure. (The particulars of the stimulation provided during the fitting procedure is discussed further with respect to spatial field information 790 in FIG. 39C). Mapping information 780 can again be specified by body region Xx, and again the GUI may provide a graphic or image 771 that illustrates different body regions in which the effect of stimulation may be felt. For example, and considering body region X1, one can record whether stimulation is felt in that region (e.g., no (0), yes (1)), the perceived intensity of stimulation in that region (e.g., 7 out of 10), and the extent to which the patient feels that the stimulation is "covering" their pain (e.g., 60%).

Further, the mapping information 760 can include a pain intensity rating, which is similar to the pain intensity provided earlier in pain information 770, but as affected by the stimulation; if stimulation therapy is effective, it would be expected that the pain intensity improves (or at least does not worsen) in mapping information 780 when compared to the pain intensity received during pain information 770 when stimulation is not present. The mapping information 780 can also include a characterization of the sensation of the stimulation as perceived by the patient. For example, a patient may report that stimulation feels like constant tingling (1), vibrating (2), massaging (3), light pressure, pulsating, a spreading field, etc.

Other mapping information 760 can quantify the strength of the simulation as perceived by the patient. For example, a paresthesia threshold can be determined. As discussed earlier, this threshold (also useful during algorithm 400) can comprise for example a lowest amplitude of the simulation that the patient can perceive. Similarly, mapping information 780 can further include a discomfort threshold, which may comprise for example a maximum amplitude of the stimulation that the patient can tolerate. Other objective measures, such as various ECAP features recorded in response to stimulation, may be included within mapping information 780 as well. Mapping information 780 can result in a mapping matrix M, which may also be viewed as a plurality of mapping vectors each containing information which characterizes the effectiveness of stimulation in different body regions Xx.

FIG. 39C shows receipt at the GUI of spatial field information 790 and patient phenotype information 800. Spatial field information 790 comprises information indicative of the stimulation used during the fitting procedure, such as the shape, size, and location of the electric field such stimulation creates in the patient's tissue, and may also include information indicative of the physiological location at which the stimulation is applied, as discussed further below. In this regard, note that during the fitting procedure, different types of stimulation may be tried for the patient, using GUI aspects shown in FIG. 5 for example.

Spatial field information 790 can comprise the types of pulses used during fitting. For example, the GUI can receive an indication of the use monophasic pulses followed by passive charge recovery (0), biphasic pulses for active charge recovery (1), biphasic pulses with additional passive charge recovery (2), etc. Such pulse types were explained earlier, and still other pulse types may be used and received at the GUI as well. The GUI may also receive information about the pole configuration used to provide the stimulation, including the number of and polarity of the poles in the configuration, such as whether a bipole is used (0; e.g., FIG. 6), a tripole (1; see U.S. Patent Application Publication 2019/0175915), a spread bipole (2; e.g., FIG. 7D). Spatial field information 790 may also include information about the size of the pole configuration and the electric field it produces in the tissue. For example, the focus distance between the poles can be received, and/or the area defined by the poles (or the estimated area of the electric field created in the tissue).

Some of the pieces of spatial field information 790 may be associated with physiological coordinates, which the fitting algorithm 740 can determined in conjunction with the use of other techniques. Physiological coordinates describe physiological positions in a common manner between patients, and with reference to common physiological structures. For example, in an SCS application, coordinate (0,0,0) may correspond to the center of the T10 vertebra, while (20,0,0)

corresponds to the center of the T9 vertebra, and (−20,0,0) to the center of the T11 vertebra. In this regard, physiological coordinates may not necessarily specify actual dimensions; for example, the actual distance between T10 and T9 in a bigger patient may be larger than that same distance in a smaller patient. Nonetheless, physiological coordinates generally describe a general anatomical position. In an SCS application, the position of the electrode array 17, and hence the physiological coordinates of the electrodes 16, are generally known relative to known physical structures, such as by the use of fluoroscopic imaging techniques that show the position of a patient's array 17/electrodes 16 relative to such structures. Although not shown (in FIG. 5 for example), such physiological structures (e.g., different known vertebrae) may be superimposed on an image of the electrode array. Depending on the manner in which they are calculated, physiological coordinates may be two dimensional (x,y), but may be three dimensional as well (x,y,z) and as shown in FIG. 39C.

Knowing the positions of anatomical structures in the patient, the physiological coordinates of the electrodes 16 relative to such structures, and the electrodes that are active to form the pole configuration in the array, the fitting algorithm 740 can determine physiological coordinates for various spatial field parameters. For example, knowing the currents at each anode pole and each cathode pole allows the fitting algorithm 740 to determine physiological coordinates that correspond to the positions of those poles, which as mentioned earlier may not correspond to the physical positions of the electrodes 16. Note that knowledge of the location of such poles can also allow for a calculation of the focus distance and field area, as described earlier.

The physiological coordinates of the anode and cathode poles also allows for the determination of still further physiological coordinates that are generally indicative of the physiological position of the electric field produced in the patient. For example, the stimulation will cause various voltages V to be formed in the patient's tissue, which voltages can be estimated in three dimensions, particularly if the resistance of the tissue is known or can be measured. This in turn allows a three-dimensional electric field E in the tissue to be determined as a first order spatial derivative, i.e., $E=dV/dx$, as well as a second order spatial derivative, $d^2V/dx^2$. A physiological coordinate indicative of the position of either of these derivatives can be useful for the fitting algorithm 740 to consider. As explained in U.S. Patent Application Publication 2020/0147390, while fibers in the dorsal column run in parallel to the long axis x of the spinal cord (i.e., a rostral-caudal direction), fibers in the dorsal horn can be oriented in many directions, including perpendicular to the long axis of the spinal cord. Dorsal horn fibers and dorsal column fibers have different responses to electrical stimulation. The strength of stimulation (i.e., depolarizing or hyperpolarizing) of the dorsal column fibers is described by the so-called "activating function" $d^2V/dx^2$ determined along the longitudinal axis (x) of the spine, because dorsal column fibers that propagate past the stimulation electrodes are more likely to be activated along the axon. This is partially because the large myelinated axons in dorsal column fibers are primarily aligned longitudinally along the spine. On the other hand, the likelihood of generating action potentials in dorsal horn fibers and neurons is better described by $dV/dx$ (otherwise known as the electric field, E), because dorsal horn fibers and neurons, often constrained to being directly underneath the electrode, may be more likely to respond at dendrites and terminals. Thus, the dorsal horn "activating function" is proportional not to the second-order derivative, but to the first-order derivative of the voltage along the fiber axis.

The physiological coordinates of these activating functions can comprise spatial field information 790 calculated and used by the fitting algorithm 740. In particular, and as shown in FIG. 39C, maximum values for these activating functions (max $dV/dt$, max $d^2V/dx^2$) can be determined at physiological coordinates, as can a maximum voltage in the tissue (max V). A volume of activation can also be determined at a physiological coordinate which is indicative of a volume of recruited neural tissue. See, e.g., U.S. Pat. Nos. 8,606,360 and 9,792,412 (discussing computation of a volume of activation). A physiological coordinate for a volume of activation can comprise a center point of that volume, such as a centroid, or any other coordinate tending to show the physiological position of the activated volume in the patient.

Providing physiological coordinate information for various relevant field parameters can be significant for the fitting algorithm 740 to consider. As just described, such physiological coordinates generally indicate of the physiological location at which stimulation is provided in a given patient, and hence generally indicates a physiological neural site of pain in the patient (see, e.g., 298, FIG. 7A). It can be of interest to know such physiological positions for a patient being fitted, as this can allow the fitting algorithm 740 to determined best 750 of the optimal stimulation parameters 420 or 420'. For example, the training data 810 may reflect when a particular field parameter (e.g., max d2V/dx2) is located at or near a particular physiological coordinate (e.g., x7,y7,z7, corresponding to a particular neural structure), higher-frequency best optimal stimulation parameters 750 may be warranted. By contrast, the location of that parameter at a different physiological coordinate (x11,y11,z11, corresponding to a different neural structure) might suggest the use of lower-frequency best optimal stimulation parameters 750. This would presumably be reflected in the training data 810. That is, training data 810 would reflect from the history of past patients that those having this field parameter proximate to (x7,y7,z7) responded better when higher-frequency stimulation was used, while those having this field parameter proximate to (x11,y11,z11) responded better when lower-frequency stimulation was used.

Patient phenotype information 800 comprises information about the patient, such as their gender, age, type or indication of the patient's disease, the duration of their disease, the duration since the patient received their implant. Information regarding postures and/or activities (postures for short) in which the patient's symptoms are particularly problematic (e.g., when sitting (1), when standing (2), etc.), can also be included as patient phenotype information 800. Although not shown in FIG. 39C, the GUI may include options to allow all problematic postures to be entered, as there may be more than one. Together, the phenotype information 800 can result in a vector Y.

As discussed earlier, different patient postures or activities (postures for short) can also affect the stimulation that would be best for a given patient, and thus selection of best 750 of the optimal stimulation parameters 420 or 420'. In this regard, FIG. 40 illustrates that fitting information 760 can be received as a function of posture. For example, fitting information 760 can be received while a patient is sitting (e.g., pain matrix P1, mapping matrix M1, spatial field vector F1), while standing (P2, M2, F2), while supine (P3, M3, F3), etc., because the fitting information 760 may be different for each of these postures. For example, a patient may experience pain in a different body region when in different postures, or may perceive that pain differently, thus resulting in pain matrices Px with different information. Likewise, the effectiveness of the stimulation may vary when in different postures, yielding mapping matrices Mx with different information. Further, the stimulation used when in different postures may be different, as reflected in different spatial field vectors Fx. (By contrast, the information within patient phenotype vector Y would be agnostic to patient posture, as FIG. 40 shows).

Such fitting information 760—e.g., pain matrix P, mapping matrix M, spatial field vector F, and/or phenotype vector P, or the individual pieces of information within each—are useful for the fitting algorithm 740 to receive and consider because such information can be suggestive of stimulation parameters that would be best for a given patient, and in particular that would be the best of the optimal stimulation parameters 420 or 420' that have been determined for the patient. Experience will teach which pieces of the fitting information 760 will comprise best predictors of the best of the optimal stimulation parameters 750, and such experience may be reflected in the training data 810 (FIG. 38) used to predict the best optimal stimulation parameters 750.

For example, the percentage of pain coverage—a piece of fitting information within the mapping matrix M (FIG. 39B)—should correlate well with the neural dose or frequency of the best optimal stimulation parameters 750. If stimulation well covers a patient's pain (a high percentage), meaning that the stimulation well recruits the patient's pain, stimulation at lower neural doses or frequencies may be appropriate, and thus the fitting algorithm 740 may select one or more (e.g., a subset) of best optimal stimulation parameters 750 having lower frequencies within optimal stimulation parameters 420 or 420 determined for the patient. By contrast, if stimulation does not well cover a patient's pain (a low percentage), stimulation at higher neural doses or frequencies within the optimal stimulation parameters 420 or 420' may be selected as best optimal stimulation parameters 750 for the patient. As such, the training data 810 may attribute high relevance to (e.g., prescribe a high weight to) the percentage of pain coverage, or to the mapping matrix M more generally, when determining best optimal stimulation parameters 750.

Figure 41A:
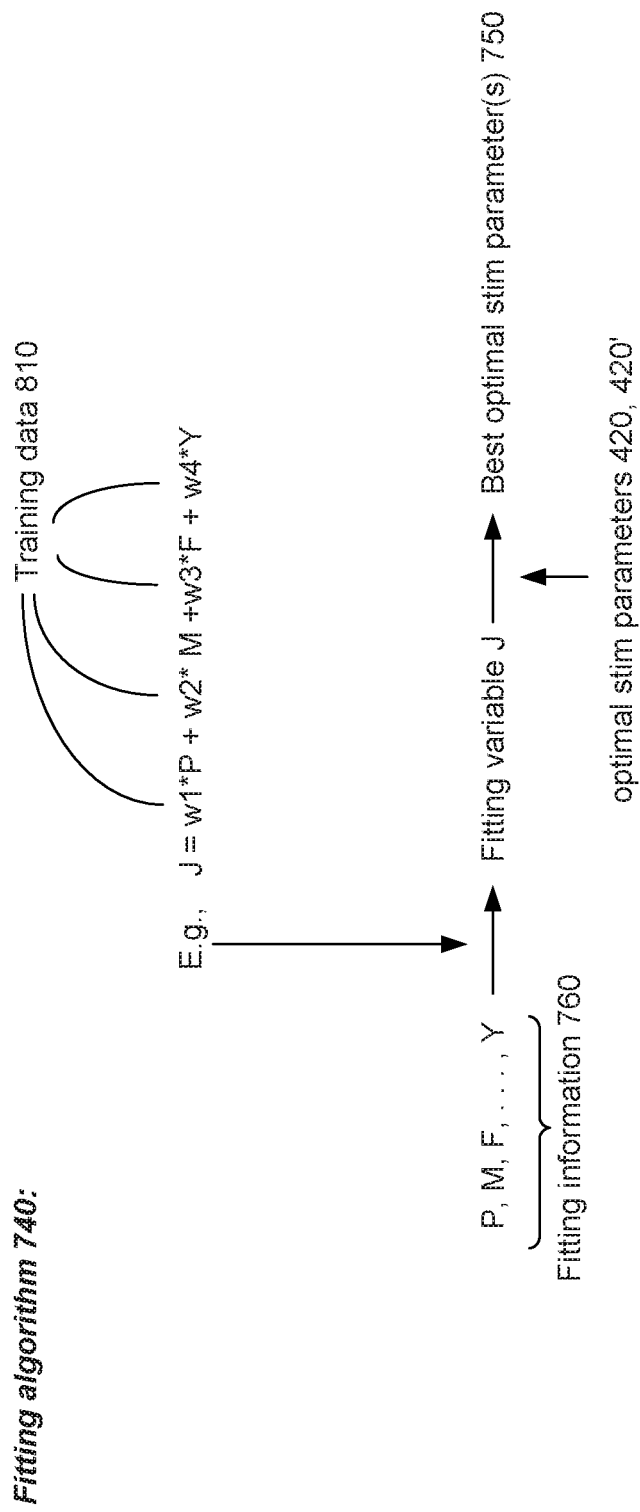
FIGS. 41A-41C show in flow chart form how the fitting algorithm can process the fitting information and the optimal stimulation parameters in light of training data to determine the best optimal stimulation parameters for the patient.
Figure 41B:
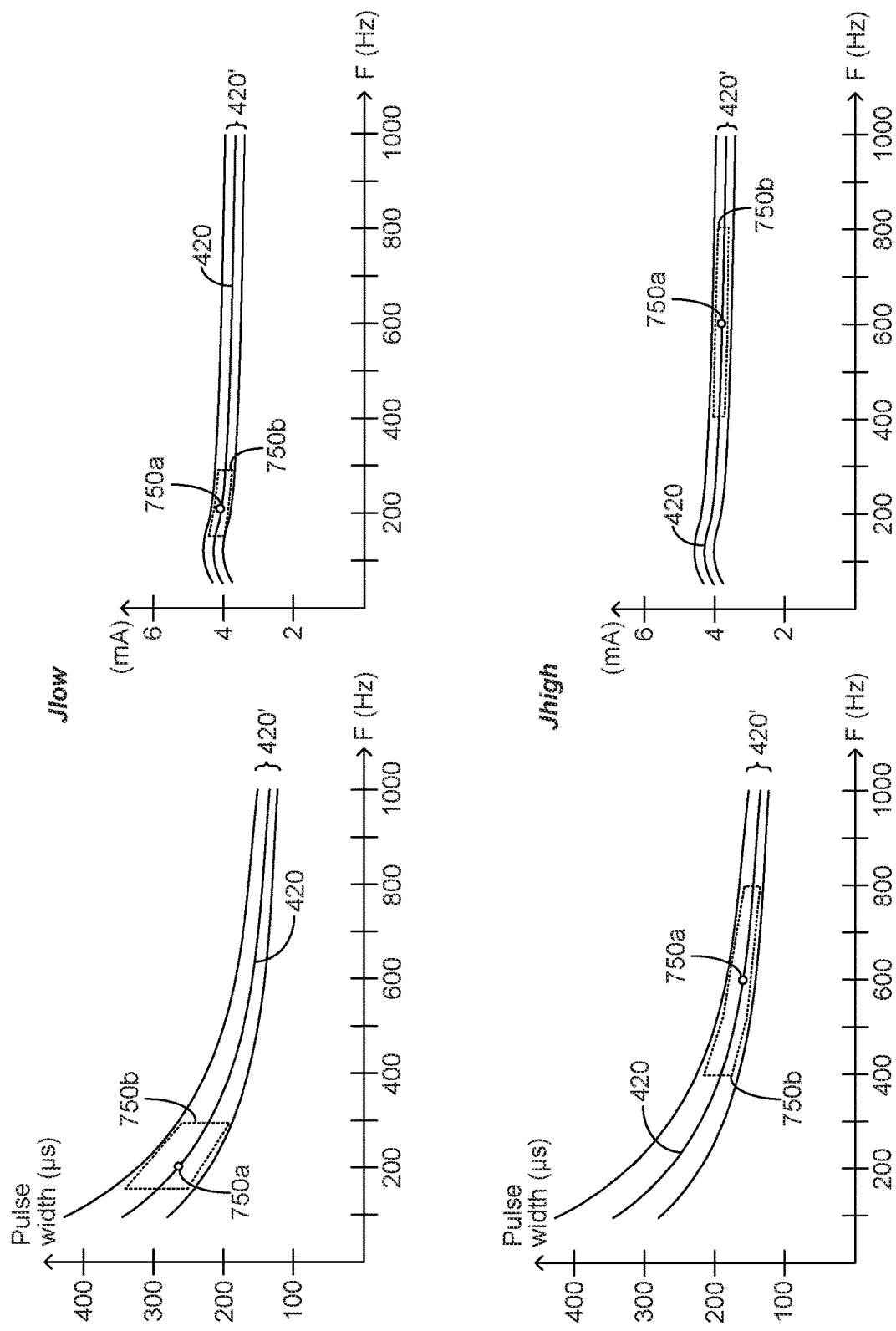

FIG. 41A shows in flow chart form how the fitting algorithm 740 can determine best optimal stimulation parameters 750 for a patient using the fitting information 760. It should be noted that FIG. 41A provides only a simple example of how fitting algorithm 740 may perform, and how training data 810 may be applied to the fitting information 760. As noted earlier, training data 810 may be arrived at by using machine learning techniques or other statistical techniques which by their nature are complicated, although understood by those skilled in the art.

In FIG. 41A, training data 810 is applied to the fitting information 760 in the form of weights, wx, which essentially assign a degree of relevance to each piece of fitting information. The weights are shown as applied to the pain matrix P, the mapping matrix M, the spatial field vector F, and the phenotype vector Y. In the example shown, a weight is applied to each of the matrices or vectors, and in this regard, it may be useful to process each matrix or vector so that they are each represented by single numbers. Although not shown, it should be understood that weights can be applied to each of the individual pieces of information that comprise the various matrices or vectors, and it is therefore not necessary that the fitting information 760 comprise matrices or vectors of information. Further, it is not strictly necessary that fitting algorithm 740 consider all of the pain information (P), mapping information (M), spatial field information (F), and patient phenotype information (Y), as some of these categories or information within them may not prove to be statistically relevant to selecting best optimal stimulation parameters 750 in an actual implementation.

Preferably, the application of the training data 810 to the fitting information 760 results in the determination of a fitting variable J. Although not shown, fitting variable J may have a variance or error associated with it, which may result from the statistical manner in which training data 810 operates. In this regard, fitting variable J may comprise either a single variable or a range of variables. The fitting algorithm 740 can use the fitting variable J to select one or more best 750 of the optimal stimulation parameters 420 or 420'. In one example, the fitting variable J may be correlated to a neural dose. For example, a high value of J may correspond to high values for frequency, because the optimal stimulation parameters 420 or 420' tend to comprise higher neural doses at higher frequencies. In the bottom graphs of FIG. 41B, the relatively high value for J results in the selection of a single point of best optimal stimulation parameters 750a, for example pulses with a frequency of 600 Hz, a pulse width of roughly 150 microseconds, and an amplitude of roughly 4 mA. Alternatively, fitting variable J, which may comprise a range in values, or which may be associated with an error term, may result in the selection of best optimal stimulation parameters 750 comprising a subset 750b of parameters, such as those corresponding to a range of frequencies (e.g., 400 to 800 Hz) and pulse widths and amplitudes associated with those frequencies from within 420 or 420'. The top of FIG. 41A by contrast shows how a lower value of J has resulted in the selection of best optimal stimulation parameters 750 from within optimal stimulation parameters 420 or 420' that have lower frequencies, and hence lower neural doses.

Figure 41C:
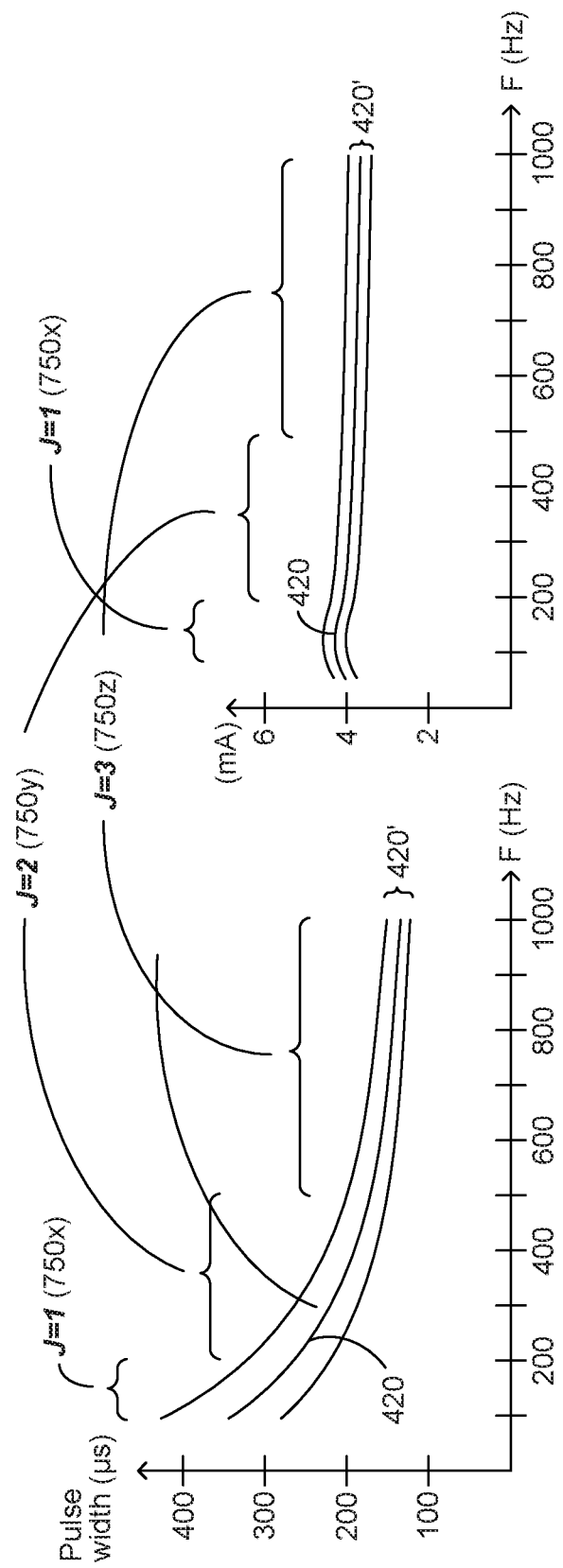

Fitting variable J may be treated more qualitatively by the fitting algorithm 740 when selecting best 750 of the optimal stimulation parameters 420 or 420'. In this regard, and as shown in FIG. 41C, the fitting algorithm 740 can classify fitting variable J into categories rather than determining J as an absolute numeric value. For example, J can be classified as '1', indicating that stimulation parameters with lower neural doses should be selected from the optimal stimulation parameters 420 or 420'. Such lower-dose parameters as just explained may comprise those at lower frequencies, and hence the fitting algorithm 740 may select for the patient a subset 750x of stimulation parameters comprising optimal stimulation parameters 420 or 420' that are at lower frequencies (e.g., 100-200 Hz), and with pulse widths and amplitudes that are consistent with those frequencies within 420 or 420'. Similarly, J may be classified as a '2', or '3', respectively suggesting the use of medium or higher neural doses, which may result in the selection of appropriate best stimulation parameters subset 750y (e.g., parameters within 420 or 420' with medium-range frequencies of 200-400 Hz) or 750z (e.g., parameters within 420 or 420' with higher-range frequencies of 400-1000 Hz). If necessary, the system (e.g., the patient's IPG or a relevant external programming device), can constrain adjustment to within these determined subsets 750x-z, similarly to what was explained earlier. As before, a single set of parameters, as opposed to a subset of parameters, could also be selected by the fitting algorithm 740.

Alternatively, to the extent that the fitting information 760 is determined as a function of patient posture x, as described earlier in FIG. 40, the fitting algorithm 740 may determine a fitting variable Jx corresponding to each patient posture x (e.g., J1 sitting, J2 standing, etc.), with each fitting variable being determined using the fitting information specific to that posture (or at least information that is not specific to any posture, such as patient phenotype information 800). For example, J1=w1*P1+w2*M1+w3*F1+w4*Y, while J2=w5*P2+w6*M2+w7*F2+w4*Y, etc. Each of these posture-specific fitting variables Jx can be used to determine best optimal stimulation parameters 750 for different patient postures. This can be useful, as it allows the best optimal stimulation parameters 750 to be adjusted as the patient changes posture. This is similar to what was described above with respect to the selection of different subsets 425 for the patient depending on a currently-detected patient posture: when a new patient posture is detected, new, best optimal stimulation parameters 750 can be applied that are associated with the detected posture.

It is preferred that the fitting algorithm 740 use the previously-determined optimal stimulation parameters 420 or 420' for a patient when selecting best optimal stimulation parameters 750 for that patient. However, this is not strictly necessary, and FIG. 42 shows an alternative fitting algorithm 740'. As before, training data 810 can be applied to a patient's fitting information 760 to determine a fitting variable J. However, fitting variable J is used to select the best optimal stimulation parameters 750 for the patient from a generic model 830. The model 830 may not be specific to the patient that provides the fitting information 760, and may represent a generic modelling of preferred stimulation parameters, such as those noticed based on empirical data to provide beneficial results over a larger subset of patients. Model 830 may comprise a range or volume of stimulation parameters that provide sub-perception stimulation, although this is not strictly necessary, and model 830 could also comprise a range or volume of stimulation parameters that provide supra-perception stimulation. Model 830 could, for example, comprise the regions 100 or relationships 98 discussed earlier with respect to FIGS. 10A-13B, the model 390 discussed with reference to FIG. 18, or other models developed in the future and indicative of beneficial stimulation parameters. Even though fitting algorithm 740' does not select best optimal stimulation parameters 750 from optimal stimulation parameters 420 or 420' determined to be useful for a specific patient, it is expected as more patients are successfully treated that model 830 and training data 810 will develop over time to allow best optimal stimulation parameters 750 to be predicted for a given patient using that patient's fitting information 760.

Various aspects of the disclosed techniques, including processes implementable in the IPG or ETS, or in external devices such as the clinician programmer or external controller to render and operate the GUI 64, can be formulated and stored as instructions in a computer-readable media associated with such devices, such as in a magnetic, optical, or solid state memory. The computer-readable media with such stored instructions may also comprise a device readable by the clinician programmer or external controller, such as in a memory stick or a removable disk, and may reside elsewhere. For example, the computer-readable media may be associated with a server or any other computer device, thus allowing instructions to be downloaded to the clinician programmer system or external controller or to the IPG or ETS, via the Internet for example.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
a spinal cord stimulator device comprising a plurality of electrodes, wherein the stimulator device is programmable to provide stimulation to a patient's tissue at at least one of the plurality of electrodes in accordance with a stimulation program; and
an external device configured to program the stimulator device with the stimulation program, wherein the external device is programmed with an algorithm configured to determine the stimulation program in accordance with a first model, wherein the first model is defined by pre-determined mean charge per second values that cause sub-perception stimulation, wherein the algorithm is configured to determine stimulation parameters for the stimulation program that yield a mean charge per second value within the first model.

2. The system of claim 1, wherein the first model comprises the mean charge per second values represented as a function of values of one of the stimulation parameters.

3. The system of claim 2, wherein the first model comprises a mathematical relationship expressing the mean charge per second values as a function of one of the stimulation parameters.

4. The system of claim 2, wherein the one of the stimulation parameters comprises frequency.

5. The system of claim 4, wherein the frequencies in the first model are equal to or lower than 1 kHz.

6. The system of claim 4, wherein the frequencies in the first model are equal to or lower than 400 Hz.

7. The system of claim 2, wherein the first model includes a range of the mean charge per second values at each of the values of the one of the stimulation parameters.

8. The system of claim 1, wherein the algorithm is further configured to determine the stimulation program in accordance with a second model, wherein the second model comprises information relating frequencies and pulse widths that cause sub-perception stimulation.

9. The system of claim 8, wherein the algorithm selects a frequency and pulse width as two of the stimulation parameters in accordance with the second model, and selects an amplitude as another stimulation parameter to yield the mean charge per second value within the first model.

10. The system of claim 1, wherein the stimulation parameters for the stimulation program comprise amplitude, pulse width, and frequency.

11. The system of claim 1, wherein the first model comprises pre-determined information relating the mean charge per second values and frequencies values that cause sub-perception stimulation.

12. The system of claim 11, wherein the first model comprises the mean charge per second values and frequency values that are on or within one or more linearly-bounded regions defined by points:
(i) (10 Hz, 6 µC/s), (10 Hz, 12 µC/s), (50 Hz, 55 µC/s), and (50 Hz, 27 µC/s); or
(ii) (50 Hz, 27 µC/s), (50 Hz, 55 µC/s), (100 Hz, 88 µC/s), and (100 Hz, 40 µC/s); or
(iii) (100 Hz, 40 µC/s), (100 Hz, 88 µC/s), (200 Hz, 151 µC/s), and (200 Hz, 67 µC/s); or (iv) (200 Hz, 67 µC/s), (200 Hz, 151 µC/s), (400 Hz, 274 µC/s), and (400 Hz, 118 µC/s); or (v) (400 Hz, 118 µC/s), (400 Hz, 274 µC/s), (600 Hz, 357 µC/s), (600 Hz, 141 µC/s); or (vi) (600 Hz, 141 µC/s), (600 Hz, 357 µC/s), (1000 Hz, 471 µC/s), (1000 Hz, 181 µC/s).

13. The system of claim 11, wherein the first model comprises the mean charge per second values and frequency values that are on or within one or more linearly-bounded regions defined by points:

(i) (10 Hz, 6 µC/s), (10 Hz, 12 µC/s), (50 Hz, 55 µC/s), and (50 Hz, 27 µC/s); or (ii) (50 Hz, 27 µC/s), (50 Hz, 55 µC/s), (100 Hz, 88 µC/s), and (100 Hz, 40 µC/s); or (iii) (100 Hz, 40 µC/s), (100 Hz, 88 µC/s), (200 Hz, 151 µC/s), and (200 Hz, 67 µC/s); or (iv) (200 Hz, 67 µC/s), (200 Hz, 151 µC/s), (400 Hz, 274 µC/s), and (400 Hz, 118 µC/s).

14. The system of claim 1, wherein the spinal cord stimulator is programmable during a programming session, and wherein the sub-perception stimulation is washed in within a period of one hour or less during the programming session.

15. The system of claim 1, wherein the spinal cord stimulator is programmable during a programming session, and wherein the sub-perception stimulation is washed in within a period of ten minutes or less during the programming session.

16. The system of claim 1, wherein the external device is configured to cause the stimulator device to cease providing the sub-perception stimulation, wherein effectiveness of the sub-perception stimulation occurs during a wash out period of ten minutes or greater after the sub-perception stimulation has ceased.

17. The system of claim 1, wherein the external device is configured to cause the stimulator device to cease providing the sub-perception stimulation, wherein effectiveness of the sub-perception stimulation occurs during a wash out period of one hour or greater after the sub-perception stimulation has ceased.

* * * * *